United States Patent
Bur et al.

(10) Patent No.: US 8,563,714 B2
(45) Date of Patent: Oct. 22, 2013

(54) BRIDGED SPIRO [2.4] HEPTANE DERIVATIVES AS ALX RECEPTOR AND/OR FPRL2 AGONISTS

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 27 days.

(21) Appl. No.: 13/321,372

(22) PCT Filed: May 17, 2010

(86) PCT No.: PCT/IB2010/052170
§ 371 (c)(1),
(2), (4) Date: Nov. 18, 2011

(87) PCT Pub. No.: WO2010/134014
PCT Pub. Date: Nov. 25, 2010

(65) Prior Publication Data
US 2012/0115841 A1 May 10, 2012

(30) Foreign Application Priority Data
May 18, 2009 (WO) .................. PCT/IB2009/052056

(51) Int. Cl.
C07C 233/58 (2006.01)
C07C 233/60 (2006.01)
C07C 233/63 (2006.01)
C07D 207/09 (2006.01)
C07D 211/26 (2006.01)
C07D 213/40 (2006.01)
C07D 231/12 (2006.01)
C07D 233/64 (2006.01)
C07D 235/14 (2006.01)
C07D 239/30 (2006.01)
C07D 249/08 (2006.01)
C07D 277/28 (2006.01)

(52) U.S. Cl.
USPC ........... 544/165; 540/543; 544/400; 548/125; 548/147; 548/212; 548/216; 548/248; 548/249; 548/267.6; 548/300.7; 548/357.5; 548/569; 548/953; 549/330; 564/153; 564/157; 560/37; 560/39; 546/15; 514/210.17; 514/218; 514/252.12; 514/237.8; 514/278; 514/364; 514/372; 514/373; 514/374; 514/377; 514/378; 514/383; 514/392; 514/394; 514/407; 514/409; 514/452; 514/462; 514/531; 514/616

(58) Field of Classification Search
None
See application file for complete search history.

(56) References Cited

U.S. PATENT DOCUMENTS

| 2006/0078559 A1 | 4/2006 | Migeotte et al. |
| 2010/0331378 A1 | 12/2010 | Bur et al. |
| 2011/0034516 A1 | 2/2011 | Bur et al. |
| 2011/0319454 A1 * | 12/2011 | Beard et al. .................. 514/352 |
| 2012/0101138 A1 | 4/2012 | Bur et al. |
| 2012/0115916 A1 | 5/2012 | Bur et al. |

FOREIGN PATENT DOCUMENTS

| WO | WO 95/02587 | 1/1995 |
| WO | WO 03/082314 | 10/2003 |
| WO | WO 2005/047899 | 5/2005 |
| WO | WO 2009/077954 | 6/2009 |
| WO | WO 2009/077990 | 6/2009 |
| WO | WO 2010/143116 | 12/2010 |
| WO | WO 2010/143158 | 12/2010 |

OTHER PUBLICATIONS

Sodin-Semrl et al, "Lipoxin $A_4$ counteracts Synergistic Activation of Human Fibroblast-like Synoviocytes" *Int J Immunopathol Pharmacol* (2004) 17:15-25.

Zhang et al., "BML-111, a lipoxin receptor agonist, modulates the immune response and reduces the severity of collagen-induced arthritis" (2008) *Inflamm Res* 57:157-162.

Jin et al., (2007) "Posttreatment with Aspiring-Triggered Lipoxin $A_4$ Analog Attenuates Lipopolysaccharide-Induced Acute Lung Injury in Mice: The Role of Heme Oxygenase-1" *Anesth Analg* 104:369-377.

Celik et al., Lipoxin $A_4$ in asthma: relation with disease severity and aspiring sensitivity (2007) *Clin Exp Allergy* 37:1494-1501, p. 1494 Only.

Planaguma et al, Airway Lipoxin $A_4$ Generation and Lipoxin $A_4$ Receptor Expression Are Decreased in Severe Asthma (2008) *Am J Respir Crit Care Med* 178:574-582).

Levy et al., "Multi-pronged Inhibition of airway hyper-responsiveness and inflammation by Lipoxin $A_4$" (2002) *Nat Med* 8:1018-1023.

Levy et al., "Lipoxin $A_4$ stable analogs reduce allergic airway responses via mechanisms distinct from CysLT1 receptor antagonism" (2007) *FASEB J* 21: pp. 1-8.

Karp et al., "Defective lipoxin-mediated anti-inflammatory activity in the cystic fibrosis airway" (2004) *Nat Immunol* 5:388-392.

(Continued)

Primary Examiner — Laura L. Stockton
(74) Attorney, Agent, or Firm — Hunton & Williams LLP

(57) ABSTRACT

The present invention relates to bridged spiro[2.4]heptane derivatives of formula (I), wherein W, Y, Z, $R^1$ and $R^2$ are as defined in the description, their preparation and their use as pharmaceutically active compounds as ALX receptor and/or FPRL2 agonists for the treatment of inflammatory and obstructive airways diseases.

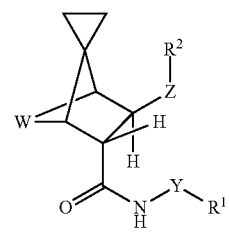

34 Claims, No Drawings

(56) References Cited

OTHER PUBLICATIONS

Gronert, "Lipoxins in the eye and their role in wound healing" (2005) *Prostaglandins Leukot Essent Fatty Acids* 73:221-229.

Gronert et al., "A Role for the Mouse 12/15-Lipoxygenase Pathaway in Promoting Epithelial Wound Healing and Host Defense" (2005) *J Biol Chem* 280:15267-15278.

Gewirtz et al., "Mechanisms of Active Intestinal Inflammation and Potential Down-regulation via Lipoxins" (2002) *Eicosanoids and other Bioactive Lipids in Cancer, Inflammation, and Radiation Injury*, Kluwer Academic/Plenum Publishers, 229-236).

Mamiya et al., "[Gly14]-Humanin improved the learning and memory impairment induced by scopolamine in vivo" (2001) *Br J Pharmacol* 134:1597-1599.

Ying et al., "Humanin, a Newly Identified Neuroprotective Factor, Uses the G Protein-Coupled Formylpeptide Receptor-Like-1 as a Functional Receptor[1]" (2004) *J Immunol* 172:7078-7085.

Miao et al., "S14G-Humanin ameliorates Aβ25-35-induced behavioral deficits by reducing neuroinflammatory responses and apoptosis in mice" (2008) *Neuropeptides* 42:557-567.

Bannenberg, Gerard L.; "Anti-inflammatory actions of lipoxins"; Expert Opin. Ther. Patents; vol. 17, No. 6, pp. 591-605; 2007 XP-002593532.

Bürli, Roland W. et al.; "Potent hFPRL1 (ALXR) agonists as potential anti-inflammatory agents"; Bioorganic & Medicinal Chemistry Letters; vol. 16, pp. 3713-3718; 2006.

Caricasole, Andrea et al.; "A novel rat gene encoding a Humanin-like peptide endowed with broad neuroprotective activity"; FASEB Journal, vol. 16, pp. 1331-1333; Aug. 2002.

Chiang, Nan et al.; "The Lipoxing Receptor ALX: Potent Ligand-Specific and Stereoselective Actions in Vivo"; Pharmacological Reviews, vol. 58, No. 3, pp. 463-487; 2006.

Coe, Jotham W. et al.; "Formation of 3-Halobenzyne: Solvent Effects and Cycloaddition Adducts"; American Chemical Society; Organic Letters, vol. 6, No. 10, pp. 1589-1592; 2004.

Devosse, Thalie et al.; "Formyl Peptide Receptor-Like 2 is Expressed and Functional in Plasmacytoid Dendritic Cells, Tissue-Specific Macrophage Subpopulations, and Eosinophils"; Journal of Immunology, vol. 182, pp. 4974-4984; 2009.

Gould, Philip L.; "Salt selection for basic drugs"; International Journal of Pharmaceutics, vol. 33, pp. 201-217; 1986.

Greene, Theodora W. et al.; "Protective Groups in Organic Synthesis"; Wiley-Interscience Publication; Third Edition; 1999; ISBN 0-471-22057-4.

Harada, Masataka et al.; "N-Formylated humanin activates both formyl peptide receptor-like 1 and 2"; Biochemical and Biophysical Research Communications vol. 324, pp. 255-261; 2004.

Hashimoto, Yuichi et al.; "Mechanisms of Neuroprotection by a Novel Rescue Factor Humanin from Swedish Mutant Amyloid Precursor Protein"; Biochmeical and Biophysical Research Communications, vol. 283, pp. 460-468; 2001.

Hartmann, Horst et al.; "High Stereoselectivity in Lewis-Acid-Catalyzed and Uncatalyzed Diels-Alder Reactions of the Fumarate of (S)-Ethyl Lactate"; Angew. Chem. Int. Ed. Engl., vol. 26, No. 11, pp. 1143-1145; 1987.

Kang, Hyun Kyu et al.; "The Synthetic Peptide Trp-Lys-Tyr-Met-Val-D-Met Inhibits Human Monocyte-Derived Dendritic Cell Maturation via Formyl Peptide Receptor and Formyl Peptide Receptor-Like 2"; The Journal of Immunology, vol. 175, pp. 685-692; 2005.

Le, Yingying et al.; "Biologically Active Peptides Interacting with the G Protein-Coupled Formylpeptide Receptors"; Protein & Peptide Letters, vol. 14, pp. 846-853; 2007.

Mamiya, Takayoshi et al.; "[Gly14]-Humanin improved the learning and memory impairment induced by scopolamine in vivo"; British Journal of Pharmacology, vol. 134, pp. 1597-1599; 2001.

Migeotte, Isabelle et al.; "Identification and characterization of an endogenous chemotactic ligand specific for FPRL2"; Journal of Experimental Medicine, vol. 201, No. 1, pp. 83-93; 2005.

Kriek, Nicole M. A. J., et al.; "Synthesis of Novel Tetrahydropyran-Based Dipeptide Isosters by Overman Rearrangement of 2,3-Didehydroglycosides"; Eur. J. Org. Chem, pp. 2418-2427; 2003.

Remington; "Pharmaceutical Manufacturing"; The Science and Practice of Pharmacy, 21st Edition, Part 5; published by Lippincott Williams & Wilkins; 2005, Table of Contents Only.

Schwab, Jan M. et al; "Lipoxins and new lipid mediators in the resolution of inflammation"; Current Opinion in Pharmacology, vol. 6, pp. 414-420; 2006.

Kariya, Shingo et al.; "Humanin inhibits cell death of serum-deprived PC12h cells"; Neurochemistry NeuroReport, vol. 13, No. 6, pp. 903-907; May 7, 2002.

Yazawa, Hiroshi et al.; "β Amyloid peptide ($A\beta_{42}$) is internalized via the G-Protein-Coupled receptor FPRL1 and forms fibrillar aggregates in macrophages[1]"; FASEB Journal, vol. 15, pp. 2454-2462; Nov. 2001.

Ying, Guoguang et al.; "Humanin, a Newly Identified Neuroprotective Factor, Uses the G Protein-Coupled Formylpeptide Receptor-Like-1 as a Functional Receptor"; Journal of Immunology, Vo. 172, pp. 7078-7085; 2004.

\* cited by examiner

BRIDGED SPIRO [2.4] HEPTANE DERIVATIVES AS ALX RECEPTOR AND/OR FPRL2 AGONISTS

CROSS-REFERENCE TO RELATED APPLICATIONS

This application is the national phase application of PCT/IB2010/052170, filed May 17, 2010, which claims the benefit of PCT/IB2009/052056, filed May 18, 2009, the contents of each of which are hereby incorporated by reference in their entirety.

FIELD OF THE INVENTION

The present invention relates to bridged spiro[2.4]heptane derivatives of formula (I) and their use as pharmaceuticals. The invention also concerns related aspects including processes for the preparation of the compounds, pharmaceutical compositions containing one or more compounds of formula (I), and especially their use as ALX receptor and/or FPRL2 agonists.

BACKGROUND OF THE INVENTION

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

BRIEF SUMMARY OF THE INVENTION

FPRL2 (alias Formyl Peptide Receptor Like-2, FPR3; disclosed in US2006/0078559 as nucleotide sequence SEQ ID NO:1 and amino acid sequence SEQ ID NO: 2) is a member of the G-protein coupled receptor family. The mRNA of FPRL2 was detected in various tissues, including heart, aorta, vein, spleen, lung, trachea, liver, pancreas, adrenal gland, cervix, rectum, small intestine, ileum chronic inflammation, placenta, spinal cord, lymph node, dorsal rot ganglia, pons, cerebral meninges, postcentral gyrus, Alzheimer brain frontal lobe and breast tumor. FPRL2 is expressed in human monocytes, macrophages, myeloid dendritic cells, plasmacytoid dendritic cells, eosinophils, but not in neutrophils (Migeotte et al, J. Exp. Med., 2005, 201, 83-89; Devosee et al., J. Immunol., 2009, 4974-4984). Humanin, and its analogues, were found to bind FPRL2 with high affinity (Harada et al., Biochem. Biophys. Res. Commun., 2004, 324, 255-261). Humanin was found to protect neuronal cells from a number of toxic insults. This includes neurotoxicity mediated by three mutant genes that cause FAD as well as Abeta (Hashimoto et al., Biochem. Biophys. Res. Commun., 2001, 283, 460-468). Humanin has also been reported to have protective activity for neurons against serum deprivation (Takahashi et al., Neuroreport, 2002, 13, 903-907) and against excitotoxic death (Caricasole et al., FASEB J., 2002, 1331-1333). Humanin has also been shown to rescue cortical neurons from prion-peptide-induced apoptosis. Humanin has been further shown to improve learning and memory impairment in mice, thereby evidencing utility as a beneficial agent for the prevention or treatment of learning or memory impairment (Mamiya et al., 2001, Br. J. Pharmacol., 134, 1597-1599). Humanin has also been shown to be protective for muscle cells and rescues human cerebrovascular smooth muscle cells from Abeta-induced toxicity. Furthermore, FPRL2 was found to recognize F2L, a Heme Binding Protein (HBP) polypeptide (Migeotte et al., US2006/0078559). Migeotte et al. (J. Exp. Med., 2005, 201, 83-89) suggested that F2L could be released from HBP after cell suffering or cell death. This molecule would thereafter mediate the recruitment of monocytes and Dendritic cells via FPRL2. Immature and mature dendritic cells (iDC and mDC, respectively) migrate to different anatomical sites, e.g., sites of antigen (Ag) deposition and secondary lymphoid organs, respectively, to fulfill their roles in the induction of primary, Ag-specific immune responses. The trafficking pattern of iDC and mDC is based on their expression of functional chemotactic receptors and the in vivo sites expressing the corresponding ligands including chemokines and/or classical chemoattractants. FPRL2 expressed by DC must be functional and mediate the effect of some known ligands on DC, suggesting that the interaction of FPRL2 and its endogenous ligand(s) may be involved in regulating DC trafficking during Ag uptake and processing in the periphery as well as the T cell-stimulating phase of the immune responses. Kang et al. (J. Immunol, 2005, 175, 685-692) demonstrated that FPRL2 ligands, *Helicobacter pylori*-derived peptide Hp(2-20) and F2L, inhibited IL-12 production in Monocyte-derived DC (MoDC) induced by LPS, supporting the notion that FPRL2 participates in the inhibition of MoDC maturation by LPS. Therefore, FPRL2 might be involved in the initiation of a variety of inflammatory diseases based on cell death and could represent an attractive target for therapeutic approaches.

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The biological properties of FPRL2 agonists include, but are not limited to, monocyte/macrophage/microglia migration/activation, regulation of lymphocyte activation, proliferation and differentiation, maturation and migration of dendritic cells, regulation of inflammation, regulation of cytokine production and/or release, regulation of proinflammatory mediator production and/or release, regulation of immune reaction.

The present invention provides bridged spiro[2.4]heptane derivatives, which are non-peptide agonists of human ALX and/or FPRL2 receptor. Different bridged spiro[2.4]heptane derivatives have been disclosed in WO9502587. The compounds are useful for the prevention or treatment of diseases, which respond to the modulation of the ALX receptor and/or FPRL2 such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

DETAILED DESCRIPTION OF PREFERRED EMBODIMENTS

Various embodiments of the invention are presented hereafter:
1) The present invention relates to compounds of the formula (I),

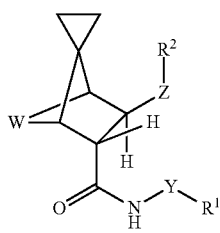

wherein
W represents —$CH_2CH_2$— or —CH=CH—;
Y represents a bond or a ($C_1$-$C_4$)alkandiyl group and $R^1$ represents
an aryl- or a heteroaryl-group, which groups are independently unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_2$)alkyl-carbonyl, ($C_1$-$C_2$)fluoroalkyl, ($C_1$-$C_2$)fluoroalkoxy, nitro, cyano and phenyl, wherein the phenyl is unsubstituted or mono-substituted with halogen; or
benzo[d][1,3]dioxolyl; or
aryloxy; or
a cyclohexyl- or a cyclohexenyl-group, which groups are independently unsubstituted or mono-substituted with ($C_1$-$C_4$)alkyl; or
($C_1$-$C_2$)alkyl-carbonyl; or
($C_1$-$C_4$)alkoxy-carbonyl;
or Y represents together with $R^1$ a ($C_4$-$C_6$)alkyl group or a amino-($C_4$-$C_6$)alkyl group;
Z represents —C(O)$NR^3$—* or —$CH_2NR^4C(O)$—*,
wherein the asterisks indicate the bond which is linked to $R^2$;
$R^2$ represents
($C_3$-$C_6$)cycloalkyl, which is unsubstituted or mono-substituted with hydroxy, hydroxy-methyl, $R^5R^6N$—$CH_2$—, heterocyclyl-methyl or —$CONH_2$; or
($C_1$-$C_6$)alkyl, which is unsubstituted or mono-substituted with fluorine, trifluoromethyl, ($C_1$-$C_4$)alkylthio, ($C_1$-$C_4$)alkoxy-carbonyl, hydroxy, cyano, —$NR^5R^6$, —COOH, —C(O)$NR^7R^8$ or optionally mono-substituted ($C_1$-$C_4$)alkoxy, wherein the substituent is selected from hydroxy and heterocyclyl; or
($C_1$-$C_6$)alkyl (preferably ($C_1$-$C_5$)alkyl), which is mono-substituted
with ($C_3$-$C_6$)cycloalkyl, which cycloalkyl is unsubstituted or mono-substituted with —$NR^5R^6$ or hydroxy;
with heterocyclyl, which heterocyclyl is unsubstituted or mono-substituted at a nitrogen atom with ($C_1$-$C_4$) alkyl, ($C_1$-$C_2$)alkyl-carbonyl or tert-butoxycarbonyl, and/or mono- or di-substituted at one or two of the carbon atoms with substituents independently selected from halogen, ($C_1$-$C_4$)alkyl and ($C_1$-$C_2$) alkoxy-($C_1$-$C_2$)alkyl; or
with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NHR^9$, —$SO_2NH_2$ and phenyl; or
($C_3$-$C_5$)fluoroalkyl, which is mono-substituted with heterocyclyl, which heterocyclyl is unsubstituted (preferred) or mono- or di-substituted at one or two of the carbon atoms with substituents independently selected from halogen and ($C_1$-$C_4$)alkyl; or
heterocyclyl, which is unsubstituted or mono-substituted at a nitrogen atom with ($C_1$-$C_6$)alkyl, benzyl or tert-butoxycarbonyl or mono-substituted at a carbon atom with pyrrolidin-1-yl-methyl; or
an aryl- or a heteroaryl-group, which groups are independently unsubstituted, mono-, di- or tri-substituted, wherein the substituents are independently selected from the group consisting of halogen, ($C_1$-$C_4$)alkyl and phenyl; or
a group selected from 1-carbamoyl-2-phenyl-ethyl, 1-methoxymethyl-2-phenyl-ethyl, 2-morpholino-2-phenyl-ethyl, 2-phenyl-vinyl, 2,2-dichloro-1-methyl-cyclopropyl;
$R^3$ represents hydrogen, ($C_1$-$C_3$)alkyl or 2-methoxy-ethyl; or
$R^2$ and $R^3$ form, together with the nitrogen that carries them, a ring of 5 to 7 members, which ring is substituted with amino-($C_1$-$C_4$)alkyl;
$R^4$ represents hydrogen or methyl;
$R^5$ represents hydrogen, ($C_1$-$C_3$)alkyl or tert-butoxycarbonyl;
$R^6$ represents hydrogen or ($C_1$-$C_3$)alkyl;
$R^7$ and $R^8$ represent independently from each other hydrogen or methyl; or $R^7$ and $R^8$ form, together with the nitrogen that carries them, a pyrrolidine or piperidine ring; and $R^9$ represents hydrogen or tert-butoxycarbonyl;

and to the salts (in particular pharmaceutically acceptable salts) of such compounds.

For avoidance of any doubt, the term "Z represents —C(O)NR$^3$—*, wherein the asterisk indicates the bond which is linked to R$^2$" means that the residue R$^2$ is linked to the nitrogen atom of the amide moiety.

The configuration of compounds of formula (I) according to embodiment 1) is such that the substituent $R^1$—Y—NH—C(O)— is in relative proximity to the group W (endo-position), whereas the substituent $R^2$—Z— is in relative proximity to the cyclopropyl-moiety (exo-position).

Formula I comprises compounds of formula $I_{St1}$ and of formula $I_{St2}$ and mixtures thereof.

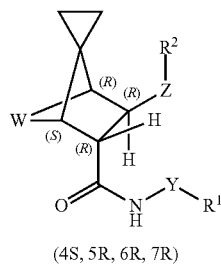

(4S, 5R, 6R, 7R)

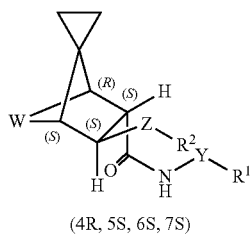

(4R, 5S, 6S, 7S)

For avoidance of any doubt, compounds of formula (I) are denominated in analogy to the following examples:

a mixture of enantiomers of structure

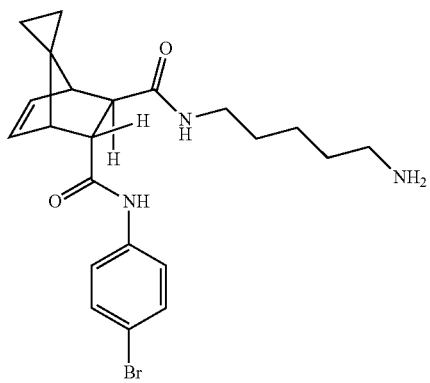 [SMILES: NCCCCCNC(=O)C1C(C(=O)Nc2ccc(Br)cc2)C2C=CC1C21CC1]

is denominated (5R*)—N$^5$-(4-Bromophenyl)-(6R*)—N$^6$-(5-amino-pentyl)-(4S*,7R*)-[4,7-ethenylene-spiro[2.4]heptane]-5,6-dicarboxamide;

the pure stereoisomer of structure

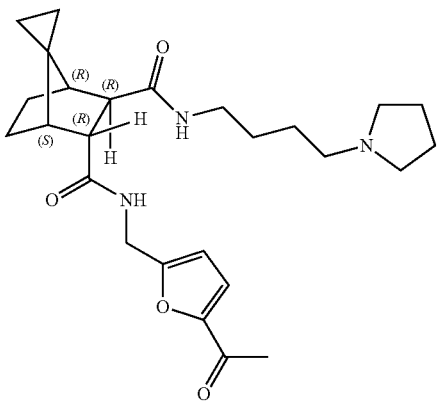

is denominated (5R)—N$^5$-(5-Acetyl-furan-2-yl-methyl)-(6R)—N$^6$-(4-pyrrolidin-1-yl-butyl)-(4S,7R)-[4,7-ethylene-spiro[2.4]heptane]-5,6-dicarboxamide; and a mixture of enantiomers of structure

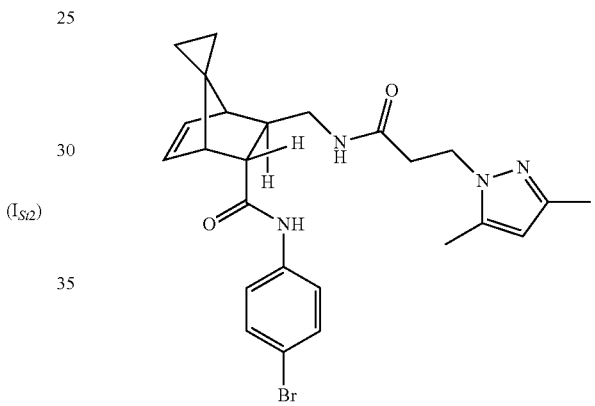

is denominated (5R*)—N$^5$-(4-Bromo-phenyl)-(6R*)-6-[(3-(3,5-dimethyl-pyrazol-1-yl)-propionylamino)-methyl]-(4S*,7R*)-[4,7-ethenylene-spiro[2.4]heptane]-5-carboxamide.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to six carbon atoms. The term "$(C_x-C_y)$alkyl" (x and y each being an integer), refers to an alkyl group as defined before containing x to y carbon atoms. For example a $(C_1-C_6)$alkyl group contains from one to six carbon atoms. Representative examples of alkyl groups include methyl, ethyl, n-propyl, iso-propyl, n-butyl, iso-butyl, sec-butyl, tert-butyl, the isomeric pentyls and the isomeric hexyls. The alkyl group may be unsubstituted or substituted as explicitly defined.

In case a $(C_1-C_4)$alkyl group is a substituent to an aryl-, a heteroaryl- or a heterocyclyl-group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred are methyl, ethyl and iso-butyl, and most preferred is methyl.

In case a $(C_1-C_6)$alkyl group is a substituent to a heterocyclyl-group, the term "$(C_1-C_6)$alkyl" means $(C_1-C_6)$alkyl groups as defined above. Examples of said groups are methyl, ethyl, n-propyl, iso-propyl, n-butyl, iso-butyl, sec-butyl, tert-butyl, the isomeric pentyls and the isomeric hexyls. Preferred are methyl, ethyl and 3-methyl-but-1-yl. Most preferred is 3-methyl-but-1-yl.

In case a $(C_1-C_4)$alkyl group is a substituent to a cyclohexyl- or a cyclohexenyl-group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred are methyl and tert-butyl, and most preferred is methyl.

In case "$R^2$" represents "$(C_1-C_6)$alkyl which is unsubstituted or mono-substituted with fluorine, trifluoromethyl, $(C_1-C_4)$alkylthio, $(C_1-C_4)$alkoxy-carbonyl, hydroxy, cyano, —$NR^5R^6$, —COOH, —$C(O)NR^7R^8$ or optionally mono-substituted $(C_1-C_4)$alkoxy, wherein the substituent is selected from hydroxy and heterocyclyl" the term "$(C_1-C_6)$alkyl" means $(C_1-C_6)$alkyl groups as defined above. Examples of said groups are methyl, ethyl, n-propyl, iso-propyl, n-butyl, iso-butyl, sec-butyl, tert-butyl, the isomeric pentyls and the isomeric hexyls. Preferred are methyl, ethyl, n-propyl, iso-propyl, n-butyl, iso-butyl, 2,2-dimethyl-prop-1-yl, 3-methyl-but-1-yl, 3,3-dimethyl-but-1-yl, pent-1-yl, pent-2-yl, 4-methyl-pent-2-yl and hex-1-yl. Most preferred are methyl, ethyl, n-propyl, n-butyl, iso-butyl, 2,2-dimethyl-prop-1-yl and pent-1-yl. The above-mentioned $(C_1-C_6)$alkyl groups are unsubstituted or mono-substituted with fluorine, trifluoromethyl, $(C_1-C_4)$alkylthio, $(C_1-C_4)$alkoxy-carbonyl, hydroxy, cyano, —$NR^5R^6$, —COOH, —$C(O)NR^7R^8$ or optionally mono-substituted $(C_1-C_4)$alkoxy, wherein the substituent is selected from hydroxy and heterocyclyl. Preferably the substituent is selected from the group consisting of fluorine, trifluoromethyl, methoxy, ethoxy, ethylthio, hydroxy, cyano, —$NR^5R^6$ or —$C(O)NR^7R^8$.

In the other case wherein "$R^2$" represents "$(C_1-C_6)$alkyl" the term means $(C_1-C_6)$alkyl groups as defined above. Examples of said groups are methyl, ethyl, n-propyl, iso-propyl, n-butyl, iso-butyl, sec-butyl, tert-butyl, the isomeric pentyls and the isomeric hexyls.

Preferred are methyl, ethyl, n-propyl, n-butyl and n-pentyl. More preferred are n-butyl and n-pentyl and most preferred is n-butyl. The above-mentioned $(C_1-C_6)$alkyl groups are mono-substituted with $(C_3-C_6)$cycloalkyl, which cycloalkyl is unsubstituted or mono-substituted with —$NR^5R^6$ or hydroxy; with heterocyclyl, which heterocyclyl is unsubstituted or mono-substituted at a nitrogen atom with $(C_1-C_4)$ alkyl, $(C_1-C_2)$alkyl-carbonyl or tert-butoxycarbonyl, and/or mono- or di-substituted at one or two of the carbon atoms with substituents independently selected from halogen, $(C_1-C_4)$ alkyl and $(C_1-C_2)$alkoxy-$(C_1-C_2)$alkyl; or with an aryl- or heteroaryl-group, which groups are independently unsubstituted, mono-, di- or tri-substituted, wherein the substituents are independently selected from the group consisting of halogen, $(C_1-C_4)$alkyl, —$CH_2NHR^9$, —$SO_2NH_2$ and phenyl. In a preferred embodiment the $(C_1-C_6)$alkyl groups are substituted with a heterocyclyl group, which is unsubstituted, mono-substituted at a nitrogen atom with methyl or ethyl or mono-substituted at a carbon atom with fluorine. In another preferred embodiment the $(C_1-C_6)$alkyl groups are substituted with an aryl- or heteroaryl-group, which groups are independently unsubstituted, mono- or di-substituted (preferably unsubstituted or mono-substituted), wherein the substituents are independently selected from the group consisting of halogen, methyl, ethyl, —$CH_2NH_2$ and —$SO_2NH_2$.

In case "$R^3$" represents "$(C_1-C_3)$alkyl" the term means $(C_1-C_3)$alkyl groups as defined above. Examples of said groups are methyl, ethyl, n-propyl and iso-propyl. Preferred are methyl, ethyl and n-propyl. Most preferred are methyl and ethyl.

In case "$R^5$" represents "$(C_1-C_3)$alkyl" the term means $(C_1-C_3)$alkyl groups as defined above. Examples of said groups are methyl, ethyl, n-propyl and iso-propyl. Preferred are methyl, ethyl and n-propyl. Most preferred are methyl and ethyl.

In case "$R^6$" represents "$(C_1-C_3)$alkyl" the term means $(C_1-C_3)$alkyl groups as defined above. Examples of said groups are methyl, ethyl, n-propyl and iso-propyl. Preferred are methyl, ethyl and n-propyl. Most preferred are methyl and ethyl.

The term "$(C_1-C_4)$alkandiyl group" as used in Y refers to a carbon chain containing from one to four carbon atoms, which is attached to the residue $R^1$ and to the amide-nitrogen atom of the rest of the molecule as depicted in formula (I). The respective two residues may be attached to the same or to different carbon atoms of the alkandiyl group. Preferred examples of $(C_1-C_4)$alkandiyl groups are methandiyl, ethan-1,1-diyl, ethan-1,2-diyl, propan-1,3-diyl and butan-1,4-diyl. More preferred are methandiyl and ethan-1,2-diyl. Most preferred is methandiyl.

In case "Y together with $R^1$" represents "$(C_4-C_6)$alkyl" the term means $(C_4-C_6)$alkyl groups as defined above. Examples of said groups are n-butyl, iso-butyl, sec-butyl, tert-butyl, the isomeric pentyls and the isomeric hexyls. Preferred are n-butyl, 3-methyl-butyl, 2-ethyl-butyl and n-pentyl. Most preferred is n-pentyl.

In case "Y together with $R^1$" represents a "amino-$(C_4-C_6)$ alkyl" group the term means a $(C_4-C_6)$alkyl group as defined above in which one hydrogen atom has been replaced with an amino group. Examples of said groups are 4-amino-butyl, 5-amino-pentyl and 6-amino-hexyl. Most preferred are 4-amino-butyl and 5-amino-pentyl.

The term "amino-$(C_1-C_4)$alkyl" refers to an $(C_1-C_4)$alkyl group as defined above in which one hydrogen atom has been replaced with an amino group. A preferred example is amino-methyl.

The term "$(C_3-C_6)$cycloalkyl", alone or in combination, means a cycloalkyl group with 3 to 6 carbon atoms. Examples of $(C_3-C_6)$cycloalkyl groups are cyclopropyl, cyclobutyl, cyclopentyl and cyclohexyl. The $(C_3-C_6)$cycloalkyl group may be unsubstituted or substituted as explicitly defined.

In case "$R^2$" represents "$(C_3-C_6)$cycloalkyl" the term means $(C_3-C_6)$cycloalkyl groups as defined above. Examples of said groups are cyclopropyl, cyclobutyl, cyclopentyl and cyclohexyl. Preferred are cyclopropyl, cyclopentyl and cyclohexyl. Most preferred are cyclopentyl and cyclohexyl. The above-mentioned $(C_3-C_6)$cycloalkyl groups are unsubstituted or mono-substituted with hydroxy, hydroxy-methyl, $R^5R^6N$—$CH_2$—, heterocyclyl-methyl or —$CONH_2$ (preferably with hydroxy or pyrrolidin-1-yl-methyl).

In case "$R^2$" represents "$(C_1-C_6)$alkyl, which is mono-substituted with $(C_3-C_6)$cycloalkyl" the term "$(C_3-C_6)$cycloalkyl" means the above-mentioned groups. Preferred are cyclopropyl and cyclohexyl. The above-mentioned $(C_3-C_6)$ cycloalkyl groups are unsubstituted or mono-substituted with —$NR^5R^6$ or hydroxy (preferably with hydroxy).

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. The alkoxy group may be unsubstituted or substituted as explicitly defined.

In case a $(C_1-C_4)$alkoxy group is a substituent to an aryl- or a heteroaryl-group, the term "$(C_1-C_4)$alkoxy" means $(C_1-C_4)$ alkoxy groups as defined above. Examples of said groups are methoxy, ethoxy, n-propoxy, iso-propoxy, n-butoxy, iso-butoxy, sec-butoxy and tert-butoxy. Preferred are methoxy, ethoxy and iso-propoxy. Most preferred is methoxy.

In case "$R^2$" represents "$(C_1-C_6)$alkyl which is mono-substituted with optionally mono-substituted $(C_1-C_4)$alkoxy" the term "optionally mono-substituted $(C_1-C_4)$alkoxy" means a $(C_1-C_4)$alkoxy group as defined above, which is unsubstituted or mono-substituted. Examples of said groups are methoxy, ethoxy, n-propoxy, iso-propoxy, n-butoxy, iso-butoxy, sec-butoxy and tert-butoxy. Preferred are methoxy and ethoxy. The above-mentioned $(C_1-C_4)$alkoxy group is unsubstituted or mono-substituted with hydroxy or heterocyclyl and preferably unsubstituted or mono-substituted with heterocyclyl.

The term "$(C_1-C_2)$alkoxy-$(C_1-C_2)$alkyl" refers to an $(C_1-C_2)$alkyl group as defined above in which one hydrogen atom has been replaced with an $(C_1-C_2)$alkoxy group as defined above. Examples of $(C_1-C_2)$alkoxy-$(C_1-C_2)$alkyl groups are methoxy-methyl, methoxy-ethyl, ethoxy-methyl and ethoxy-ethyl. Preferred is methoxy-methyl.

The term "alkylthio", used alone or in combination, refers to an alkyl-S— group wherein the alkyl group is as defined before. The term "$(C_x-C_y)$alkylthio" (x and y each being an integer) refers to an alkylthio group as defined before containing x to y carbon atoms. For example a $(C_1-C_4)$alkylthio group contains from one to four carbon atoms. Representative examples of alkylthio groups include methylthio, ethylthio, n-propylthio, iso-propylthio, n-butylthio, iso-butylthio, sec-butylthio and tert-butylthio. Preferred are methylthio and ethylthio. Most preferred is ethylthio.

The term "$(C_1-C_2)$alkyl-carbonyl", used alone or in combination, refers to a $(C_1-C_2)$alkyl-C(O)— group wherein the $(C_1-C_2)$alkyl group is as defined before. Representative examples of $(C_1-C_2)$alkyl-carbonyl groups include methyl-carbonyl (acetyl) and ethyl-carbonyl (propionyl). Preferred is acetyl.

The term "$(C_1-C_4)$alkoxy-carbonyl", used alone or in combination, refers to a $(C_1-C_4)$ alkoxy-C(O)— group wherein the $(C_1-C_4)$alkoxy group is as defined before. Representative examples of $(C_1-C_4)$alkoxy-carbonyl groups include methoxy-carbonyl, ethoxy-carbonyl, n-propoxy-carbonyl, iso-propoxy-carbonyl, n-butoxy-carbonyl, iso-butoxy-carbonyl, sec-butoxy-carbonyl and tert-butoxy-carbonyl. Preferred are methoxy-carbonyl and tert-butoxy-carbonyl. Most preferred is methoxy-carbonyl.

The term "$(C_x-C_y)$fluoroalkyl" (x and y each being an integer) refers to an alkyl group as defined before containing x to y carbon atoms in which one or more (and possibly all) hydrogen atoms have been replaced with fluorine. The fluoroalkyl group may be unsubstituted or substituted as explicitly defined.

In case a $(C_1-C_2)$fluoroalkyl group is a substituent to an aryl- or a heteroaryl-group, the term "$(C_1-C_2)$fluoroalkyl" means $(C_1-C_2)$fluoroalkyl groups as defined above. Examples of said groups are trifluoromethyl, difluoromethyl and 2,2,2-trifluoroethyl. Preferred are trifluoromethyl and 2,2,2-trifluoroethyl. Most preferred is trifluoromethyl.

In case "$R^2$" represents "$(C_3-C_5)$fluoroalkyl" the term means a $(C_3-C_5)$fluoroalkyl group as defined above. Examples of said groups are 2-fluoro-propyl, 2,2-difluoro-propyl, 2-fluoro-butyl, 2,2-difluoro-butyl, 3-fluoro-butyl, 3,3-difluoro-butyl, 2-fluoro-pentyl, 2,2-difluoro-pentyl, 3-fluoro-pentyl, 3,3-difluoro-pentyl, 4-fluoro-pentyl and 4,4-difluoro-pentyl. Preferred are 3-fluoro-butyl and 3,3-difluoro-butyl. Most preferred is 3-fluoro-butyl. The above-mentioned $(C_3-C_5)$fluoroalkyl groups are mono-substituted with heterocyclyl.

The term "$(C_x-C_y)$fluoroalkoxy" (x and y each being an integer) refers to an alkoxy group as defined before containing x to y carbon atoms in which one or more (and possibly all) hydrogen atoms have been replaced with fluorine. For example a $(C_1-C_2)$fluoroalkoxy group contains from one to two carbon atoms in which one to five hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term halogen means fluoro, chloro, bromo or iodo.

In case the halogen is a substituent to an aryl- or a heteroaryl-group, the term means preferably fluoro, chloro or bromo and most preferably chloro or bromo.

In case the halogen is a substituent to a heterocyclyl-group, the term means most preferably fluoro.

The term "aryl", used alone or in any combination, means a phenyl or a naphthyl group. Preferred is a phenyl group. The aryl group may be unsubstituted or substituted as explicitly defined.

In case $R^1$ represents "aryl" the term means the above-mentioned groups (preferably phenyl), which groups are independently unsubstituted, mono-, di- or tri-substituted (preferably unsubstituted, mono- or di-substituted and most preferably mono- or di-substituted), wherein the substituents are independently selected from the group consisting of halogen, $(C_1-C_4)$alkyl, $(C_1-C_4)$alkoxy, $(C_1-C_2)$alkyl-carbonyl, $(C_1-C_2)$fluoroalkyl, $(C_1-C_2)$fluoroalkoxy, nitro, cyano and phenyl, wherein the phenyl is unsubstituted or mono-substituted with halogen. Preferably the substituents are independently selected from the group consisting of halogen, $(C_1-C_4)$ alkyl, $(C_1-C_4)$alkoxy, $(C_1-C_2)$alkyl-carbonyl, trifluoromethyl and trifluoromethoxy (and most preferably from fluoro, bromo, methoxy and trifluoromethyl). Examples of such aryl groups are phenyl, 4-methyl-phenyl, 2,4-dimethyl-phenyl, 2,5-dimethyl-phenyl, 3,4-dimethyl-phenyl, 3,5-dimethyl-phenyl, 2-methoxy-phenyl, 4-methoxy-phenyl, 2,4-dimethoxy-phenyl, 3,4-dimethoxy-phenyl, 4-ethoxy-phenyl, 2-iso-propoxy-phenyl, 4-iso-propoxy-phenyl, 3-acetyl-phenyl, 4-acetyl-phenyl, 4-trifluoromethyl-phenyl, 3-difluoromethoxy-phenyl, 4-trifluoromethoxy-phenyl, 4-fluoro-phenyl, 2,3,5-trifluoro-phenyl, 2,4,6-trifluoro-phenyl, 4-chloro-phenyl, 2,4-dichloro-phenyl, 3-bromo-phenyl, 4-bromo-phenyl, 4-iodo-phenyl, 3-chloro-2-fluoro-phenyl, 2-chloro-3,6-difluoro-phenyl, 2-bromo-4-fluoro-phenyl, 3-bromo-4-fluoro-phenyl, 4-bromo-2-fluoro-phenyl, 4-bromo-3-fluoro-phenyl, 4-bromo-2,3-difluoro-phenyl, 4-bromo-2,5-difluoro-phenyl, 4-bromo-2,6-difluoro-phenyl, 4-bromo-3,5-difluoro-phenyl, 4-bromo-3-chloro-phenyl, 5-methyl-2-methoxy-phenyl, 4-bromo-2-methyl-phenyl, 2-chloro-6-fluoro-3-methyl-phenyl, 2,3-difluoro-4-methoxy-phenyl, 2,6-difluoro-4-methoxy-phenyl, 3,5-difluoro-4-methoxy-phenyl, 3-fluoro-4-methoxy-phenyl, 3-chloro-4- methoxy-phenyl, 3-bromo-4-methoxy-phenyl, 2-fluoro-3-trifluoromethyl-phenyl, 2-fluoro-5-trifluoromethyl-phenyl, 3-fluoro-5-trifluoromethyl-phenyl, 4-fluoro-3-trifluoromethyl-phenyl, 2-chloro-5-trifluoromethyl-phenyl and 4-bromo-3-trifluoromethyl-phenyl (and preferably 4-methoxyphenyl, 4-trifluoromethylphenyl, 2,4-dichloro-phenyl, 4-bromophenyl, 4-bromo-2-fluoro-phenyl, 4-bromo-3-fluoro-phenyl and 4-bromo-2,6-difluoro-phenyl).

In case $R^2$ represents "aryl" the term means the above-mentioned groups (preferably phenyl), which groups are independently unsubstituted, mono-, di- or tri-substituted (preferably mono- or di-substituted), wherein the substituents are independently selected from the group consisting of halogen, $(C_1-C_4)$alkyl and phenyl (and preferably from halogen). Examples of such aryl groups are 4-bromophenyl and 2-chloro-3-fluorophenyl.

In case $R^2$ represents "$(C_1-C_6)$alkyl, which is mono-substituted with an aryl group" the term "aryl" means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, —$CH_2NHR^9$, —$SO_2NH_2$ and phenyl. Preferably the substituents are independently selected from the group consisting of halogen, —$CH_2NHR^9$ and —$SO_2NH_2$ (and most preferably from —$CH_2NH_2$ and —$SO_2NH_2$). Examples of such aryl groups are 4-fluorophenyl, 2-chlorophenyl, 3-aminomethyl-phenyl, 4-aminomethyl-phenyl, 3-(tert-butoxycarbonylamino-methyl)-phenyl, 4-(tert-butoxycarbonylamino-methyl)-phenyl and 4-sulfamoyl-phenyl (and preferably 3-aminomethyl-phenyl, 4-aminomethyl-phenyl and 4-sulfamoyl-phenyl).

The term "aryloxy", used alone or in combination, refers to an aryl-O— group wherein the aryl group is as defined before. A preferred example of an aryloxy group is phenoxy.

The term "heteroaryl", used alone or in any combination, means a 5- to 10-membered monocyclic or bicyclic aromatic ring containing 1, 2 or 3 heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl and phthalazinyl. The heteroaryl group may be unsubstituted or substituted as explicitly defined.

In case $R^1$ represents "heteroaryl" the term means the above-mentioned groups. Preferred heteroaryl groups as used in $R^1$ are furanyl (notably furan-2-yl), oxazolyl (notably oxazol-2-yl and oxazol-5-yl), isoxazolyl (notably isoxazol-3-yl), oxadiazolyl (notably[1,2,5]oxadiazolyl), thienyl (notably thiophen-2-yl and thiophen-3-yl), thiazolyl (notably thiazol-2-yl, thiazol-4-yl and thiazol-5-yl), thiadiazolyl (notably [1,2,4]thiadiazol-5-yl and[1,3,4]thiadiazol-5-yl), imidazolyl (notably imidazol-1-yl and imidazol-2-yl), pyridyl (notably pyridin-2-yl and pyridin-3-yl), pyrimidyl (notably pyrimidin-5-yl), pyrazinyl (notably pyrazin-2-yl), indolyl (notably indol-1-yl and indol-5-yl), benzimidazolyl (notably benzimidazol-2-yl), benzoxazolyl (notably benzoxazol-6-yl), benzothiazolyl (notably benzothiazol-2-yl and benzothiazol-5-yl), benzoisothiazolyl (notably benzoisothiazol-5-yl) and benzo[2,1,3]oxadiazolyl (notably benzo[2,1,3]oxadiazol-4-yl). Most preferred heteroaryl groups are furanyl (notably furan-2-yl), thiazolyl (notably thiazol-2-yl), pyridyl (notably pyridin-2-yl and pyridin-3-yl), pyrazinyl (notably pyrazin-2-yl) and benzothiazolyl (notably benzothiazol-5-yl). The above-mentioned heteroaryl groups as used in $R^1$ are unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy, $(C_1-C_2)$alkyl-carbonyl, $(C_1-C_2)$fluoroalkyl, $(C_1-C_2)$fluoroalkoxy, nitro, cyano and phenyl, wherein the phenyl is unsubstituted or mono-substituted with halogen. Preferably the substituents are independently selected from the group consisting of halogen, $(C_1-C_4)$alkyl, $(C_1-C_2)$alkyl-carbonyl, $(C_1-C_2)$fluoroalkyl, nitro, cyano and phenyl, wherein the phenyl is unsubstituted or mono-substituted with halogen. Most preferably the substituents are independently selected from halogen, methyl and acetyl. Examples of such unsubstituted, mono-, di- or tri-substituted heteroaryl groups as used in $R^1$ are furan-2-yl, 5-acetyl-furan-2-yl (preferred), 5-methyl-furan-2-yl, 4-methyl-oxazol-2-yl, 2-acetyl-oxazol-4-yl, 2-acetyl-oxazol-5-yl, 4-acetyl-oxazol-2-yl, 5-methyl-isoxazol-3-yl, 5-iso-butyl-isoxazol-3-yl, 5-tert-butyl-isoxazol-3-yl, 5-acetyl-thiophen-2-yl, 5-bromo-thiophen-3-yl, 5-chloro-thiazol-2-yl, 2-bromo-thiazol-5-yl, 4-bromo-thiazol-2-yl, 5-bromo-thiazol-2-yl (preferred), 4-methyl-thiazol-2-yl, 5-methyl-thiazol-2-yl, 4,5-dimethyl-thiazol-2-yl, 4-tert-butyl-thiazol-2-yl, 2-acetyl-thiazol-4-yl, 2-acetyl-thiazol-5-yl, 4-acetyl-thiazol-2-yl, 5-acetyl-thiazol-2-yl, 4-trifluoromethyl-thiazol-2-yl, 5-nitro-thiazol-2-yl, 5-cyano-thiazol-2-yl, 4-(4-chloro-phenyl)-thiazol-2-yl, 4-methyl-[1,2,5]oxadiazol-3-yl, 3-phenyl-[1,2,4]thiadiazol-5-yl, 2-trifluoromethyl-[1,3,4]thiadiazol-5-yl, imidazol-1-yl, 4,5-dimethyl-imidazol-2-yl (preferred), pyridin-2-yl, 2-methoxy-pyridin-4-yl, 2,6-dichloro-pyridin-4-yl, 5-bromo-pyridin-2-yl (preferred), 5-methyl-pyridin-2-yl (preferred), 5-trifluoromethyl-pyridin-2-yl, 6-chloro-pyridin-3-yl (preferred), 6-bromo-pyridin-3-yl (preferred), 6-bromo-5-fluoro-pyridin-3-yl, 6-methoxy-pyridin-3-yl, 6-trifluoromethyl-pyridin-3-yl, 2-chloro-pyrimidin-5-yl, 5-bromo-pyrazin-2-yl (preferred), indol-1-yl, 2-methyl-indol-1-yl, indol-5-yl, 1-methyl-benzimidazol-2-yl, benzoxazol-6-yl, benzothiazol-2-yl, 6-fluoro-benzothiazol-2-yl, 6-chloro-benzothiazol-2-yl, benzothiazol-5-yl (preferred), 2-methyl-benzothiazol-5-yl, 3-methyl-benzoisothiazol-5-yl and benzo[2,1,3]oxadiazol-4-yl.

In case $R^2$ represents "heteroaryl" the term means the above-mentioned groups. Preferred heteroaryl groups as used in $R^2$ are isoxazolyl (notably isoxazol-4-yl), pyrazolyl (notably pyrazol-3-yl, pyrazol-4-yl and pyrazol-5-yl) and pyridyl (notably pyridin-3-yl). The above-mentioned heteroaryl groups as used in $R^2$ are unsubstituted, mono-, di- or tri-substituted (preferably mono-substituted), wherein the substituents are independently selected from the group consisting of halogen, $(C_1-C_4)$alkyl and phenyl. Preferably the substituents are independently selected from the group consisting of methyl and phenyl. Examples of such unsubstituted, mono-, di- or tri-substituted heteroaryl groups as used in $R^2$ are 5-phenyl-isoxazol-4-yl (preferred), 1,5-dimethyl-pyrazol-3-yl, 5-chloro-1,3-dimethyl-pyrazol-4-yl, 1-phenyl-pyrazol-5-yl (preferred) and 4-methyl-pyridin-3-yl.

In case $R^2$ represents "$(C_1-C_6)$alkyl, which is mono-substituted with a heteroaryl group" the term "heteroaryl" means the above-mentioned groups. Preferred heteroaryl groups are furanyl (notably furan-3-yl), isoxazolyl (notably isoxazol-4-yl), thiazolyl (notably thiazol-4-yl), imidazolyl (notably imidazol-1-yl and imidazol-2-yl), pyrazolyl (notably pyrazol-1-yl, pyrazol-3-yl, pyrazol-4-yl and pyrazol-5-yl), triazolyl (notably [1,2,4]triazol-1-yl), pyridyl (notably pyridin-2-yl and pyridin-3-yl), indolyl (notably indol-3-yl) and benzimidazolyl (notably benzimidazol-2-yl). The above-mentioned heteroaryl groups are unsubstituted, mono-, di- or tri-substituted (preferably unsubstituted, mono- or disubstituted), wherein the substituents are independently selected from the group consisting of halogen, $(C_1-C_4)$alkyl, —$CH_2NHR^9$, —$SO_2NH_2$ and phenyl. Preferably the substituents are independently selected from the group consisting of $(C_1-C_4)$alkyl and phenyl. Examples of such unsubstituted, mono-, di- or tri-substituted heteroaryl groups are furan-3-yl, 5-methyl-3-phenyl-isoxazol-4-yl, 2-methyl-thiazol-4-yl, 2,5-dimethyl-thiazol-4-yl, imidazol-1-yl (preferred), 4,5-dimethyl-imidazol-2-yl (preferred), pyrazol-1-yl (preferred), 3,5-dimethyl-pyrazol-1-yl (preferred), 1-ethyl-5-methyl-pyrazol-3-yl (preferred), 5-methyl-pyrazol-4-yl, 1-ethyl-3-methyl-pyrazol-5-yl, [1,2,4]triazol-1-yl (preferred), pyridin-2-yl, pyridin-3-yl, indol-3-yl), benzimidazol-2-yl (preferred) and 1-methyl-benzimidazol-2-yl.

The term "heterocyclyl", used alone or in combination, means a 4- to 7-membered (notably 4- to 6-membered) saturated monocyclic ring containing 1 or 2 heteroatoms independently selected from the group consisting of sulfur, oxygen and nitrogen (preferably oxygen and nitrogen), wherein one or two methylene groups adjacent to a nitrogen atom are optionally replaced by carbonyl groups. Examples of such heterocyclyl groups are azetidinyl, oxetanyl, pyrrolidinyl, pyrrolidinonyl, tetrahydrofuranyl, tetrahydrothiophenyl, imidazolidinonyl, oxazolidinyl, oxazolidinonyl, thiazolidinyl, thiazolidinonyl, piperidinyl, piperidonyl, piperazinyl, piperazinonyl, piperazine-dionyl, tetrahydro-2H-pyranyl, morpholinyl, morpholinonyl, thiomorpholinyl, thiomorpholinonyl, dioxanyl, 1,4-diazepanyl and 1,4-diazepanonyl. Preferred examples are azetidinyl, pyrrolidinyl, pyrrolidinonyl, tetrahydrofuranyl, imidazolidinonyl, piperidinyl, piperidonyl, piperazinyl, tetrahydro-2H-pyranyl, morpholinyl, dioxanyl and 1,4-diazepanyl. The heterocyclyl group may be unsubstituted or substituted as explicitly defined.

In case $R^2$ represents "$(C_3-C_6)$cycloalkyl, which is mono-substituted with heterocyclyl-methyl" the term "heterocyclyl" means the above-mentioned groups. Preferred heterocyclyl groups are azetidinyl (notably azetidin-1-yl), pyrrolidinyl (notably pyrrolidin-1-yl) and piperidinyl (notably piperidin-1-yl). Most preferred is pyrrolidinyl (notably pyrrolidin-1-yl).

In case $R^2$ represents "heterocyclyl" the term means the above-mentioned groups. Preferred heterocyclyl groups as used in $R^2$ are azetidinyl (notably azetidin-3-yl), pyrrolidinyl (notably pyrrolidin-3-yl), piperidinyl (notably piperidin-3-yl and piperidin-4-yl) and tetrahydro-2H-pyranyl (notably tetrahydro-2H-pyran-3-yl). Most preferred are pyrrolidin-3-yl, piperidin-3-yl, piperidin-4-yl and tetrahydro-2H-pyran-3-yl. The above-mentioned heterocyclyl groups are unsubstituted or mono-substituted at a nitrogen atom with $(C_1-C_6)$alkyl, benzyl or tert-butoxycarbonyl or mono-substituted at a carbon atom with pyrrolidin-1-yl-methyl. Examples of such unsubstituted or mono-substituted heterocyclyl groups are azetidin-3-yl, 1-tert-butoxycarbonyl-azetidin-3-yl, pyrrolidin-3-yl (preferred), 1-tert-butoxycarbonyl-pyrrolidin-3-yl, piperidin-3-yl (preferred), 1-tert-butoxycarbonyl-piperidin-3-yl, piperidin-4-yl (preferred), 1-methyl-piperidin-4-yl, 1-ethyl-piperidin-4-yl, 1-(3-methyl-butyl)-piperidin-4-yl, 1-benzyl-piperidin-4-yl, 1-tert-butoxycarbonyl-piperidin-4-yl and 6-(pyrrolidin-1-ylmethyl)-tetrahydro-2H-pyran-3yl.

In case $R^2$ represents "$(C_1-C_6)$alkyl, which is mono-substituted with heterocyclyl" the term "heterocyclyl" means the above-mentioned groups. Preferred heterocyclyl groups are azetidinyl (notably azetidin-1-yl), pyrrolidinyl (notably pyrrolidin-1-yl and pyrrolidin-2-yl), pyrrolidinonyl (notably pyrrolidin-2-on-1-yl), tetrahydrofuranyl (notably tetrahydrofuran-2-yl), imidazolidinonyl (notably imidazolidin-2-on-1-yl), piperidinyl (notably piperidin-1-yl, piperidin-2-yl, piperidin-3-yl and piperidin-4-yl), piperazinyl (notably piperazin-1-yl), morpholinyl (notably morpholin-4-yl), dioxanyl (notably 1,4-dioxan-2-yl) and 1,4-diazepanyl (notably 1,4-diazepan-1-yl). Most preferred are azetidinyl (notably azetidin-1-yl), pyrrolidinyl (notably pyrrolidin-1-yl and pyrrolidin-2-yl), tetrahydrofuranyl (notably tetrahydrofuran-2-yl), imidazolidinonyl (notably imidazolidin-2-on-1-yl), piperidinyl (notably piperidin-1-yl, piperidin-2-yl and piperidin-4-yl), piperazinyl (notably piperazin-1-yl), morpholinyl (notably morpholin-4-yl) and 1,4-diazepanyl (notably 1,4-diazepan-1-yl). The above-mentioned heterocyclyl groups are unsubstituted or mono-substituted at a nitrogen atom with $(C_1-C_4)$alkyl, $(C_1-C_2)$alkyl-carbonyl or tert-butoxycarbonyl, and/or mono- or di-substituted at one or two of the carbon atoms with substituents independently selected from halogen, $(C_1-C_4)$alkyl and $(C_1-C_2)$alkoxy-$(C_1-C_2)$alkyl. Preferably the heterocyclyl groups are unsubstituted or mono-substituted at a nitrogen atom with $(C_1-C_4)$alkyl (notably methyl or ethyl), or mono- or di-substituted at one or two of the carbon atoms with substituents independently selected from fluorine, methyl and methoxymethyl. Examples of such unsubstituted or substituted heterocyclyl groups are azetidin-1-yl, pyrrolidin-1-yl, 3-fluoro-pyrrolidin-1-yl (notably (R)-3-fluoro-pyrrolidin-1-yl and (S)-3-fluoro-pyrrolidin-1-yl), 3,3-difluoro-pyrrolidin-1-yl, 2,5-dimethyl-pyrrolidin-1-yl, 2-methoxymethyl-pyrrolidin-1-yl, pyrrolidin-2-yl, 1-methyl-pyrrolidin-2-yl, 1-ethyl-pyrrolidin-2-yl, 1-tert-butoxycarbonyl-pyrrolidin-2-yl, pyrrolidin-2-on-1-yl, tetrahydrofuran-2-yl, imidazolidin-2-on-1-yl, piperidin-1-yl, piperidin-2-yl, piperidin-3-yl, 1-tert-butoxycarbonyl-piperidin-3-yl, piperidin-4-yl, 1-tert-butoxycarbonyl-piperidin-4-yl, 4-methyl-piperazin-1-yl, 4-ethyl-piperazin-1-yl, 4-acetyl-piperazin-1-yl, morpholin-4-yl, 1,4-dioxan-2-yl and 4-methyl-1,4-diazepan-1-yl. Preferred examples of such unsubstituted or mono-substituted heterocyclyl groups are azetidin-1-yl, pyrrolidin-1-yl, (R)-3-fluoro-pyrrolidin-1-yl, (S)-3-fluoro-pyrrolidin-1-yl, 3,3-difluoro-pyrrolidin-1-yl, 2,5-dimethyl-pyrrolidin-1-yl, 2-methoxymethyl-pyrrolidin-1-yl, pyrrolidin-2-yl, 1-methyl-pyrrolidin-2-yl, tetrahydrofuran-2-yl, imidazolidin-2-on-1-yl, piperidin-1-yl, piperidin-2-yl, piperidin-4-yl, 4-methyl-piperazin-1-yl, morpholin-4-yl, 1,4-dioxan-2-yl and 4-methyl-1,4-diazepan-1-yl.

In case $R^2$ represents "$(C_1-C_6)$alkyl, which is mono-substituted with optionally mono-substituted $(C_1-C_4)$alkoxy, wherein the substituent is heterocyclyl" the term "heterocyclyl" means the above-mentioned groups. Preferred heterocyclyl groups are azetidinyl (notably azetidin-1-yl), pyrrolidinyl (notably pyrrolidin-1-yl) and piperidinyl (notably piperidin-1-yl). Most preferred is pyrrolidin-1-yl.

In case $R^2$ represents "$(C_3-C_5)$fluoroalkyl, which is mono-substituted with heterocyclyl" the term "heterocyclyl" means the above-mentioned groups. Preferred heterocyclyl groups are azetidinyl (notably azetidin-1-yl), pyrrolidinyl (notably pyrrolidin-1-yl and pyrrolidin-2-yl), pyrrolidinonyl (notably pyrrolidin-2-on-1-yl), tetrahydrofuranyl (notably tetrahydrofuran-2-yl), imidazolidinonyl (notably imidazolidin-2-on-1-yl), piperidinyl (notably piperidin-1-yl, piperidin-3-yl and piperidin-4-yl), piperazinyl (notably piperazin-1-yl), morpholinyl (notably morpholin-4-yl), dioxanyl (notably 1,4-dioxan-2-yl) and 1,4-diazepanyl (notably 1,4-diazepan-1-yl). More preferred heterocyclyl groups are azetidinyl (notably azetidin-1-yl), pyrrolidinyl (notably pyrrolidin-1-yl) and piperidinyl (notably piperidin-1-yl). Most preferred is pyrrolidin-1-yl. The above-mentioned heterocyclyl groups are unsubstituted (preferred) or mono- or di-substituted at one or two of the carbon atoms with substituents independently selected from halogen (notably fluoro) and ($C_1$-$C_4$)alkyl (notably methyl).

The term "a ring of 5 to 7 members", as used in "$R^2$ and $R^3$ form, together with the nitrogen that carries them, a ring of 5 to 7 members", refers to a heterocyclic ring selected from pyrrolidinyl (notably pyrrolidin-1-yl), piperidinyl (notably piperidin-1-yl) and azepanyl (notably azepan-1-yl). Preferred is piperidinyl (notably piperidin-1-yl). The ring with 5 to 7 members is substituted with amino-($C_1$-$C_4$)alkyl.

For compounds of formula $I_p$ the following definitions are preferred:

The term "alkyl", used alone or in combination, refers to a straight or branched chain alkyl group containing one to six carbon atoms. The term "($C_x$-$C_y$)alkyl" (x and y each being an integer), refers to an alkyl group as defined before containing x to y carbon atoms. For example a ($C_1$-$C_6$)alkyl group contains from one to six carbon atoms. Representative examples of alkyl groups include methyl, ethyl, n-propyl, iso-propyl, n-butyl, iso-butyl, sec-butyl, tert-butyl, the isomeric pentyls and the isomeric hexyls. The alkyl group may be unsubstituted or substituted as explicitly defined.

In case a ($C_1$-$C_4$)alkyl group is a substituent to an aryl-, a heteroaryl- or a heterocyclyl-group, the term "($C_1$-$C_4$)alkyl" means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl, ethyl and iso-butyl, and most preferred is methyl.

In case a ($C_1$-$C_6$)alkyl group is a substituent to a heterocyclyl-group, the term "($C_1$-$C_6$)alkyl" means ($C_1$-$C_6$)alkyl groups as defined above. Examples of said groups are methyl, ethyl, n-propyl, iso-propyl, n-butyl, iso-butyl, sec-butyl, tert-butyl, the isomeric pentyls and the isomeric hexyls. Preferred are methyl, ethyl and 3-methyl-but-1-yl. Most preferred is 3-methyl-but-1-yl.

In case "Y together with $R^1$" represents "($C_4$-$C_6$)alkyl" the term means ($C_4$-$C_6$)alkyl groups as defined above. Examples of said groups are n-butyl, iso-butyl, sec-butyl, tert-butyl, the isomeric pentyls and the isomeric hexyls. Preferred are n-butyl, 3-methyl-butyl, 2-ethyl-butyl and n-pentyl. Most preferred is n-pentyl.

In case "$R^2$" represents "($C_1$-$C_6$)alkyl" the term means ($C_1$-$C_6$)alkyl groups as defined above. Examples of said groups are methyl, ethyl, n-propyl, iso-propyl, n-butyl, iso-butyl, sec-butyl, tert-butyl, the isomeric pentyls and the isomeric hexyls. Preferred are methyl, ethyl, n-propyl, iso-propyl, n-butyl, iso-butyl, 2,2-dimethyl-prop-1-yl, 3-methyl-but-1-yl, 3,3-dimethyl-but-1-yl, pent-1-yl, pent-2-yl, 4-methyl-pent-2-yl and hex-1-yl. Most preferred are ethyl, n-propyl, n-butyl, iso-butyl, 2,2-dimethyl-prop-1-yl and pent-1-yl. The above-mentioned ($C_1$-$C_6$)alkyl groups are unsubstituted or mono-substituted with fluorine, trifluoromethyl, ($C_1$-$C_4$)alkoxy, ($C_1$-$C_4$)alkylthio, ($C_1$-$C_4$)alkoxy-carbonyl, hydroxy, cyano, —$NR^5R^6$ or —$C(O)NR^7R^8$. Preferably the substituent is selected from the group consisting of fluorine, trifluoromethyl, methoxy, ethoxy, ethylthio, hydroxy, cyano, —$NR^5R^6$ or —$C(O)NH_2$.

In case "$R^2$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl, ethyl, n-propyl and n-butyl. Most preferred is n-butyl. The above-mentioned ($C_1$-$C_4$)alkyl groups are mono-substituted with ($C_3$-$C_6$)cycloalkyl; with heterocyclyl, which is unsubstituted or mono-substituted at a nitrogen atom with ($C_1$-$C_4$)alkyl or tert-butoxycarbonyl; or with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NHR^9$, —$SO_2NH_2$ and phenyl. In a preferred embodiment the ($C_1$-$C_4$)alkyl groups are substituted with a heterocyclyl group, which is unsubstituted or mono-substituted at a nitrogen atom with methyl or ethyl. In another preferred embodiment the ($C_1$-$C_4$)alkyl groups are substituted with an aryl- or heteroaryl-group, which groups are independently unsubstituted, mono- or di-substituted (preferably unsubstituted or mono-substituted), wherein the substituents are independently selected from the group consisting of halogen, methyl, ethyl, —$CH_2NH_2$ and —$SO_2NH_2$.

In case "$R^3$" represents "($C_1$-$C_3$)alkyl" the term means ($C_1$-$C_3$)alkyl groups as defined above. Examples of said groups are methyl, ethyl, n-propyl and iso-propyl. Preferred are methyl, ethyl and n-propyl. Most preferred are methyl and ethyl.

In case "$R^5$" represents "($C_1$-$C_3$)alkyl" the term means ($C_1$-$C_3$)alkyl groups as defined above. Examples of said groups are methyl, ethyl, n-propyl and iso-propyl. Preferred are methyl, ethyl and n-propyl. Most preferred are methyl and ethyl.

In case "$R^6$" represents "($C_1$-$C_3$)alkyl" the term means ($C_1$-$C_3$)alkyl groups as defined above. Examples of said groups are methyl, ethyl, n-propyl and iso-propyl. Preferred are methyl, ethyl and n-propyl. Most preferred are methyl and ethyl.

The term "($C_1$-$C_4$)alkandiyl group" as used in Y refers to a carbon chain containing from one to four carbon atoms, which is attached to the residue $R^1$ and to the amide-nitrogen atom of the rest of the molecule as depicted in formula (I). The respective two residues may be attached to the same or to different carbon atoms of the alkandiyl group. Preferred examples of ($C_1$-$C_4$)alkandiyl groups are methandiyl, ethan-1,1-diyl, ethan-1,2-diyl, propan-1,3-diyl and butan-1,4-diyl. More preferred are methandiyl and ethan-1,2-diyl. Most preferred is methandiyl.

The term "($C_3$-$C_6$)cycloalkyl", alone or in combination, means a cycloalkyl group with 3 to 6 carbon atoms. Examples of ($C_3$-$C_6$)cycloalkyl groups are cyclopropyl, cyclobutyl, cyclopentyl and cyclohexyl. The ($C_3$-$C_6$) cycloalkyl group may be unsubstituted or substituted as explicitly defined.

In case "$R^2$" represents "($C_3$-$C_6$)cycloalkyl" the term means ($C_3$-$C_6$)cycloalkyl groups as defined above. Examples of said groups are cyclopropyl, cyclobutyl, cyclopentyl and cyclohexyl. Preferred are cyclopropyl, cyclopentyl and cyclohexyl. Most preferred are cyclopentyl and cyclohexyl. The above-mentioned ($C_3$-$C_6$) cycloalkyl groups are unsubstituted or mono-substituted with hydroxy (preferred) or —$CONH_2$.

In case "$R^2$" represents "($C_1$-$C_4$)alkyl, which is mono-substituted with ($C_3$-$C_6$)cycloalkyl" the term "($C_3$-$C_6$) cycloalkyl" means the above-mentioned groups. A preferred ($C_3$-$C_6$)cycloalkyl group is cyclopropyl.

The term "alkoxy", used alone or in combination, refers to an alkyl-O— group wherein the alkyl group is as defined before. The term "($C_x$-$C_y$)alkoxy" (x and y each being an integer) refers to an alkoxy group as defined before containing x to y carbon atoms. For example a ($C_1$-$C_4$) alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are methoxy and ethoxy. Most preferred is methoxy.

The term "alkylthio", used alone or in combination, refers to an alkyl-S— group wherein the alkyl group is as defined before. The term "($C_x$-$C_y$)alkylthio" (x and y each being an integer) refers to an alkylthio group as defined before containing x to y carbon atoms. For example a ($C_1$-$C_4$)alkylthio group contains from one to four carbon atoms. Representative examples of alkylthio groups include methylthio, ethylthio, n-propylthio, iso-propylthio, n-butylthio, iso-butylthio, sec-butylthio and tert-butylthio. Preferred are methylthio and ethylthio. Most preferred is ethylthio.

The term "($C_1$-$C_2$)alkyl-carbonyl", used alone or in combination, refers to a ($C_1$-$C_2$)alkyl-C(O)— group wherein the ($C_1$-$C_2$)alkyl group is as defined before. Representative examples of ($C_1$-$C_2$)alkyl-carbonyl groups include methyl-carbonyl (acetyl) and ethyl-carbonyl (propionyl). Preferred is acetyl.

The term "($C_1$-$C_4$)alkoxy-carbonyl", used alone or in combination, refers to a ($C_1$-$C_4$) alkoxy-C(O)— group wherein the ($C_1$-$C_4$)alkoxy group is as defined before. Representative examples of ($C_1$-$C_4$)alkoxy-carbonyl groups include methoxy-carbonyl, ethoxy-carbonyl, n-propoxy-carbonyl, iso-propoxy-carbonyl, n-butoxy-carbonyl, iso-butoxy-carbonyl, sec-butoxy-carbonyl and tert-butoxy-carbonyl. Preferred are methoxy-carbonyl and tert-butoxy-carbonyl. Most preferred is methoxy-carbonyl.

The term "($C_x$-$C_y$)fluoroalkyl" (x and y each being an integer) refers to an alkyl group as defined before containing x to y carbon atoms in which one or more (and possibly all) hydrogen atoms have been replaced with fluorine. For example a ($C_1$-$C_2$)fluoroalkyl group contains from one to two carbon atoms in which one to five hydrogen atoms have been replaced with fluorine. Representative examples of fluoroalkyl groups include trifluoromethyl, difluoromethyl and 2,2,2-trifluoroethyl. Preferred are trifluoromethyl and 2,2,2-trifluoroethyl. Most preferred is trifluoromethyl.

The term "($C_x$-$C_y$)fluoroalkoxy" (x and y each being an integer) refers to an alkoxy group as defined before containing x to y carbon atoms in which one or more (and possibly all) hydrogen atoms have been replaced with fluorine. For example a ($C_1$-$C_2$)fluoroalkoxy group contains from one to two carbon atoms in which one to five hydrogen atoms have been replaced with fluorine. Representative examples of fluoroalkoxy groups include trifluoromethoxy, difluoromethoxy and 2,2,2-trifluoroethoxy. Preferred are ($C_1$)fluoroalkoxy groups such as trifluoromethoxy and difluoromethoxy. Most preferred is trifluoromethoxy.

The term halogen means fluoro, chloro, bromo or iodo, preferably fluoro, chloro or bromo and most preferably chloro or bromo.

The term "aryl", used alone or in any combination, means a phenyl or a naphthyl group. Preferred is a phenyl group. The aryl group may be unsubstituted or substituted as explicitly defined.

In case $R^1$ represents "aryl" the term means the above-mentioned groups (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, ($C_1$-$C_4$)alkyl, ($C_1$-$C_4$)alkoxy, ($C_1$-$C_2$)alkyl-carbonyl, ($C_1$-$C_2$)fluoroalkyl, ($C_1$-$C_2$)fluoroalkoxy, nitro, cyano and phenyl, wherein the phenyl is unsubstituted or mono-substituted with halogen. Preferably the substituents are independently selected from the group consisting of halogen, ($C_1$-$C_4$) alkyl, ($C_1$-$C_4$)alkoxy, ($C_1$-$C_2$)alkyl-carbonyl, trifluoromethyl and trifluoromethoxy (and most preferably from fluoro, bromo, methoxy and trifluoromethyl). Examples of such aryl groups are phenyl, 4-methylphenyl, 2-methoxyphenyl, 4-methoxyphenyl, 4-acetylphenyl, 4-trifluoromethyl-phenyl, 4-trifluoromethoxyphenyl, 3-bromophenyl, 4-bromophenyl, 4-bromo-2-fluoro-phenyl and 4-iodophenyl (and preferably 4-methoxyphenyl, 4-trifluoromethylphenyl, 4-bromophenyl and 4-bromo-2-fluoro-phenyl).

In case $R^2$ represents "aryl" the term means the above-mentioned groups (preferably phenyl), which groups are independently unsubstituted, mono-, di- or tri-substituted (preferably mono- or di-substituted and most preferably di-substituted), wherein the substituents are independently selected from the group consisting of halogen, ($C_1$-$C_4$)alkyl and phenyl (and preferably from halogen). Examples of such aryl groups are 4-bromophenyl and 2-chloro-3-fluorophenyl.

In case $R^2$ represents "($C_1$-$C_4$)alkyl, which is mono-substituted with an aryl group" the term "aryl" means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, ($C_1$-$C_4$)alkyl, —$CH_2NHR^9$, —$SO_2NH_2$ and phenyl. Preferably the substituents are independently selected from the group consisting of halogen, —$CH_2NHR^9$ and —$SO_2NH_2$ (and most preferably from —$CH_2NH_2$ and —$SO_2NH_2$). Examples of such aryl groups are 4-fluorophenyl, 2-chlorophenyl, 3-aminomethyl-phenyl, 4-aminomethyl-phenyl, 3-(tert-butoxycarbonylamino-methyl) phenyl, 4-(tert-butoxycarbonylamino-methyl)-phenyl and 4-sulfamoyl-phenyl (and preferably 3-aminomethyl-phenyl, 4-aminomethyl-phenyl and 4-sulfamoyl-phenyl).

The term "aryloxy", used alone or in combination, refers to an aryl-O— group wherein the aryl group is as defined before. A preferred example of an aryloxy group is phenoxy.

The term "heteroaryl", used alone or in combination, means a 5- to 10-membered monocyclic or bicyclic aromatic ring containing 1, 2 or 3 heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl and phthalazinyl. The heteroaryl group may be unsubstituted or substituted as explicitly defined.

In case R¹ represents "heteroaryl" the term means the above-mentioned groups. Preferred heteroaryl groups as used in R¹ are furanyl (notably furan-2-yl), oxazolyl (notably oxazol-5-yl), isoxazolyl (notably isoxazol-3-yl), thienyl (notably thiophen-2-yl and thiophen-3-yl), thiazolyl (notably thiazol-2-yl), thiadiazolyl (notably[1,2,4]thiadiazol-5-yl), imidazolyl (notably imidazol-1-yl and imidazol-2-yl), pyridyl (notably pyridin-2-yl and pyridin-3-yl), pyrimidyl (notably pyrimidin-5-yl), indolyl (notably indol-1-yl and indol-5-yl), benzimidazolyl (notably benzimidazol-2-yl), benzothiazolyl (notably benzothiazol-2-yl and benzothiazol-5-yl), benzoisothiazolyl (notably benzoisothiazol-5-yl) and benzo[2,1,3]oxadiazolyl (notably benzo[2,1,3]oxadiazol-4-yl). Most preferred heteroaryl groups are furanyl (notably furan-2-yl), thiazolyl (notably thiazol-2-yl), pyridyl (notably pyridin-2-yl and pyridin-3-yl) and benzothiazolyl (notably benzothiazol-5-yl). The above-mentioned heteroaryl groups as used in R¹ are unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy, $(C_1-C_2)$alkyl-carbonyl, $(C_1-C_2)$fluoro-alkyl, $(C_1-C_2)$fluoroalkoxy, nitro, cyano and phenyl, wherein the phenyl is unsubstituted or mono-substituted with halogen. Preferably the substituents are independently selected from the group consisting of halogen, $(C_1-C_4)$alkyl, $(C_1-C_2)$alkyl-carbonyl, nitro, cyano and phenyl, wherein the phenyl is unsubstituted or mono-substituted with halogen. Most preferably the substituents are independently selected from halogen, methyl and acetyl. Examples of such unsubstituted, mono-, di- or tri-substituted heteroaryl groups as used in R¹ are furan-2-yl, 5-acetyl-furan-2-yl (preferred), 5-methyl-furan-2-yl, 2-acetyl-oxazol-5-yl, 5-iso-butyl-isoxazol-3-yl, 5-tert-butyl-isoxazol-3-yl, 5-acetyl-thiophen-2-yl, 5-bromo-thiophen-3-yl, 5-chloro-thiazol-2-yl, 5-bromo-thiazol-2-yl (preferred), 5-methyl-thiazol-2-yl, 4-tert-butyl-thiazol-2-yl, 4-acetyl-thiazol-2-yl, 5-nitro-thiazol-2-yl, 5-cyano-thiazol-2-yl, 4-(4-chloro-phenyl)-thiazol-2-yl, 3-phenyl-[1,2,4]thiadiazol-5-yl, imidazol-1-yl, 4,5-dimethyl-imidazol-2-yl (preferred), 5-bromo-pyridin-2-yl (preferred), 5-methyl-pyridin-2-yl (preferred), 6-chloro-pyridin-3-yl (preferred), 6-bromo-pyridin-3-yl (preferred), 2-chloro-pyrimidin-5-yl, indol-1-yl, 2-methyl-indol-1-yl, indol-5-yl, 1-methyl-benzimidazol-2-yl, benzothiazol-2-yl, 6-fluoro-benzothiazol-2-yl, 6-chloro-benzothiazol-2-yl, benzothiazol-5-yl (preferred), 2-methyl-benzothiazol-5-yl, 3-methyl-benzoisothiazol-5-yl and benzo[2,1,3]oxadiazol-4-yl.

In case R² represents "heteroaryl" the term means the above-mentioned groups. Preferred heteroaryl groups as used in R² are isoxazolyl (notably isoxazol-4-yl), pyrazolyl (notably pyrazol-3-yl, pyrazol-4-yl and pyrazol-5-yl) and pyridyl (notably pyridin-3-yl). The above-mentioned heteroaryl groups as used in R² are unsubstituted, mono-, di- or tri-substituted (preferably mono-substituted), wherein the substituents are independently selected from the group consisting of halogen, $(C_1-C_4)$alkyl and phenyl. Preferably the substituents are independently selected from the group consisting of methyl and phenyl. Examples of such unsubstituted, mono-, di- or tri-substituted heteroaryl groups as used in R² are 5-phenyl-isoxazol-4-yl (preferred), 1,5-dimethyl-pyrazol-3-yl, 5-chloro-1,3-dimethyl-pyrazol-4-yl, 1-phenyl-pyrazol-5-yl(preferred) and 4-methyl-pyridin-3-yl.

In case R² represents "$(C_1-C_4)$alkyl, which is mono-substituted with a heteroaryl group" the term "heteroaryl" means the above-mentioned groups. Preferred heteroaryl groups are furanyl (notably furan-3-yl), isoxazolyl (notably isoxazol-4-yl), thiazolyl (notably thiazol-4-yl), imidazolyl (notably imidazol-1-yl and imidazol-2-yl), pyrazolyl (notably pyrazol-1-yl, pyrazol-3-yl, pyrazol-4-yl and pyrazol-5-yl), triazolyl (notably [1,2,4]triazol-1-yl), pyridyl (notably pyridin-2-yl and pyridin-3-yl), indolyl (notably indol-3-yl) and benzimidazolyl (notably benzimidazol-2-yl). The above-mentioned heteroaryl groups are unsubstituted, mono-, di- or tri-substituted (preferably unsubstituted, mono- or disubstituted), wherein the substituents are independently selected from the group consisting of halogen, $(C_1-C_4)$alkyl, $—CH_2NHR^9$, $—SO_2NH_2$ and phenyl. Preferably the substituents are independently selected from the group consisting of $(C_1-C_4)$alkyl and phenyl. Examples of such unsubstituted, mono-, di- or tri-substituted heteroaryl groups are furan-3-yl, 5-methyl-3-phenyl-isoxazol-4-yl, 2-methyl-thiazol-4-yl, 2,5-dimethyl-thiazol-4-yl, imidazol-1-yl (preferred), 4,5-dimethyl-imidazol-2-yl (preferred), pyrazol-1-yl (preferred), 3,5-dimethyl-pyrazol-1-yl (preferred), 1-ethyl-5-methyl-pyrazol-3-yl (preferred), 5-methyl-pyrazol-4-yl, 1-ethyl-3-methyl-pyrazol-5-yl, [1,2,4]triazol-1-yl (preferred), pyridin-2-yl, pyridin-3-yl, indol-3-yl), benzimidazol-2-yl (preferred) and 1-methyl-benzimidazol-2-yl.

The term "heterocyclyl", used alone or in combination, means a 4- to 6-membered saturated monocyclic ring containing 1 or 2 heteroatoms independently selected from the group consisting of sulfur, oxygen and nitrogen (preferably oxygen and nitrogen), wherein one or two methylene groups adjacent to a nitrogen atom are optionally replaced by carbonyl groups. Examples of such heterocyclyl groups are azetidinyl, oxetanyl, pyrrolidinyl, pyrrolidonyl, tetrahydrofuranyl, tetrahydrothiophenyl, imidazolidinonyl, oxazolidinyl, oxazolidinonyl, thiazolidinyl, thiazolidinonyl, piperidinyl, piperidonyl, piperazinyl, piperazinonyl, piperazine-dionyl, morpholinyl, morpholinonyl, thiomorpholinyl, thiomorpholinonyl and dioxanyl. Preferred examples are azetidinyl, pyrrolidinyl, pyrrolidonyl, tetrahydrofuranyl, imidazolidinonyl, piperidinyl, piperidonyl, piperazinyl, morpholinyl and dioxanyl. The heterocyclyl group may be unsubstituted or substituted as explicitly defined.

In case R² represents "heterocyclyl" the term means the above-mentioned groups. Preferred heterocyclyl groups as used in R² are azetidinyl (notably azetidin-3-yl), pyrrolidinyl (notably pyrrolidin-3-yl) and piperidinyl (notably piperidin-3-yl and piperidin-4-yl). The above-mentioned heterocyclyl groups are unsubstituted or mono-substituted at a nitrogen atom with $(C_1-C_6)$alkyl, benzyl or tert-butoxycarbonyl. Examples of such unsubstituted or mono-substituted heterocyclyl groups are 1-tert-butoxycarbonyl-azetidin-3-yl, pyrrolidin-3-yl (preferred), 1-tert-butoxycarbonyl-pyrrolidin-3-yl, piperidin-3-yl (preferred), 1-tert-butoxycarbonyl-piperidin-3-yl, piperidin-4-yl (preferred), 1-methyl-piperidin-4-yl, 1-ethyl-piperidin-4-yl, 1-(3-methyl-butyl)-piperidin-4-yl, 1-benzyl-piperidin-4-yl and 1-tert-butoxycarbonyl-piperidin-4-yl.

In case R² represents "$(C_1-C_4)$alkyl, which is mono-substituted with heterocyclyl" the term "heterocyclyl" means the above-mentioned groups. Preferred heterocyclyl groups are pyrrolidinyl (notably pyrrolidin-1-yl and pyrrolidin-2-yl), pyrrolidonyl (notably pyrrolidon-1-yl), tetrahydrofuranyl (notably tetrahydrofuran-2-yl), imidazolidinonyl (notably imidazolidin-2-on-1-yl), piperidinyl (notably piperidin-3-yl and piperidin-4-yl), piperazinyl (notably piperazin-1-yl), morpholinyl (notably morpholin-4-yl) and dioxanyl (notably 1,4-dioxan-2-yl). The above-mentioned heterocyclyl groups are unsubstituted or mono-substituted at a nitrogen atom with ($C_1$-$C_4$)alkyl (preferred) or tert-butoxycarbonyl. Examples of such unsubstituted or mono-substituted heterocyclyl groups are pyrrolidin-1-yl, pyrrolidin-2-yl, 1-methyl-pyrrolidin-2-yl, 1-ethyl-pyrrolidin-2-yl, 1-tert-butoxycarbonyl-pyrrolidin-2-yl, pyrrolidon-1-yl, tetrahydrofuran-2-yl, imidazolidin-2-on-1-yl, 1-tert-butoxycarbonyl-piperidin-3-yl, piperidin-4-yl, 1-tert-butoxycarbonyl-piperidin-4-yl, 4-methyl-piperazin-1-yl, morpholin-4-yl and 1,4-dioxan-2-yl. Preferred examples of such unsubstituted or mono-substituted heterocyclyl groups are pyrrolidin-1-yl, pyrrolidin-2-yl, 1-methyl-pyrrolidin-2-yl, tetrahydrofuran-2-yl, imidazolidin-2-on-1-yl, piperidin-4-yl, 4-methyl-piperazin-1-yl and 1,4-dioxan-2-yl.

2) A further embodiment of the invention relates to bridged spiro[2.4]heptane derivatives according to embodiment 1) which are also compounds of formula ($I_P$)

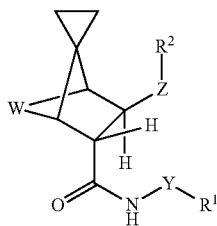

wherein

W represents —$CH_2CH_2$— or —CH=CH—;

Y represents a bond or a ($C_1$-$C_4$)alkandiyl group and $R^1$ represents an aryl- or a heteroaryl-group, which groups are independently unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_2$)alkyl-carbonyl, ($C_1$-$C_2$)fluoroalkyl, ($C_1$-$C_2$)fluoroalkoxy, nitro, cyano and phenyl, wherein the phenyl is unsubstituted or mono-substituted with halogen; or aryloxy; or cyclohexyl, which is unsubstituted or mono-substituted with methyl; or ($C_1$-$C_2$)alkyl-carbonyl; or ($C_1$-$C_4$)alkoxy-carbonyl;

or Y represents together with $R^1$ a ($C_4$-$C_6$)alkyl group;

Z represents —C(O)$NR^3$—* or —$CH_2NR^4$C(O)—*, wherein the asterisks indicate the bond which is linked to $R^2$;

$R^2$ represents ($C_3$-$C_6$)cycloalkyl, which is unsubstituted or mono-substituted with hydroxy or —$CONH_2$; or ($C_1$-$C_6$)alkyl, which is unsubstituted or mono-substituted with fluorine, trifluoromethyl, ($C_1$-$C_4$)alkoxy, ($C_1$-$C_4$) alkylthio, ($C_1$-$C_4$)alkoxy-carbonyl, hydroxy, cyano, —$NR^5R^6$ or —C(O)$NR^7R^8$; or ($C_1$-$C_4$)alkyl, which is mono-substituted with ($C_3$-$C_6$)cycloalkyl; with heterocyclyl, which is unsubstituted or mono-substituted at a nitrogen atom with ($C_1$-$C_4$)alkyl or tert-butoxycarbonyl; or with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NHR^9$, —$SO_2NH_2$ and phenyl; or heterocyclyl, which is unsubstituted or mono-substituted at a nitrogen atom with ($C_1$-$C_6$)alkyl, benzyl or tert-butoxycarbonyl; or an aryl- or a heteroaryl-group, which groups are independently unsubstituted, mono-, di- or tri-substituted, wherein the substituents are independently selected from the group consisting of halogen, ($C_1$-$C_4$)alkyl and phenyl; or a group selected from 1-carbamoyl-2-phenyl-ethyl, 1-methoxymethyl-2-phenyl-ethyl, 2-morpholino-2-phenyl-ethyl, 1-(1-piperidinecarbonyl)-ethyl, 2-phenyl-vinyl, 2,2-dichloro-1-methyl-cyclopropyl;

$R^3$ represents hydrogen, ($C_1$-$C_3$)alkyl or 2-methoxy-ethyl;

$R^4$ represents hydrogen or methyl;

$R^5$ represents hydrogen, ($C_1$-$C_3$)alkyl or tert-butoxycarbonyl;

$R^6$ represents hydrogen or ($C_1$-$C_3$)alkyl;

$R^7$ and $R^8$ represent independently from each other hydrogen or methyl; and $R^6$ represents hydrogen or tert-butoxycarbonyl;

and to the salts (in particular pharmaceutically acceptable salts) of such compounds.

3) A further embodiment of the invention relates to bridged spiro[2.4]heptane derivatives according to embodiment 1), wherein W represents —$CH_2CH_2$— or —CH=CH—;

Y represents a bond or a ($C_1$-$C_4$)alkandiyl group;

$R^1$ represents an aryl- or a heteroaryl-group, which groups are independently unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_2$)alkyl-carbonyl, ($C_1$-$C_2$)fluoroalkyl, ($C_1$-$C_2$)fluoroalkoxy, nitro, cyano and phenyl, wherein the phenyl is unsubstituted or mono-substituted with halogen;

Z represents —C(O)$NR^3$—* or —$CH_2NR^4$C(O)—*, wherein the asterisks indicate the bond which is linked to $R^2$;

$R^2$ represents ($C_3$-$C_6$)cycloalkyl, which is unsubstituted or mono-substituted with hydroxy, pyrrolidin-1-yl-methyl or —$CONH_2$; or ($C_1$-$C_6$)alkyl, which is unsubstituted or mono-substituted with fluorine, trifluoromethyl, ($C_1$-$C_4$)alkylthio, ($C_1$-$C_4$)alkoxy-carbonyl, hydroxy, cyano, —$NR^5R^6$, —C(O)$NR^7R^8$ or optionally mono-substituted ($C_1$-$C_4$) alkoxy, wherein the substituent is selected from hydroxy and heterocyclyl; or ($C_1$-$C_5$)alkyl, which is mono-substituted with heterocyclyl, which heterocyclyl is unsubstituted or mono-substituted at a nitrogen atom with ($C_1$-$C_4$) alkyl, or mono- or di-substituted at one or two of the carbon atoms with substituents independently selected from halogen, ($C_1$-$C_4$)alkyl and ($C_1$-$C_2$) alkoxy-($C_1$-$C_2$)alkyl; or with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NH_2$ and —$SO_2NH_2$; or ($C_3$-$C_5$)fluoroalkyl, which is mono-substituted with heterocyclyl, which heterocyclyl is unsubstituted (preferred) or mono- or di-substituted at one or two of the carbon atoms with substituents independently selected from halogen and ($C_1$-$C_4$)alkyl; or heterocyclyl, which is unsubstituted or mono-substituted at a nitrogen atom with ($C_1$-$C_6$)alkyl, benzyl or tert-butoxycarbonyl or mono-substituted at a carbon atom with pyrrolidin-1-yl-methyl; or an aryl- or a heteroaryl-group, which groups are independently unsubstituted, mono-, or di-substituted, wherein the substituents are independently selected from the group consisting of halogen, ($C_1$-$C_4$)alkyl and phenyl;

$R^3$ represents hydrogen, ($C_1$-$C_3$)alkyl or 2-methoxy-ethyl; or $R^2$ and $R^3$ form, together with the nitrogen that carries them, a piperidine ring, which ring is substituted with amino-($C_1$-$C_4$)alkyl (preferably amino-methyl);

$R^4$ represents hydrogen or methyl;

$R^5$ represents hydrogen, ($C_1$-$C_3$)alkyl or tert-butoxycarbonyl;

$R^6$ represents hydrogen or ($C_1$-$C_3$)alkyl;

$R^7$ and $R^8$ represent independently from each other hydrogen or methyl; or $R^7$ and $R^8$ form, together with the nitrogen that carries them, a pyrrolidine ring;

and to the salts (in particular pharmaceutically acceptable salts) of such compounds.

4) A further embodiment of the invention relates to bridged spiro[2.4]heptane derivatives according to any one of embodiments 1) to 3), wherein W represents —$CH_2CH_2$— or —CH=CH—;

Y represents a bond or a ($C_1$-$C_4$)alkandiyl group;

$R^1$ represents an aryl- or a heteroaryl-group, which groups are independently unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_2$)alkyl-carbonyl, ($C_1$-$C_2$)fluoroalkyl, ($C_1$-$C_2$)fluoroalkoxy, nitro, cyano and phenyl, wherein the phenyl is unsubstituted or mono-substituted with halogen;

Z represents —C(O)$NR^3$—* or —$CH_2NR^4$C(O)—*, wherein the asterisks indicate the bond which is linked to $R^2$;

$R^2$ represents ($C_3$-$C_6$)cycloalkyl, which is unsubstituted or mono-substituted with hydroxy or —$CONH_2$; or ($C_1$-$C_6$)alkyl, which is unsubstituted or mono-substituted with fluorine, trifluoromethyl, ($C_1$-$C_4$)alkoxy, ($C_1$-$C_4$)alkylthio, ($C_1$-$C_4$)alkoxy-carbonyl, hydroxy, cyano, —$NR^5R^6$ or —C(O)$NR^7R^8$; or ($C_1$-$C_4$)alkyl, which is mono-substituted with heterocyclyl, which is unsubstituted or mono-substituted at a nitrogen atom with ($C_1$-$C_4$)alkyl; or ($C_1$-$C_4$)alkyl, which is mono-substituted with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NH_2$ and —$SO_2NH_2$; or heterocyclyl, which is unsubstituted or mono-substituted at a nitrogen atom with ($C_1$-$C_6$)alkyl, benzyl or tert-butoxycarbonyl; or an aryl- or a heteroaryl-group, which groups are independently unsubstituted, mono- or di-substituted, wherein the substituents are independently selected from the group consisting of halogen, ($C_1$-$C_4$)alkyl and phenyl;

$R^3$ represents hydrogen, ($C_1$-$C_3$)alkyl or 2-methoxy-ethyl;

$R^4$ represents hydrogen or methyl;

$R^5$ represents hydrogen, ($C_1$-$C_3$)alkyl or tert-butoxycarbonyl;

$R^6$ represents hydrogen or ($C_1$-$C_3$)alkyl; and $R^7$ and $R^8$ represent independently from each other hydrogen or methyl;

and to the salts (in particular pharmaceutically acceptable salts) of such compounds.

5) A further embodiment of the invention relates to bridged spiro[2.4]heptane derivatives according to any one of embodiments 1) or 3), wherein W represents —$CH_2CH_2$— or —CH=CH—;

Y represents a bond;

$R^1$ represents an aryl- or a heteroaryl-group, which groups are independently unsubstituted, mono-, di- or tri-substituted, wherein the substituents are independently selected from the group consisting of halogen (preferably bromo), ($C_1$-$C_4$) alkyl (preferably methyl), ($C_1$-$C_4$)alkoxy (preferably methoxy), ($C_1$-$C_2$)alkyl-carbonyl (preferably acetyl), and ($C_1$-$C_2$) fluoroalkyl (preferably trifluoromethyl);

Z represents —C(O)$NR^3$—*, wherein the asterisk indicates the bond which is linked to $R^2$;

$R^2$ represents ($C_3$-$C_6$)cycloalkyl, which is unsubstituted or mono-substituted with hydroxy or pyrrolidin-1-yl-methyl; or ($C_1$-$C_6$)alkyl, which is unsubstituted or mono-substituted with fluorine, trifluoromethyl, ($C_1$-$C_4$)alkylthio (preferably ethylthio), hydroxy, cyano, —$NR^5R^6$, —C(O)$NH_2$ or optionally mono-substituted ($C_1$-$C_4$)alkoxy (preferably methoxy or ethoxy), wherein the substituent is selected from hydroxy and heterocyclyl; or ($C_1$-$C_5$)alkyl, which is mono-substituted with heterocyclyl, which heterocyclyl is unsubstituted or mono-substituted at a nitrogen atom with methyl or ethyl (preferably methyl), or mono- or di-substituted at one or two of the carbon atoms with substituents independently selected from fluorine, methyl and methoxy-methyl; or with an aryl- or heteroaryl-group, which groups are independently unsubstituted, mono- or di-substituted, wherein the substituents are independently selected from the group consisting of ($C_1$-$C_4$)alkyl (preferably methyl) and —$CH_2NH_2$; or ($C_3$-$C_5$)fluoroalkyl, which is mono-substituted with heterocyclyl (preferably pyrrolidin-1-yl); or heterocyclyl, which is unsubstituted or mono-substituted at a carbon atom with pyrrolidin-1-yl-methyl;

$R^3$ represents hydrogen, ($C_1$-$C_3$)alkyl (preferably methyl or ethyl) or 2-methoxy-ethyl;

$R^5$ represents hydrogen, ($C_1$-$C_3$)alkyl (preferably methyl or ethyl) or tert-butoxycarbonyl; and $R^6$ represents hydrogen or ($C_1$-$C_3$)alkyl (preferably methyl or ethyl);

and to the salts (in particular pharmaceutically acceptable salts) of such compounds.

6) A further embodiment of the invention relates to bridged spiro[2.4]heptane derivatives according to any one of embodiments 1) to 5), wherein W represents —$CH_2CH_2$— or —CH=CH—;

Y represents a bond;

$R^1$ represents an aryl- or a heteroaryl-group, which groups are independently unsubstituted or mono-substituted, wherein the substituent is selected from the group consisting of halogen (preferably bromo), $(C_1-C_4)$alkyl (preferably methyl), $(C_1-C_4)$alkoxy (preferably methoxy), $(C_1-C_2)$alkyl-carbonyl (preferably acetyl) and $(C_1-C_2)$fluoroalkyl (preferably trifluoromethyl);

Z represents —C(O)NR$^3$—*, wherein the asterisk indicates the bond which is linked to R$^2$;

R$^2$ represents $(C_3-C_6)$cycloalkyl, which is unsubstituted or mono-substituted with hydroxy; or $(C_1-C_6)$alkyl, which is unsubstituted or mono-substituted with fluorine, trifluoromethyl, $(C_1-C_4)$alkoxy (preferably methoxy or ethoxy), $(C_1-C_4)$alkylthio (preferably ethylthio), hydroxy, cyano, —NR$^5$R$^6$ or —C(O)NH$_2$; or $(C_1-C_4)$alkyl, which is mono-substituted with heterocyclyl, which is unsubstituted or mono-substituted at a nitrogen atom with methyl; or $(C_1-C_4)$alkyl, which is mono-substituted with an aryl- or heteroaryl-group, which groups are independently unsubstituted, mono- or di-substituted, wherein the substituents are independently selected from the group consisting of $(C_1-C_4)$alkyl (preferably methyl) and —CH$_2$NH$_2$; or heterocyclyl;

R$^3$ represents hydrogen, $(C_1-C_3)$alkyl (preferably methyl or ethyl) or 2-methoxy-ethyl;

R$^5$ represents hydrogen, $(C_1-C_3)$alkyl (preferably methyl or ethyl) or tert-butoxycarbonyl; and R$^6$ represents hydrogen or $(C_1-C_3)$alkyl (preferably methyl or ethyl);

and to the salts (in particular pharmaceutically acceptable salts) of such compounds.

7) A further embodiment of the invention relates to bridged spiro[2.4]heptane derivatives according to any one of embodiments 1) to 6), wherein W represents —CH$_2$CH$_2$—;

and to the salts (in particular pharmaceutically acceptable salts) of such compounds.

8) A further embodiment of the invention relates to bridged spiro[2.4]heptane derivatives according to any one of embodiments 1) to 6), wherein W represents —CH═CH—;

and to the salts (in particular pharmaceutically acceptable salts) of such compounds.

9) A further embodiment of the invention relates to bridged spiro[2.4]heptane derivatives according to any one of embodiments 1) to 8), wherein Y represents a bond;

and to the salts (in particular pharmaceutically acceptable salts) of such compounds.

10) A further embodiment of the invention relates to bridged spiro[2.4]heptane derivatives according to any one of embodiments 1) to 4) or 7) to 8), wherein Y represents a $(C_1-C_4)$alkandiyl group (preferably methandiyl);

and to the salts (in particular pharmaceutically acceptable salts) of such compounds.

11) A further embodiment of the invention relates to bridged spiro[2.4]heptane derivatives according to any one of embodiments 1) to 4) or 7) to 10), wherein R$^1$ represents an aryl- or a heteroaryl-group, which groups are independently unsubstituted, mono-, di- or tri-substituted, wherein the substituents are independently selected from the group consisting of halogen, $(C_1-C_4)$alkyl, $(C_1-C_4)$alkoxy, $(C_1-C_2)$alkyl-carbonyl, $(C_1-C_2)$fluoroalkyl, $(C_1-C_2)$fluoroalkoxy, nitro, cyano and phenyl, wherein the phenyl is unsubstituted or mono-substituted with halogen;

and to the salts (in particular pharmaceutically acceptable salts) of such compounds.

12) A further embodiment of the invention relates to bridged spiro[2.4]heptane derivatives according to any one of embodiments 1) to 11), wherein R$^1$ represents an aryl- or a heteroaryl-group, which groups are independently unsubstituted or mono-substituted, wherein the substituent is selected from the group consisting of halogen (preferably bromo), $(C_1-C_4)$alkyl (preferably methyl), $(C_1-C_4)$alkoxy (preferably methoxy), $(C_1-C_2)$alkyl-carbonyl (preferably acetyl) and $(C_1-C_2)$fluoroalkyl (preferably trifluoromethyl);

and to the salts (in particular pharmaceutically acceptable salts) of such compounds.

13) A further embodiment of the invention relates to bridged spiro[2.4]heptane derivatives according to any one of embodiments 1), 2) or 7) to 10), wherein R$^1$ represents aryloxy (preferably phenoxy), cyclohexyl, 4-methyl-cyclohexyl, $(C_1-C_2)$alkyl-carbonyl (preferably acetyl) or $(C_1-C_4)$alkoxy-carbonyl (preferably methoxy-carbonyl);

and to the salts (in particular pharmaceutically acceptable salts) of such compounds.

14) A further embodiment of the invention relates to bridged spiro[2.4]heptane derivatives according to any one of embodiments 1), 7) or 8), wherein Y represents together with R$^1$ a $(C_4-C_6)$alkyl group or a amino-$(C_4-C_6)$alkyl group;

and to the salts (in particular pharmaceutically acceptable salts) of such compounds.

15) A further embodiment of the invention relates to bridged spiro[2.4]heptane derivatives according to any one of embodiments 1), 2), 7) or 8), wherein Y represents together with R$^1$ a $(C_4-C_6)$alkyl group;

and to the salts (in particular pharmaceutically acceptable salts) of such compounds.

16) A further embodiment of the invention relates to bridged spiro[2.4]heptane derivatives according to any one of embodiments 1), 7) or 8), wherein Y represents together with R$^1$ a amino-$(C_4-C_6)$alkyl group;

and to the salts (in particular pharmaceutically acceptable salts) of such compounds.

17) A further embodiment of the invention relates to bridged spiro[2.4]heptane derivatives according to any one of embodiments 1), 7) or 8), wherein Y represents a $(C_1-C_2)$alkandiyl group (preferably ethan-1,2-diyl) and R$^1$ represents an aryl-group, which group is unsubstituted, mono-, di- or tri-substituted, wherein the substituents are independently selected from the group consisting of halogen (preferably fluoro, chloro and bromo), $(C_1-C_4)$alkyl (preferably methyl) and $(C_1-C_4)$alkoxy (preferably methoxy); or benzo[d][1,3]dioxolyl;

and to the salts (in particular pharmaceutically acceptable salts) of such compounds.

18) A further embodiment of the invention relates to bridged spiro[2.4]heptane derivatives according to any one of embodiments 1) to 17), wherein Z represents —C(O)NR$^3$—*, wherein the asterisk indicates the bond which is linked to R$^2$;

and to the salts (in particular pharmaceutically acceptable salts) of such compounds.

19) A further embodiment of the invention relates to bridged spiro[2.4]heptane derivatives according to any one of embodiments 1) to 4) or 7) to 17), wherein Z represents —CH$_2$NR$^4$C(O)—*, wherein the asterisk indicates the bond which is linked to R$^2$; and to the salts (in particular pharmaceutically acceptable salts) of such compounds.

20) A further embodiment of the invention relates to bridged spiro[2.4]heptane derivatives according to any one of embodiments 1), 3) or 7) to 19), wherein
R$^2$ represents
(C$_3$-C$_6$)cycloalkyl, which is unsubstituted or mono-substituted with hydroxy, pyrrolidin-1-yl-methyl or —CONH$_2$; or
(C$_1$-C$_6$)alkyl, which is unsubstituted or mono-substituted with fluorine, trifluoromethyl, (C$_r$-C$_4$)alkylthio, (C$_1$-C$_4$)alkoxy-carbonyl, hydroxy, cyano, —NR$^5$R$^6$, —C(O)NR$^7$R$^8$ or optionally mono-substituted (C$_1$-C$_4$)alkoxy, wherein the substituent is selected from hydroxy and heterocyclyl; or
(C$_1$-C$_5$)alkyl, which is mono-substituted with heterocyclyl, which heterocyclyl is unsubstituted or mono-substituted at a nitrogen atom with (C$_1$-C$_4$)alkyl, or mono- or di-substituted at one or two of the carbon atoms with substituents independently selected from halogen, (C$_1$-C$_4$)alkyl and (C$_1$-C$_2$)alkoxy-(C$_1$-C$_2$)alkyl; or
(C$_1$-C$_5$)alkyl, which is mono-substituted with an aryl- or heteroaryl-group, which groups are independently unsubstituted, mono-, di- or tri-substituted, wherein the substituents are independently selected from the group consisting of halogen, (C$_1$-C$_4$)alkyl, —CH$_2$NH$_2$ and —SO$_2$NH$_2$; or
(C$_3$-C$_5$)fluoroalkyl, which is mono-substituted with heterocyclyl; or
heterocyclyl, which is unsubstituted or mono-substituted at a nitrogen atom with (C$_1$-C$_6$)alkyl, benzyl or tert-butoxycarbonyl or mono-substituted at a carbon atom with pyrrolidin-1-yl-methyl; or
an aryl- or a heteroaryl-group, which groups are independently unsubstituted, mono-, or di-substituted, wherein the substituents are independently selected from the group consisting of halogen, (C$_1$-C$_4$)alkyl and phenyl;
and to the salts (in particular pharmaceutically acceptable salts) of such compounds.

21) A further embodiment of the invention relates to bridged spiro[2.4]heptane derivatives according to any one of embodiments 1) to 4) or 7) to 19), wherein
R$^2$ represents
(C$_3$-C$_6$)cycloalkyl, which is unsubstituted or mono-substituted with hydroxy or —CONH$_2$; or
(C$_1$-C$_6$)alkyl, which is unsubstituted or mono-substituted with fluorine, trifluoromethyl,
(C$_1$-C$_4$)alkoxy, (C$_1$-C$_4$)alkylthio, (C$_1$-C$_4$)alkoxy-carbonyl, hydroxy, cyano, —NR$^5$R$^6$ or —C(O)NR$^7$R$^8$; or
(C$_1$-C$_4$)alkyl, which is mono-substituted with heterocyclyl, which is unsubstituted or mono-substituted at a nitrogen atom with (C$_1$-C$_4$)alkyl; or
(C$_1$-C$_4$)alkyl, which is mono-substituted with an aryl- or heteroaryl-group, which groups are independently unsubstituted, mono-, di- or tri-substituted, wherein the substituents are independently selected from the group consisting of halogen, (C$_1$-C$_4$)alkyl, —CH$_2$NH$_2$ and —SO$_2$NH$_2$; or
heterocyclyl, which is unsubstituted or mono-substituted at a nitrogen atom with (C$_r$-C$_6$)alkyl, benzyl or tert-butoxycarbonyl; or
an aryl- or a heteroaryl-group, which groups are independently unsubstituted, mono- or di-substituted, wherein the substituents are independently selected from the group consisting of halogen, (C$_1$-C$_4$)alkyl and phenyl;
and to the salts (in particular pharmaceutically acceptable salts) of such compounds.

22) A further embodiment of the invention relates to bridged spiro[2.4]heptane derivatives according to any one of embodiments 1), 3) or 7) to 19), wherein
R$^2$ represents
(C$_3$-C$_6$)cycloalkyl, which is unsubstituted or mono-substituted with hydroxy or pyrrolidin-1-yl-methyl; or
(C$_1$-C$_6$)alkyl, which is unsubstituted or mono-substituted with fluorine, trifluoromethyl, (C$_1$-C$_4$)alkylthio (preferably ethylthio), hydroxy, cyano, —NR$^5$R$^6$, —C(O)NH$_2$ or optionally mono-substituted (C$_1$-C$_4$)alkoxy (preferably methoxy or ethoxy), wherein the substituent is selected from hydroxy and heterocyclyl; or
(C$_1$-C$_5$)alkyl, which is mono-substituted with heterocyclyl, which heterocyclyl is unsubstituted or mono-substituted at a nitrogen atom with methyl or ethyl (preferably methyl), or mono- or di-substituted at one or two of the carbon atoms with substituents independently selected from fluorine, methyl and methoxy-methyl; or
(C$_1$-C$_5$)alkyl, which is mono-substituted with an aryl- or heteroaryl-group, which groups are independently unsubstituted, mono- or di-substituted, wherein the substituents are independently selected from the group consisting of (C$_1$-C$_4$)alkyl (preferably methyl) and —CH$_2$NH$_2$; or
(C$_3$-C$_5$)fluoroalkyl, which is mono-substituted with heterocyclyl (preferably pyrrolidin-1-yl); or
heterocyclyl, which is unsubstituted or mono-substituted at a carbon atom with pyrrolidin-1-yl-methyl;
and to the salts (in particular pharmaceutically acceptable salts) of such compounds.

23) A further embodiment of the invention relates to bridged spiro[2.4]heptane derivatives according to any one of embodiments 1) to 19), wherein
R$^2$ represents
(C$_3$-C$_6$)cycloalkyl, which is unsubstituted or mono-substituted with hydroxy; or
(C$_1$-C$_6$)alkyl, which is unsubstituted or mono-substituted with fluorine, trifluoromethyl, (C$_1$-C$_4$)alkoxy (preferably methoxy or ethoxy), (C$_1$-C$_4$)alkylthio (preferably ethylthio), hydroxy, cyano, —NR$^5$R$^6$ or —C(O)NH$_2$; or
(C$_1$-C$_4$)alkyl, which is mono-substituted with heterocyclyl, which is unsubstituted or mono-substituted at a nitrogen atom with methyl; or
(C$_1$-C$_4$)alkyl, which is mono-substituted with an aryl- or heteroaryl-group, which groups are independently unsubstituted, mono- or di-substituted, wherein the substituents are independently selected from the group consisting of (C$_1$-C$_4$)alkyl (preferably methyl) and —CH$_2$NH$_2$; or
heterocyclyl;
and to the salts (in particular pharmaceutically acceptable salts) of such compounds.

24) A further embodiment of the invention relates to bridged spiro[2.4]heptane derivatives according to any one of embodiments 1), 3), 5) or 7) to 19), wherein
R$^2$ represents (C$_3$-C$_6$)cycloalkyl (preferably cyclopentyl or cyclohexyl), which is unsubstituted or mono-substituted with hydroxy, hydroxy-methyl, amino-methyl, pyrrolidin-1-yl-methyl or —CONH$_2$ (and preferably unsubstituted or mono-substituted with hydroxy or pyrrolidin-1-yl-methyl);
and to the salts (in particular pharmaceutically acceptable salts) of such compounds.

25) A further embodiment of the invention relates to bridged spiro[2.4]heptane derivatives according to any one of embodiments 1) to 19), wherein
R$^2$ represents (C$_3$-C$_6$)cycloalkyl (preferably cyclopentyl or cyclohexyl), which is unsubstituted or mono-substituted with hydroxy;

and to the salts (in particular pharmaceutically acceptable salts) of such compounds.

26) A further embodiment of the invention relates to bridged spiro[2.4]heptane derivatives according to any one of embodiments 1), 3) or 7) to 19), wherein
$R^2$ represents $(C_1-C_6)$alkyl, which is unsubstituted or mono-substituted with fluorine, trifluoromethyl, $(C_1-C_4)$alkylthio, hydroxy, cyano, —$NR^5R^6$, —$C(O)NR^7R^8$ or optionally mono-substituted $(C_1-C_4)$alkoxy, wherein the substituent is selected from hydroxy and heterocyclyl;
and to the salts (in particular pharmaceutically acceptable salts) of such compounds.

27) A further embodiment of the invention relates to bridged spiro[2.4]heptane derivatives according to any one of embodiments 1) to 19), wherein
$R^2$ represents $(C_1-C_6)$alkyl, which is unsubstituted or mono-substituted with fluorine, trifluoromethyl, $(C_1-C_4)$alkoxy, $(C_1-C_4)$alkylthio, hydroxy, cyano, —$NR^5R^6$ or —$C(O)NH_2$ (preferably fluorine, trifluoromethyl, methoxy, ethoxy, hydroxy, cyano, —$NR^5R^6$ or —$C(O)NH_2$);
and to the salts (in particular pharmaceutically acceptable salts) of such compounds.

28) A further embodiment of the invention relates to bridged spiro[2.4]heptane derivatives according to any one of embodiments 1), 3), 5) or 7) to 19), wherein
$R^2$ represents $(C_2-C_5)$alkyl, which is unsubstituted or mono-substituted with fluorine, trifluoromethyl, hydroxy, —$NR^5R^6$, —$C(O)NR^7R^8$, methoxy, ethoxy or 2-(pyrrolidin-1-yl)-ethoxy;
and to the salts (in particular pharmaceutically acceptable salts) of such compounds.

29) A further embodiment of the invention relates to bridged spiro[2.4]heptane derivatives according to any one of embodiments 1), 3) or 7) to 19), wherein
$R^2$ represents
$(C_1-C_5)$alkyl, which is mono-substituted with heterocyclyl, which heterocyclyl is unsubstituted or mono-substituted at a nitrogen atom with $(C_1-C_4)$alkyl (preferably methyl or ethyl), or mono- or di-substituted at one or two of the carbon atoms with substituents independently selected from halogen, $(C_1-C_4)$alkyl and $(C_1-C_2)$alkoxy-$(C_1-C_2)$alkyl (preferably from fluorine, methyl and methoxy-methyl); or
$(C_1-C_5)$alkyl, which is mono-substituted with an aryl- or heteroaryl-group, which groups are independently unsubstituted, mono- or di-substituted, wherein the substituents are independently selected from the group consisting of halogen, $(C_1-C_4)$alkyl, —$CH_2NH_2$ and —$SO_2NH_2$ (and preferably from methyl and —$CH_2NH_2$);
and to the salts (in particular pharmaceutically acceptable salts) of such compounds.

30) A further embodiment of the invention relates to bridged spiro[2.4]heptane derivatives according to any one of embodiments 1) to 19), wherein
$R^2$ represents $(C_1-C_4)$alkyl, which is mono-substituted with heterocyclyl, which is unsubstituted or mono-substituted at a nitrogen atom with methyl; or
$(C_1-C_4)$alkyl, which is mono-substituted with an aryl- or heteroaryl-group, which groups are independently unsubstituted, mono- or di-substituted, wherein the substituents are independently selected from the group consisting of $(C_1-C_4)$alkyl (preferably methyl) and —$CH_2NH_2$;
and to the salts (in particular pharmaceutically acceptable salts) of such compounds.

31) A further embodiment of the invention relates to bridged spiro[2.4]heptane derivatives according to any one of embodiments 1), 3), 5) or 7) to 19), wherein
$R^2$ represents $(C_1-C_5)$alkyl, which is mono-substituted with heterocyclyl, which heterocyclyl is unsubstituted or mono-substituted at a nitrogen atom with methyl or ethyl (preferably methyl), or mono- or di-substituted at one or two of the carbon atoms with substituents independently selected from fluorine, methyl and methoxy-methyl;
and to the salts (in particular pharmaceutically acceptable salts) of such compounds.

32) A further embodiment of the invention relates to bridged spiro[2.4]heptane derivatives according to any one of embodiments 1) to 19), wherein
$R^2$ represents $(C_1-C_4)$alkyl (preferably methyl or n-butyl and most preferably n-butyl), which is mono-substituted with heterocyclyl, which is unsubstituted (preferred) or mono-substituted at a nitrogen atom with methyl;
and to the salts (in particular pharmaceutically acceptable salts) of such compounds.

33) A further embodiment of the invention relates to bridged spiro[2.4]heptane derivatives according to any one of embodiments 29) to 32), wherein
the heterocyclyl is selected from the group consisting of azetidinyl (preferably azetidin-1-yl), pyrrolidinyl (preferably pyrrolidin-1-yl and pyrrolidin-2-yl), tetrahydrofuranyl (preferably tetrahydrofuran-2-yl), imidazolidinonyl (preferably imidazolidin-2-on-1-yl), piperidinyl (preferably piperidin-1-yl, piperidin-2-yl and piperidin-4-yl), piperazinyl (preferably piperazin-1-yl), morpholinyl (preferably morpholin-4-yl) and 1,4-diazepanyl (preferably 1,4-diazepan-1-yl);
and to the salts (in particular pharmaceutically acceptable salts) of such compounds.

34) A further embodiment of the invention relates to bridged spiro[2.4]heptane derivatives according to any one of embodiments 1) to 19), wherein
$R^2$ represents $(C_1-C_5)$alkyl (preferably $(C_1-C_3)$alkyl), which is mono-substituted with an aryl- or heteroaryl-group, which groups are independently unsubstituted, mono- or di-substituted (preferably unsubstituted or mono-substituted), wherein the substituents are independently selected from the group consisting of halogen, $(C_1-C_4)$alkyl, —$CH_2NH_2$ and —$SO_2NH_2$ (and preferably from methyl and —$CH_2NH_2$);
and to the salts (in particular pharmaceutically acceptable salts) of such compounds.

35) A further embodiment of the invention relates to bridged spiro[2.4]heptane derivatives according to any one of embodiments 1) to 19), wherein
$R^2$ represents $(C_1-C_4)$alkyl (preferably methyl, ethyl or n-propyl), which is mono-substituted with an aryl- or heteroaryl-group, which groups are independently unsubstituted, mono- or di-substituted (preferably unsubstituted or mono-substituted), wherein the substituents are independently selected from the group consisting of $(C_1-C_4)$alkyl (preferably methyl) and —$CH_2NH_2$;
and to the salts (in particular pharmaceutically acceptable salts) of such compounds.

36) A further embodiment of the invention relates to bridged spiro[2.4]heptane derivatives according to any one of embodiments 1) to 19), wherein
$R^2$ represents $(C_1-C_5)$alkyl (preferably $(C_1-C_3)$alkyl), which is mono-substituted with a heteroaryl-group, which is unsubstituted, mono- or di-substituted (preferably unsubstituted or di-substituted) with $(C_1-C_4)$alkyl (preferably methyl);
and to the salts (in particular pharmaceutically acceptable salts) of such compounds.

37) A further embodiment of the invention relates to bridged spiro[2.4]heptane derivatives according to any one of embodiments 1), 3), 5) or 7) to 19), wherein $R^2$ represents $(C_3-C_5)$fluoroalkyl, which is mono-substituted with heterocyclyl (preferably pyrrolidin-1-yl);
and to the salts (in particular pharmaceutically acceptable salts) of such compounds.

38) A further embodiment of the invention relates to bridged spiro[2.4]heptane derivatives according to embodiment 37), wherein
$(C_3-C_5)$fluoroalkyl means 3-fluorobutyl (preferred) or 3,3-difluorobutyl;
and to the salts (in particular pharmaceutically acceptable salts) of such compounds.

39) A further embodiment of the invention relates to bridged spiro[2.4]heptane derivatives according to any one of embodiments 1), 3) or 7) to 19), wherein
$R^2$ represents heterocyclyl, which is unsubstituted or mono-substituted at a nitrogen atom with $(C_1-C_6)$alkyl or mono-substituted at a carbon atom with pyrrolidin-1-yl-methyl;
and to the salts (in particular pharmaceutically acceptable salts) of such compounds.

40) A further embodiment of the invention relates to bridged spiro[2.4]heptane derivatives according to any one of embodiments 1) to 4) or 6 to 19), wherein
$R^2$ represents heterocyclyl, which is unsubstituted (preferred) or mono-substituted at a nitrogen atom with $(C_1-C_6)$alkyl;
and to the salts (in particular pharmaceutically acceptable salts) of such compounds.

41) A further embodiment of the invention relates to bridged spiro[2.4]heptane derivatives according to any one of embodiments 1) to 18) or 20) to 40), wherein
$R^3$ represents hydrogen (preferred), methyl, ethyl or 2-methoxy-ethyl;
and to the salts (in particular pharmaceutically acceptable salts) of such compounds.

42) A further embodiment of the invention relates to bridged spiro[2.4]heptane derivatives according to any one of embodiments 1), 3) or 7) to 19), wherein
$R^2$ and $R^3$ form, together with the nitrogen that carries them, a piperidine ring, which ring is substituted with amino-$(C_1-C_4)$alkyl (preferably amino-methyl);
and to the salts (in particular pharmaceutically acceptable salts) of such compounds.

43) A further embodiment of the invention relates to bridged spiro[2.4]heptane derivatives according to any one of embodiments 1) to 4), 7) to 17) or 19) to 40), wherein $R^4$ represents hydrogen;
and to the salts (in particular pharmaceutically acceptable salts) of such compounds.

44) A further embodiment of the invention relates to bridged spiro[2.4]heptane derivatives according to any one of embodiments 1) to 23), 26) to 28), 41) or 43), wherein
$R^5$ represents hydrogen, methyl or ethyl;
and to the salts (in particular pharmaceutically acceptable salts) of such compounds.

45) A further embodiment of the invention relates to bridged spiro[2.4]heptane derivatives according to any one of embodiments 1) to 23), 26) to 28), 41), 43) or 44), wherein
$R^6$ represents hydrogen, methyl or ethyl;
and to the salts (in particular pharmaceutically acceptable salts) of such compounds.

46) A further embodiment of the invention relates to bridged spiro[2.4]heptane derivatives according to any one of embodiments 1) to 4), 7) to 21), 26), 28), 41) or 43), wherein
$R^7$ and $R^8$ represent hydrogen;
and to the salts (in particular pharmaceutically acceptable salts) of such compounds.

47) A further embodiment of the invention relates to bridged spiro[2.4]heptane derivatives according to any one of embodiments 1), 2), 7) to 19), 41) or 43), wherein
$R^9$ represents hydrogen;
and to the salts (in particular pharmaceutically acceptable salts) of such compounds.

48) A further embodiment of the invention relates to bridged spiro[2.4]heptane derivatives according to any one of embodiments 1) to 47), wherein the absolute configuration of the stereogenic centers is as depicted in formula $I_{St1}$ above;
and to the salts (in particular pharmaceutically acceptable salts) of such compounds.

49) A further embodiment of the invention relates to bridged spiro[2.4]heptane derivatives according to any one of embodiments 1) to 47), wherein the absolute configuration of the stereogenic centers is as depicted in formula $I_{St2}$ above;
and to the salts (in particular pharmaceutically acceptable salts) of such compounds.

50) Preferred compounds of formula (I) as defined in embodiment 1) are selected from the group consisting of:
(5R*)—$N^5$-(4-Bromophenyl)-(6R*)—$N^6$-(5-amino-pentyl)-(4S*,7R*)-[4,7-ethenylene-spiro[2.4]heptane]-5,6-dicarboxamide;
(5R)—$N^5$-(4-Bromophenyl)-(6R)—$N^6$-(4-pyrrolidin-1-yl-butyl)-(4S,7R)-[4,7-ethenylene-spiro[2.4]heptane]-5,6-dicarboxamide;
(5R*)—$N^5$-(4-Bromophenyl)-(6R*)—$N^6$-(piperidin-4-yl)-(4S*,7R*)-[4,7-ethenylene-spiro[2.4]heptane]-5,6-dicarboxamide;
(5R*)—$N^5$-(4-Bromophenyl)-(6R*)—$N^6$-(3-iso-butyl)-(4S*,7R*)-[4,7-ethenylene-spiro[2.4]heptane]-5,6-dicarboxamide;
(5R*)—$N^5$-(4-Bromophenyl)-(6R*)—$N^6$-(4-amino-butyl)-(4S*,7R*)-[4,7-ethenylene-spiro[2.4]heptane]-5,6-dicarboxamide;
(5R)—$N^5$-(4-Bromophenyl)-(6R)—$N^6$-(2-N,N-dimethyl-amino-ethyl)-(4S,7R)-[4,7-ethenylene-spiro[2.4]heptane]-5,6-dicarboxamide;
(5R*)—$N^5$-(4-Bromophenyl)-(6R*)—$N^6$-((3-aminomethyl-phenyl)-methyl)-(4S*,7R*)-[4,7-ethenylene-spiro[2.4]heptane]-5,6-dicarboxamide;
(5R*)—$N^5$-(4-Bromophenyl)-(6R*)—$N^6$-(4-piperidinyl-methyl)-(4S*,7R*)-[4,7-ethenylene-spiro[2.4]heptane]-5,6-dicarboxamide;
(5R*)—$N^5$-(4-Bromophenyl)-(6R*)—$N^6$-(pyrrolidin-3-yl)-(4S*,7R*)-[4,7-ethenylene-spiro[2.4]heptane]-5,6-dicarboxamide;
(5R*)—$N^5$-(4-Bromophenyl)-(6R*)—$N^6$-(2,2-dimethyl-3-amino-propyl)-(4S*,7R*)-[4,7-ethenylene-spiro[2.4]heptane]-5,6-dicarboxamide;
(5R*)—$N^5$-(4-Bromophenyl)-(6R*)—$N^6$-(4-(N,N-diethyl-amino)-butyl)-(4S*,7R*)-[4,7-ethenylene-spiro[2.4]heptane]-5,6-dicarboxamide;
(5R)—$N^5$-(4-Bromophenyl)-(6R)—$N^6$-(3-hydroxy-propyl)-(4S,7R)-[4,7-ethenylene-spiro[2.4]heptane]-5,6-dicarboxamide;
(5R)—$N^5$-(4-Bromophenyl)-(6R)—$N^6$-(2-carbamoyl-ethyl)-(4S,7R)-[4,7-ethenylene-spiro[2.4]heptane]-5,6-dicarboxamide;
(5R*)—$N^5$-(4-Bromophenyl)-(6R*)—$N^6$—(N-tert-butoxy-carbonyl-pyrrolidin-3-yl)-(4S*,7R*)-[4,7-ethenylene-spiro[2.4]heptane]-5,6-dicarboxamide;

(5R*)—N5-(4-Bromophenyl)-(6R*)—N6-(cyclopentyl)-(4S*,7R*)-[4,7-ethenylene-spiro[2.4]heptane]-5,6-dicarboxamide;

(5R*)—N5-(4-Bromophenyl)-(6R*)—N6-(3-amino-propyl)-(4S*,7R*)-[4,7-ethenylene-spiro[2.4]heptane]-5,6-dicarboxamide;

(5R*)—N5-(4-Bromophenyl)-(6R*)—N6-(3-ethoxy-propyl)-(4S*,7R*)-[4,7-ethenylene-spiro[2.4]heptane]-5,6-dicarboxamide;

(5R*)—N5-(4-Bromophenyl)-(6R*)—N6-(2-pyrrolidinyl-methyl)-(4S*,7R*)-[4,7-ethenylene-spiro[2.4]heptane]-5,6-dicarboxamide;

(5R*)—N5-(4-Bromophenyl)-(6R*)—N6-(2,2,2-trifluoro-ethyl)-(4S*,7R*)-[4,7-ethenylene-spiro[2.4]heptane]-5,6-dicarboxamide;

(5R*)—N5-(4-Bromophenyl)-(6R*)—N6-(2-fluoro-ethyl)-(4S*,7R*)-[4,7-ethenylene-spiro[2.4]heptane]-5,6-dicarboxamide;

(5R*)—N5-(4-Bromophenyl)-(6R*)—N6-(2-(N-methyl-amino)-ethyl)-(4S*,7R*)-[4,7-ethenylene-spiro[2.4]heptane]-5,6-dicarboxamide;

(5R*)—N5-(4-Bromophenyl)-(6R*)—N6-(2-tetrahydro-furanyl-methyl)-(4S*,7R*)-[4,7-ethenylene-spiro[2.4]heptane]-5,6-dicarboxamide;

(5R*)—N5-(4-Bromophenyl)-(6R*)—N6-(4-hydroxy-cyclohexyl)-(4S*,7R*)-[4,7-ethenylene-spiro[2.4]heptane]-5,6-dicarboxamide;

(5R*)—N5-(4-Bromophenyl)-(6R*)—N6-(2-ethylsulfanyl-ethyl)-(4S*,7R*)-[4,7-ethenylene-spiro[2.4]heptane]-5,6-dicarboxamide;

(5R*)—N5-(4-Bromophenyl)-(6R*)—N6-(5-(N,N-diethyl-amino)-pent-2-yl)-(4S*,7R*)-[4,7-ethenylene-spiro[2.4]heptane]-5,6-dicarboxamide;

(5R*)—N5-(4-Bromophenyl)-(6R*)—N6-(piperidin-3-yl)-(4S*,7R*)-[4,7-ethenylene-spiro[2.4]heptane]-5,6-dicarboxamide;

(5R*)—N5-(4-Bromophenyl)-(6R*)—N6-(2-tert-butoxycarbonyl-amino-ethyl)-(4S*,7R*)-[4,7-ethenylene-spiro[2.4]heptane]-5,6-dicarboxamide;

(5R*)—N5-(4-Bromophenyl)-(6R*)—N6-(1-hydroxy-prop-2-yl)-(4S*,7R*)-[4,7-ethenylene-spiro[2.4]heptane]-5,6-dicarboxamide;

(5R*)—N5-(4-Bromophenyl)-(6R*)—N6-(2-imidazolidin-2-on-1-yl-ethyl)-(4S*,7R*)-[4,7-ethenylene-spiro[2.4]heptane]-5,6-dicarboxamide;

(5R*)—N5-(4-Bromophenyl)-(6R*)—N6-(3-pyrrolidin-1-yl-propyl)-(4S*,7R*)-[4,7-ethenylene-spiro[2.4]heptane]-5,6-dicarboxamide;

(5R)—N5-(4-Bromophenyl)-(6R)—N6-(2-methoxy-ethyl)-(4S,7R)-[4,7-ethenylene-spiro[2.4]heptane]-5,6-dicarboxamide;

(5R*)—N5-(4-Bromophenyl)-(6R*)—N6-(3-(1H-benzoimidazol-2-yl)-propyl)-(4S*,7R*)-[4,7-ethenylene-spiro[2.4]heptane]-5,6-dicarboxamide;

(5R*)—N5-(4-Bromophenyl)-(6R*)—N6-(2-(1-methyl-pyrrolidin-2-yl)-ethyl)-(4S*,7R*)-[4,7-ethenylene-spiro[2.4]heptane]-5,6-dicarboxamide;

(5R*)—N5-(4-Bromophenyl)-(6R*)—N6-(2-hydroxy-ethyl)-(4S*,7R*)-[4,7-ethenylene-spiro[2.4]heptane]-5,6-dicarboxamide;

(5R*)—N5-(4-Bromophenyl)-(6R*)—N6,N6-bis-(2-methoxy-ethyl)-(4S*,7R*)-[4,7-ethenylene-spiro[2.4]heptane]-5,6-dicarboxamide;

(5R*)—N5-(4-Bromophenyl)-(6R*)—N6-(cyano-methyl)-(4S*,7R*)-[4,7-ethenylene-spiro[2.4]heptane]-5,6-dicarboxamide;

(5R*)—N5-(4-Bromophenyl)-(6R*)—N6-(3-1H-pyrazol-1-yl-propyl)-(4S*,7R*)-[4,7-ethenylene-spiro[2.4]heptane]-5,6-dicarboxamide;

(5R*)—N5-(4-Bromophenyl)-(6R*)—N6-[(4-aminomethyl-phenyl)-methyl]-(4S*,7R*)-[4,7-ethenylene-spiro[2.4]heptane]-5,6-dicarboxamide;

(5R*)—N5-(4-Bromophenyl)-(6R*)—N6-ethyl-N6-(2-diethylamino-ethyl)-(4S*,7R*)-[4,7-ethenylene-spiro[2.4]heptane]-5,6-dicarboxamide;

(5R*)—N5-(4-Bromophenyl)-(6R*)—N6-(3-1H-imidazol-1-yl-propyl)-(4S*,7R*)-[4,7-ethenylene-spiro[2.4]heptane]-5,6-dicarboxamide;

(5R*)—N5-(4-Bromophenyl)-(6R*)—N6-([1,4]-dioxan-2-yl-methyl)-(4S*,7R*)-[4,7-ethenylene-spiro[2.4]heptane]-5,6-dicarboxamide;

(5R*)—N5-(4-Bromophenyl)-(6R*)—N6-(4-hydroxy-butyl)-(4S*,7R*)-[4,7-ethenylene-spiro[2.4]heptane]-5,6-dicarboxamide;

(5R*)—N5-(4-Bromophenyl)-(6R*)—N6-(3-(4-methyl-piperazin-1-yl)-propyl)-(4S*,7R*)-[4,7-ethenylene-spiro[2.4]heptane]-5,6-dicarboxamide;

(5R*)—N5-(4-Bromophenyl)-(6R*)—N6-(2-amino-ethyl)-(4S*,7R*)-[4,7-ethenylene-spiro[2.4]heptane]-5,6-dicarboxamide;

(5R*)—N5-(4-Bromophenyl)-(6R*)—N6-methyl-N6-(2-dimethylamino-ethyl)-(4S*,7R*)-[4,7-ethenylene-spiro[2.4]heptane]-5,6-dicarboxamide;

(5R*)—N5-(4-Bromophenyl)-(6R*)—N6-(4-tert-butoxycarbonyl-amino-butyl)-(4S*,7R*)-[4,7-ethenylene-spiro[2.4]heptane]-5,6-dicarboxamide;

(5R*)—N5-(4-Bromophenyl)-(6R*)—N6-(2-(methyl-tert-butoxycarbonyl-amino)-ethyl)-(4S*,7R*)-[4,7-ethenylene-spiro[2.4]heptane]-5,6-dicarboxamide;

(5R*)—N5-(4-Bromophenyl)-(6R*)—N6-(2-pyrrolidin-1-yl-ethyl)-(4S*,7R*)-[4,7-ethenylene-spiro[2.4]heptane]-5,6-dicarboxamide;

(5R*)—N5-(4-Bromophenyl)-(6R*)—N6-(2-1H-[1,2,4]-triazol-1-yl-ethyl)-(4S*,7R*)-[4,7-ethenylene-spiro[2.4]heptane]-5,6-dicarboxamide;

(5R*)—N5-(4-Bromophenyl)-(6R*)—N6-(furan-3-yl-methyl)-(4S*,7R*)-[4,7-ethenylene-spiro[2.4]heptane]-5,6-dicarboxamide;

(5R*)—N5-(4-Bromophenyl)-(6R*)—N6-(5-dimethylamino-pentyl)-(4S*,7R*)-[4,7-ethenylene-spiro[2.4]heptane]-5,6-dicarboxamide;

(5R*)—N5-(4-Bromophenyl)-(6R*)—N6-(3-dimethylamino-propyl)-(4S*,7R*)-[4,7-ethenylene-spiro[2.4]heptane]-5,6-dicarboxamide;

(5R*)—N5-(4-Bromophenyl)-(6R*)—N6-(3-methoxy-propyl)-(4S*,7R*)-[4,7-ethenylene-spiro[2.4]heptane]-5,6-dicarboxamide;

(5R*)—N5-(4-Bromophenyl)-(6R*)—N6-[(1-ethyl-pyrrolidin-2-yl)-methyl]-(4S*,7R*)-[4,7-ethenylene-spiro[2.4]heptane]-5,6-dicarboxamide;

(5R*)—N5-(4-Bromophenyl)-(6R*)—N6-(3-1H-[1,2,4]-triazol-1-yl-propyl)-(4S*,7R*)-[4,7-ethenylene-spiro[2.4]heptane]-5,6-dicarboxamide;

(5R*)—N5-(4-Bromophenyl)-(6R*)—N6-(N-tert-butoxycarbonyl-piperidin-3-yl)-(4S*,7R*)-[4,7-ethenylene-spiro[2.4]heptane]-5,6-dicarboxamide;

(5R*)—N5-(4-Bromophenyl)-(6R*)—N6-(3-(N-tert-butoxycarbonyl-amino)-propyl)-(4S*,7R*)-[4,7-ethenylene-spiro[2.4]heptane]-5,6-dicarboxamide;

(5R*)—N5-(4-Bromophenyl)-(6R*)—N6-(3-methyl-butyl)-(4S*,7R*)-[4,7-ethenylene-spiro[2.4]heptane]-5,6-dicarboxamide;

(5R*)—N⁵-(4-Bromophenyl)-(6R*)—N⁶-[(2S)-1-hydroxy-4-methyl-pent-2-yl]-(4S*,7R*)-[4,7-ethenylene-spiro[2.4]heptane]-5,6-dicarboxamide;
(5R*)—N⁵-(4-Bromophenyl)-(6R*)—N⁶-(2-(methoxy-carbonyl)-ethyl)-(4S*,7R*)-[4,7-ethenylene-spiro[2.4]heptane]-5,6-dicarboxamide;
(5R*)—N⁵-(4-Bromophenyl)-(6R*)—N⁶-(2-(4-aminosulfonyl-phenyl)-ethyl)-(4S*,7R*)-[4,7-ethenylene-spiro[2.4]heptane]-5,6-dicarboxamide;
(5R*)—N⁵-(4-Bromophenyl)-(6R*)—N⁶-(2-(1-ethyl-5-methyl-1H-pyrazol-3-yl)-ethyl)-(4S*,7R*)-[4,7-ethenylene-spiro[2.4]heptane]-5,6-dicarboxamide;
(5R)—N⁵-(4-Bromophenyl)-(6R)—N⁶,N⁶-bis-(2-methoxy-ethyl)-(4S,7R)-[4,7-ethenylene-spiro[2.4]heptane]-5,6-dicarboxamide;
(5R*)—N⁵-(4-Bromophenyl)-(6R*)—N⁶-(2-(4,5-dimethyl-1H-imidazol-2-yl)-ethyl)-(4S*,7R*)-[4,7-ethenylene-spiro[2.4]heptane]-5,6-dicarboxamide;
(5R*)—N⁵-(4-Bromophenyl)-(6R*)—N⁶-[(1S)-1-carbamoyl-ethyl]-(4S*,7R*)-[4,7-ethenylene-spiro[2.4]heptane]-5,6-dicarboxamide;
(5R*)—N⁵-(4-Bromophenyl)-(6R*)—N⁶-(2-diethyl-aminoethyl)-(4S*,7R*)-[4,7-ethenylene-spiro[2.4]heptane]-5,6-dicarboxamide;
(5R*)—N⁵-(4-Bromophenyl)-(6R*)—N⁶-(pentyl)-(4S*,7R*)-[4,7-ethenylene-spiro[2.4]heptane]-5,6-dicarboxamide;
(5R*)—N⁵-(4-Bromophenyl)-(6R*)—N⁶-(5-tert-butoxycarbonyl-amino-pentyl)-(4S*,7R*)-[4,7-ethenylene-spiro[2.4]heptane]-5,6-dicarboxamide;
(5R*)—N⁵-(4-Bromophenyl)-(6R*)—N⁶—(N-(3-methyl-butyl)-piperidin-4-yl)-(4S*,7R*)-[4,7-ethenylene-spiro[2.4]heptane]-5,6-dicarboxamide;
(5R*)—N⁵-(4-Bromophenyl)-(6R*)—N⁶-(2-pyridin-2-yl-ethyl)-(4S*,7R*)-[4,7-ethenylene-spiro[2.4]heptane]-5,6-dicarboxamide;
(5R*)—N⁵-(4-Bromophenyl)-(6R*)—N⁶-(2,2-dimethyl-3-N-tert-butoxycarbonyl-amino-propyl)-(4S*,7R*)-[4,7-ethenylene-spiro[2.4]heptane]-5,6-dicarboxamide;
(5R*)—N⁵-(4-Bromophenyl)-(6R*)—N⁶-(1-phenyl-1H-pyrazol-5-yl)-(4S*,7R*)-[4,7-ethenylene-spiro[2.4]heptane]-5,6-dicarboxamide;
(5R*)—N⁵-(4-Bromophenyl)-(6R*)—N⁶-(cyclopropyl)-(4S*,7R*)-[4,7-ethenylene-spiro[2.4]heptane]-5,6-dicarboxamide;
(5R*)—N⁵-(4-Bromophenyl)-(6R*)—N⁶-(butyl)-(4S*,7R*)-[4,7-ethenylene-spiro[2.4]heptane]-5,6-dicarboxamide;
(5R*)—N⁵-(4-Bromophenyl)-(6R*)—N⁶-(hexyl)-(4S*,7R*)-[4,7-ethenylene-spiro[2.4]heptane]-5,6-dicarboxamide;
(5R*)—N⁵-(4-Bromophenyl)-(6R*)—N⁶-(2-(1-ethyl-3-methyl-1H-pyrazol-5-yl)-ethyl)-(4S*,7R*)-[4,7-ethenylene-spiro[2.4]heptane]-5,6-dicarboxamide;
(5R*)—N⁵-(4-Bromophenyl)-(6R*)—N⁶-(2-phenyl-2-morpholino-ethyl)-(4S*,7R*)-[4,7-ethenylene-spiro[2.4]heptane]-5,6-dicarboxamide;
(5R*)—N⁵-(4-Bromophenyl)-(6R*)—N⁶-(3-diethyl-amino-propyl)-(4S*,7R*)-[4,7-ethenylene-spiro[2.4]heptane]-5,6-dicarboxamide;
(5R*)—N⁵-(4-Bromophenyl)-(6R*)—N⁶—(N-tert-butoxycarbonyl-pyrrolidin-2-yl-methyl)-(4S*,7R*)-[4,7-ethenylene-spiro[2.4]heptane]-5,6-dicarboxamide;
(5R*)—N⁵-(4-Bromophenyl)-(6R*)—N⁶-(2-morpholino-ethyl)-(4S*,7R*)-[4,7-ethenylene-spiro[2.4]heptane]-5,6-dicarboxamide;
(5R*)—N⁵-(4-Bromophenyl)-(6R*)—N⁶-(2-carbamoyl-cyclohexyl)-(4S*,7R*)-[4,7-ethenylene-spiro[2.4]heptane]-5,6-dicarboxamide;
(5R*)—N⁵-(4-Bromophenyl)-(6R*)—N⁶-(1-piperidin-1-yl-propan-1-on-2-yl)-(4S*,7R*)-[4,7-ethenylene-spiro[2.4]heptane]-5,6-dicarboxamide;
(5R*)—N⁵-(4-Bromophenyl)-(6R*)—N⁶—(N-benzyl-piperidin-4-yl)-(4S*,7R*)-[4,7-ethenylene-spiro[2.4]heptane]-5,6-dicarboxamide;
(5R*)—N⁵-(4-Bromophenyl)-(6R*)—N⁶-methyl-N⁶-hexyl-(4S*,7R*)-[4,7-ethenylene-spiro[2.4]heptane]-5,6-dicarboxamide;
(5R*)—N⁵-(4-Bromophenyl)-(6R*)—N⁶-(3,3-dimethyl-butyl)-(4S*,7R*)-[4,7-ethenylene-spiro[2.4]heptane]-5,6-dicarboxamide;
(5R*)—N⁵-(4-Bromophenyl)-(6R*)—N⁶—(N-methyl-piperidin-4-yl)-(4S*,7R*)-[4,7-ethenylene-spiro[2.4]heptane]-5,6-dicarboxamide;
(5R*)—N⁵-(4-Bromophenyl)-(6R*)—N⁶-(3-morpholino-propyl)-(4S*,7R*)-[4,7-ethenylene-spiro[2.4]heptane]-5,6-dicarboxamide;
(5R*)—N⁵-(4-Bromophenyl)-(6R*)—N⁶-(3-(5-methyl-1H-pyrazol-4-yl)-propyl)-(4S*,7R*)-[4,7-ethenylene-spiro[2.4]heptane]-5,6-dicarboxamide;
(5R*)—N⁵-(4-Bromophenyl)-(6R*)—N⁶-(3-tert-butoxycarbonyl-propyl)-(4S*,7R*)-[4,7-ethenylene-spiro[2.4]heptane]-5,6-dicarboxamide;
(5R*)—N⁵-(4-Bromophenyl)-(6R*)—N⁶-{[(3-N-tert-butoxycarbonyl-aminomethyl)-phenyl]-methyl}-(4S*,7R*)-[4,7-ethenylene-spiro[2.4]heptane]-5,6-dicarboxamide;
(5R*)—N⁵-(4-Bromophenyl)-(6R*)—N⁶-propyl-N⁶-(cyclopropylmethyl)-(4S*,7R*)-[4,7-ethenylene-spiro[2.4]heptane]-5,6-dicarboxamide;
(5R*)—N⁵-(4-Bromophenyl)-(6R*)—N⁶—(N-tert-butoxycarbonyl-piperidin-4-yl-methyl)-(4S*,7R*)-[4,7-ethenylene-spiro[2.4]heptane]-5,6-dicarboxamide;
(5R*)—N⁵-(4-Bromophenyl)-(6R*)—N⁶-(cyclohexyl)-(4S*,7R*)-[4,7-ethenylene-spiro[2.4]heptane]-5,6-dicarboxamide;
(5R*)—N⁵-(4-Bromophenyl)-(6R*)—N⁶—(N-tert-butoxycarbonyl-piperidin-4-yl)-(4S*,7R*)-[4,7-ethenylene-spiro[2.4]heptane]-5,6-dicarboxamide;
(5R*)—N⁵-(4-Bromophenyl)-(6R*)—N⁶-[(1S)-1-carbamoyl-2-phenyl-ethyl]-(4S*,7R*)-[4,7-ethenylene-spiro[2.4]heptane]-5,6-dicarboxamide;
(5R*)—N⁵-(4-Bromophenyl)-(6R*)—N⁶-[(2S)-3,3-dimethyl-1-(methylamino)-1-oxobutan-2-yl]-(4S*,7R*)-[4,7-ethenylene-spiro[2.4]heptane]-5,6-dicarboxamide;
(5R*)—N⁵-(4-Bromophenyl)-(6R*)—N⁶-[(4-N-tert-butoxycarbonyl-aminomethyl-phenyl)-methyl]-(4S*,7R*)-[4,7-ethenylene-spiro[2.4]heptane]-5,6-dicarboxamide;
(5R*)—N⁵-(4-Bromophenyl)-(6R*)—N⁶—(N-tert-butoxycarbonyl-azetidin-3-yl)-(4S*,7R*)-[4,7-ethenylene-spiro[2.4]heptane]-5,6-dicarboxamide;
(5R*)—N⁵-(4-Bromophenyl)-(6R*)—N⁶-(2-(N-tert-butoxycarbonyl-piperidin-3-yl)-ethyl)-(4S*,7R*)-[4,7-ethenylene-spiro[2.4]heptane]-5,6-dicarboxamide;
(5R*)—N⁵-(4-Bromophenyl)-(6R*)—N⁶-[(1S)-2-methoxy-1-benzyl-ethyl]-(4S*,7R*)-[4,7-ethenylene-spiro[2.4]heptane]-5,6-dicarboxamide;
(5R*)—N⁵-(4-Bromophenyl)-(6R*)—N⁶-[(5-methyl-3-phenyl-isoxazol-4-yl)-methyl]-(4S*,7R*)-[4,7-ethenylene-spiro[2.4]heptane]-5,6-dicarboxamide;
(5R*)—N⁵-(4-Bromophenyl)-(6R*)—N⁶-(2-carbamoyl-ethyl)-(4S*,7R*)-[4,7-ethylene-spiro[2.4]heptane]-5,6-dicarboxamide;

(5R*)—N⁵-(4-Bromophenyl)-(6R*)—N⁶-(3-methoxy-propyl)-(4S*,7R*)-[4,7-ethylene-spiro[2.4]heptane]-5,6-dicarboxamide;

(5R*)—N⁵-(4-Bromophenyl)-(6R*)—N⁶-(tetrahydrofuran-2-yl-methyl)-(4S*,7R*)-[4,7-ethylene-spiro[2.4]heptane]-5,6-dicarboxamide;

(5R*)—N⁵-(4-Bromophenyl)-(6R*)—N⁶-[(2-imidazolidin-2-on-1-yl)-ethyl]-(4S*,7R*)-[4,7-ethylene-spiro[2.4]heptane]-5,6-dicarboxamide;

(5R*)—N⁵-(4-Bromophenyl)-(6R*)—N⁶-(cyclopropyl)-(4S*,7R*)-[4,7-ethylene-spiro[2.4]heptane]-5,6-dicarboxamide;

(5R*)—N⁵-(4-Bromophenyl)-(6R*)—N⁶-(3-hydroxy-propyl)-(4S*,7R*)-[4,7-ethylene-spiro[2.4]heptane]-5,6-dicarboxamide;

(5R*)—N⁵-(4-Bromophenyl)-(6R*)—N⁶-(3-(1H-imidazol-1-yl)-propyl)-(4S*,7R*)-[4,7-ethylene-spiro[2.4]heptane]-5,6-dicarboxamide;

(5R*)—N⁵-(4-Bromophenyl)-(6R*)—N⁶-(5-(dimethyl-amino)-pentyl)-(4S*,7R*)-[4,7-ethylene-spiro[2.4]heptane]-5,6-dicarboxamide;

(5R*)—N⁵-(4-Bromophenyl)-(6R*)—N⁶-(3-pyrrolidin-1-yl-propyl)-(4S*,7R*)-[4,7-ethylene-spiro[2.4]heptane]-5,6-dicarboxamide;

(5R*)—N⁵-(4-Bromophenyl)-(6R*)—N⁶-(3-(4-methyl-piperazin-1-yl)-propyl)-(4S*,7R*)-[4,7-ethylene-spiro[2.4]heptane]-5,6-dicarboxamide;

(5R*)—N⁵-(4-Bromophenyl)-(6R*)—N⁶-(2-(4,5-dimethyl-1H-imidazol-2-yl)-ethyl)-(4S*,7R*)-[4,7-ethylene-spiro[2.4]heptane]-5,6-dicarboxamide;

(5R)—N⁵-(4-Bromophenyl)-(6R)—N⁶-(4-pyrrolidin-1-yl-butyl)-(4S,7R)-[4,7-ethylene-spiro[2.4]heptane]-5,6-dicarboxamide;

(5R*)—N⁵-(2-Bromopyridin-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Methoxyphenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Chloro-pyridin-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(Benzothiazol-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Bromophenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Bromo-pyridin-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Bromo-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Methyl-pyridin-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-Pentyl-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-[(4-Methyl-phenyl)-methyl]-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Methoxycarbonyl-ethyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(Cyclohexyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Methyl-cyclohex-1-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-oxo-hexyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Nitro-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Chloro-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Cyano-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(Furan-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(1-(4-Bromophenyl)-ethyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Trifluoromethoxyphenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Phenoxy-ethyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-Methyl-butyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-Butyl-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Methyl-furan-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Methyl-benzothiazol-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Phenyl-ethyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-oxo-pentyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-(1H-Imidazol-1-yl)-propyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Chloro-pyrimidin-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-Bromophenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(Benzothiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-tert-Butyl-isoxazol-3-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-Methyl-benzo[d]isothiazol-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N$^5$-(1H-Indol-5-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(6-Fluoro-benzothiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-Ethyl-butyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-(4-Chlorophenyl)-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(Benzo[2,1,3]oxadiazol-4-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-tert-Butyl-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(3-Phenyl-[1,2,4]thiadiazol-5-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(6-Chloro-benzothiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(3-(2-Methyl-1H-indol-1-yl)-propyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(1-Methyl-1H-benzoimidazol-2-yl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(1H-Indol-1-yl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(2-Methoxy-phenyl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-Bromo-phenyl)-(6R*)-6-[(3-(3,5-dimethyl-pyrazol-1-yl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(5-phenyl-isoxazole-4-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(4-(2-oxo-pyrrolidin-1-yl)-butyrylamino)-methyl]-(4S*,7R*)-[4,7-ethenylene-spiro[2.4]heptane]-5-carboxamide;

(5R*)—N$^5$-(4-Bromo-phenyl)-(6R*)-6-[(2-(2-chloro-phenyl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-methoxy-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(N,N-dimethyl-aminocarbonyl)-propionyl-amino)-methyl]-(4S*,7R*)-[4,7-ethenylene-spiro[2.4]heptane]-5-carboxamide;

(5R*)—N$^5$-(4-Bromo-phenyl)-(6R*)-6-{[(2,2-dichloro-1-methyl-cyclopropylcarbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(4-methoxycarbonyl-butanoyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-(pentanoylamino-methyl)-(4S*,7R*)-[4,7-ethenylene-spiro[2.4]heptane]-5-carboxamide;

(5R*)—N$^5$-(4-Bromo-phenyl)-(6R*)-6-[(2-(2,5-dimethyl-thiazol-4-yl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(1-phenyl-1H-pyrazole-5-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(3-aminocarbonyl-propionyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(4-methyl-pyridine-3-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(isobutyrylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(N-ethyl-piperidine-4-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(3-pyridin-3-yl-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-{[N-(3-methoxy-propionyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(2-chloro-3-fluoro-phenyl-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(4-pyrrolidin-1-yl-butanoylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(1,5-dimethyl-1H-pyrazole-3-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(cyclopentyl-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(2-(2-methyl-thiazol-4-yl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(2-(N,N-dimethyl-amino)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-{[N-(2-(2-chloro-phenyl)-acetyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-{[N-(1,5-dimethyl-1H-pyrazole-3-carbonyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-[(2-cyclopropyl-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(1-methyl-1H-benzoimidazol-2-yl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-1H-indol-3-yl-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(butanoylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(4-fluoro-phenyl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-phenyl-acryloylamino)-methyl]-(4S*,7R*)-[4,7-ethenylene-spiro[2.4]heptane]-5-carboxamide;

(5R*)—N⁵-(4-Bromo-phenyl)-(6R*)-6-{[(5-chloro-1,3-dimethyl-1H-pyrazole-4-carbonyl)-amino]-methyl}-(4S*,7R*)-[4,7-ethenylene-spiro[2.4]heptane]-5-carboxamide;

(5R*)—N⁵-(4-Acetyl-thiazol-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Acetyl-phenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Methyl-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Acetyl-thiophen-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R)—N⁵-(5-Acetyl-furan-2-yl-methyl)-(6R)—N⁶-(4-pyrrolidin-1-yl-butyl)-(4S,7R)-[4,7-ethenylene-spiro[2.4]heptane]-5,6-dicarboxamide;

(5R)—N⁵-(5-Acetyl-furan-2-yl-methyl)-(6R)—N⁶-(4-pyrrolidin-1-yl-butyl)-(4S,7R)-[4,7-ethylene-spiro[2.4]heptane]-5,6-dicarboxamide;

(5R*)—N⁵-(4-Trifluoromethyl-phenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Acetyl-oxazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-(4,5-Dimethyl-1H-imidazol-2-yl)-ethyl)-(6R*)—N⁶-(4-bromophenyl)-(4S*,7R*)-[4,7-ethenylene-spiro[2.4]heptane]-5,6-dicarboxamide;

(5R*)—N⁵-(4-Iodophenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-(iso-Butyl)-isoxazol-3-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Bromo-thiophen-4-yl-methyl)-(6R*)—N⁶-(4-pyrrolidin-1-yl-butyl)-(4S*,7R*)-[4,7-ethenylene-spiro[2.4]heptane]-5,6-dicarboxamide; and (5R*)—N⁵-(2-Fluoro-4-bromophenyl-methyl)-(6R*)—N⁶-(4-pyrrolidin-1-yl-butyl)-(4S*,7R*)-[4,7-ethenylene-spiro[2.4]heptane]-5,6-dicarboxamide;

or salts (in particular pharmaceutically acceptable salts) of such compounds;

it is to be understood for any of the above listed compounds, that a stereogenic center, which is not specifically assigned, may be in absolute (R) — or absolute (S)-configuration and that a double bond, which is not specifically assigned, may be in (E)- or (Z)-configuration. Especially, for a compound mentioned in the above list to have the relative (4S*,5R*,6R*,7R*)-configuration it is to be understood that also the respective enantiomer with the absolute (4R,5S,6S,7S)-configuration and/or the respective enantiomer with the absolute (4S,5R,6R,7R)-configuration is encompassed.

51) Further preferred compounds of formula (I) as defined in embodiment 1) are selected from the group consisting of:

(5R*)—N⁵-(4-Bromophenyl)-(6R*)—N⁶-(3-dimethylamino-3-oxopropyl)-(4S*,7R*)-[4,7-ethenylene-spiro[2.4]heptane]-5,6-dicarboxamide;

(5R*)—N⁵-(4-Bromophenyl)-(6R*)—N⁶-(4-amino-4-oxobutyl)-(4S*,7R*)-[4,7-ethenylene-spiro[2.4]heptane]-5,6-dicarboxamide;

(5R*)—N⁵-(4-Bromophenyl)-(6R*)—N⁶-(3-pyrrolidino-3-oxopropyl)-(4S*,7R*)-[4,7-ethenylene-spiro[2.4]heptane]-5,6-dicarboxamide;

(5R*)—N⁵-(4-Bromophenyl)-(6R*)—N⁶-(2-amino-2-oxoethyl)-(4S*,7R*)-[4,7-ethenylene-spiro[2.4]heptane]-5,6-dicarboxamide;

(5R)—N⁵-(4-Bromophenyl)-(6R)—N⁶-(4-(4-ethyl-piperazin-1-yl)-butyl)-(4S,7R)-[4,7-ethenylene-spiro[2.4]heptane]-5,6-dicarboxamide;

(5R)—N⁵-(4-Bromophenyl)-(6R)—N⁶-(4-piperidino-butyl)-(4S,7R)-[4,7-ethenylene-spiro[2.4]heptane]-5,6-dicarboxamide;

(5R)—N⁵-(4-Bromophenyl)-(6R)—N⁶-(4-(azetidin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-morpholino-butyl)-(4S,7R)-[4,7-ethenylene-spiro[2.4]heptane]-5,6-dicarboxamide;

(5R)—N⁵-(4-Bromophenyl)-(6R)—N⁶-(4-(4-methyl-1,4-diazepan-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-(4-methyl-piperazin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-pyrrolidino-4-oxobutyl)-(4S,7R)-[4,7-ethenylene-spiro[2.4]heptane]-5,6-dicarboxamide;

(5R)—N⁵-(4-Bromophenyl)-(6R)—N⁶-(2-(2-(pyrrolidin-1-yl)ethoxy)ethyl)-(4S,7R)-[4,7-ethenylene-spiro[2.4]heptane]-5,6-dicarboxamide;

(5R)—N⁵-(4-Bromophenyl)-(6R)—N⁶-((3R,6S)-6-(pyrrolidin-1-ylmethyl)tetrahydro-2H-pyran-3-yl)-(4S,7R)-[4,7-ethenylene-spiro[2.4]heptane]-5,6-dicarboxamide;

(5R)—N⁵-(4-Bromophenyl)-(6R)—N⁶-(4-(4-acetyl-piperazin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(cis-4-(pyrrolidin-1-yl-methyl)-cyclohexyl)-(4S,7R)-[4,7-ethenylene-spiro[2.4]heptane]-5,6-dicarboxamide;

(5R)—N⁵-(4-Bromophenyl)-(6R)—N⁶-(4-((3R)-fluoropyrrolidino)butyl)-(4S,7R)-[4,7-ethenylene-spiro[2.4]heptane]-5,6-dicarboxamide;

(5R)—N⁵-(4-Bromophenyl)-(6R)—N⁶-(4-((3S)-fluoropyrrolidino)butyl)-(4S,7R)-[4,7-ethenylene-spiro[2.4]heptane]-5,6-dicarboxamide;

(5R)—N⁵-(4-Bromophenyl)-(6R)—N⁶-(5-pyrrolidino-pentyl)-(4S,7R)-[4,7-ethenylene-spiro[2.4]heptane]-5,6-dicarboxamide;

(5R)—N⁵-(4-Bromophenyl)-(6R)—N⁶-(trans-4-(pyrrolidin-1-yl-methyl)-cyclohexyl)-(4S,7R)-[4,7-ethenylene-spiro[2.4]heptane]-5,6-dicarboxamide;

(5R*)—N⁵-(4-Bromophenyl)-(6R*)—N⁶-(3-methylamino-3-oxopropyl)-(4S*,7R*)-[4,7-ethenylene-spiro[2.4]heptane]-5,6-dicarboxamide;

(5R*)—N⁵-(2-Acetyl-thiazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R)—N⁵-(5-Bromo-thiazol-2-yl)-(6R)—N⁶-(4-pyrrolidin-1-yl-butyl)-(4S,7R)-[4,7-ethenylene-spiro[2.4]heptane]-5,6-dicarboxamide;

(5R*)—N⁵-(2,6-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2,3-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-Fluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3,5-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Chloro-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Fluoro-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Trifluoromethoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Isopropoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Bromo-thiazol-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Acetyl-oxazol-4-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Bromo-phenyl-methyl)-(6R*)—N⁶-(3-pyrrolidin-1-yl-propyl)-(4S*,7R*)-[4,7-ethenylene-spiro[2.4]heptane]-5,6-dicarboxamide;

(5R*)—N⁵-(5-Bromo-thiazol-2-yl)-(6R*)—N⁶-(3-pyrrolidin-1-yl-propyl)-(4S*,7R*)-[4,7-ethenylene-spiro[2.4]heptane]-5,6-dicarboxamide;

(5R)—N⁵-(5-Bromo-thiazol-2-yl)-(6R)—N⁶-(4-pyrrolidin-1-yl-butyl)-(4S,7R)-[4,7-ethylene-spiro[2.4]heptane]-5,6-dicarboxamide;

(5R)—N⁵-(5-Bromo-thiazol-2-yl)-(6R)—N⁶-(3-amino-3-oxopropyl)-(4S,7R)-[4,7-ethylene-spiro[2.4]heptane]-5,6-dicarboxamide;

(5R)—N⁵-(5-Bromo-thiazol-2-yl)-(6R)—N⁶-(3-amino-3-oxopropyl)-(4S,7R)-[4,7-ethenylene-spiro[2.4]heptane]-5,6-dicarboxamide;

(5R)—N⁵-(4-Bromo-phenyl-methyl)-(6R)—N⁶-(3-amino-3-oxopropyl)-(4S,7R)-[4,7-ethenylene-spiro[2.4]heptane]-5,6-dicarboxamide;

(5R)—N⁵-(2-Bromo-pyrid-5-yl)-(6R)—N⁶-(3-amino-3-oxopropyl)-(4S,7R)-[4,7-ethenylene-spiro[2.4]heptane]-5,6-dicarboxamide;

(5R*)—N⁵-(4-Acetyl-oxazol-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(isobutyl)-(4S*,7R*)-[4,7-ethenylene-spiro[2.4]heptane]-5,6-dicarboxamide;

(5R*)—N⁵-(5-Bromo-thiazol-2-yl)-(6R*)—N⁶-(isobutyl)-(4S*,7R*)-[4,7-ethenylene-spiro[2.4]heptane]-5,6-dicarboxamide;

(5R*)—N⁵-(4-Bromo-phenyl-methyl)-(6R*)—N⁶-(isobutyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(3-(1H-benzoimidazol-2-yl)-propyl)-(4S*,7R*)-[4,7-ethenylene-spiro[2.4]heptane]-5,6-dicarboxamide;

(5R*)—N⁵-(5-Bromo-thiazol-2-yl)-(6R*)—N⁶-(3-(1H-benzoimidazol-2-yl)-propyl)-(4S*,7R*)-[4,7-ethenylene-spiro[2.4]heptane]-5,6-dicarboxamide;

(5R*)—N⁵-(4-Bromo-phenyl-methyl)-(6R*)—N⁶-(3-(1H-benzoimidazol-2-yl)-propyl)-(4S*,7R*)-[4,7-ethenylene-spiro[2.4]heptane]-5,6-dicarboxamide;

(5R*)—N⁵-(2-Methoxy-pyrid-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Bromo-pyrazin-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Trifluoromethyl-pyridin-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Methyl-pyridin-5-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(Benzo[d]oxazol-6-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Methyl-isoxazol-3-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Methyl-thiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Trifluoromethyl-1,3,4-thiadiazol-2-yl)-(6R*)—N⁶-(4-pyrrolidin-1-yl-butyl)-(4S*,7R*)-[4,7-ethenylene-spiro[2.4]heptane]-5,6-dicarboxamide;

(5R)—N⁵-(2-Bromo-pyridin-5-yl)-(6R)—N⁶-(4-pyrrolidin-1-yl-butyl)-(4S,7R)-[4,7-ethenylene-spiro[2.4]heptane]-5,6-dicarboxamide;

(5R*)—N⁵-(5-Bromo-thiazol-2-yl)-(6R*)—N⁶-(2-fluoro-ethyl)-(4S*,7R*)-[4,7-ethenylene-spiro[2.4]heptane]-5,6-dicarboxamide;

(5R*)—N⁵-(5-Bromo-thiazol-2-yl)-(6R*)—N⁶-((2-imidazolidin-2-on)-1-yl-ethyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(3-amino-3-oxopropyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(4-diethylamino-butyl)-(4S*,7R*)-[4,7-ethenylene-spiro[2.4]heptane]-5,6-dicarboxamide;

(5R*)—N⁵-(4-Bromophenyl-methyl)-(6R*)—N⁶-(3-ethoxy-propyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(3-pyrrolidino-propyl)-(4S*,7R*)-[4,7-ethenylene-spiro[2.4]heptane]-5,6-dicarboxamide;

(5R*)—N⁵-(5-Bromothiazol-2-yl)-(6R*)—N⁶-(3-(4-methylpiperazin-1-yl)-propyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(2-dimethylamino-ethyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(3-dimethylamino-propyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-(3-(4-methylpiperazin-1-yl)-propyl)-(4S*,7R*)-[4,7-ethenylene-spiro[2.4]heptane]-5,6-dicarboxamide;

(5R*)—N⁵-(4-Acetyl-thiazol-2-yl-methyl)-(6R*)—N⁶-((2-imidazolidin-2-on)-1-yl-ethyl)-(4S*,7R*)-[4,7-ethenylene-spiro[2.4]heptane]-5,6-dicarboxamide;

(5R*)—N⁵-(5-Bromothiazol-2-yl)-(6R*)—N⁶-(4-diethylamino-butyl)-(4S*,7R*)-[4,7-ethenylene-spiro[2.4]heptane]-5,6-dicarboxamide;

(5R*)—N⁵-(4-Bromophenyl-methyl)-(6R*)—N⁶-(2-fluoro-ethyl)-(4S*,7R*)-[4,7-ethenylene-spiro[2.4]heptane]-5,6-dicarboxamide;

(5R*)—N⁵-(4-Bromophenyl-methyl)-(6R*)—N⁶-(4-diethylamino-butyl)-(4S*,7R*)-[4,7-ethenylene-spiro[2.4]heptane]-5,6-dicarboxamide;

($5R^*$)—$N^5$-(4-Bromophenyl-methyl)-($6R^*$)—$N^6$-(3-(4-methylpiperazin-1-yl)-propyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(2-dimethylamino-ethyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-((2-imidazolidin-2-on)-1-yl-ethyl)-($4S^*,7R^*$)-[4,7-ethenylene-spiro[2.4]heptane]-5,6-dicarboxamide;

($5R^*$)—$N^5$-(5-Bromothiazol-2-yl)-($6R^*$)—$N^6$-(2-methoxyethyl)-($4S^*,7R^*$)-[4,7-ethenylene-spiro[2.4]heptane]-5,6-dicarboxamide;

($5R^*$)—$N^5$-(5-Bromothiazol-2-yl)-($6R^*$)—$N^6$-(3-dimethylamino-propyl)-($4S^*,7R^*$)-[4,7-ethenylene-spiro[2.4]heptane]-5,6-dicarboxamide;

(5R)—$N^5$-(2-Bromopyrid-5-yl)-(6R)—$N^6$-(3-amino-3-oxopropyl)-(4S,7R)-[4,7-ethylene-spiro[2.4]heptane]-5,6-dicarboxamide;

(5R)—$N^5$-(2-Bromopyrid-5-yl)-(6R)—$N^6$-(4-pyrrolidino-butyl)-(4S,7R)-[4,7-ethylene-spiro[2.4]heptane]-5,6-dicarboxamide;

(5R)—$N^5$-(5-Bromopyrid-2-yl)-(6R)—$N^6$-(3-amino-3-oxopropyl)-(4S,7R)-[4,7-ethenylene-spiro[2.4]heptane]-5,6-dicarboxamide;

(5R)—$N^5$-(2-Chloropyrid-5-yl)-(6R)—$N^6$-(3-amino-3-oxopropyl)-(4S,7R)-[4,7-ethenylene-spiro[2.4]heptane]-5,6-dicarboxamide;

(5R)—$N^5$-(4-Bromo-2-fluorophenyl-methyl)-(6R)—$N^6$-(3-amino-3-oxopropyl)-(4S,7R)-[4,7-ethenylene-spiro[2.4]heptane]-5,6-dicarboxamide;

(5R)—$N^5$-(2-Bromothiazol-5-yl-methyl)-(6R)—$N^6$-(3-amino-3-oxopropyl)-(4S,7R)-[4,7-ethenylene-spiro[2.4]heptane]-5,6-dicarboxamide;

(5R)—$N^5$-(4-Bromo-2-fluorophenyl-methyl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Methoxyphenyl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Bromophenyl-methyl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Methoxyphenyl)-(6R)—$N^6$-(3-hydroxyl-3-oxopropyl)-(4S,7R)-[4,7-ethenylene-spiro[2.4]heptane]-5,6-dicarboxamide;

(5R)—$N^5$-(4-Bromo-3-fluorophenyl)-(6R)—$N^6$-(4-pyrrolidino-butyl)-(4S,7R)-[4,7-ethenylene-spiro[2.4]heptane]-5,6-dicarboxamide;

(5R)—$N^5$-(2-Chloro-pyridin-5-yl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Methoxyphenyl)-(6R)—$N^6$-(3-amino-3-oxopropyl)-(4S,7R)-[4,7-ethenylene-spiro[2.4]heptane]-5,6-dicarboxamide;

(5R)—$N^5$-(4-Bromophenyl-methyl)-(6R)—$N^6$-(3-amino-3-oxopropyl)-(4S,7R)-[4,7-ethylene-spiro[2.4]heptane]-5,6-dicarboxamide;

(5R)—$N^5$-(4-Bromo-2-fluorophenyl-methyl)-(6R)—$N^6$-(3-amino-3-oxopropyl)-(4S,7R)-[4,7-ethylene-spiro[2.4]heptane]-5,6-dicarboxamide;

(5R)—$N^5$-(4-Methoxyphenyl)-(6R)—$N^6$-(3-amino-3-oxopropyl)-(4S,7R)-[4,7-ethenylene-spiro[2.4]heptane]-5,6-dicarboxamide;

(5R)—$N^5$-(5-Bromo-pyridin-2-yl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Bromo-2-fluorophenyl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Bromo-2-methylphenyl)-(6R)—$N^6$-(4-pyrrolidino-butyl)-(4S,7R)-[4,7-ethenylene-spiro[2.4]heptane]-5,6-dicarboxamide;

(5R)—$N^5$-(4-Bromo-3-chlorophenyl)-(6R)—$N^6$-(4-pyrrolidino-butyl)-(4S,7R)-[4,7-ethenylene-spiro[2.4]heptane]-5,6-dicarboxamide;

(5R)—$N^5$-(2-Chloro-pyridin-5-yl)-(6R)—$N^6$-(3-amino-3-oxopropyl)-(4S,7R)-[4,7-ethylene-spiro[2.4]heptane]-5,6-dicarboxamide;

($5R^*$)—$N^5$-(4-Acetyl-thiazol-2-yl-methyl)-($6R^*$)—$N^6$-(3-amino-propyl)-($4S^*,7R^*$)-[4,7-ethenylene-spiro[2.4]heptane]-5,6-dicarboxamide;

($5R^*$)—$N^5$-(4-Acetyl-thiazol-2-yl-methyl)-($6R^*$)—$N^6$-(piperidin-4-yl-methyl)-($4S^*,7R^*$)-[4,7-ethenylene-spiro[2.4]heptane]-5,6-dicarboxamide;

($5R^*$)—$N^5$-(5-Bromo-thiazol-2-yl)-($6R^*$)—$N^6$-(2-methylamino-ethyl)-($4S^*,7R^*$)-[4,7-ethenylene-spiro[2.4]heptane]-5,6-dicarboxamide;

($5R^*$)—$N^5$-(5-Bromo-thiazol-2-yl)-($6R^*$)—$N^6$-(5-aminopentyl)-($4S^*,7R^*$)-[4,7-ethenylene-spiro[2.4]heptane]-5,6-dicarboxamide;

($5R^*$)—$N^5$-(5-Bromo-thiazol-2-yl)-($6R^*$)—$N^6$-(4-(aminomethyl)phenyl-methyl)-($4S^*,7R^*$)-[4,7-ethenylene-spiro[2.4]heptane]-5,6-dicarboxamide;

($5R^*$)—$N^5$-(5-Bromo-thiazol-2-yl)-($6R^*$)—$N^6$-(2,2-dimethyl-3-amino-propyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(2-methylamino-ethyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(piperidin-4-yl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(3-aminopropyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(3-(aminomethyl)phenyl-methyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(4-(aminomethyl)phenyl-methyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(2,2-dimethyl-3-amino-propyl)-($4S^*,7R^*$)-[4,7-ethenylene-spiro[2.4]heptane]-5,6-dicarboxamide;

($5R^*$)—$N^5$-(4-Bromophenyl-methyl)-($6R^*$)—$N^6$-(piperidin-4-yl-methyl)-($4S^*,7R^*$)-[4,7-ethenylene-spiro[2.4]heptane]-5,6-dicarboxamide;

(5R)—$N^5$-(2-Bromo-thiazol-5-yl-methyl)-(6R)—$N^6$-(4-pyrrolidino-butyl)-(4S,7R)-[4,7-ethenylene-spiro[2.4]heptane]-5,6-dicarboxamide;

(5R)—$N^5$-(5-Methyl-pyridin-2-yl)-(6R)—$N^6$-(3-amino-3-oxopropyl)-(4S,7R)-[4,7-ethenylene-spiro[2.4]heptane]-5,6-dicarboxamide;

(5R)—$N^5$-(4-Bromo-2,5-difluorophenyl)-(6R)—$N^6$-(4-pyrrolidino-butyl)-(4S,7R)-[4,7-ethylene-spiro[2.4]heptane]-5,6-dicarboxamide;

(5R)—$N^5$-(4-Bromo-2,6-difluorophenyl)-(6R)—$N^6$-(4-pyrrolidino-butyl)-(4S,7R)-[4,7-ethylene-spiro[2.4]heptane]-5,6-dicarboxamide;

(5R)—$N^5$-(4-Bromo-2,3-difluorophenyl)-(6R)—$N^6$-(4-pyrrolidino-butyl)-(4S,7R)-[4,7-ethylene-spiro[2.4]heptane]-5,6-dicarboxamide;

(5R)—N⁵-(4-Bromo-2,6-difluorophenyl-methyl)-(6R)—N⁶-(4-pyrrolidin-1-yl-butyl)-(4S,7R)-[4,7-ethenylene-spiro[2.4]heptane]-5,6-dicarboxamide;

(5R)—N⁵-(4-Bromo-2-fluorophenyl-methyl)-(6R)—N⁶-(4-pyrrolidino-butyl)-(4S,7R)-[4,7-ethylene-spiro[2.4]heptane]-5,6-dicarboxamide;

(5R)—N⁵-(4-Bromo-2-fluorophenyl-methyl)-(6R)—N⁶-(5-amino-pentyl)-(4S,7R)-[4,7-ethenylene-spiro[2.4]heptane]-5,6-dicarboxamide;

(5R)—N⁵-(4-Bromo-2-fluorophenyl-methyl)-(6R)—N⁶-(4-amino-butyl)-(4S,7R)-[4,7-ethenylene-spiro[2.4]heptane]-5,6-dicarboxamide;

(5R)—N⁵-(4-Bromo-3-fluorophenyl-methyl)-(6R)—N⁶-(4-pyrrolidino-butyl)-(4S,7R)-[4,7-ethylene-spiro[2.4]heptane]-5,6-dicarboxamide;

(5R)—N⁵-(5-Bromo-thiazol-2-yl)-(6R)—N⁶-(5-amino-pentyl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yl-methyl)-(4S,7R)-[4,7-ethenylene-spiro[2.4]heptane]-5,6-dicarboxamide;

(5R)—N⁵-(5-Bromo-thiazol-2-yl)-(6R)—N⁶,N⁶-(3-(aminomethyl)pentane-1,5-diyl)-(4S,7R)-[4,7-ethenylene-spiro[2.4]heptane]-5,6-dicarboxamide;

(5R)—N⁵-(4-Bromo-2-fluorophenyl-methyl)-(6R)—N⁶-(5-amino-pentyl)-(4S,7R)-[4,7-ethylene-spiro[2.4]heptane]-5,6-dicarboxamide;

(5R)—N⁵-(4-Bromo-2,3-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-3,5-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-2,5-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yl)-(4S,7R)-[4,7-ethylene-spiro[2.4]heptane]-5,6-dicarboxamide;

(5R)—N⁵-(5-Bromo-thiazol-2-yl)-(6R)—N⁶-(isobutyl)-(4S,7R)-[4,7-ethylene-spiro[2.4]heptane]-5,6-dicarboxamide;

(5R)—N⁵-(5-Bromo-thiazol-2-yl)-(6R)—N⁶-(4-tert-butoxycarbonyl-amino-butyl)-(4S,7R)-[4,7-ethylene-spiro[2.4]heptane]-5,6-dicarboxamide;

(5R)—N⁵-(5-Bromo-thiazol-2-yl)-(6R)—N⁶-(5-tert-butoxycarbonyl-amino-pentyl)-(4S,7R)-[4,7-ethylene-spiro[2.4]heptane]-5,6-dicarboxamide;

(5R)—N⁵-(5-Bromo-thiazol-2-yl)-(6R)—N⁶-(5-amino-pentyl)-(4S,7R)-[4,7-ethylene-spiro[2.4]heptane]-5,6-dicarboxamide;

(5R)—N⁵-(5-Bromo-thiazol-2-yl)-(6R)—N⁶-(4-amino-butyl)-(4S,7R)-[4,7-ethylene-spiro[2.4]heptane]-5,6-dicarboxamide;

(5R)—N⁵-(5-Bromo-thiazol-2-yl)-(6R)—N⁶,N⁶-(3-(aminomethyl)pentane-1,5-diyl)-(4S,7R)-[4,7-ethylene-spiro[2.4]heptane]-5,6-dicarboxamide;

(5R)—N⁵-(5-Bromo-thiazol-2-yl)-(6R)—N⁶-(piperidin-4-yl-methyl)-(4S,7R)-[4,7-ethylene-spiro[2.4]heptane]-5,6-dicarboxamide;

(5R)—N⁵-(2-Bromo-3-fluoro-pyridin-5-yl)-(6R)—N⁶-(4-pyrrolidino-butyl)-(4S,7R)-[4,7-ethenylene-spiro[2.4]heptane]-5,6-dicarboxamide;

(5R*)—N⁵-(4-Aminobutyl)-(6R*)—N⁶-(4-bromophenyl)-(4S*,7R*)-[4,7-ethenylene-spiro[2.4]heptane]-5,6-dicarboxamide;

(5R*)—N⁵-(5-Aminopentyl)-(6R*)—N⁶-(4-bromophenyl)-(4S*,7R*)-[4,7-ethenylene-spiro[2.4]heptane]-5,6-dicarboxamide;

(5R*)—N⁵-(2-(Cyclohexen-1-yl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-tert-Butyl-cyclohexyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(Pyridin-2-yl ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Acetyl-thiazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Trifluoromethyl-thiazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,4,6-Trifluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,4-Dimethyl phenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(2-Acetyl-thiazol-4-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Chloro-2-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Methyl-oxazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(5-Acetyl-thiazol-2-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Acetylphenyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,3,5-Trifluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(4-Methyl-1,2,5-oxadiazol-3-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Fluoro-3-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3,5-Dimethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Acetylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Difluoromethoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N$^5$-[(2-Methoxypyridin-4-yl)methyl]-(6R*)—N$^6$-(4-pyrrolidino-butyl)-(4S*,7R*)-[4,7-ethenylene-spiro[2.4]heptane]-5,6-dicarboxamide;

(5R*)—N$^5$-(3-Fluoro-5-trifluoromethylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(4-Acetylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Chloro-5-trifluoromethylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Fluoro-5-trifluoromethylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(4-Fluoro-3-trifluoromethylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-[(2,6-Dichloropyridin-4-yl)methyl]-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2,5-Dimethylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(4,5-Dimethyl-thiazol-2-yl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Methoxy-5-methylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Chloro-3,6-difluorophenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Isopropoxyphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-Chloro-6-fluoro-3-methylphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(3-Chloro-4-methoxyphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(3,4-Dimethoxyphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2,4-Dimethoxyphenyl-methyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(3,4-Dimethoxyphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(4-Methoxyphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(4-Bromophenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(3,4-Dimethylphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(4-Methylphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(4-Fluorophenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(Benzo[d][1,3]dioxol-5-yl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(3-Bromo-4-methoxyphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(2-(2,4-Dimethylphenyl)ethyl)-(6R*)—N$^6$-(4-pyrrolidino-butyl)-(4S*,7R*)-[4,7-ethenylene-spiro[2.4]heptane]-5,6-dicarboxamide;

(5R*)—N$^5$-(4-Ethoxyphenyl-methyl)-(6R*)—N$^6$-(4-pyrrolidino-butyl)-(4S*,7R*)-[4,7-ethenylene-spiro[2.4]heptane]-5,6-dicarboxamide;

(5R)—N$^5$-(2-(4-Chlorophenyl)ethyl)-(6R)—N$^6$-(4-pyrrolidino-butyl)-(4S,7R)-[4,7-ethenylene-spiro[2.4]heptane]-5,6-dicarboxamide;

(5R)—N$^5$-(2-(4-Chlorophenyl)ethyl)-(6R)—N$^6$-(2-dimethylamino-ethyl)-(4S,7R)-[4,7-ethenylene-spiro[2.4]heptane]-5,6-dicarboxamide;

(5R)—N$^5$-(2-(4-Chlorophenyl)ethyl)-(6R)—N$^6$-(2-(pyridin-2-yl)ethyl)-(4S,7R)-[4,7-ethenylene-spiro[2.4]heptane]-5,6-dicarboxamide;

(5R)—N$^5$-(2-(4-Chlorophenyl)ethyl)-(6R)—N$^6$-(2-(4-aminosulfonyl-phenyl)-ethyl)-(4S,7R)-[4,7-ethenylene-spiro[2.4]heptane]-5,6-dicarboxamide;

(5R)—N$^5$-(2-(2,4-Dichlorophenyl)ethyl)-(6R)—N$^6$-(4-pyrrolidino-butyl)-(4S,7R)-[4,7-ethenylene-spiro[2.4]heptane]-5,6-dicarboxamide;

(5R)—N$^5$-(2-(4-Chlorophenyl)ethyl)-(6R)—N$^6$—(N-isopentyl-piperidin-4-yl)-(4S,7R)-[4,7-ethenylene-spiro[2.4]heptane]-5,6-dicarboxamide;

(5R)—N$^5$-(4-Bromo-3,5-difluorophenyl)-(6R)—N$^6$-(4-pyrrolidino-butyl)-(4S,7R)-[4,7-ethenylene-spiro[2.4]heptane]-5,6-dicarboxamide;

(5R)—N$^5$-(4-Bromo-thiazol-2-yl)-(6R)—N$^6$-(4-pyrrolidino-butyl)-(4S,7R)-[4,7-ethenylene-spiro[2.4]heptane]-5,6-dicarboxamide;

(5R)—N$^5$-(4-Bromo-3-trifluoromethylphenyl)-(6R)—N$^6$-(4-pyrrolidino-butyl)-(4S,7R)-[4,7-ethenylene-spiro[2.4]heptane]-5,6-dicarboxamide;

(5R*)—N$^5$-[(4-Acetyl-thiazol-2-yl)methyl]-(6R*)—N$^6$-(2-methylamino-ethyl)-(4S*,7R*)-[4,7-ethenylene-spiro[2.4]heptane]-5,6-dicarboxamide;

(5R)—N$^5$-(4-Bromophenyl)-(6R)—N$^6$-(4-(2,5-dimethylpyrrolidin-1-yl)butyl)-(4S,7R)-[4,7-ethenylene-spiro[2.4]heptane]-5,6-dicarboxamide;

(5R)—N$^5$-(4-Bromophenyl)-(6R)—N$^6$-(4-(pyrrolidin-1-yl)pentyl)-(4S,7R)-[4,7-ethenylene-spiro[2.4]heptane]-5,6-dicarboxamide;

(5R)—N$^5$-(4-Bromophenyl)-(6R)—N$^6$-(3-fluoro-4-(pyrrolidin-1-yl)butyl)-(4S,7R)-[4,7-ethenylene-spiro[2.4]heptane]-5,6-dicarboxamide;

(5R)—N$^5$-(4-Bromophenyl)-(6R)—N$^6$-(4-(2-(methoxymethyl)pyrrolidin-1-yl)butyl)-(4S,7R)-[4,7-ethenylene-spiro[2.4]heptane]-5,6-dicarboxamide;

(5R)—N$^5$-(4-Bromophenyl)-(6R)—N$^6$-(4-(3,3-difluoropyrrolidin-1-yl)butyl)-(4S,7R)-[4,7-ethenylene-spiro[2.4]heptane]-5,6-dicarboxamide;

(5R)—N$^5$-(2-Bromo-3-fluoro-pyridin-5-yl)-(6R)—N$^6$-(4-pyrrolidino-butyl)-(4S,7R)-[4,7-ethylene-spiro[2.4]heptane]-5,6-dicarboxamide;

(5R)—N$^5$-(5-Bromothiazol-2-yl)-(6R)—N$^6$-(2-hydroxyethyl)-(4S,7R)-[4,7-ethylene-spiro[2.4]heptane]-5,6-dicarboxamide;

(5R)—N$^5$-(5-Bromothiazol-2-yl)-(6R)—N$^6$-(3-hydroxypropyl)-(4S,7R)-[4,7-ethylene-spiro[2.4]heptane]-5,6-dicarboxamide;

(5R)—N⁵-(5-Bromothiazol-2-yl)-(6R)—N⁶-(4-hydroxybutyl)-(4S,7R)-[4,7-ethylene-spiro[2.4]heptane]-5,6-dicarboxamide;
(5R)—N⁵-(5-Bromothiazol-2-yl)-(6R)—N⁶-(2-methyl-3-hydroxyprop-2-yl)-(4S,7R)-[4,7-ethylene-spiro[2.4]heptane]-5,6-dicarboxamide;
(5R)—N⁵-(5-Bromothiazol-2-yl)-(6R)—N⁶-(2-(2-hydroxyethoxy)ethyl)-(4S,7R)-[4,7-ethylene-spiro[2.4]heptane]-5,6-dicarboxamide;
(5R)—N⁵-(5-Bromothiazol-2-yl)-(6R)—N⁶-(4-hydroxy-cyclohexyl)-(4S,7R)-[4,7-ethylene-spiro[2.4]heptane]-5,6-dicarboxamide;
(5R)—N⁵-(5-Bromothiazol-2-yl)-(6R)—N⁶-[(1-hydroxy-cyclohexyl)methyl]-(4S,7R)-[4,7-ethylene-spiro[2.4]heptane]-5,6-dicarboxamide;
(5R)—N⁵-(5-Bromothiazol-2-yl)-(6R)—N⁶-(trans-4-(hydroxymethyl)-cyclohexyl)-(4S,7R)-[4,7-ethylene-spiro[2.4]heptane]-5,6-dicarboxamide;
(5R)—N⁵-(5-Bromothiazol-2-yl)-(6R)—N⁶-(cis-4-(hydroxymethyl)-cyclohexyl)-(4S,7R)-[4,7-ethylene-spiro[2.4]heptane]-5,6-dicarboxamide;
(5R)—N⁵-(5-Bromothiazol-2-yl)-(6R)—N⁶-(pyrrolidin-3-yl)-(4S,7R)-[4,7-ethylene-spiro[2.4]heptane]-5,6-dicarboxamide;
(5R)—N⁵-(5-Bromothiazol-2-yl)-(6R)—N⁶-(2-(N-methylamino)-ethyl)-(4S,7R)-[4,7-ethylene-spiro[2.4]heptane]-5,6-dicarboxamide;
(5R)—N⁵-(5-Bromothiazol-2-yl)-(6R)—N⁶-(3-(N-methylamino)-propyl)-(4S,7R)-[4,7-ethylene-spiro[2.4]heptane]-5,6-dicarboxamide;
(5R)—N⁵-(5-Bromothiazol-2-yl)-(6R)—N⁶-(piperidin-3-yl)-(4S,7R)-[4,7-ethylene-spiro[2.4]heptane]-5,6-dicarboxamide;
(5R)—N⁵-(5-Bromothiazol-2-yl)-(6R)—N⁶-[(pyrrolidin-2-yl)-methyl]-(4S,7R)-[4,7-ethylene-spiro[2.4]heptane]-5,6-dicarboxamide;
(5R)—N⁵-(5-Bromothiazol-2-yl)-(6R)—N⁶-[(piperidin-2-yl)-methyl]-(4S,7R)-[4,7-ethylene-spiro[2.4]heptane]-5,6-dicarboxamide;
(5R)—N⁵-(5-Bromothiazol-2-yl)-(6R)—N⁶-[(piperidin-3-yl)-methyl]-(4S,7R)-[4,7-ethylene-spiro[2.4]heptane]-5,6-dicarboxamide;
(5R)—N⁵-(5-Bromothiazol-2-yl)-(6R)—N⁶-(azetidin-3-yl)-(4S,7R)-[4,7-ethylene-spiro[2.4]heptane]-5,6-dicarboxamide;
(5R)—N⁵-(4-Bromophenyl)-(6R)—N⁶-(cis-4-(aminomethyl)-cyclohexyl)-(4S,7R)-[4,7-ethenylene-spiro[2.4]heptane]-5,6-dicarboxamide;
(5R)—N⁵-(4-Bromophenyl)-(6R)—N⁶-(trans-4-(aminomethyl)-cyclohexyl)-(4S,7R)-[4,7-ethenylene-spiro[2.4]heptane]-5,6-dicarboxamide; and
(5R*)—N⁵-(2-Trifluoromethyl-pyridin-5-yl)-(6R*)—N⁶-(4-pyrrolidin-1-yl-butyl)-(4S*,7R*)-[4,7-ethenylene-spiro[2.4]heptane]-5,6-dicarboxamide;

or salts (in particular pharmaceutically acceptable salts) of such compounds;

it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration. Especially, for a compound mentioned in the above list to have the relative (4S*,5R*,6R*,7R*)-configuration it is to be understood that also the respective enantiomer with the absolute (4R,5S,6S,7S)-configuration and/or the respective enantiomer with the absolute (4S,5R,6R,7R)-configuration is encompassed.

The present invention also includes isotopically labelled, especially ²H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially ²H (deuterium) labelled compounds of formula (I) and salts thereof are within the scope of the present invention. Substitution of hydrogen with the heavier isotope ²H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 51), or pharmaceutically acceptable salts thereof, are suitable for use as medicaments. In particular, compounds of formula (I) modulate the ALX receptor and/or FPRL2, i.e. they act as ALX receptor agonists and/or as FPRL2 agonists, and are useful for the prevention or treatment of diseases which respond to the activation of the ALX receptor and/or FPRL2 such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 51), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:
1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.
3) Further inflammatory diseases, obstructive airway diseases and allergic conditions include bronchiectasis, and pneumoconiosis of whatever type or genesis.
4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.
5) In a further embodiment the compounds of formula (I) according to any one of embodiments 1) to 51), or pharmaceutically acceptable salts thereof, are particularly suitable for the prevention or treatment of inflammatory diseases. Inflammatory diseases include one, several or all of the following groups of diseases and disorders:
   5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.
   5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.
   5c) Further inflammatory diseases also relate to diseases or conditions having an inflammatory component. Diseases or conditions having an inflammatory component include, but are not limited to, diseases and conditions affecting the eye such as uveits (anterior, intermediate and posterior), Behçet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).
   5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 51), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 51), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4v, GUN-7wt, AG204, AG206, AG208, HCM305, HCM308, HCM342, mSTD104, and HCM309.

Further, the compounds of formula (I) according to any one of embodiments 1) to 51), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 51), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 51), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 51), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 51), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 51), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 51), or pharmaceutically acceptable salts thereof, are suitable for the modulation of immune responses.

The modulation of immune responses includes, but is not limited to, methods based on the administration to a subject a composition of at least one antigen and at least one compound of formula (I) according to any one of embodiments 1) to 51), or pharmaceutically acceptable salts thereof. In some cases, the antigen-containing composition is administrated first, followed by administration of a composition of at least one compounds of formula (I) according to any one of embodiments 1) to 51), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 51), or pharmaceutically acceptable salts thereof, and the antigen, as compared to sole administration of the antigen;
2) A greater sensitivity to small amounts of antigen (e.g., toxin or pathogen) or antigens that do not habitually induce strong immune responses; and
3) More effective anti-tumor therapies.

Further, the compounds of formula (I) according to any one of embodiments 1) to 51), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 51), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection);

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;
3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);
4) HIV-mediated retroviral infections such as diseases and disorders caused by HIV-1 and HIV-2 strains such as GUN-4v, GUN-7wt, AG204, AG206, AG208, HCM305, HCM308, HCM342, mSTD104, and HCM309;
5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;
6) Neurological disorders such as stroke, cerebral ischemia, Alzheimer's disease, and Parkinson's disease;
7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);
8) Amyloid-mediated disorders;
9) Cystic fibrosis, wound healing and inflammatory diseases caused by pathogenic organisms.

The invention also relates to the use of a compound of formula (I) according to any one of embodiments 1) to 51) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 51).

A pharmaceutical composition according to the present invention contains at least one compound of formula (I) according to any one of embodiments 1) to 51) (or a pharmaceutically acceptable salt thereof) as the active agent and optionally carriers and/or diluents and/or adjuvants.

The compounds of formula (I) according to any one of embodiments 1) to 51) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 51), or a pharmaceutically acceptable salt thereof.

Any reference to a compound of formula I, $I_P$, $I_{ST1}$ or $I_{ST2}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_P$, to the compounds of formula $I_{ST1}$ and the compounds of formula $I_{ST2}$ as well as to the salts and pharmaceutically acceptable salts of the compounds of formula I, of formula $I_P$, of formula $I_{ST1}$ or of formula $I_{ST2}$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$, $R^6$, $R^7$, $R^8$, $R^9$, W, Y and Z are as defined for formula (I). Other abbreviations used are defined in the experimental section.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups $R^1$, $R^2$, $R^3$, $R^4$, $R^5$, $R^6$, $R^7$, $R^8$, $R^9$, W, Y and Z might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

A. Synthesis of Final Products

Sections A.a) to A.g) hereafter describe general methods for preparing compounds of formula (I).

A.a) The compounds of formula (I) wherein Z represents —C(O)NR³—* can be prepared from carboxylic acids of structure 1 by reaction with an appropriate amine $R^2R^3NH$ using standard amide coupling conditions such as EDC/HOBt/DMAP, or DCC/HOAt, or PyBOP, or HATU/

DMAP in the presence of a base such as DIPEA at a temperature about rt in a suitable solvent such as CH$_2$Cl$_2$. Alternatively, the compounds of formula (I) can be prepared by coupling carboxylic acids of structure 1 with an appropriate amine R$^2$R$^3$NH using POCl$_3$ in a suitable solvent such as DCE/pyridine (1:1). Alternatively, the compounds of formula (I) can be prepared by coupling carboxylic acids of structure 1 via formation of the acyl chloride (using standard conditions such as oxalyl chloride and a catalytic amount of DMF in a solvent such as toluene). Alternatively, the compounds of formula (I) can be prepared from esters of structure 2 wherein R$^{10}$ represents (C$_1$-C$_2$)alkyl with an appropriate amine R$^2$R$^3$NH using AlMe$_3$ in a suitable solvent such as CH$_2$Cl$_2$.

Structure 1

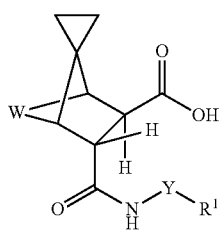

Structure 2

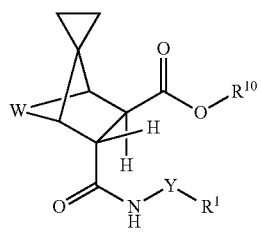

A.b) Alternatively, the compounds of formula (I) wherein Z represents —C(O)NR$^3$—* may be prepared from carboxylic acids of structure 3 with an appropriate amine R$^1$—Y—NH$_2$ using standard amide coupling conditions such as EDC/HOBt/DMAP or DCC/HOAt in the presence of a base such as DIPEA at a temperature about rt in a suitable solvent such as CH$_2$Cl$_2$. Alternatively, the compounds of formula (I) can be prepared by coupling carboxylic acids of structure 3 with an appropriate amine R$^1$—Y—NH$_2$ using POCl$_3$ in a suitable solvent such as DCE/pyridine (1:1).

Structure 3

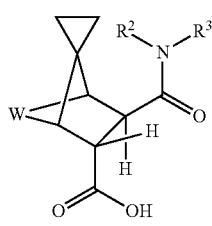

A.c) Alternatively, the compounds of formula (I) wherein Z represents —CH$_2$—NR$^4$C(O)—* can be prepared from amines of structure 4 with an appropriate carboxylic acid R$^2$COOH using standard amide coupling conditions such as EDC/HOBt/DMAP or DCC/HOAt in the presence of a base such as DIPEA at a temperature about rt in a suitable solvent such as CH$_2$Cl$_2$.

Structure 4

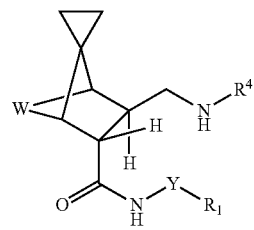

A.d) Alternatively, the compounds of formula (I) wherein R$^1$ represents or contains a (C$_1$-C$_2$)alkyl-carbonyl group may be prepared by deprotection of a ketal of structure 5, wherein A represents a bond (in case Y represents a (C$_1$-C$_4$)alkandiyl group) or an aryl- or a heteroaryl-group, using an acid such as diluted aqueous HCl in a solvent such as THF at a temperature about rt.

Structure 5

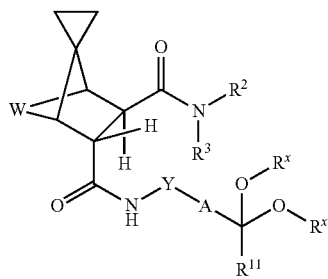

R$^{11}$ Represents (C$_1$-C$_2$)alkyl and R$^x$ Represents (C$_1$-C$_2$)alkyl or both R$^x$ Together form an ethane-1,2-diyl Bridge A.e) Alternatively, the compounds of formula (I) wherein R$^1$ represents or contains a (C$_1$-C$_2$)alkyl-carbonyl group may be prepared by deprotection of a silyl-protected alcohol of structure 6, wherein A represents a bond (in case Y represents a (C$_1$-C$_4$)alkandiyl group) or an aryl- or a heteroaryl-group, using for example TBAF in a suitable solvent such as THF, followed by oxidation using for example MnO$_2$ in a suitable solvent such as AcCN.

Structure 6

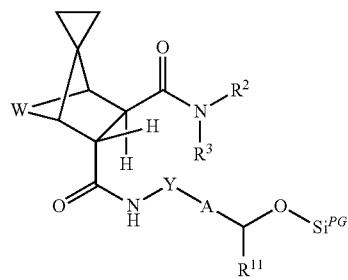

R$^{11}$ Represents (C$_1$-C$_2$)alkyl and Si$^{PG}$ Represents an Appropriate Silyl Protecting Group Such as TMS, TIPS, TBDMS or TBDPS (Preferably TBDMS)

A.f) Alternatively, the compounds of formula (I) wherein R$^2$ contains a primary or secondary amino group may be prepared by deprotection of the corresponding protected amine such as N-tert-butoxycarbonyl protected amine using an acid such as HCl in a solvent mixture such as dioxane and $CH_2Cl_2$ at a temperature about rt.

A.g) Alternatively, the compounds of formula (I) wherein $R^2$ contains an amide group (—$C(O)NR^7R^8$) may be prepared by saponification of the corresponding ester followed by activation of the resulting carboxylic acid via a mixed anhydride for example using ethyl chloroformate and a base such as $Et_3N$ in a suitable solvent such as THF at a temperature ranging from 0° C. to rt, and subsequent reaction with an appropriate amine $R^7R^8NH$.

B. Synthesis of Intermediates

B1. Synthesis of Spiro Compounds

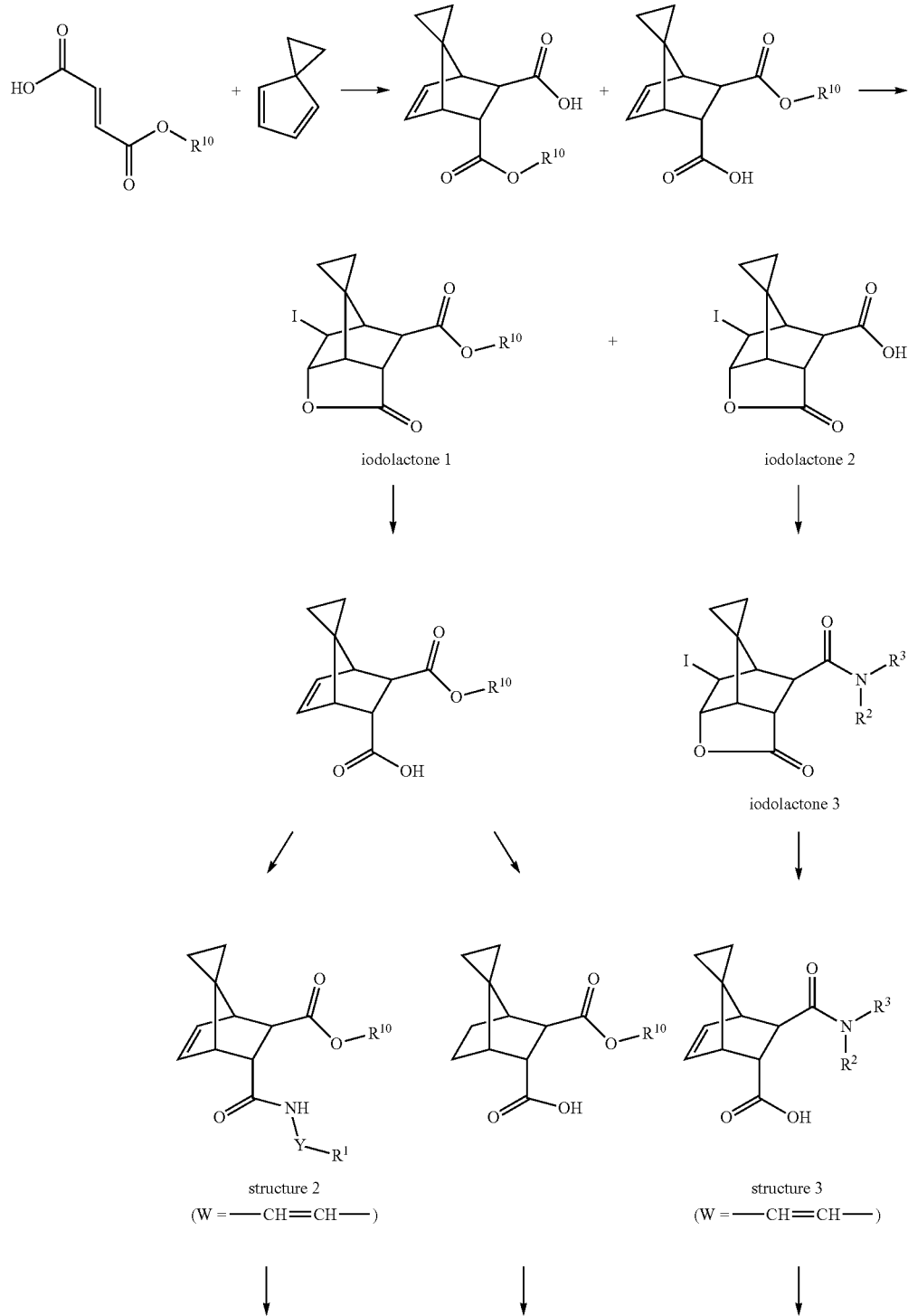

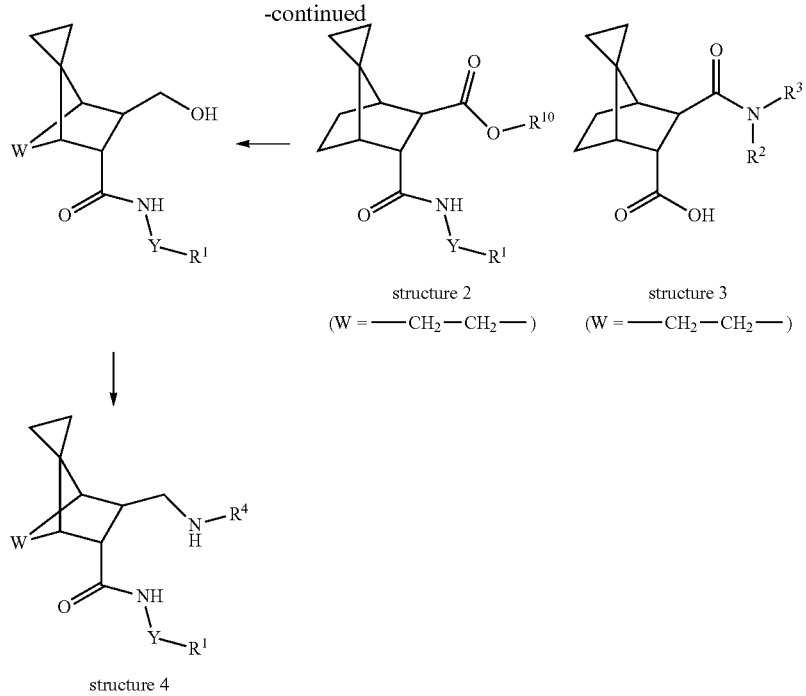

structure 4

R[10] represents (C$_1$-C$_2$)alkyl

Compounds of structure 1 can be obtained by saponification of the ester moiety of compounds of structure 2 using a base such as LiOH or NaOH in a solvent such as a mixture of water and an organic solvent such as THF or EtOH.

Compounds of structure 2 wherein W represents —CH=CH— can be prepared by the following sequence (see scheme 1): a) Diels-Alder reaction between spiro[2.4]hepta-4,6-diene (prepared according to J. W. Coe et al. *Org. Letters* 2004, 6, 1589) and commercially available (E)-but-2-enedioic acid monoethyl ester in a suitable solvent such as MeOH to obtain a mixture of endo and exo products; b) iodolactonization using KI and I$_2$ in the presence of a base such as NaHCO$_3$ in a solvent such as CH$_2$Cl$_2$ at a temperature about rt to enable separation of the isomers (iodolactone 1 (ester) and iodolactone 2 (carboxylic acid)); c) retro-iodolactonization of the resulting iodolactone 1 using an excess of zinc in a solvent such as AcOH at a temperature about 65° C.; and d) amide coupling of the resulting carboxylic acid with an appropriate amine R[1]—Y—NH$_2$ via formation of the acyl chloride (using standard conditions such as oxalyl chloride and a catalytic amount of DMF in a solvent such as toluene or CH$_2$Cl$_2$) in the presence of a base such as DIPEA, Et$_3$N or pyridine and in a suitable solvent such as CH$_2$Cl$_2$, THF or acetone or via activation of the carboxylic acid using standard amide coupling conditions such as EDC/HOBt/DMAP in the presence of a base such as DIPEA in a suitable solvent such as CH$_2$Cl$_2$. It is to be understood that, in case the substituent R[1] represents or contains a (C$_1$-C$_2$)alkylcarbonyl group, the respective keto-function may be protected in the amines used in step d) as a ketal or as a silylated alcohol; the obtained intermediates may then be transferred to compounds of structure 5 or 6 respectively (see below).

Compounds of structure 2 wherein W represents —CH$_2$—CH$_2$— can be prepared by the following sequence (see scheme 1): a) Diels-Alder reaction between spiro[2.4]hepta-4,6-diene and commercially available (E)-but-2-enedioic acid monoethyl ester in a suitable solvent such as MeOH to obtain a mixture of endo and exo products; b) iodolactonization using KI and I$_2$ in the presence of a base such as NaHCO$_3$ in a solvent such as CH$_2$Cl$_2$ at a temperature about rt to enable separation of the isomers (iodolactone 1 (ester) and iodolactone 2 (carboxylic acid)); c) retro-iodolactonization of the resulting iodolactone 1 using an excess of zinc in a solvent such as AcOH at a temperature about 65° C.; d) reduction of the double bond using cyclohexene in the presence of Pd/C in a suitable solvent such as THF; and e) amide coupling of the resulting carboxylic acid with an appropriate amine R[1]—Y—NH$_2$ via formation of the acyl chloride (using standard conditions such as oxalyl chloride and a catalytic amount of DMF in a solvent such as toluene or CH$_2$Cl$_2$) in the presence of a base such as DIPEA, Et$_3$N or pyridine and in a suitable solvent such as CH$_2$Cl$_2$, THF or acetone or via activation of the carboxylic acid using standard amide coupling conditions such as EDC/HOBt/DMAP in the presence of a base such as DIPEA in a suitable solvent such as CH$_2$Cl$_2$. In case the substituent R[1] represents or contains a (C$_1$-C$_2$)alkylcarbonyl group, the respective keto-function may be protected as described above (compounds of structure 2 wherein W represents —CH=CH—).

Compounds of structure 3 wherein W represents —CH=CH— can be prepared by the following sequence (see scheme 1): a) amide coupling of iodolactone 2 with an appropriate amine R[2]R[3]NH, wherein R[2], if containing a primary or secondary amine function, might require protection for example as a N-tert-butoxycarbonyl protected amine, via formation of the acyl chloride (using standard conditions such as oxalyl chloride and a catalytic amount of DMF in a solvent such as toluene) in the presence of a base such as DIPEA and in a suitable solvent such as CH$_2$Cl$_2$ or via activation of the carboxylic acid using standard amide coupling conditions such as EDC/HOBt/DMAP in the presence of a base such as DIPEA in a suitable solvent such as CH$_2$Cl$_2$; and b) retro-iodolactonization of the resulting iodolactone 3 using an excess of zinc in a solvent such as AcOH at a temperature about 65° C.

Compounds of structure 3 wherein W represents —CH$_2$—CH$_2$— can be prepared by reduction of the double bond of compounds of structure 3 wherein W represents —CH=CH— using for example hydrogen in the presence of Pd/C in a suitable solvent such as EtOH or cyclohexene in the presence of Pd/C in a suitable solvent such as THF (see scheme 1).

Compounds of structure 4 can be prepared by reduction of the ester of compounds of structure 2 using a reducing agent such as LiBH$_4$ in a suitable solvent such as THF at a temperature about 65° C. followed by formation of the corresponding sulfonate (e.g. triflate) by reaction of the alcohol with a sulfonyl chloride or anhydride derivative (e.g. trifluoromethane sulfonic anhydride) in a suitable solvent such as CH$_2$Cl$_2$ in the presence of a base such as DIPEA at a temperature ranging from −78° C. to 0° C. and subsequent reaction with R$^4$NH$_2$ in a suitable solvent such as CH$_2$Cl$_2$ at a temperature ranging from −78° C. to rt. Alternatively the intermediate sulfonate can be converted into the corresponding azide using sodium azide in a suitable solvent such as DMF at a temperature about 80° C. and subsequent reduction of the azide to the amine using Ph$_3$P in a suitable solvent such as THF/H$_2$O.

Compounds of structures 5 and 6 can be prepared from carboxylic esters of structure 2 wherein R$^1$ represents or contains a masked (C$_1$-C$_2$)alkyl-carbonyl group (for example a silylated alcohol or an acetal protected ketone) by saponification of the ester moiety using a base such as LiOH or NaOH in a solvent such as a mixture of water and an organic solvent such as THF or EtOH, followed by reaction of the obtained carboxylic acid with an appropriate amine R$^2$R$^3$NH using standard amide coupling conditions such as EDC /HOBt/ DMAP or DCC/HOAt in the presence of a base such as DIPEA at a temperature about rt in a suitable solvent such as CH$_2$Cl$_2$. Alternatively, compounds of structures 5 and 6 can be prepared from esters of structure 2 wherein R$^1$ represents or contains a masked (C$_1$-C$_2$)alkyl-carbonyl group with an appropriate amine R$^2$R$^3$NH using AlMe$_3$ in a suitable solvent such as CH$_2$Cl$_2$. Compounds of structure 2 wherein R$^1$ represents or contains a masked (C$_1$-C$_2$)alkyl-carbonyl group can be prepared according to scheme 1 using an appropriate amine R$^1$—Y—NH$_2$, wherein R$^1$ represents or contains a masked (C$_1$-C$_2$)alkyl-carbonyl group (see above).

Alternatively, compounds of structures 5 and 6 can be prepared from compounds of structure 3 by reaction with an appropriate amine R$^1$—Y—NH$_2$ wherein R$^1$ represents or contains a masked (C$_1$-C$_2$)alkyl-carbonyl group as defined above using standard amide coupling conditions such as EDC/HOBt/DMAP or DCC/HOAt in the presence of a base such as DIPEA at a temperature about rt in a suitable solvent such as CH$_2$Cl$_2$.

Scheme 2

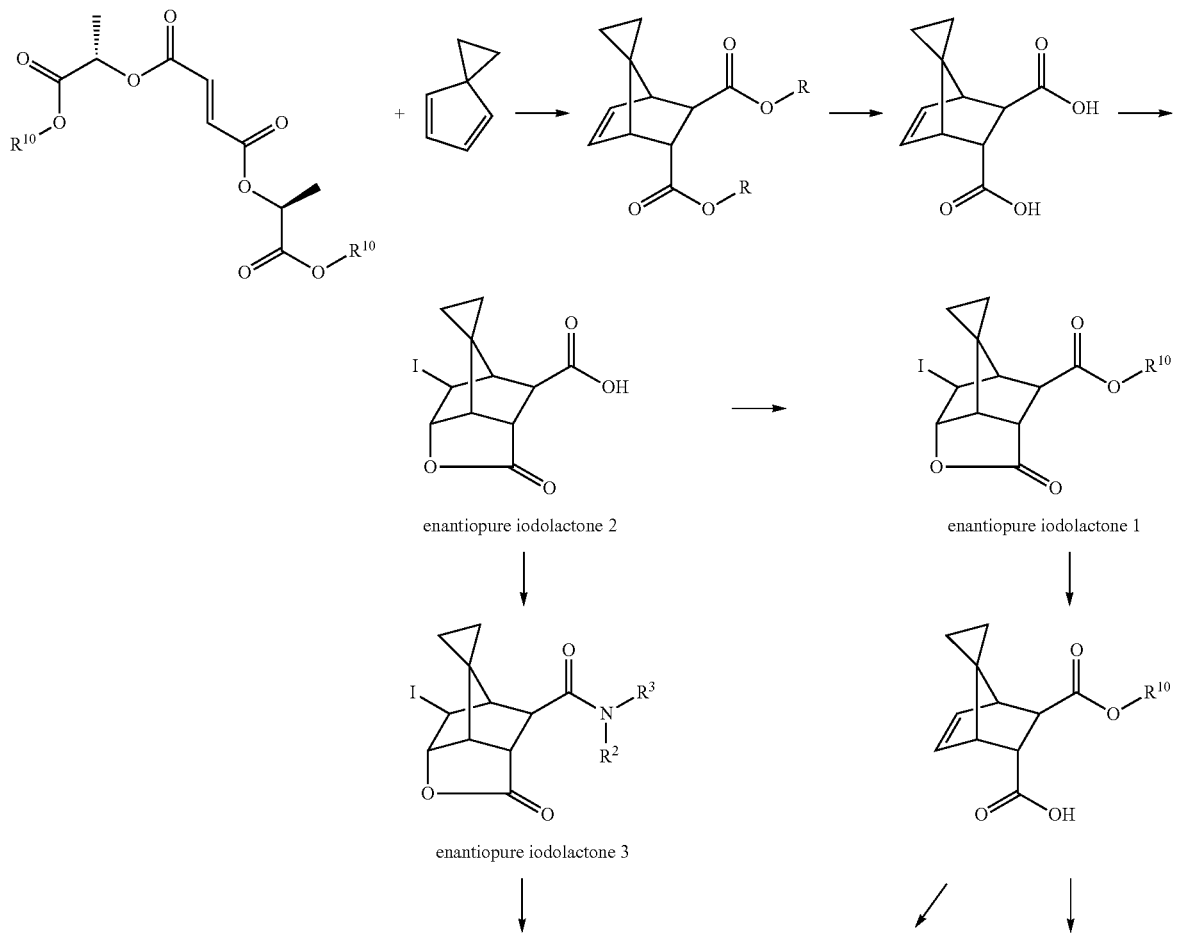

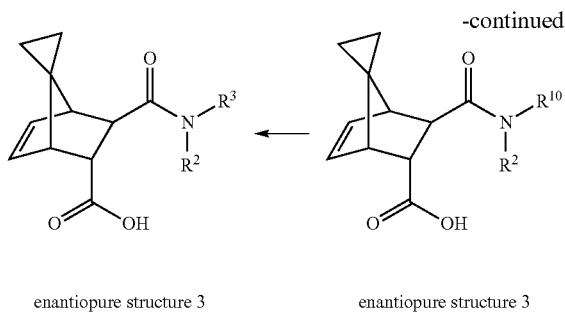

enantiopure structure 3
(W = —CH₂—CH₂—)

enantiopure structure 3
(W = —CH=CH—)

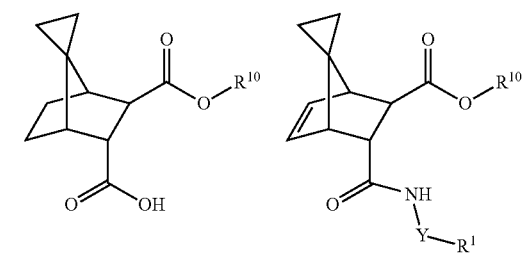

enantiopure structure 2
(W = —CH=CH—)

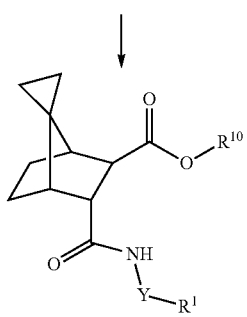

enantiopure structure 2
(W = —CH₂—CH₂—)

$R^{10}$ represents ($C_1$-$C_2$)alkyl and R represnets (S)—CH(Me)COO$R^{10}$

Enantiopure compounds of structure 1 can be obtained by saponification of the ester moiety of enantiopure compounds of structure 2 using a base such as LiOH or NaOH in a solvent such as a mixture of water and an organic solvent such as THF or EtOH.

Enantiopure compounds of structure 2 wherein W represents —CH=CH— can be prepared by the following sequence (see scheme 2): a) Diels-Alder reaction between spiro[2.4]hepta-4,6-diene and commercially available (E)-1,2-bis-[((1S)-1-ethoxycarbonyl-ethoxy)-carbonyl]-ethene in a suitable solvent such as hexane; the assignment of the stereogenic centers of the obtained intermediates was made based on a literature reference (G. Helmchen et al., *Angew. Chem. Int. Ed.* 1987, 26, 1143), describing the Diels-Alder reaction between cyclopentadiene and (E)-1,2-bis-[((1S)-1-ethoxycarbonyl-ethoxy)-carbonyl]-ethene; b) saponification of the ester moieties using a base such as LiOH in a suitable solvent such as a mixture of THF and water; c) iodolactonization using KI and $I_2$ in the presence of a base such as $NaHCO_3$ in a solvent such as $CH_2Cl_2$ at a temperature about rt to give enantiopure iodolactone 2; d) esterification of the resulting carboxylic acid using standard conditions such as $TMSCH_2N_2$ in a suitable solvent such as MeOH or via formation of the acyl chloride (using standard conditions such as oxalyl chloride and a catalytic amount of DMF in a solvent such as toluene or $CH_2Cl_2$) and subsequent reaction with MeOH; e) retro-iodolactonization of the resulting iodolactone ester using an excess of zinc in a solvent such as AcOH at a temperature about 65° C.; and f) amide coupling of the resulting carboxylic acid with an appropriate amine $R^1$—Y—$NH_2$ via formation of the acyl chloride (using standard conditions such as oxalyl chloride and a catalytic amount of DMF in a solvent such as toluene or $CH_2Cl_2$) in the presence of a base such as DIPEA, $Et_3N$ or pyridine and in a suitable solvent such as $CH_2Cl_2$, THF or acetone or via activation of the carboxylic acid using standard amide coupling conditions such as EDC/HOBt/DMAP in the presence of a base such as DIPEA in a suitable solvent such as $CH_2Cl_2$. It is to be understood that, in case the substituent $R^1$ represents or contains a ($C_1$-$C_2$)alkylcarbonyl group, the respective keto-function may be protected in the amines used in step f) as a ketal or as a silylated alcohol.

Enantiopure compounds of structure 2 wherein W represents —$CH_2$—$CH_2$— can be prepared by the following sequence (see scheme 2): a) esterification of enantiopure iodolactone 2 using standard conditions such as $TMSCH_2N_2$ in a suitable solvent such as MeOH or via formation of the acyl chloride (using standard conditions such as oxalyl chloride and a catalytic amount of DMF in a solvent such as toluene or $CH_2Cl_2$) and subsequent reaction with MeOH to give enantiopure iodolactone 1; b) retro-iodolactonization of the resulting iodolactone ester using an excess of zinc in a solvent such as AcOH at a temperature about 65° C.; c) reduction of the double bond using cyclohexene in the presence of Pd/C in a suitable solvent such as THF; and d) amide coupling of the resulting carboxylic acid with an appropriate amine $R^1$—Y—$NH_2$ via formation of the acyl chloride (using standard conditions such as oxalyl chloride and a catalytic amount of DMF in a solvent such as toluene or $CH_2Cl_2$) in the presence of a base such as DIPEA, $Et_3N$ or pyridine and in a suitable solvent such as $CH_2Cl_2$, THF or acetone or via activation of the carboxylic acid using standard amide coupling conditions such as EDC/HOBt/DMAP in the presence of a base such as DIPEA in a suitable solvent such as $CH_2Cl_2$. It is to be understood that, in case the substituent $R^1$ represents or contains a ($C_1$-$C_2$)alkylcarbonyl group, the respective keto-function may be protected in the amines used in step d) as a ketal or as a silylated alcohol.

Enantiopure compounds of structure 3 wherein W represents —CH=CH— can be prepared by the following sequence (see scheme 2): a) amide coupling of enantiopure iodolactone 2 with an appropriate amine $R^2R^3NH$, wherein $R^2$, if containing a primary or secondary amine function, might require protection for example as a N-tert-butoxycarbonyl protected amine, via formation of the acyl chloride (using standard conditions such as oxalyl chloride and a catalytic amount of DMF in a solvent such as toluene) in the presence of a base such as DIPEA and in a suitable solvent such as $CH_2Cl_2$ or via activation of the carboxylic acid using standard amide coupling conditions such as EDC/HOBt/DMAP in the presence of a base such as DIPEA in a suitable solvent such as $CH_2Cl_2$; and b) retro-iodolactonization of the resulting enantiopure iodolactone 3 using an excess of zinc in a solvent such as AcOH at a temperature about 65° C.

Enantiopure compounds of structure 3 wherein W represents —$CH_2$—$CH_2$— can be prepared by reduction of the double bond of enantiopure compounds of structure 3 wherein W represents —CH═CH— with, for instance, hydrogen in the presence of Pd/C in a suitable solvent such as EtOH or cyclohexene in the presence of Pd/C in a suitable solvent such as THF (see scheme 2).

Enantiopure compounds of structure 4 wherein W represents —CH═CH— or —$CH_2$—$CH_2$— can be prepared from enantiopure compounds of structure 2 by analogy to the synthesis described in scheme 1.

Enantiopure compounds of structures 5 and 6 wherein W represents —CH═CH— or —$CH_2$—$CH_2$— can be prepared by analogy to scheme 1.

In a general way, enantiopure compounds of structure 1 can be obtained either in analogy to the synthesis of racemic compounds of structure 1 starting from enantiopure iodolactone 1 or 2 or by chiral HPLC purification of a mixture of enantiomers.

B2. Synthesis of Amines $R^1$—Y—$NH_2$

Amines of formula $R^1$—Y—$NH_2$, if not commercially available, may be prepared for instance by the following sequence: a) conversion of alcohol $R^1$—Y—OH into the corresponding mesylate or chloride using for example MsCl in the presence of a base such as $Et_3N$ and DMAP in a suitable solvent such as $CH_2Cl_2$; b) conversion of the mesylate or chloride into the corresponding azide using for example $NaN_3$ in a solvent such as DMF at a temperature about 80° C.; c) reduction of the azide moiety either using $Ph_3P$ and water in a solvent such as THF at a temperature about 60° C., or by hydrogenation using a metal catalyt such as Pd/C in a suitable solvent such as MeOH. The paragraphs below describe the synthesis of some of these amines.

1-(5-Aminomethyl-furan-2-yl)-ethanone may be prepared using the following sequence: a) protection of commercially available 5-hydroxymethyl-2-furaldehyde using 3,4-dihydro-2H-pyran in the presence of pyridinium toluene-4-sulfonate in a solvent such as $CH_2Cl_2$; b) methylation of the aldehyde using for example methylmagnesium chloride in a solvent such as THF at a temperature about 0° C.; c) oxidation of the resulting secondary alcohol using an oxidizing agent such as $MnO_2$ in a solvent such as $CH_2Cl_2$ at a temperature about 45° C.; d) removal of the protecting group using an acid such as Amberlyst 15 in a suitable solvent such as MeOH at a temperature about 35° C.; e) chlorination of the alcohol using for example Ms-Cl in the presence of a base such as $Et_3N$ and DMAP in a solvent such as $CH_2Cl_2$ at a temperature ranging from 0° C. to rt; f) formation of the corresponding azide using $NaN_3$ in a solvent such as DMF at a temperature about 80° C.; and g) reduction of the azide moiety using $Ph_3P$ and water in a solvent such as THF at a temperature about 60° C.

3-(2-Methyl-[1,3]dioxolan-2-yl)-propylamine may be prepared using the following sequence: a) condensation of commercially available methyl vinyl ketone and nitromethane in the presence of a catalyst such as activated $KF/Al_2O_3$; b) protection of the resulting ketone with ethylene glycol and a catalyst such as p-TsOH in a solvent such as toluene at a temperature about 120° C.; and c) reduction of the nitro group using a metal catalyst such as Pd/C in a solvent such as MeOH under an $H_2$ atmosphere.

4-(2-Methyl-[1,3]dioxolan-2-yl)butylamine may be prepared using the following sequence: a) condensation of commercially available ethyl acetoacetate and acrylonitrile in the presence of a base such as sodium ethylate; b) decarboxylation using a base such as $Na_2CO_3$ in a solvent such as water at a temperature about 100° C.; c) protection of the resulting ketone with ethylene glycol and a catalyst such as p-TsOH in a solvent such as toluene at a temperature about 120° C.; and d) reduction of the nitrile using a reducing agent such as $LiAlH_4$ in a solvent such as $Et_2O$ at a temperature about 35° C.

[4-(2-Methyl-[1,3]dioxolan-2-yl)-thiazol-2-yl]-methylamine may be prepared using the following sequence: a) reaction of commercially available 2,4-dibromo-thiazole with an organolithium reagent such as n-butyl lithium in a solvent such as ether at a temperature about −78° C. and subsequent formylation with N,N-dimethylformamide at a temperature ranging from −78° C. to rt; b) reduction with a reducing agent such as $NaBH_4$ in a solvent such as MeOH at a temperature about rt; c) protection of the alcohol with a protecting group such as tert-butyldimethylsilyl chloride in the presence of a base such as imidazole in a solvent such as dichloromethane; d) reaction of the protected alcohol with an organolithium reagent such as n-butyl lithium in a solvent such as ether at a temperature about −78° C. and subsequent acetylation with N,N-dimethylacetamide at a temperature ranging from −78° C. to rt; e) ketal formation in the presence of trimethylorthoformate and a catalyst such as $LiBF_4$ in a solvent such as ethylene glycol at a temperature about 95° C.; f) deprotection of the silyl protecting group under standard conditions such as TBAF in a solvent such as THF at a temperature about rt or 0° C.; g) mesylation using a reagent such as methanesulfonyl chloride in a solvent such as $CH_2Cl_2$ in the presence of a base such as $Et_3N$ and DMAP at a temperature about 0° C.; h) formation of the corresponding azide using $NaN_3$ in a solvent such as DMF at a temperature about 80° C.; and i) reduction of the azide moiety using $Ph_3P$ and water in a solvent such as THF at a temperature about 60° C.

[5-(2-Methyl-[1,3]dioxolan-2-yl)thiophen-2-yl]-methylamine may be prepared using the following sequence: a) lithiation of commercially available 2-methyl-2-thiophen-2-yl-[1,3]dioxolane with an organolithium reagent such as n-butyl lithium in the presence of N,N,N',N'-tetramethyl-ethylenediamine in a solvent such as THF at a temperature about -78° C. and subsequent addition of DMF; b) reduction with a reducing agent such as $NaBH_4$ in a solvent such as MeOH at a temperature about 0° C.; c) chlorination of the alcohol using for example Ms-Cl in presence of a base such as $Et_3N$ and DMAP in a solvent such as $CH_2Cl_2$ at a temperature about 0° C.; d) formation of the corresponding azide using $NaN_3$ in a solvent such as DMF at a temperature about 80° C.; and e) reduction of the azide moiety using $Ph_3P$ and water in a solvent such as THF at a temperature about 60° C.

2-[1-(tert-Butyl-dimethyl-silanyloxy)-ethyl]-oxazol-5-yl-methylamine may be prepared using the following sequence: a) reaction of commercially available 1,3-oxazole with an organomagnesium reagent such as iso-propylmagnesium chloride in a solvent such as THF at a temperature about −10° C. and subsequent acetylation with N-methoxy-N-methyl-acetamide at a temperature ranging from −10° C. to rt; b) reduction of the ketone with a reducing agent such as $NaBH_4$ in a solvent such as MeOH at a temperature ranging from 0° C. to rt; c) protection of the alcohol with a protecting group such as tert-butyldimethylsilyl chloride in the presence of a base such as imidazole in a solvent such as THF; d) reaction of the protected alcohol with an organolithium reagent such as tert-butyllithium in a solvent such as THF at a temperature ranging from −78° C. to −40° C. and subsequent formylation with N,N-dimethylformamide at a temperature ranging from −78° C. to rt; e) reduction of the aldehyde with a reducing agent such as $NaBH_4$ in a solvent such as MeOH at a temperature ranging from 0° C. to rt; f) chlorination using a reagent such as methanesulfonyl chloride in a solvent such as $CH_2Cl_2$ in the presence of a base such as $Et_3N$ and DMAP at a temperature about 0° C.; g) formation of the corresponding azide using $NaN_3$ in a solvent such as DMF at a temperature about 80° C.; and h) reduction of the azide moiety using $Ph_3P$ and water in a solvent such as THF at a temperature about 60° C.

4-Bromo-2,3-difluorobenzylamine can be prepared using the following sequence: a) reaction of commercially available 1,2-difluorobenzene and trimethylsilyl chloride in the presence of a base such as lithium diisopropylamide in a suitable solvent such as THF at a temperature about −78° C.; b) conversion of the resulting (2,3-difluoro-1,4-phenylene)-bis(trimethylsilane) to the corresponding 1,4-dibromo-2,3-difluorobenzene using a source of bromine such as bromine at a temperature ranging from 0° C. to 58° C.; c) reaction with an organolithium reagent such as n-butyllithium in a solvent such as THF at a temperature ranging about −78° C. and subsequent carboxylation with solid carbon dioxide for example at a temperature ranging from −78° C. to rt; d) reduction of the resulting carboxylic acid to the corresponding benzyl alcohol using a suitable reducing agent such as borane in a suitable solvent such as THF at a temperature ranging from 0° C. to 50° C.; e) mesylation using a reagent such as methanesulfonyl chloride in a solvent such as $CH_2Cl_2$ in the presence of a base such as $Et_3N$ and DMAP at a temperature about 0° C.; f) formation of the corresponding azide using $NaN_3$ in a solvent such as DMF at a temperature about 80° C.; and g) reduction of the azide moiety using $Ph_3P$ and water in a solvent such as THF at a temperature about 60° C.

B3. Synthesis of Amines $R^2$—$NH_2$

Amines of formula $R^2$—$NH_2$, if not commercially available, may be prepared for instance by the following sequence: a) conversion of alcohol $R^2$—OH into the corresponding mesylate or chloride using for example MsCl in the presence of a base such as $Et_3N$ and DMAP in a suitable solvent such as $CH_2Cl_2$ or conversion of alcohol $R^2$—OH into the corresponding iodide using for example iodine and $Ph_3P$ in the presence of a base such as imidazole in a suitable solvent such as $CH_2Cl_2$; b) conversion of the mesylate, chloride or iodide into the corresponding azide using for example $NaN_3$ in a solvent such as DMF at a temperature about 80° C.; c) reduction of the azide moiety either using $Ph_3P$ and water in a solvent such as THF at a temperature about 60° C., or by hydrogenation using a metal catalyst such as Pd/C in a suitable solvent such as MeOH.

Alternatively, if not commercially available, amines of formula $R^2$—$NH_2$, which are also amines of formula $R^{2a}CH_2$—$NH_2$, may be prepared by reduction of nitriles $R^{2a}$—CN either using a reducing agent such as $LiAlH_4$ in a suitable solvent such as THF at a temperature ranging from 0° C. to rt, or by hydrogenation using a metal catalyt such as Pd/C in a suitable solvent such as MeOH.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5-10 μm) column. Typical conditions of chiral HPLC are an isocratic mixture of eluent A (EtOH, in presence or absence of an amine such as $Et_3N$ or diethylamine) and eluent B (hexane), at a flow rate of 0.8 to 150 mL/min.

For instance, enantiopure compounds of structure 2 may be obtained by chiral HPLC separation of a mixture of enantiomers; for example, (5R)—$N^5$-(4-bromo-phenyl)-(6R)-6-ethoxycarbonyl-(4S,7R)-[4,7-ethenylene-spiro[2.4]heptane]-5-carboxamide may be obtained by chiral HPLC separation of (5R*)—$N^5$-(4-bromo-phenyl)-(6R*)-6-ethoxycarbonyl-(4S*,7R*)-[4,7-ethenylene-spiro[2.4]heptane]-5-carboxamide. Preferably such separations are performed using a Deicel ChiralPak AD-H column with a mixture of EtOH and hexane (15/85) as eluent.

EXPERIMENTAL PART

Abbreviations (as used herein and in the description above)

| | |
|---|---|
| Ac | acetyl |
| AcCN | acetonitrile |
| AcOH | acetic acid |
| $AlMe_3$ | trimethyl aluminium |
| aq. | aqueous |
| atm | atmosphere |
| Boc | tert-butoxycarbonyl |
| bp | boiling point |
| (n-)Bu | butyl |
| BuLi | n-butyllithium |
| ca. | About |
| Cbz | benzyloxycarbonyl |
| COAD | chronic obstructive airway disease |
| COLD | chronic obstructive lung disease |
| COPD | chronic obstructive pulmonary disease |
| DAD | diode array detector |
| DC | dendritic cells |
| DCC | N,N'-dicyclohexylcarbodiimide |
| PL-DCC | polymer supported N,N'-dicyclohexylcarbodiimide |
| DCE | 1,2-dichloroethane |
| DIPEA | diisopropylethylamine |
| DMAP | 4-N,N-dimethylaminopyridine |
| DMEM | dulbecco's modified eagle's medium |
| DMF | dimethylformamide |
| DMSO | dimethylsulfoxide |
| EA | ethyl acetate |
| $EC_{50}$ | half maximal effective concentration |
| EDC | N-(3-dimethylaminopropyl)-N'-ethyl-carbodiimide |
| ELSD | evaporative light-scattering detection |
| eq. | equivalent(s) |
| ES+ | electro-spray, positive ionization |
| Et | ethyl |
| Ether or $Et_2O$ | diethylether |
| $Et_3N$ | triethylamine |
| EtOH | ethanol |
| FA | formic acid |
| FAD | familial autosomic dominant |
| FC | flash column chromatography on silica gel |
| FLIPR | fluorescence imaging plate reader |
| FPRL1 | formyl-peptide receptor like-1 |
| FPRL2 | formyl-peptide receptor like-2 |
| h | hour(s) |
| HATU | 2-(7-aza-1H-benzotriazol-1-yl)-1,1,3,3-tetramethyluronium hexafluorophosphate |
| HBSS | hanks' balanced salt solution |
| HEPES | 4-(2-hydroxyethyl)-1-piperazineethanesulfonic acid |
| hept | heptane |
| HIV | human immunodeficiency virus |
| HOBt | hydroxybenzotriazole |
| HOAt | 7-aza-1-hydroxybenzotriazole |
| HPLC | high performance liquid chromatography |
| LC-MS | liquid chromatography - mass spectrometry |

| | |
|---|---|
| lem | emission wavelength |
| lex | excitation wavelength |
| LPS | lipopolysaccharide |
| Me | methyl |
| MeOH | methanol |
| min | minute(s) |
| mM | millimolar |
| µM | micromolar |
| mRNA | messenger ribonucleic acid |
| MPLC | medium pressure liquid chromatography |
| MS | mass spectrometry |
| Ms | methanesulfonyl |
| nm | nanometer |
| nM | nanomolar |
| NMR | nuclear magnetic resonance |
| OAc | acetate |
| org. | organic |
| p | para |
| p-TsOH | para-toluene sulfonic acid |
| PG | protecting group |
| PyBOP | benzotriazol-1-yl-oxy-tris-pyrrolidino-phosphonium-hexafluoro-phosphate |
| rf | retention factor |
| rpm | rotation per minute |
| rt | room temperature |
| sat. | saturated |
| SCX | strong cation exchanger |
| TBA | tetra-n-butylammonium |
| TBAF | tetra-n-butylammonium fluoride |
| TBME | tert-butyl methyl ester |
| TBDMS | tert-butyl-dimethyl-silyl |
| TBDPS | tert-butyl-diphenyl-silyl |
| t-Bu | tert-butyl |
| TFA | trifluoroacetic acid |
| THF | tetrahydrofuran |
| TIPS | tri-isopropyl-silyl |
| TLC | thin layer chromatography |
| TMS | trimethyl-silyl |
| $t_R$ | retention time |
| UV | ultra violet |
| Vis | visible |

I Chemistry

General. All temperatures are stated in degrees Celsius (° C.). Unless otherwise indicated, the reactions take place at rt.

As SCX material SiliaBond® SCX from Silicycle was used.

As polymer supported DCC, PL-DCC from Polymer Laboratories was used.

As polymer supported $SO_2Cl$, PL-$SO_2Cl$ from Polymer Laboratories was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EA, $Et_2O$, hept, hexane, $CH_2Cl_2$, $CHCl_3$, MeOH, $NH_4OH$ or mixtures thereof.

MPLC were performed using Isolute® SPE Flash SI II columns from international sorbent technology, elution with EA, $Et_2O$, hept, hexane, $CH_2Cl_2$, $CHCl_3$, MeOH, $NH_4OH$ or mixtures thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 µm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 01b (if not indicated otherwise): Analytical: Thermo Finnigan MSQ Surveyor MS with Agilent 1100 Binary Pump and DAD. Column: Xbridge C18 5 µM, 4.6×50 mm ID from Waters. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions $O_2$ (if not indicated otherwise): Analytical: Thermo Finnigan MSQ Plus MS with Agilent 1100 Binary Pump and DAD. Column: Zorbax SB-AQ 5 µm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 05 (if not indicated otherwise): Analytical: Dionex GHP 3200 Binary Pump, MS: Thermo MSQ Plus, DAD: Dionex PDA 3000, ELSD: Sedere Sedex 85, column: Xbridge C18 5 µM, 4.6×50 mm ID from Waters, thermostated in the Dionex TCC-3200 compartment. Eluents: A: $H_2O$+0.04% TFA; B: AcCN. Method: Gradient: 5% B→95% B over 1 min. Flow: 4.5 mL/min. Detection: UV/Vis and/or ELSD, and MS, $t_R$ is given in min.

LC-MS-conditions 05b (if not indicated otherwise): Analytical: Dionex GHP 3200 Binary Pump, MS: Thermo MSQ Plus, DAD: Dionex PDA 3000, ELSD: Sedere Sedex 85. Column: Zorbax Extend C18 1.8 µM, 4.6×20 mm from Agilent Technologies, thermostated in the Dionex TCC-3200 compartment. Eluents: A: $H_2O$+0.04% TFA; B: AcCN. Method: Gradient: 2% B→95% B over 1.20 min. Flow: 4.5 mL/min. Detection: UV/Vis and/or ELSD, and MS, $t_R$ is given in min.

LC-MS-conditions 05c (if not indicated otherwise): Analytical: Dionex GHP 3200 Binary Pump, MS: Thermo MSQ Plus, DAD: Dionex PDA 3000, ELSD: Sedere Sedex 85. Column: Zorbax SB-AQ 1.8 µm, 4.6×20 mm ID from Agilent Technologies, thermostated in the Dionex TCC-3200 compartment. Eluents: A: $H_2O$+0.04% TFA; B: AcCN. Method: Gradient: 5% B→95% B over 1 min. Flow: 4.5 mL/min. Detection: UV/Vis and/or ELSD, and MS, $t_R$ is given in min.

LC-MS-conditions 06 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis C18 2.7 µm, 3×30 mm ID from Sigma-Aldrich, thermostated in the Dionex TCC-3000 compartment. Eluents: A: $H_2O$+0.05% FA; B: AcCN. Method: Gradient: 5% B→95% B over 1.40 min. Flow: 3.0 mL/min. Detection: UV/Vis and/or ELSD, and MS, $t_R$ is given in min.

LC-MS-conditions 07 (if not indicated otherwise): Analytical. Pump: Dionex HPG-32001RS, MS: Thermo MSQ Plus, DAD: Dionex DAD-3000RS, ELSD: Sedere Sedex 85. Column: Xbridge C18 2.5 µM, 4.6×30 mm ID from Waters, thermostated in the Dionex TCC-3200 compartment. Eluents: A: $H_2O$+0.04% TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions 07b (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-Aq 3.5 µM, 4.6×50 mm ID from Agilent Technologies, thermostated in the Dionex TCC-3200 compartment. Eluents: A: $H_2O$+0.04% TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions 07c (if not indicated otherwise): Analytical. Pump: Dionex HPG-3200RS, MS: Thermo MSQ Plus, DAD: Dionex DAD-3000RS, ELSD: Sedere Sedex 85. Column: Atlantis T3 5 µM, 4.6×30 mm ID from Waters, thermostated in the Dionex TCC-3200 compartment. Eluents: A: $H_2O+0.04\%$ TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions 07d (if not indicated otherwise): Analytical. Pump: Dionex HPG-3200RS, MS: Thermo MSQ Plus, DAD: Dionex DAD-3000RS, ELSD: Sedere Sedex 85. Column: Ascentis Express C18 2.7 μm, 4.6×30 mm ID from Sigma-Aldrich, thermostated in the Dionex TCC-3200 compartment. Eluents: A: $H_2O+0.04\%$ TFA; B: AcCN. Method: Gradient: 2% B→95% B over 1.20 min. Flow: 4.5 mL/min. Detection: UV/Vis and/or ELSD, and MS, $t_R$ is given in min.

LC-MS-conditions 04 (if not indicated otherwise): Analytical. Pump: Dionex HPG-3200RS, MS: Thermo MSQ Plus, DAD: Dionex DAD-3000RS, ELSD: Sedere Sedex 85. Column: Xbridge C18 5 μM, 4.6×50 mm ID from Waters, thermostated in the Dionex TCC-3200 compartment. Eluents: A: $H_2O/NH_3$ ($c(NH_3)$=13 mmol/L); B: AcCN. Method: Gradient: 2% B→95% B over 1.20 min. Flow: 4.5 mL/min. Detection: UV/Vis and/or ELSD, and MS, $t_R$ is given in min.

LC-MS-conditions FA (if not indicated otherwise): Analytical. Pump: Waters Acquity Binary Solvent Manager, MS: Waters SQ Detector, DAD: Acquity HPLC PDA Detector, ELSD: Acquity HPLC ELSD. Column: Acquity HPLC BEH C18 1.7 μm 2.1×50 mm ID from Waters, thermostated in the Acquity HPLC Column Manager. Eluents: A: $H_2O+0.05\%$ FA; B: AcCN+0.05% FA. Method: Gradient: 2% B→98% B over 2.00 min. Flow: 1.2 mL/min. Detection: UV/Vis and/or ELSD, and MS, $t_R$ is given in min.

LC-MS-conditions TFA (if not indicated otherwise): Analytical. Pump: Waters Acquity Binary Solvent Manager, MS: Waters SQ Detector, DAD: Acquity HPLC PDA Detector, ELSD: Acquity HPLC ELSD. Column: Acquity HPLC BEH C18 1.7 μm 2.1×50 mm ID from Waters, thermostated in the Acquity HPLC Column Manager. Eluents: A: $H_2O+0.05\%$ TFA; B: AcCN+0.05% TFA. Method: Gradient: 2% B→98% B over 2.00 min. Flow: 1.2 mL/min. Detection: UV/Vis and/or ELSD, and MS, $t_R$ is given in min.

HPLC preparative: X-Bridge C18 5 μm, 50×19 mm ID from Waters. Eluents: A: $H_2O+0.5\%$ $NH_4OH$; B: AcCN; Gradient: 10% B 90% B over 5 min. Flow: 40.0 mL/min. Detection: UV/Vis and/or ELSD, and MS, $t_R$ is given in min.

HPLC chiral, analytical: a) Regis Whelk column, 4.6×250 mm, 10 μm. Eluent A: EtOH+0.05% $Et_3N$. Eluent B: hexane. Flow: 1 mL/min. b) ChiralPak AD, 4.6×250 mm, 5 μm. Eluent A: EtOH+0.05% $Et_3N$. Eluent B: hexane. Flow: 1 mL/min. c) ChiralCel OD, 4.6×250 mm, 10 μm. Eluent A: EtOH+0.1% $Et_3N$. Eluent B: hexane. Flow: 0.8 mL/min. Detection: UV/Vis, $t_R$ is given in min.

HPLC chiral, preparative: a) Regis Whelk 01 column, 50×250 mm. Flow: 100 mL/min. b) ChiralPak AD, 20×250 mm. Flow: 10 mL/min. c) ChiralCel OD, 20 μm, 50 mm×250 mm. Flow: 100 mL/min. Detection: UV/Vis, $t_R$ is given in min.

GC-MS-conditions 01: Thermo Trace GC Ultra, Thermo DSQ II MS detector, Thermo TriPlus Autosampler, Column: Zebron ZB-5 MS, 15 m×0.25 mm ID, 0.25 μm film, Column flow: 2.0 mL/min, Carrier gas: Helium, Split ratio: 20, SSL Inlet Temperature: 200° C., Temperature gradient: 60° C. to 300° C. from 0.0 min to 4.0 min, 300° C. isotherm from 4.0 min to 5.0 min, Ionization: chemical ionization with $CH_4$ as reagent gas.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

As continuous-flow hydrogenation reactor H-Cube® from ThalesNano was used.

The following examples illustrate the invention but do not at all limit the scope thereof.

General Procedures

General Procedure A: Amide Coupling (1):

In a glass vial, under inert atmosphere ($N_2$), to an amine (3.0 eq.) in $CH_2Cl_2$ (0.3 M) were added DMAP (0.25 eq.), EDC.HCl (2.0 eq.) and DIPEA (1.0-3.0 eq., when necessary). A solution of the carboxylic acid (1.0 eq.) in $CH_2Cl_2$ (0.1 M) was then added and the reaction mixture stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by FC or HPLC gave the desired compound.

General Procedure B: Amide Coupling (2):

In a glass vial, under inert atmosphere ($N_2$), a mixture of the carboxylic acid (1.0 eq.), an amine (3.0 eq.) and HOAt or HOBt (1.0 eq.) in $CH_2Cl_2$ (10 mL per 0.5 mmol of HOAt) was added to PL-DCC Resin (4.0 eq.) in $CH_2Cl_2$ (0.2 M) in the presence of PS-DIPEA when needed. The reaction mixture was stirred at rt for 2 days. The reaction mixture was filtered over an Isolute® Phase Separator syringe washed with $CH_2Cl_2$ (3×1 mL) and the solvent was removed under reduced pressure. Purification of the residue by FC or HPLC gave the desired compound.

General Procedure C: Amide Coupling (3):

In a glass vial, under inert atmosphere ($N_2$), a mixture of the carboxylic acid (1.0 eq.) and an amine (1.0 eq.) in DCE/pyridine (1:1, 0.2 M) was cooled to −10° C. $POCl_3$ (2.5 eq.) in DCE/pyridine (1:1, 1.2 M) was added and the reaction mixture was stirred at −10° C. for 1 h. The reaction mixture was poured on a syringe containing diatomaceous earth (Isolute® HM-N from Separtis) treated with 1 M NaOH (1.0 mL per g of Isolute®). The product was eluted with $CH_2Cl_2$ (3×2 mL) and the solvent was removed under reduced pressure. Purification of the residue by FC or HPLC gave the desired compound.

General Procedure D: Amide Coupling (4):

In a glass vial, under inert atmosphere ($N_2$), to a mixture of the amine (1.0 eq.) and a carboxylic acid (1.2 eq.) in $CH_2Cl_2$ (10 mL per mmol of acid) was added a solution of HOBt (1.25 eq.), DMAP (0.25 eq.), EDC HCl (1.5-2.0 eq.) and DIPEA (4.0-5.0 eq.) in $CH_2Cl_2$ (6 mL per mmol of HOBt). The reaction mixture was stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by FC or HPLC gave the desired compound.

General Procedure E: Amide Coupling (5):

In a flame dried round-bottomed flask equipped with a magnetic stir bar and under inert atmosphere ($N_2$), to a solution of the carboxylic acid (1.0 eq.) in $CH_2Cl_2$ (0.2 M) were added an amine (1.0-2.0 eq.), EDC HCl (2.0-3.0 eq.), DIPEA (3.0-6.0 eq., when necessary) and DMAP (0.25 eq.). The reaction mixture was stirred at rt until completion of the reaction. Water was then added, the layers separated and the aq. layer extracted with $CH_2Cl_2$ (3×). The combined org. extracts were dried over $MgSO_4$, filtered, and concentrated under reduced pressure. Purification of the residue by FC or HPLC gave the desired compound.

General Procedure F: Weinreb Amidation:

In a flame dried round-bottomed flask equipped with a magnetic stir bar and under inert atmosphere ($N_2$), to a solution of an amine (2.0 eq.) in $CH_2Cl_2$ (0.4 M) was added $AlMe_3$ (1.0 M in heptane, 6.0 eq.). The reaction mixture was stirred at rt for 1 h and was then cooled to 0° C. A solution of the ester (1.0 eq.) in $CH_2Cl_2$ (0.2 M) was added and the reaction mixture stirred at rt until completion of the reaction. Aq. sat. $NaHCO_3$ was carefully added, the layers separated and the aq. layer extracted with $CH_2Cl_2$ (3×). The combined org. extracts were dried over $MgSO_4$, filtered, and concentrated under reduced pressure. Purification of the residue by FC or HPLC gave the desired compound.

General Procedure G: Dioxolane Deprotection:

In a glass vial, under inert atmosphere ($N_2$), a 0.06 M solution of the dioxolane (1.0 eq.) in THF was treated with 1N HCl (2.7 eq.) and the reaction mixture was stirred at rt until completion. Aq. 1N NaOH was added and the product extracted with EA (3×). The combined org. extracts were dried over $MgSO_4$, filtered, and concentrated under reduced pressure. Purification of the residue by FC or HPLC gave the desired compound.

General Procedure H: Boc Deprotection:

In a glass vial, under inert atmosphere ($N_2$), a 0.06 M solution of the Boc-protected amine (1.0 eq.) in $CH_2Cl_2$ (+1 drop of MeOH) was treated with 4N HCl in dioxane (15 mL/mmol amine) and the reaction mixture was stirred at rt for 1 h. The reaction mixture was then concentrated under reduced pressure and the residue purified by FC or HPLC to give the desired compound.

General Procedure I: Amide Coupling (6):

In a flame dried round-bottomed flask equipped with a magnetic stir bar and under inert atmosphere ($N_2$), to a solution of the carboxylic acid (1.0 eq.) in $CH_2Cl_2$ (0.2 M) were added HOBt (1.2 eq.), DMAP (0.25 eq.), EDC HCl (2.5 eq.) and DIPEA (4.0 eq.). The reaction mixture was stirred at rt for 30 min. A solution of an amine (1.0 eq.) in $CH_2Cl_2$ (0.2 M) was then added and the reaction mixture stirred at rt overnight. Water was added, the layers separated, and the org. layer dried over $MgSO_4$, filtered, and concentrated under reduced pressure. Purification of the residue by FC or HPLC gave the desired compound.

General Procedure J: Amide Coupling (7):

In a flame dried round-bottomed flask equipped with a magnetic stir bar and under inert atmosphere ($N_2$), to a solution of the carboxylic acid (1.0 eq.) in $CH_2Cl_2$ (0.1 M) were added oxalyl chloride (1.1 eq.) and a few drops of DMF. The reaction mixture was stirred at rt until completion. A solution of an amine (2.2 eq.) in $CH_2Cl_2$ (0.4 M) was then added and the reaction mixture stirred at rt until completion of the reaction. Water and $CH_2Cl_2$ were then added, the layers separated and the aq. layer extracted with $CH_2Cl_2$ (2×). The combined org. extracts were dried over $Na_2SO_4$, filtered, and concentrated under reduced pressure. Purification of the residue by FC or HPLC gave the desired compound.

General Procedure K: Amide Coupling (8):

In a flame dried round-bottomed flask equipped with a magnetic stir bar and under inert atmosphere ($N_2$), a mixture of the carboxylic acid (1.0 eq.), an amine (1.0 eq.) and HOBt (1.2 eq.) in $CH_2Cl_2$ (1 mL per 0.3 mmol of HOBt) was added to PL-DCC Resin (2.0 eq.) in $CH_2Cl_2$ (0.2 M). The reaction mixture was stirred at rt for 1 day. The reaction mixture was filtered and the solvent was removed under reduced pressure. Purification of the residue by FC or HPLC gave the desired compound.

General Procedure L: Amide Coupling (9):

In a flame dried round-bottomed flask equipped with a magnetic stir bar and under inert atmosphere ($N_2$), to a mixture of the carboxylic acid (1.0 eq.), an amine (1.1 eq.) and HATU (1.2 eq.) in THF/DMF 4:1 (1 mL per 0.2 mmol of HATU) was added DIPEA (3.0 eq.). The reaction mixture was stirred at rt for 1 day. Water was then added and the mixture extracted with EA (3×). The combined org. extracts were washed with brine, dried over $MgSO_4$, filtered and concentrated under reduced pressure. Purification of the residue by FC or HPLC gave the desired compound.

General Procedure M: Carboxamide Formation:

In a flame dried round-bottomed flask equipped with a magnetic stir bar and under inert atmosphere ($N_2$), the ester (1.0 eq.) was dissolved in THF (0.2 M) and treated with aq. 1N NaOH (2.0 eq.) at rt until completion of the reaction. The reaction mixture was poured into aq. 1N HCl and extracted with EA (3×). The combined organic extracts were dried over $MgSO_4$, filtered and concentrated under reduced pressure. To a solution of the crude carboxylic acid (1.0 eq.) and $Et_3N$ (1.0 eq.) in dry THF (0.1 M) was added ethyl chloroformate (1.0 eq.) at 0° C. The reaction mixture was stirred at 0° C. for 15 min and an amine (aq. $NH_3$ (excess) or $MeNH_2$ (1.0 eq.)) was then added. The reaction mixture was stirred at 0° C. until completion of the reaction then concentrated under reduced pressure. The residue was partitioned between water and $CH_2Cl_2$, the layers separated and the aq. layer extracted with $CH_2Cl_2$ (2×). The combined org. extracts were dried over $MgSO_4$, filtered and concentrated under reduced pressure. Purification of the residue by FC or HPLC gave the desired compound.

General Procedure N: Amide Coupling (10):

In a glass vial, under inert atmosphere ($N_2$), to a solution of the carboxylic acid (1.0 eq.) in $CH_2Cl_2$ (0.25 M) were added HOBt (1.20 eq.), DMAP (0.25 eq.), EDC HCl (2.5 eq.) and DIPEA (4.0 eq.). The reaction mixture was stirred at rt for 30 min. An amine (2.0 eq.) was then added and the reaction mixture stirred at rt until completion of the reaction. DMF (0.3 vol. $CH_2Cl_2$) and $PL-SO_2Cl_2$ (1.0 eq.) were added and after stirring at rt for 1 h the mixture was filtered ($CH_2Cl_2$) and concentrated under reduced pressure. Purification of the residue by FC or HPLC gave the desired compound.

SYNTHESIS OF INTERMEDIATES

Spiro[2.4]hepta-4,6-diene

In a flame dried round-bottomed flask equipped with a magnetic stir bar and under inert atmosphere ($N_2$), a mixture of benzyltriethylammonium chloride (18.0 g, 78 mmol) in 50% aqueous NaOH solution (1.2 L) was heated to 45° C. A chilled solution of cyclopentadiene (formed by cracking of cyclopentadiene dimer at 180° C., 140 mL, 1.70 mol) in 1,2-dichloroethane (122 mL, 1.55 mol) was added to the stirred NaOH solution while keeping the internal temperature below 55° C. After completion of the addition (ca. 1.75 h), the reaction mixture was stirred at 50° C. for 2 h and allowed to cool down to rt. The layers were separated, the organic layer washed with 1M NaOH, dried ($Na_2SO_4$) and filtered. The crude brown liquid was distilled under reduced pressure (85-95 mbar) and the title compound was obtained as a colorless liquid (bp=45-50° C. at 80 mbar). $^1H$ NMR (400 MHz, $CDCl_3$) δ 6.58 (m, 2H), 6.19 (m, 2H), 1.71 (s, 4H).

Diels Alder Reaction—formation of (5R)-5-ethoxy-carbonyl-(4S*,7R*)-[4,7-ethenylene-spiro[2.4]heptane]-(6R*)-6-carboxylic acid and (6R*)-6-ethoxy-carbonyl-(4S*,7R*)-[4,7-ethenylene-spiro[2.4]heptane]-(5R*)-5-carboxylic acid

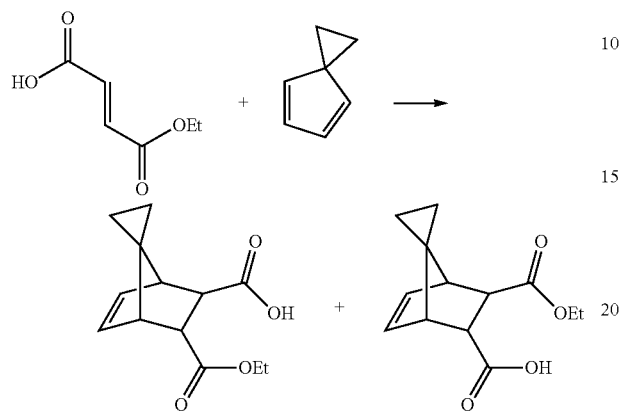

In a flame dried round-bottomed flask equipped with a magnetic stir bar and under inert atmosphere (N$_2$), a solution of (E)-but-2-enedioic acid monoethyl ester (63.8 g, 0.44 mol) in MeOH (425 mL) was treated with spiro[2.4]hepta-4,6-diene (57.6 mL, 0.57 mol) at rt. The reaction mixture was stirred at this temperature for 11 days. The mixture was concentrated under reduced pressure and the crude residue recrystallized from EA and pentane. (6R*)-6-Ethoxycarbonyl-(4S*,7R*)-[4,7-ethenylene-spiro[2.4]heptane]-(5R*)-5-carboxylic acid (exo product) was obtained as a white solid. The mother liquor was then concentrated under reduced pressure, the residue purified by FC (heptane/acetone, 2-5% of acetone) and the product obtained as a mixture of endo/exo products (yellow solid). TLC:rf (7:3 hept-acetone)=0.29. LC-MS-conditions 02: $t_R$=0.89 min; [M+H]$^+$=373.99. $^1$H NMR (400 MHz, CDCl$_3$) δ 6.42 (m, 1H), 6.24 (dd, J=5.8, 2.5 Hz, 1H), 4.20 (qd, J=7.3, 1.3 Hz, 2H), 3.74 (t, J=4.0 Hz, 1H), 2.82 (d, J=4.5 Hz, 1H), 2.74 (br s, 1H), 2.69 (br s, 1H), 1.30 (t, J=7.0 Hz, 3H), 0.50 (m, 4H) for pure isomer. $^1$H NMR (400 MHz, CDCl$_3$) δ 6.40 (m, 1Ha+1Hb), 6.23 (dd, J=5.8, 2.8 Hz, 1Ha), 6.16 (dd, J=5.8, 2.8 Hz, 1Hb), 4.18 (qd, J=7.0, 1.3 Hz, 2Ha), 4.12 (qd, J=7.3, 2.0 Hz, 2Hb), 3.73 (t, J=4.3 Hz, 1Ha), 3.62 (t, J=4.3 Hz, 1Hb), 2.92 (d, J=4.5 Hz, 1Hb), 2.81 (d, J=4.5 Hz, 1Ha), 2.75 (br s, 1Hb), 2.72 (br s, 1Ha), 2.67 (br s, 1Ha+1Hb), 1.28 (t, J=7.3 Hz, 3Ha), 1.25 (t, J=7.0 Hz, 3Hb), 0.50 (m, 4Ha+Hb) for mixture of stereoisomers.

Iodolactonization—formation of (±)-iodolactones 1 (R$^{10}$=Et) and 2

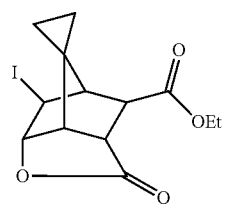 [SMILES: CCOC(=O)C1C2C(=O)OC3C(I)C1C1(CC1)C32]

To a solution of 6-ethoxycarbonyl-(4S*,7R*)-[4,7-ethenylene-spiro[2.4]heptane]-5-carboxylic acid (15.00 g, 63.5 mmol, mixture of isomers as obtained above) in CH$_2$Cl$_2$ (95 mL) were added NaHCO$_3$ (5.87 g, 69.8 mmol), water (286 mL), KI (39.00 g, 234.9 mmol) and I$_2$ (3.55 g, 11.0 mmol). The reaction mixture was stirred at rt overnight. The reaction was quenched by the addition of sat. aq. Na$_2$S$_2$O$_3$. The layers were separated and the aq. layer extracted with CH$_2$Cl$_2$ (3×). The combined org. extracts were successively washed with aq. sat. NaHCO$_3$ and brine, then dried over Na$_2$SO$_4$, filtered, and concentrated under reduced pressure to give (±)-iodolactone 1 (R$^{10}$=Et) (ethyl ester) as a pale yellow oil. TLC:rf (4:1 hept-acetone)=0.25. LC-MS-conditions 02: $t_R$=1.02 min; [M+H]$^+$=363.53.

The aq. layer was then acidified (pH=1) and extracted with EA. The combined organic extracts were dried over Na$_2$SO$_4$, filtered, and concentrated under reduced pressure. The crude solid was purified by FC to give (±)-iodolactone 2 (carboxylic acid) as a white solid. TLC:rf (70:30:1.1 hept-acetone-MeOH)=0.15. LC-MS-conditions 02: $t_R$=0.86 min; [M+AcCN+H]$^+$=376.49.

Retro-iodolactonization—formation of (6R*)-6-ethoxycarbonyl-(4S*,7R*)-[4,7-ethenylene-spiro[2.4]heptane]-(5R*)-5-carboxylic acid In a flame dried round-bottomed flask equipped with a magnetic stir bar and under inert atmosphere (N$_2$), to a solution of (±)-iodolactone 1 (R$^{10}$=Et) (5.00 g, 13.8 mmol) in acetic acid (50 mL) was added zinc powder (13.54 g, 207.1 mmol). The reaction mixture was stirred at 65° C. for 2 h, cooled down to rt, filtered and partitioned between water and EA. The layers were separated and the aq. layer extracted with EA (3×). The combined org. extracts were washed with brine, dried over MgSO$_4$, filtered, and concentrated under reduced pressure. The crude residue was purified by FC (hept-EA, 1:0->1:1) and the title compound was obtained as a white solid. TLC:rf (7:3 hept-EA)=0.18. LC-MS-conditions 02: $t_R$=0.89 min; [M+H]$^+$=237.30.

Amide Coupling (with 4-bromo-aniline)—formation of (5R*)—N$^5$-(4-bromo-phenyl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere (N$_2$), to a solution of (6R*)-6-ethoxycarbonyl-(4S*,7R*)-[4,7-ethenylene-spiro[2.4]heptane]-(5R*)-5-carboxylic acid (17.9 g, 75.6 mmol) in dry toluene (350 mL) were added a few drops of DMF and oxalyl chloride (10.1 mL, 113.5 mmol). The reaction mixture was stirred at reflux for 40 minutes, cooled down to rt, concentrated under reduced pressure and the residue dried under high vacuum.

To a solution of this acyl chloride in dry CH$_2$Cl$_2$ (350 mL) were added 4-bromoaniline (26.8 g, 151.3 mmol) and DIPEA (38.8 mL, 151.3 mmol). The reaction mixture was stirred at rt for 2 h. 1N HCl was added, the layers separated, and the aq. layer extracted with $CH_2Cl_2$ (3×). The combined org. extracts were washed with brine, dried over $MgSO_4$, filtered, and concentrated under reduced pressure. The crude residue was triturated with MeOH and the title compound obtained as a pale brown solid. TLC:rf (7:3 hept-EA)=0.46. LC-MS-conditions 02: $t_R$=1.09 min; $[M+H]^+$=390.30.

Saponification—formation of (5R*)—$N^5$-(4-bromo-phenyl)-(6R*)-6-hydroxycarbonyl-(4S*,7R*)-[4,7-ethenylene-spiro[2.4]heptane]-5-carboxamide A mixture of (5R*)—$N^5$-(4-bromo-phenyl)-(6R*)-6-ethoxycarbonyl-(4S*,7R*)-[4,7-ethenylene-spiro[2.4]heptane]-5-carboxamide (2.70 g, 6.92 mmol) in EtOH (69 mL) and 1N NaOH (69 mL) was stirred at 80° C. for 1 h. The reaction mixture was then cooled down to rt and EtOH was removed under reduced pressure. The residue was partitioned between 2N HCl and EA. The layers were separated and the aq. layer extracted with EA (3×). The combined org. extracts were washed with brine, dried over $MgSO_4$, filtered, and concentrated under reduced pressure to give the title compound as a yellow solid. LC-MS-conditions 02: $t_R$=0.98 min; $[M+H]^+$=362.20.

Amide coupling (with beta-alanine methyl ester hydrochloride)—formation of (5R*)—$N^5$-(4-bromo-phenyl)-(6R*)—$N^6$-(2-methoxycarbonyl-ethyl)-(4S*,7R*)-[4,7-ethenylene-spiro[2.4]heptane]-5,6-dicarboxamide In a flame dried round-bottomed flask equipped with a magnetic stir bar and under inert atmosphere ($N_2$), to a solution of (5R*)—$N^5$-(4-bromo-phenyl)-(6R*)-6-hydroxycarbonyl-(4S*,7R*)-[4,7-ethenylene-spiro[2.4]heptane]-5-carboxamide (200 mg, 0.55 mmol) in dry toluene (1.7 mL) were added a few drops of DMF and oxalyl chloride (1.1 eq.). The reaction mixture was stirred at rt for 90 min, concentrated under reduced pressure and the residue co-evaporated with toluene (2×). The residue was then redissolved in $CH_2Cl_2$ (0.7 mL) and added to a mixture of beta-alanine methyl ester hydrochloride (85 mg, 0.61 mmol) and DIPEA (0.28 mL, 3.0 eq.) at rt. The reaction mixture was stirred at rt for 20 minutes, diluted with $CH_2Cl_2$ and washed with aq. 1N HCl. The layers were separated, and the aq. layer back-extracted with $CH_2Cl_2$ (2×). The combined org. extracts were washed with aq. sat. $NaHCO_3$, dried over $Na_2SO_4$, filtered, and concentrated under reduced pressure. The crude residue was purified by FC (hept-EA) and the title compound obtained as a white solid. TLC:rf (6:4 hept-EA)=0.35. LC-MS-conditions 02: $t_R$=0.98 min; $[M+H]^+$=446.90.

(5R*)-5-Hydroxycarbonyl-(6R*)—$N^6$-(4-bromo-phenyl)-(4S*,7R*)-[4,7-ethenylene-spiro[2.4]heptane]-6-carboxamide In a flame dried round-bottomed flask equipped with a magnetic stir bar and under inert atmosphere ($N_2$), to a solution of (±)-iodolactone 2 (1.00 g, 2.99 mmol) in dry toluene (17 mL) were added a few drops of DMF and oxalyl chloride (0.38 mL, 4.49 mmol). The reaction mixture was stirred at reflux for 20 minutes, cooled down to rt, concentrated under reduced pressure and the residue dried under high vacuum.

To a solution of this acyl chloride in dry $CH_2Cl_2$ (5 mL) were added 4-bromoaniline (730 mg, 4.24 mmol) and DIPEA (1.5 mL, 8.98 mmol). The reaction mixture was stirred at rt for 20 min. 1N HCl was added, the layers separated, and the aq. layer extracted with $CH_2Cl_2$ (3×). The combined org. extracts were washed with brine, dried over $Na_2SO_4$, filtered, and concentrated under reduced pressure. The crude residue was purified by FC (hept-EA, 7:3) and the pure amide was obtained as a pale orange foam. TLC:rf (7:3 hept-EA)=0.21. LC-MS-conditions 02: $t_R$=1.08 min. In a flame dried round-bottomed flask equipped with a magnetic stir bar and under inert atmosphere ($N_2$), to a solution of the above iodolactone (1.29 g, 2.64 mmol) in acetic acid (10 mL) was added zinc powder (2.59 g, 39.64 mmol). The reaction mixture was stirred at 65° C. for 2 h, cooled down to rt, filtered and partitioned between water and EA. The layers were separated and the aq. layer extracted with EA (3×). The combined org. extracts were washed with brine, dried over $MgSO_4$, filtered, and concentrated under reduced pressure. The crude residue was purified by FC (hept-EA, 4:6) and the title compound was obtained as a white foam. TLC: rf (4:6 hept-EA)=0.43. LC-MS-conditions 02: $t_R$=0.98 min; $[M+H]^+$=362.31.

Double bond reduction—formation of (6R*)-6-ethoxycarbonyl-(4S*,7R*)-[4,7-ethylene-spiro[2.4]heptane]-(5R*)-5-carboxylic acid In a flame dried round-bottomed flask equipped with a magnetic stir bar and under inert atmosphere ($N_2$), a deoxygenated suspension of (6R*)-6-ethoxycarbonyl-(4S*,7R*)-[4,7-ethenylene-spiro[2.4]heptane]-(5R*)-5-carboxylic acid (2.00 g, 8.46 mmol), Pd/C 10% (339 mg) and cyclohexene (1.72 mL, 7.93 mmol) in dry THF (31 mL) was stirred at reflux for 4 h. The reaction mixture was filtered through celite and the filter cake washed with EtOH. The filtrate was concentrated under reduced pressure and the title compound obtained as a white solid. TLC:rf (7:3 hept-EA)=0.26. LC-MS-conditions 02: $t_R$=0.93 min; $[M+H]^+$=239.34.

Amide coupling (with 4-bromo-aniline)—formation of (5R*)—$N^5$-(4-bromo-phenyl)-(6R*)-6-ethoxycarbonyl-(4S*,7R*)-[4,7-ethylene-spiro[2.4]heptane]-5-carboxamide In a flame dried round-bottomed flask equipped with a magnetic stir bar and under inert atmosphere ($N_2$), to a solution of (6R*)-6-ethoxycarbonyl-(4S*,7R*)-[4,7-ethylene-spiro[2.4]heptane]-(5R*)-5-carboxylic acid (2.00 g, 8.46 mmol) in dry toluene (40 mL) were added a few drops of DMF and oxalyl chloride (1.13 mL, 12.70 mmol). The reaction mixture was stirred at reflux for 40 minutes, cooled down to rt, concentrated under reduced pressure and the residue dried under high vacuum.

To a solution of this acyl chloride in dry $CH_2Cl_2$ (40 mL) were added 4-bromoaniline (3.00 g, 16.93 mmol) and DIPEA (4.35 mL, 25.40 mmol). The reaction mixture was stirred at rt for 1 h. 1N HCl was added, the layers separated, and the aq. layer extracted with $CH_2Cl_2$ (3×). The combined org. extracts were washed with brine, dried over $MgSO_4$, filtered, and concentrated under reduced pressure. The crude residue was purified by FC (hept-EA, 7:3) and the title compound obtained as a pale brown solid. TLC:rf (7:3 hept-EA)=0.46. LC-MS-conditions 02: $t_R$=1.13 min; $[M+H]^+$=392.30.

Saponification—formation of (5R*)—$N^5$-(4-bromo-phenyl)-(6R*)-6-hydroxycarbonyl-(4S*,7R*)-[4,7-ethylene-spiro[2.4]heptane]-5-carboxamide A mixture of (5R*)—$N^5$-(4-bromo-phenyl)-(6R*)-6-ethoxycarbonyl-(4S*,7R*)-[4,7-ethylene-spiro[2.4]heptane]-5-carboxamide (2.78 g, 7.09 mmol) in EtOH (71 mL) and 1N NaOH (71 mL) was stirred at 80° C. for 1 h. The reaction mixture was then cooled down to rt and EtOH was removed under reduced pressure. The residue was partitioned between 2N HCl and EA. The layers were separated and the aq. layer extracted with EA (3×). The combined org. extracts were washed with brine, dried over $MgSO_4$, filtered, and concentrated under reduced pressure to give the title compound as an orange powder. TLC:rf (7:3 hept-EA)=0.18. LC-MS-conditions 02: $t_R$=1.01 min; $[M+H]^+$=364.30.

Amide coupling (with 4-pyrrolidin-1-yl-butylamine)—formation of (±)-iodolactone 3 ($R^2$=4-pyrrolidin-1-yl-butyl and $R^3$=H)

In a flame dried round-bottomed flask equipped with a magnetic stir bar and under inert atmosphere ($N_2$), to a solution of (±)-iodolactone 2 (6.92 g, 20.71 mmol) in dry $CH_2Cl_2$ (42 mL) were added a few drops of DMF and oxalyl chloride (1.96 mL, 22.78 mmol). The reaction mixture was stirred at rt for 30 min, after which 4-(1-pyrrolidino)-butylamine (3.00 g, 20.71 mmol) and DIPEA (3.55 mL, 20.71 mmol) were added. The reaction mixture was stirred at rt for 15 minutes, diluted with $CH_2Cl_2$ and washed with sat. aq. $NH_4Cl$. The layers were separated, and the aq. layer extracted with $CH_2Cl_2$ (3×). The combined org. extracts were washed with brine, dried over $Na_2SO_4$, filtered, and concentrated under reduced pressure. The crude residue was purified by FC($CH_2Cl_2$/MeOH, 95:5) and the title compound obtained as a white solid. TLC: rf (95:5 $CH_2Cl_2$/MeOH)=0.12. LC-MS-conditions 02: $t_R$=0.74 min; $[M+H]^+$=459.30.

Retro-iodolactonization—formation of (5R*)-5-hydroxycarbonyl-(6R*)—$N^6$-(4-pyrrolidin-1-yl -butyl)-(4S*,7R*)-[4,7-ethenylene-spiro[2.4]heptane]-6-carboxamide In a flame dried round-bottomed flask equipped with a magnetic stir bar and under inert atmosphere ($N_2$), to a solution of (±)-iodolactone 3 ($R^2$=4-pyrrolidin-1-yl-butyl and $R^3$=H) (7.11 g, 15.51 mmol) in acetic acid (100 mL) was added zinc powder (15.21 g, 232.70 mmol). The reaction mixture was stirred at 65° C. for 2 h, cooled down to rt, filtered, washed with $CH_2Cl_2$ and the filtrate concentrated under reduced pressure. The crude residue was purified by FC(C-18 reverse phase silica, $H_2O$/MeOH, 1:0 then 0:1) and the title compound was obtained as a white solid. LC-MS-conditions 02: $t_R$=0.64 min; $[M+H]^+$=333.34.

Ester reduction—formation of (5R*)—$N^5$-(4-bromo-phenyl)-(6R*)-6-(hydroxymethyl)-(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (5R*)—$N^5$-(4-bromo-phenyl)-(6R*)-6-ethoxycarbonyl-(4S*,7R*)-[4,7-ethenylene-spiro[2.4]heptane]-5-carboxamide (10.00 g, 25.62 mmol) in dry THF (120 mL) was added $LiBH_4$ (2.55 g, 64.06 mmol). The reaction mixture was stirred at 65° C. for 2.5 h and cooled down to rt. Sat. aq. $NH_4Cl$ and EA were added, the layers separated and the aq. layer extracted with EA (3×). The combined org. extracts were washed with brine, dried over $MgSO_4$, filtered, and concentrated under reduced pressure. The crude residue was purified by FC (hept-EA, 7:3) and the title compound was obtained as a white solid. TLC:rf (7:3 hept-EA)=0.25. LC-MS-conditions 02: $t_R$=0.99 min; $[M+H]^+$=348.30.

Amine formation via triflate—formation of (5R*)—$N^5$-(4-bromo-phenyl)-(6R*)-6-(amino-methyl)-(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (5R*)—$N^5$-(4-bromo-phenyl)-(6R*)-6-(hydroxymethyl)-(4S*,7R*)-[4,7-ethenylene-spiro[2.4]heptane]-5-carboxamide (1.00 g, 2.87 mmol) in dry $CH_2Cl_2$ (20 mL) was added DIPEA (1.23 mL, 7.18 mmol). The reaction mixture was cooled to −78° C. and trifluoromethane sulfonic anhydride (0.55 mL, 3.33 mmol) was added dropwise. The reaction mixture was stirred at −78° C. for 1 h. $NH_3$ in dioxane (0.5 M, 15 mL, 7.50 mmol) was then added and the reaction mixture allowed to warm up to rt and stirred at this temperature overnight. Water was added, the layers separated and the org. layer successively washed with sat. aq. $NaHCO_3$ and brine, dried over $MgSO_4$, filtered, and concentrated under reduced pressure. The title compound was obtained as an orange solid. TLC:rf (9:1:0.1 $CH_2Cl_2$-MeOH—$NH_4OH$) =0.28. LC-MS-conditions 02: $t_R$=0.82 min; $[M+H]^+$=347.24.

Amine formation via triflate—formation of (5R*)—$N^5$-(4-bromo-phenyl)-(6R*)-6-[(methyl-amino)-methyl]-(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (5R*)—$N^5$-(4-bromo-phenyl)-(6R*)-6-(hydroxymethyl)-(4S*,7R*)-[4,7-ethenylene-spiro[2.4]heptane]-5-carboxamide (120 mg, 0.35 mmol) in dry $CH_2Cl_2$ (2.4 mL) was added DIPEA (0.15 mL, 0.86 mmol). The reaction mixture was cooled to −78° C. and trifluoromethane sulfonic anhydride (0.09 mL, 0.57 mmol) was added dropwise. The reaction mixture was stirred at −78° C. for 1 h. Methylamine (2 M in THF, 1.73 mL, 3.46 mmol) was then added and the reaction mixture allowed to warm up to rt and stirred at this temperature for 1 h30. Water and EA were added, the layers separated and the org. layer successively washed with sat. aq. $NaHCO_3$ and brine, dried over $MgSO_4$, filtered, and concentrated under reduced pressure. The title compound was obtained as an orange solid. LC-MS-conditions 02: $t_R$=0.82 min; $[M+H]^+$= 361.29.

1-(5-Hydroxymethyl-furan-2-yl)-ethanone

In a flame dried round-bottomed flask under inert atmosphere ($N_2$), to a mixture of 5-hydroxymethyl-2-furaldehyde (100 g, 0.79 mol) and pyridinium toluene-4-sulfonate (10 g, 0.04 mol) in $CH_2Cl_2$ (1 L) was added 3,4-dihydro-2H-pyran (150 mL, 1.62 mol) while keeping the internal temperature below 28° C. (water bath). The reaction mixture was stirred at rt for 5 h. Water (1 L) was added, the layers separated and the org. layer washed with water (500 mL) and evaporated to dryness to give crude 5-(tetrahydro-pyran-2-yloxymethyl)-furan-2-carbaldehyde as a yellow oil.

Crude 5-(tetrahydro-pyran-2-yloxymethyl)-furan-2-carbaldehyde (171 g) was dissolved in THF (1 L) and cooled to 1° C. Methylmagnesium chloride (3 M in THF, 325 mL, 0.97 mol) was then added while keeping the internal temperature below 5° C. After the addition, the reaction mixture was stirred at rt for 1 h. Water (1 L), TBME (1 L) and 40% aq. citric acid (200 mL) were added, the layers separated and the org. layer washed with water (500 mL) and evaporated to dryness to give crude 1-[5-(tetrahydro-pyran-2-yloxymethyl)-furan-2-yl]-ethanol. Part of the crude material (96 g, 0.43 mol) was dissolved in $CH_2Cl_2$ (1 L) and treated with $MnO_2$ (371 g, 4.26 mol) at rt. The reaction mixture was heated to 45° C. and stirred at this temperature for 24 h. The mixture was then filtered over celite and the filter cake washed with $CH_2Cl_2$. The filtrate was evaporated to dryness to give crude 1-[5-(tetrahydro-pyran-2-yloxymethyl)-furan-2-yl]-ethanone as a yellow oil.

Crude 1-[5-(tetrahydro-pyran-2-yloxymethyl)-furan-2-yl]-ethanone (89 g, 0.40 mol) was dissolved in MeOH (500 mL) and treated with Amberlyst 15 (15 g) at rt. The reaction mixture was stirred at 35° C. for 1 h, cooled to rt and filtered over celite. $Et_3N$ (1 mL) was added and the mixture was evaporated to dryness. The residue was stripped with methylcyclohexane and 1-(5-hydroxymethyl-furan-2-yl)ethanone was obtained as a yellow oil that solidified on standing.

1-(5-Aminomethyl-furan-2-yl)-ethanone

In a flame dried round-bottomed flask equipped with a magnetic stir bar and under inert atmosphere ($N_2$), a solution of 1-(5-hydroxymethyl-furan-2-yl)-ethanone (2.00 g, 14.27 mmol) in dry $CH_2Cl_2$ (29 mL) was treated at 0° C. with $Et_3N$ (2.58 mL, 18.55 mmol) followed by DMAP (178 mg, 1.43 mmol) and Ms-Cl (1.33 mL, 17.13 mmol). After stirring at rt for 3 h, the reaction was quenched with water. The layers were separated and the aq. layer extracted with $CH_2Cl_2$ (3×). The org. layer was dried over $MgSO_4$, filtered, and the solvents were removed under reduced pressure to give crude 1-(5-chloromethyl-furan-2-yl)-ethanone as a brown oil. Part of this crude material (2.33 g, 14.72 mmol) was dissolved in dry DMF (50 mL) and treated with $NaN_3$ (2.90 g, 44.16 mmol) at 80° C. for 24 h. The reaction mixture was then cooled down to rt and partitioned between EA and water. The layers were separated and the aq. layer extracted with EA (1×). The combined org. extracts were dried over $Na_2SO_4$, filtered and concentrated under reduced pressure to give crude 1-(5-azidomethyl-furan-2-yl)-ethanone as a brown oil. LC-MS-conditions 02: $t_R$=0.81 min; [M+AcCN+H]$^+$=207.50.

To a solution of the crude azide (500 mg, 3.03 mmol) in THF (15 mL) were added $Ph_3P$ (polymer-supported, 3.0 mmol/g, 1.5 eq.) and water (5 mL). The reaction mixture was stirred at 60° C. until reaction completion, cooled down to rt and filtered. Sat. aq. $NaHCO_3$ and EA were then added, the layers separated and the aq. layer extracted with EA (1×). The combined organic extracts were dried over $Na_2SO_4$, filtered and concentrated under reduced pressure. The crude residue was purified by FC (9:1 $CH_2Cl_2$/MeOH) and the title compound was obtained as an orange oil. LC-MS-conditions 02: $t_R$=0.27 min; [M+AcCN+H]$^+$=181.61.

5-Nitro-pentan-2-one

In a flame dried round-bottomed flask equipped with a magnetic stir bar and under inert atmosphere ($N_2$), to a solution of methyl vinyl ketone (2.32 mL, 28.53 mmol) in nitromethane (29.6 mL) was added activated $KF/Al_2O_3$ (323 mg, prepared by mixing KF and basic $Al_2O_3$ in water followed by concentrating and drying) at 0° C. The reaction mixture was then allowed to warm up to rt and stirred at this temperature for 18 h. The mixture was filtered through neutral $Al_2O_3$ and washed with $CH_2Cl_2$. The filtrated was concentrated under reduced pressure to give the title compound as a colorless oil.

2-Methyl-2-(3-nitro-propyl)-[1,3]dioxolane

In a flame dried round-bottomed flask equipped with a magnetic stir bar and a Dean-Stark apparatus and under inert atmosphere ($N_2$), crude 5-nitro-pentan-2-one (28.53 mmol) was dissolved in dry toluene (28 mL). Ethylene glycol (10.2 mL, 183.02 mmol) and p-TsOH (696 mg, 3.66 mmol) were added and the reaction mixture stirred at 120° C. for 5 h. The reaction mixture was then cooled down to rt and sat. aq. $NaHCO_3$ was added. The layers were separated and the org. layer washed with brine (2×), dried over $Na_2SO_4$, filtered, and concentrated under reduced pressure. The crude residue was purified by FC (hept-EA, 4:1) to give the title compound as a pale brown oil. TLC:rf (4:1 hept-EA)=0.21.

3-(2-Methyl-[1,3]dioxolan-2-yl)-propylamine

In a flame dried round-bottomed flask equipped with a magnetic stir bar, a mixture of 2-methyl-2-(3-nitro-propyl)-[1,3]dioxolane (1.80 g, 10.27 mmol) and Pd/C 10% (176 mg) in dry MeOH (35 mL) was stirred at rt under atmospheric $H_2$ for 11 h. The reaction mixture was then filtered and concentrated under reduced pressure to give the title compound as a colorless oil. LC-MS-conditions 02: $t_R$=0.25 min; [M+H]$^+$=146.41.

2-Acetyl-4-cyano-butyric acid ethyl ester

In a flame dried round-bottomed flask equipped with a magnetic stir bar and under inert atmosphere ($N_2$), to sodium ethylate (prepared from 62 mg sodium in 8 mL of EtOH) was added ethyl acetoacetate (9.7 mL, 76.1 mmol). Acrylonitrile (5 mL, 76.1 mmol) was then added dropwise at 40-45° C. and the reaction mixture was stirred at this temperature overnight. Ethanol was removed and the residue washed with 65 mL of water containing 3.5 mL of acetic acid, diluted with $CH_2Cl_2$ and dried over $Na_2SO_4$, filtered and concentrated under reduced pressure. The crude residue was distilled (bp=95-105° C. at 1 atm) to give the title compound. TLC:rf (7:3 hept-EA)=0.29.

5-Oxo-hexanenitrile

A mixture of 2-acetyl-4-cyano-butyric acid ethyl ester (5.70 g, 31.1 mmol) and $Na_2CO_3$ (5.52 g, 52.1 mmol) in water (55 mL) was stirred at reflux for 4 h. After cooling, $K_2CO_3$ (1.9 g) was added and the reaction mixture extracted with $Et_2O$ (3×) then with $CH_2Cl_2$ (4×). The combined organic extracts were dried over $Na_2SO_4$, filtered, and concentrated under reduced pressure. The crude residue was purified by FC (hept-EA, 65:35) to give the title compound as a colorless oil. TLC:rf (65:35 hept-EA)=0.21.

4-(2-Methyl-[1,3]dioxolan-2-yl)-butyronitrile

In a flame dried round-bottomed flask equipped with a magnetic stir bar and a Dean-Stark apparatus and under inert atmosphere ($N_2$), 5-oxo-hexanenitrile (1.69 g, 15.2 mmol) was dissolved in dry toluene (10 mL). Ethylene glycol (4.24 mL, 76.0 mmol) and p-TsOH (289 mg, 1.5 mmol) were added and the reaction mixture stirred at 120° C. for 5 h. The reaction mixture was then cooled down to rt and sat. aq. $NaHCO_3$ was added. The layers were separated and the aq. layer extracted with $CH_2Cl_2$ (2×). The combined organic extracts were dried over $Na_2SO_4$, filtered, and concentrated under reduced pressure to give the title compound as a pale yellow oil. LC-MS-conditions 02: $t_R$=0.94 min.

4-(2-Methyl-[1,3]dioxolan-2-yl)-butylamine

In a flame dried round-bottomed flask equipped with a magnetic stir bar and under inert atmosphere ($N_2$), a solution of 4-(2-methyl-[1,3]dioxolan-2-yl)-butyronitrile (2.23 g, 14.4 mmol) in dry $Et_2O$ (2.5 mL) was added to a suspension of $LiAlH_4$ (1.36 g, 35.9 mmol) in dry $Et_2O$ (50 mL). The reaction mixture was stirred at reflux for 3 h, cooled down to rt and treated with water (2 mL), 15% aq. NaOH (2 mL) and water (4 mL). The precipitate was filtered off and washed with $Et_2O$. The filtrate was dried over $Na_2SO_4$, filtered and concentrated under reduced pressure to give the title compound as a light brown oil. LC-MS-conditions 02: $t_R$=0.32 min; $[M+H]^+$=160.29.

4-Bromo-thiazole-2-carbaldehyde

In a flame dried round-bottomed flask equipped with a magnetic stir bar and under inert atmosphere ($N_2$), a solution of commercially available 2,4-dibromo-thiazole (3.50 g, 14.41 mmol) in dry $Et_2O$ (120 mL) was treated with n-BuLi (5.9 mL of a 2.5 M solution in hexanes, 14.72 mmol) at −78° C. The reaction mixture was stirred at this temperature for 30 min. N,N-Dimethylformamide (1.35 mL, 14.47 mmol) was then added and the mixture allowed to warm to rt over a period of 1 h. The reaction was quenched by the addition of sat. aq. $NH_4Cl$ (50 mL). The layers were separated and the aq. layer extracted with $Et_2O$ (3×50 mL). The combined org. extracts dried over $Na_2SO_4$, filtered, and the solvents were removed under reduced pressure. Purification of the residue by FC (10:1->3:1 hept-EA) gave the title compound as a pale yellow solid. TLC:rf (1:1 hept-EA)=0.21. LC-MS-conditions 02: $t_R$=0.81 min.

(4-Bromo-thiazol-2-yl)-methanol

In a flame dried round-bottomed flask equipped with a magnetic stir bar and under inert atmosphere ($N_2$), 4-bromo-thiazole-2-carbaldehyde (1.68 g, 8.75 mmol) was dissolved in MeOH (10 mL). $NaBH_4$ (428 mg, 10.86 mmol) was added portionwise at 0° C. and the reaction mixture stirred at rt for 1 h. Water (10 mL) was added and the mixture extracted with EA (3×20 mL). The combined org. extracts were dried over $Na_2SO_4$, filtered, and the solvents were removed under reduced pressure. Purification of the residue by FC (6:1->2:1 hept-EA) gave the title compound as a pale yellow solid. TLC:rf (1:1 hept-EA)=0.31. LC-MS-conditions 02: $t_R$=0.62 min $[M+H]^+$=194.31.

4-Bromo-2-(tert-butyl-dimethyl-silanyloxymethyl)-thiazole

In a flame dried round-bottomed flask equipped with a magnetic stir bar and under inert atmosphere ($N_2$), (4-bromo-thiazol-2-yl)-methanol (1.37 g, 7.06 mmol) was dissolved in dry $CH_2Cl_2$ (21 mL). tert-Butyldimethylsilyl chloride (1.17 g, 7.77 mmol) was added at 0° C. followed by imidazole (985 mg, 14.47 mmol). The reaction mixture was stirred at rt for 2 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure to give the title compound as a colorless oil. TLC:rf (1:1 hept-EA)=0.80.

1-[2-(tert-Butyl-dimethyl-silanyloxymethyl)-thiazol-4-yl]-ethanone

In a flame dried round-bottomed flask equipped with a magnetic stir bar and under inert atmosphere ($N_2$), to a solution of 4-bromo-2-(tert-butyl-dimethyl-silanyloxymethyl)-thiazole (1.94 g, 6.29 mmol) in dry $Et_2O$ (50 mL) was added n-BuLi (2.76 mL of a 2.5 M solution in hexanes, 6.92 mmol) at −78° C. The reaction mixture was then stirred for 30 min at −78° C. before N,N-dimethylacetamide (1.17 mL, 12.58 mmol) was added dropwise. The reaction mixture was allowed to warm up to rt over a period of 1 h and stirred at this temperature for 20 min. Sat. aq. $NH_4Cl$ (20 mL) was added, the layers separated and the aq. layer extracted with $Et_2O$ (3×30 mL). The combined org. extracts were dried over $Na_2SO_4$, filtered, and the solvent was removed under reduced pressure. Purification of the residue by FC (20:1->5:1 hept-EA) gave the title compound as a yellow solid. TLC:rf (1:1 hept-EA)=0.51. LC-MS-conditions 02: $t_R$=1.11 min; $[M+H]^+$=272.39.

2-(tert-Butyl-dimethyl-silanyloxymethyl)-4-(2-methyl-[1,3]dioxolan-2-yl)-thiazole In a flame dried round-bottomed flask equipped with a magnetic stir bar and under inert atmosphere ($N_2$), a solution of 1-[2-(tert-butyl-dimethyl-silanyloxymethyl)-thiazol-4-yl]-ethanone (1.77 g, 6.52 mmol) in ethylene glycol (7 mL) was treated with trimethylorthoformate (1.46 mL, 13.29 mmol) followed by $LiBF_4$ (125 mg, 1.30 mmol). The reaction mixture was heated at 95° C. for 4 h. Sat. aq. $Na_2CO_3$ (5 mL) was added and the mixture was extracted with $Et_2O$ (2×20 mL). The org. extracts were dried over $Na_2SO_4$, filtered, and the solvent was removed under reduced pressure. Purification of the residue by FC (20:1->3:1 hept-EA) gave the title compound as a brown oil. TLC:rf (1:1 hept-EA)=0.56. LC-MS-conditions 02: $t_R$=1.11 min; $[M+H]^+$=316.36.

[4-(2-Methyl-[1,3]dioxolan-2-yl)-thiazol-2-yl]-methanol

In a flame dried round-bottomed flask equipped with a magnetic stir bar and under inert atmosphere ($N_2$), a solution of 2-(tert-butyl-dimethyl-silanyloxymethyl)-4-(2-methyl-[1,3]dioxolan-2-yl)-thiazole (1.30 g, 4.12 mmol) in dry THF (10 mL) was treated at 0° C. with TBAF (6.2 mL of a 1M solution in THF, 6.20 mmol). The reaction mixture was stirred at 0° C. for 5 min and at rt for 1 h30. The mixture was then diluted with EA (10 mL), washed with brine (3×10 mL), dried over $MgSO_4$, filtered and concentrated under reduced pressure. Purification of the residue by FC (5:1->1:3 hept-EA) gave the title compound as a yellow oil. TLC:rf (1:2 hept-EA)=0.20. LC-MS-conditions 02: $t_R$=0.59 min; $[M+H]^+$=202.48.

[4-(2-Methyl-[1,3]dioxolan-2-yl)-thiazol-2-yl]-methylamine

In a flame dried round-bottomed flask equipped with a magnetic stir bar and under inert atmosphere ($N_2$), a solution of [4-(2-methyl-[1,3]dioxolan-2-yl)-thiazol-2-yl]-methanol (745 mg, 3.70 mmol) in dry $CH_2Cl_2$ (5 mL) was treated at 0° C. with $Et_3N$ (0.67 mL, 4.79 mmol) followed by DMAP (46 mg, 0.37 mmol) and Ms-Cl (0.37 mL, 4.67 mmol). After stirring at 0° C. for 1 h30, the reaction was quenched with water (5 mL). The org. layer was dried over $MgSO_4$, filtered, and the solvents were removed under reduced pressure to give crude methanesulfonic acid 4-(2-methyl-[1,3]dioxolan-2-yl)

thiazol-2-ylmethyl ester as a yellow oil. Part of this crude material (200 mg, 0.72 mmol) was dissolved in dry DMF (2.5 mL) and treated with NaN$_3$ (50 mg, 0.76 mmol) at 80° C. for 24 h. The reaction mixture was then cooled down to rt and partitioned between EA and water. The layers were separated and the org. layer dried over MgSO$_4$, filtered and concentrated under reduced pressure to give crude 2-azidomethyl-4-(2-methyl-[1,3]dioxolan-2-yl)thiazole as a yellow oil. LC-MS-conditions 02: $t_R$=0.82 min; [M+H]$^+$=227.46.

To a solution of the crude azide (160 mg, 0.71 mmol) in THF (4.5 mL) were added Ph$_3$P (371 mg, 1.41 mmol) and water (1 mL). The reaction mixture was stirred at 60° C. for 4 h and cooled down to rt. Sat. aq. NaHCO$_3$ and EA were then added, the layers separated and the aq. layer extracted with EA (1×). The combined organic extracts were dried over MgSO$_4$, filtered and concentrated under reduced pressure. The crude residue was purified by FC (1:0->9:1 CH$_2$Cl$_2$-MeOH) to give the title compound as a yellow oil. LC-MS-conditions 02: $t_R$=0.37 min; [M+H]$^+$=201.54.

[5-(2-Methyl-[1,3]dioxolan-2-yl)-thiophen-2-yl]-methanol

In a flame dried round-bottomed flask equipped with a magnetic stir bar and under inert atmosphere (N$_2$), to a solution of commercially available 2-methyl-2-thiophen-2-yl-[1,3]dioxolane (5.00 g, 28.49 mmol) in THF (145.0 mL) at −78° C. was added dropwise N,N,N',N'-tetramethyl-ethylendiamine (4.41 mL, 29.06 mmol) followed by n-BuLi (18.14 mL of a 1.6 M solution in hexanes, 29.06 mmol), maintaining the temperature at −78° C. The reaction mixture was then stirred for 2 h at −78° C. before DMF (6.74 mL, 87.22 mmol) was added dropwise. The cooling bath was removed and the reaction mixture was stirred for 16 h. The reaction mixture was poured in sat. aq. NaH$_4$Cl (200 mL) and extracted with EA (2×200 mL). The combined org. extracts were dried over MgSO$_4$, filtered, and the solvent was removed under reduced pressure to give crude 5-(2-methyl-[1,3]dioxolan-2-yl)-thiophene-2-carbaldehyde as an yellow oil. LC-MS-conditions 02: $t_R$=0.87 min; [M+AcCN+H]$^+$=240.32. The crude material was dissolved, under inert atmosphere (N$_2$) in MeOH (51.2 mL) and treated at 0° C., portionwise, over 20 min, with NaBH$_4$ (1.35 g, 34.19 mmol in five equal portions). The reaction mixture was stirred at rt for 45 min. The reaction mixture was poured in water (90 mL) and the aq. layer was extracted with EA (2×225 mL). The combined org. extracts were dried over MgSO$_4$, filtered, and the solvents were removed under reduced pressure. Purification of the residue by FC (50:50 hept-EA) gave the title compound. TLC:rf (50:50 hept-EA)=0.40. LC-MS-conditions 02: $t_R$=0.72 min; [M+H]$^+$=201.46.

[5-(2-Methyl-[1,3]dioxolan-2-yl)-thiophen-2-yl]-methylamine

In a flame dried round-bottomed flask equipped with a magnetic stir bar and under inert atmosphere (N$_2$), a solution of [5-(2-methyl-[1,3]dioxolan-2-yl)thiophen-2-yl]-methanol (5.00 g, 25.0 mmol) in dry CH$_2$Cl$_2$ (46 mL) was treated at 0° C. with Et$_3$N (4.5 mL, 32.5 mmol) followed by DMAP (305 mg, 2.5 mmol) and Ms-Cl (2.3 mL, 30.0 mmol). After stirring at rt for 2 h, the reaction was quenched with water (50 mL). The org. layer was dried over MgSO$_4$, filtered, and the solvents were removed under reduced pressure to give crude 2-(5-chloromethyl-thiophen-2-yl)-2-methyl-[1,3]dioxolane as a yellow oil. Part of this crude material (953 mg, 4.36 mmol) was dissolved in dry DMF (15 mL) and treated with NaN$_3$ (859 mg, 13.08 mmol) at 80° C. for 24 h. The reaction mixture was then cooled down to rt and partitioned between EA and water. The layers were separated and the org. layer dried over Na$_2$SO$_4$, filtered and concentrated under reduced pressure to give crude 2-azidomethyl-5-(2-methyl-[1,3]dioxolan-2-yl)thiophene as a yellow oil. LC-MS-conditions 02: $t_R$=0.97 min; [M+H]$^+$=226.50.

To a solution of the crude azide (150 mg, 0.67 mmol) in THF (6 mL) were added Ph$_3$P (polymer-supported, 1.6 mmol/g, 2.0 eq.) and water (2 mL). The reaction mixture was stirred at 60° C. until reaction completion, cooled down to rt and filtered. Sat. aq. NaHCO$_3$ and EA were then added, the layers separated and the aq. layer extracted with EA (1×). The combined organic extracts were dried over MgSO$_4$, filtered and concentrated under reduced pressure. The title compound was obtained as a yellow oil. LC-MS-conditions 01: $t_R$=0.50 min; [M+H]$^+$=199.99.

1-Oxazol-2-yl-ethanone

In a flame dried round-bottomed flask equipped with a magnetic stir bar and under inert atmosphere (N$_2$), a solution of commercially available 1,3-oxazole (3.25 mL, 48.49 mmol) in dry THF (34.00 mL) was treated with isopropyl-magnesium chloride (24.00 mL of a 2.0 M solution in THF, 48.00 mmol) at −15° C. (while the internal temperature was kept below −10° C.). The reaction mixture was stirred at this temperature for 40 min. A solution of N-methoxy-N-methyl-lacetamide (4.12 mL, 38.79 mmol) in dry THF (10 mL) was then added dropwise while keeping the internal temperature below −14° C. The reaction mixture was allowed to warm to rt and stirred at this temperature overnight. The reaction was quenched by the addition of 20% aq. NH$_4$Cl (150 mL). The layers were separated and the aq. layer extracted with Et$_2$O (3×100 mL). The combined org. extracts dried over MgSO$_4$, filtered, and the solvents were removed under reduced pressure. Purification of the residue by FC (6:4 hexane-Et$_2$O) gave the title compound as an orange oil. TLC:rf (6:4 hexane-Et$_2$O)=0.27. LC-MS-conditions 02: $t_R$=0.47 min.

1-Oxazol-2-yl-ethanol

In a flame dried round-bottomed flask equipped with a magnetic stir bar and under inert atmosphere (N$_2$), 1-oxazol-2-yl-ethanone (1.76 g, 15.84 mmol) was dissolved in MeOH (30 mL). NaBH$_4$ (811 mg, 20.59 mmol) was added portionwise at 0° C. and the reaction mixture stirred at rt for 1 h30. Water (30 mL) was added and the MeOH removed under reduced pressure. The mixture was then extracted with EA (7×50 mL). The combined org. extracts were dried over MgSO$_4$, filtered, and the solvents were removed under reduced pressure. The title compound was obtained as a pale yellow oil. LC-MS-conditions 02: $t_R$=0.33 min.

2-[1-(tert-Butyl-dimethyl-silanyloxy)-ethyl]-oxazole

In a flame dried round-bottomed flask equipped with a magnetic stir bar and under inert atmosphere (N$_2$), 1-oxazol-2-yl-ethanol (1.21 g, 10.71 mmol) was dissolved in dry THF (50 mL). tert-Butyldimethylsilyl chloride (3.23 g, 21.43 mmol) was added at rt followed by imidazole (1.46 g, 21.43 mmol). The reaction mixture was stirred at rt for 16 h. Sat. aq. NH$_4$Cl (100 mL) and EA (100 mL) were added, the layers separated and the aq. layer extracted with EA (1×100 mL). The combined org. extracts were dried over MgSO$_4$, filtered, and the solvent removed under reduced pressure. Purification of the residue by FC (4:1 hexane-Et$_2$O) gave the title compound as a colorless oil. TLC:rf (4:1 hexane-Et$_2$O)=0.39. LC-MS-conditions 02: $t_R$=1.08 min; [M+H]$^+$=228.56.

2-[1-(tert-Butyl-dimethyl-silanyloxy)-ethyl]-oxazole-5-carbaldehyde

In a flame dried round-bottomed flask equipped with a magnetic stir bar and under inert atmosphere (N$_2$), to a solution of 2-[1-(tert-butyl-dimethyl-silanyloxy)-ethyl]-oxazole (733 mg, 3.22 mmol) in dry THF (16 mL) was added tert-BuLi (2.62 mL of a 1.6 M solution in pentane, 4.19 mmol) at −78° C. The reaction mixture was then stirred for 1 h at −40° C. and cooled to −78° C. before N,N-dimethylformamide (0.49 mL, 6.44 mmol) was added dropwise. The reaction mixture was allowed to warm up to rt over a period of 1 h and stirred at this temperature for 2 h. Water (30 mL) and sat. aq. NH$_4$Cl (20 mL) were added, the layers separated and the aq. layer extracted with EA (2×30 mL). The combined org. extracts were dried over MgSO$_4$, filtered, and the solvent was removed under reduced pressure. Purification of the residue by FC (4:1 hept-EA) gave the title compound as a colorless oil. TLC:rf (4:1 hept-EA)=0.33. LC-MS-conditions 02: $t_R$=1.08 min; [M+H]$^+$=256.37.

2-[1-(tert-Butyl-dimethyl-silanyloxy)-ethyl]-oxazol-5-yl-methanol

In a flame dried round-bottomed flask equipped with a magnetic stir bar and under inert atmosphere (N$_2$), 2-[1-(tert-butyl-dimethyl-silanyloxy)-ethyl]-oxazole-5-carbaldehyde (457 mg, 1.79 mmol) was dissolved in MeOH (8 mL). NaBH$_4$ (92 mg, 2.33 mmol) was added portionwise at 0° C. and the reaction mixture stirred at rt for 20 min. Water (16 mL) was added and the MeOH removed under reduced pressure. The mixture was then extracted with EA (2×20 mL). The combined org. extracts were dried over MgSO$_4$, filtered, and the solvents were removed under reduced pressure. The title compound was obtained as a colorless oil. LC-MS-conditions 02: $t_R$=0.97 min; [M+H]$^+$=258.37.

2-[1-(tert-Butyl-dimethyl-silanyloxy)-ethyl]-oxazol-5-yl-methylamine

In a flame dried round-bottomed flask equipped with a magnetic stir bar and under inert atmosphere (N$_2$), a solution of 2-[1-(tert-butyl-dimethyl-silanyloxy)-ethyl]-oxazol-5-yl-methanol (760 mg, 2.95 mmol) in dry CH$_2$Cl$_2$ (15 mL) was treated at 0° C. with Et$_3$N (0.53 mL, 3.82 mmol) followed by DMAP (36 mg, 0.30 mmol) and Ms-Cl (0.30 mL, 3.73 mmol). After stirring at 0° C. until reaction completion, the reaction was quenched with water (50 mL). The org. layer was dried over Na$_2$SO$_4$, filtered, and the solvents were removed under reduced pressure to give crude 2-[1-(tert-butyl-dimethyl-silanyloxy)-ethyl]-5-chloromethyl-oxazole as a yellow oil. The crude material (2.95 mmol) was dissolved in dry DMF (15 mL) and treated with NaN$_3$ (205 mg, 3.01 mmol) at 80° C. for 40 h. The reaction mixture was then cooled down to rt and partitioned between EA and water. The layers were separated and the org. layer dried over MgSO$_4$, filtered and concentrated under reduced pressure to give crude 5-azidomethyl-2-[1-(tert-butyl-dimethyl-silanyloxy)-ethyl]-oxazole as a yellow oil. LC-MS-conditions 02: $t_R$=1.12 min; [M+H]$^+$=283.55.

To a solution of the crude azide (700 mg, 2.48 mmol) in THF (12 mL) were added Ph$_3$P (polymer-supported, 1.6 mmol/g, 3.0 eq.) and water (4 mL). The reaction mixture was stirred at 60° C. until reaction completion, cooled down to rt and filtered. Sat. aq. NaHCO$_3$ and EA were then added, the layers separated and the aq. layer extracted with EA (1×). The combined organic extracts were dried over MgSO$_4$, filtered and concentrated under reduced pressure. The crude residue was purified by FC (1:0->9:1 CH$_2$Cl$_2$-MeOH+2% Et$_3$N) to give the title compound as a yellow oil. LC-MS-conditions 01: $t_R$=0.75 min; [M+H]$^+$=257.08.

(2-Bromo-thiazol-5-yl)-methanol

In a flame dried round-bottomed flask equipped with a magnetic stir bar and under inert atmosphere (N$_2$), 2-bromo-thiazole-5-carbaldehyde (10.66 g, 55.51 mmol) was dissolved in MeOH (150 mL). NaBH$_4$ (2.71 g, 68.91 mmol) was added portionwise at 0° C. and the reaction mixture stirred at 0° C. for 1 h. Water (10 mL) was added and the mixture extracted with EA (3×70 mL). The combined org. extracts were dried over Na$_2$SO$_4$, filtered, and the solvents were removed under reduced pressure to give crude (2-bromo-thiazol-5-yl)-methanol as an orange oil. TLC:rf (1:1 hept-EA)=0.25. LC-MS-conditions 01: $t_R$=0.56 min [M+H]$^+$=193.81.

2-Bromo-5-(tert-butyl-dimethyl-silanyloxymethyl)-thiazole

In a flame dried round-bottomed flask equipped with a magnetic stir bar and under inert atmosphere (N$_2$), (2-bromo-thiazol-5-yl)-methanol (10.65 g, 54.88 mmol) was dissolved in dry CH$_2$Cl$_2$ (150 mL). tert-Butyldimethylsilyl chloride (9.58 g, 60.37 mmol) was added at 0° C. followed by imidazole (7.66 g, 112.51 mmol). The reaction mixture was stirred at rt until completion of the reaction. Water (100 mL) was added, the layers separated and the org. layer dried over MgSO$_4$, filtered, and the solvent removed under reduced pressure. Purification of the residue by FC (1:0 to 30:1 hept-EA) gave the title compound as a yellow oil. TLC:rf (9:1 hept-EA)=0.46. LC-MS-conditions 01: $t_R$=1.13 min [M+H]$^+$=309.90.

1-[5-(tert-Butyl-dimethyl-silanyloxymethyl)-thiazol-2-yl]-ethanone

In a flame dried round-bottomed flask equipped with a magnetic stir bar and under inert atmosphere (N$_2$), to a solution of n-BuLi (4.3 mL of a 2.5 M solution in hexanes, 10.75 mmol) in dry Et$_2$O (15 mL) was added a solution of 2-bromo-5-(tert-butyl-dimethyl-silanyloxymethyl)-thiazole (3.03 g, 9.83 mmol) in dry Et$_2$O (10 mL) at −78° C. The reaction mixture was then stirred for 30 min at −78° C. before N,N-dimethylacetamide (1.9 mL, 20.43 mmol) was added dropwise. The reaction mixture was stirred at −78° C. for 1 h. Sat. aq. NH$_4$Cl (20 mL) was added, the layers separated and the aq. layer extracted with Et$_2$O (2×30 mL). The combined org. extracts were dried over Na$_2$SO$_4$, filtered, and the solvent was removed under reduced pressure to give the title compound as an orange oil. TLC:rf (2:1 hept-EA)=0.60. LC-MS-conditions 02: $t_R$=1.14 min; [M+H]$^+$=272.32.

(2-(2-Methyl-[1,3]dioxolan-2-yl)thiazol-5-yl)methanol

In a flame dried round-bottomed flask equipped with a magnetic stir bar and under inert atmosphere (N$_2$), a solution of 1-[5-(tert-butyl-dimethyl-silanyloxymethyl)-thiazol-2-yl]-ethanone (1.00 g, 3.68 mmol) in ethylene glycol (4 mL) was treated with trimethylorthoformate (0.82 mL, 7.51 mmol) followed by LiBF$_4$ (70 mg, 0.74 mmol). The reaction mixture was heated at 95° C. for 2 days. Sat. aq. Na$_2$CO$_3$ (5 mL) was added and the mixture was extracted with Et$_2$O (3×20 mL). The org. extracts were dried over Na$_2$SO$_4$, filtered, and the solvent was removed under reduced pressure. The crude residue (mixture of silylated/desilylated products) in dry THF (10 mL) was treated at rt with TBAF (1.1 mL of a 1M solution in THF, 1.10 mmol). The reaction mixture was stirred at rt until completion of the reaction. The mixture was then diluted with EA, washed with brine, dried over MgSO$_4$, filtered and concentrated under reduced pressure. Purification of the residue by FC (4:1->1:2 hept-EA) gave the title compound as a pale yellow solid. TLC: rf (EA)=0.47. LC-MS-conditions 02: $t_R$=0.60 min; [M+H]$^+$=202.46.

(2-(2-Methyl-[1,3]dioxolan-2-yl)thiazol-5-yl)methanamine

In a flame dried round-bottomed flask equipped with a magnetic stir bar and under inert atmosphere (N$_2$), a solution of (2-(2-methyl-[1,3]dioxolan-2-yl)thiazol-5-yl)methanol (389 mg, 1.93 mmol) in dry CH$_2$Cl$_2$ (10 mL) was treated at 0° C. with Et$_3$N (0.35 mL, 2.50 mmol) followed by DMAP (24 mg, 0.19 mmol) and Ms-Cl (0.19 mL, 2.40 mmol). After stirring at 0° C. for 1 h, the reaction was quenched with water (10 mL). The org. layer was dried over MgSO$_4$, filtered, and the solvents were removed under reduced pressure. Purification by FC (1:1->1:2 hept-EA+1% Et$_3$N) gave pure (2-(2-methyl-[1,3]dioxolan-2-yl)thiazol-5-yl)methyl methanesulfonate as a pale yellow oil. Part of this material (140 mg, 0.50 mmol) was dissolved in dry DMF (1 mL) and treated with NaN$_3$ (35 mg, 0.53 mmol) at 80° C. for 1 h30. The reaction mixture was then cooled down to rt and partitioned between EA and water. The layers were separated and the org. layer dried over MgSO$_4$, filtered and concentrated under reduced pressure to give crude 5-(azidomethyl)-2-(2-methyl-[1,3]dioxolan-2-yl)thiazole as a brown oil. LC-MS-conditions 01: $t_R$=0.80 min; [M+H]$^+$=226.96.

To a solution of the crude azide (113 mg, 0.50 mmol) in THF (6 mL) were added polymer supported Ph$_3$P (262 mg, 1.00 mmol) and water (2 mL). The reaction mixture was stirred at 60° C. for 1 h, cooled down to rt, filtered and concentrated under reduced pressure. The residue was redissolved in CH$_2$Cl$_2$/MeOH 9:1, dried over MgSO$_4$, filtered and concentrated under reduced pressure to give the title compound as an orange oil. LC-MS-conditions 02: $t_R$=0.48 min.

1-(2-Bromo-thiazol-5-yl)-ethanol

In a flame dried round-bottomed flask equipped with a magnetic stir bar and under inert atmosphere (N$_2$), a solution of commercially available 2-bromo-thiazole-5-carbaldehyde (1.96 g, 10.00 mmol) in CH$_2$Cl$_2$ (20 mL) was treated at 0° C. with trimethylaluminum (15 mL of a 2M solution in toluene, 30.00 mmol). The reaction mixture was then stirred at 0° C. for 45 min. CH$_2$Cl$_2$ (100 mL) was then added followed by sat. aq. NH$_4$Cl (100 mL). The mixture was then treated with 1N HCl (50 mL) and the aq. layer was extracted with CH$_2$Cl$_2$ (150 mL). The combined org. extracts were dried over MgSO$_4$, filtered, and the solvents were removed under reduced pressure to give the title compound as an orange oil. TLC: rf (1:1 hept-EA)=0.38. LC-MS-conditions 02: $t_R$=0.70 min; [M+H]$^+$=208.38.

1-(2-Bromo-thiazol-5-yl)-ethanone

In a flame dried round-bottomed flask equipped with a magnetic stir bar and under inert atmosphere (N$_2$), a solution of 1-(2-bromo-thiazol-5-yl)-ethanol (14.85 g, 71.37 mmol) in CH$_3$CN (160 mL) was treated at rt with MnO$_2$ (34.47 g, 356.84 mmol) and the reaction mixture was stirred for 20 h at rt before being filtered through Celite. The solvent was removed under reduced pressure to give the title compound as a yellow solid. TLC:rf (1:1 hept-EA)=0.54. LC-MS-conditions 02: $t_R$=0.79 min.

2-Bromo-5-(2-methyl-[1,3]dioxolan-2-yl)-thiazole

In a flame dried round-bottomed flask equipped with a magnetic stir bar and a condenser under inert atmosphere (N$_2$), a solution of 1-(2-bromo-thiazol-5-yl)-ethanone (16.22 g, 78.71 mmol) in ethylene glycol (85 mL) was treated with trimethylorthoformate (18 mL, 164.19 mmol) followed by LiBF$_4$ (1.51 g, 15.74 mmol). The reaction mixture was heated at 95° C. for 2 days. Sat. aq. NaHCO$_3$ was added and the mixture was extracted with Et$_2$O (3×). The org. extracts were washed with brine, dried over MgSO$_4$, filtered, and the solvent was removed under reduced pressure. Purification of the residue by FC (20:1 to 3:1 hept-EA) gave the title compound as a yellow solid. TLC:rf (1:1 hept-EA)=0.63. LC-MS-conditions 02: $t_R$=0.89 min; [M+H]$^+$=250.24.

5-(2-Methyl-[1,3]dioxolan-2-yl)-thiazole-2-carbaldehyde

In a flame dried round-bottomed flask equipped with a magnetic stir bar and under inert atmosphere (N$_2$), a solution of 2-bromo-5-(2-methyl-[1,3]dioxolan-2-yl)thiazole (5.00 g, 20.00 mmol) in dry Et$_2$O (40 mL) was added to a n-BuLi (8.40 mL of a 2.5M solution in hexanes, 21.00 mmol) at −78° C. The reaction mixture was then stirred for 30 min at −78° C. before DMF (2.5 mL, 32.29 mmol) was added dropwise. The reaction mixture was stirred at −60° C. for 1 h. Sat. aq. NH$_4$Cl (100 mL) was added, followed by aq. 1N HCl (50 mL). The layers separated and the aq. layer extracted with Et$_2$O (5×). The combined org. extracts were dried over Na$_2$SO$_4$, filtered, and the solvent was removed under reduced pressure to give the title compound as an orange oil. TLC:rf (1:1 hept-EA)=0.50. LC-MS-conditions 01: $t_R$=0.78 min; [M+H]$^+$=199.93.

[5-(2-Methyl-[1,3]dioxolan-2-yl)-thiazol-2-yl]-methanol

In a flame dried round-bottomed flask equipped with a magnetic stir bar and under inert atmosphere (N$_2$), 5-(2-methyl-[1,3]dioxolan-2-yl)thiazole-2-carbaldehyde (5.12 g, 25.70 mmol) was dissolved in MeOH (60 mL). NaBH$_4$ (1.26 g, 31.89 mmol) was added portionwise at 0° C. and the reaction mixture stirred at 0° C. for 1 h. Water was added and the mixture extracted with EA (3×). The combined org. extracts were dried over Na$_2$SO$_4$, filtered, and the solvents were removed under reduced pressure to give the title compound as an orange oil. TLC:rf (1:1 hept-EA)=0.31. LC-MS-conditions 02: $t_R$=0.64 min; [M+H]$^+$=202.52.

(5-(2-Methyl-[1,3]dioxolan-2-yl)thiazol-2-yl)methanamine

In a flame dried round-bottomed flask equipped with a magnetic stir bar and under inert atmosphere (N$_2$), a solution of [5-(2-methyl-[1,3]dioxolan-2-yl)-thiazol-2-yl]-methanol (500 mg, 2.48 mmol) in dry CH$_2$Cl$_2$ (15 mL) was treated at 0° C. with Et$_3$N (0.45 mL, 3.21 mmol) followed by DMAP (31 mg, 0.25 mmol) and Ms-Cl (0.25 mL, 3.14 mmol). After stirring at 0° C. for 1 h, the reaction was quenched with water (10 mL). The org. layer was dried over MgSO₄, filtered, and the solvents were removed under reduced pressure to give crude (5-(2-methyl-[1,3]dioxolan-2-yl)-thiazol-2-yl)methyl methanesulfonate as a brown oil. This material was dissolved in dry DMF (10 mL) and treated with NaN₃ (175 mg, 2.66 mmol) at 80° C. until completion of the reaction. The reaction mixture was then cooled down to rt and partitioned between EA and water. The layers were separated and the org. layer dried over MgSO₄, filtered and concentrated under reduced pressure to give crude 2-(azidomethyl)-5-(2-methyl-[1,3]dioxolan-2-yl)-thiazole as a yellow oil. LC-MS-conditions 02: $t_R$=0.86 min; [M+H]⁺=227.47.

To a solution of the crude azide (565 mg, 2.50 mmol) in THF (12 mL) were added polymer-supported Ph₃P (2.0 eq.) and water (4 mL). The reaction mixture was stirred at 60° C. until completion of the reaction, cooled down to rt, filtered and partitioned between EA and sat. aq. NaHCO₃. The layers were separated and the aq. layer extracted with EA. The combined org. extracts were dried over MgSO₄, filtered and concentrated under reduced pressure to give the title compound as a brown oil after purification by FC (CH₂Cl₂-MeOH 1:0 to 9:1). LC-MS-conditions 01: $t_R$=0.38 min; [M+H]⁺=200.96.

(4-Bromothiazol-2-yl)methanamine

In a flame dried round-bottomed flask equipped with a magnetic stir bar and under inert atmosphere (N₂), a solution of (4-bromo-thiazol-2-yl)-methanol (695 mg, 3.58 mmol) in dry CH₂Cl₂ (10 mL) was treated at 0° C. with Et₃N (0.67 mL, 4.74 mmol) followed by DMAP (44 mg, 0.36 mmol) and Ms-Cl (0.36 mL, 4.65 mmol). After stirring at 0° C. for 1 h, the reaction was quenched with water (10 mL). The org. layer was dried over MgSO₄, filtered, and the solvents were removed under reduced pressure to give crude (4-bromothiazol-2-yl)methyl methanesulfonate as a brown oil. The crude material was dissolved in dry DMF (6 mL) and treated with NaN₃ (257 mg, 3.91 mmol) at 80° C. until completion of the reaction. The reaction mixture was then cooled down to rt and partitioned between EA and water. The layers were separated and the org. layer dried over MgSO₄, filtered and concentrated under reduced pressure to give crude 2-(azidomethyl)-4-bromothiazole as a yellow oil. LC-MS-conditions 01: $t_R$=0.83 min.

To a solution of the crude azide in THF (12 mL) were added polymer supported Ph₃P (5.16 mmol) and water (4 mL). The reaction mixture was stirred at 60° C. until completion of the reaction, cooled down to rt and filtered. The filtrate was partitioned between EA and aq. sat. NaHCO₃, the layers separated and the aq. layer extracted with EA. The combined org. extracts were dried over MgSO₄, filtered and concentrated under reduced pressure to give the title compound as an orange oil. LC-MS-conditions 02: $t_R$=0.24 min; [M+H]⁺=192.85.

(E)-2-Methyl-3-phenylacrylamide

In a flame dried round-bottomed flask equipped with a magnetic stir bar and under inert atmosphere (N₂), a solution of alpha-methylcinnamic acid (19.0 g, 116 mmol) and Et₃N (17.1 mL, 122 mmol) in dry THF (500 mL) was treated with ethyl chloroformate (11.4 mL, 117 mmol) at 0° C. The reaction mixture was stirred at 0° C. for 15 min then aq. NH₃ (250 mL) in THF (150 mL) was added. The reaction mixture was vigorously stirred at 0° C. for 30 min and at rt for 1 h30. The layers were then separated, the aq. layer extracted with CH₂Cl₂ (2×) and the combined organic extracts were concentrated under reduced pressure. The residue was partitioned between water and CH₂Cl₂, the layers separated and the aq. layer extracted with CH₂Cl₂ (2×). The combined org. extracts were dried (MgSO₄), filtered and concentrated under reduced pressure to give the title compound as a white solid. LC-MS-conditions 01: $t_R$=0.75 min; [M+H]⁺=162.07.

(E)-2-(1-Phenylprop-1-en-2-yl)oxazole-4-carboxylic acid ethyl ester

In a flame dried round-bottomed flask equipped with a magnetic stir bar and under inert atmosphere (N₂), a suspension of (E)-2-methyl-3-phenylacrylamide (29.4 g, 0.18 mol) and NaHCO₃ (68.7 g, 0.82 mol) in THF (500 mL) was treated with 3-bromo-2-oxo-propionic acid ethyl ester (35.6 mL, 0.24 mol) and the reaction mixture was heated at reflux for 20 h. 3-Bromo-2-oxo-propionic acid ethyl ester (10.0 mL, 0.68 mol) was added again and the reaction mixture was stirred at reflux for 10 h. The reaction mixture was then filtered over celite and the solvents were evaporated under reduced pressure. The residue was dissolved in THF (500 mL) and treated at 0° C., dropwise, with trifluoroacetic anhydride (78.0 mL, 0.55 mol). The reaction mixture was then stirred at rt overnight. Sat. aq. Na₂CO₃ was added and the mixture was extracted with EA (4×), dried over MgSO₄, filtered, and the solvent was removed under reduced pressure. Purification of the residue by FC (0:1->1:9 EA-Hept) gave the title compound as a brown oil. TLC:rf (1:9 EA-Hept)=0.13. LC-MS-conditions 01: $t_R$=1.02 min; [M+H]⁺=257.97.

2-Acetyl-oxazole-4-carboxylic acid ethyl ester

In a flame dried round-bottomed flask equipped with a magnetic stir bar and under inert atmosphere (N₂), a solution of NaIO₄ (23 g, 108 mmol) in water (150 mL) was slowly added to a vigorously stirred suspension of silica gel (110 g) in acetone (500 mL). The mixture was then concentrated under reduced pressure and the lumpy solid slurried in CH₂Cl₂ and the solvent was evaporated under reduced pressure. CH₂Cl₂ (500 mL) was added and the reaction mixture was treated at rt with (E)-2-(1-phenylprop-1-en-2-yl)oxazole-4-carboxylic acid ethyl ester (8.3 g, 32 mmol) and RuCl₃ hydrate (1.1 g, 2 mmol). The reaction mixture was stirred at rt in the dark for 60 min, filtered and concentrated under reduced pressure. Purification of the residue by FC (1:0 to 1:5 petroleum ether-Et₂O) gave the title compound as a pale yellow solid. TLC:rf (1:1 EA-Hept)=0.52. LC-MS-conditions 01: $t_R$=0.70 min; [M+H]⁺=183.99.

2-(2-Methyl-[1,3]dioxolan-2-yl)-oxazole-4-carboxylic acid ethyl ester

In a flame dried round-bottomed flask equipped with a magnetic stir bar and under inert atmosphere (N₂), a solution of 2-acetyl-oxazole-4-carboxylic acid ethyl ester (7.0 g, 38.0 mmol) in ethylene glycol (42.7 mL) was treated with trimethylorthoformate (10.5 mL, 96.0 mmol) followed by LiBF₄ (0.73 g, 8.0 mmol). The reaction mixture was heated at 95° C. until completion of the reaction. Aq. 0.5 M Na₂CO₃ was added and the mixture was extracted with Et₂O. The org. layer was washed with aq. 0.5 M Na₂CO₃ (2×), dried over Na₂SO₄, filtered, and the solvent was removed under reduced pressure to give the title compound as a yellow oil. LC-MS-conditions 01: $t_R$=0.76 min; [M+H]⁺=227.99.

(2-(2-Methyl-[1,3]dioxolan-2-yl)oxazol-4-yl)methanol

In a flame dried round-bottomed flask equipped with a magnetic stir bar and under inert atmosphere (N₂), to an ice-cold solution of 2-(2-methyl-[1,3]dioxolan-2-yl)-oxazole-4-carboxylic acid ethyl ester (5.05 g, 22.2 mmol) in dry THF (80 mL) was added an ice-cold solution of LiAlH$_4$ (1.0 M in THF, 24.7 mL, 24.7 mmol). The reaction mixture was stirred at 0° C. until completion of the reaction. Water (2.0 mL) was carefully added at 0° C. followed by aq. 1 M NaOH (2.0 mL) and water (2.0 mL). The resulting suspension was stirred at rt for 1 h, filtered (+EA) and the filtrate concentrated under reduced pressure to give the title compound as a yellow oil. TLC: rf (EA)=0.18. LC-MS-conditions 05c: $t_R$=0.22 min; [M+H]$^+$=186.30.

(2-(2-Methyl-[1,3]dioxolan-2-yl)oxazol-4-yl)methanamine

In a flame dried round-bottomed flask equipped with a magnetic stir bar and under inert atmosphere (N$_2$), a solution of (2-(2-methyl-[1,3]dioxolan-2-yl)oxazol-4-yl)methanol (235 mg, 1.27 mmol) in dry CH$_2$Cl$_2$ (10 mL) was treated at 0° C. with Et$_3$N (0.24 mL, 1.68 mmol) followed by DMAP (16 mg, 0.13 mmol) and Ms-Cl (0.13 mL, 1.65 mmol). After stirring at 0° C. for 1 h, the reaction was quenched with water (10 mL). The org. layer was dried over MgSO$_4$, filtered, and the solvents were removed under reduced pressure to give crude (2-(2-methyl-[1,3]dioxolan-2-yl)oxazol-4-yl)methyl methanesulfonate as a brown oil. The crude material was dissolved in dry DMF (6 mL) and treated with NaN$_3$ (93 mg, 1.41 mmol) at 80° C. until completion of the reaction. The reaction mixture was then cooled down to rt and partitioned between EA and water. The layers were separated and the org. layer dried over MgSO$_4$, filtered and concentrated under reduced pressure to give crude 4-(azidomethyl)-2-(2-methyl-1,3-dioxolan-2-yl)oxazole as a brown oil. To a solution of the crude azide in THF (6 mL) were added polymer-supported Ph$_3$P (1.2 eq.) and water (2 mL). The reaction mixture was stirred at 60° C. until completion of the reaction, cooled down to rt and filtered. The filtrate was partitioned between EA and aq. sat. NaHCO$_3$ and the layers separated. The aq. layer was concentrated under reduced pressure, the residue triturated in EtOH and the solid filtered off. The filtrate was dried over Na$_2$SO$_4$, filtered and concentrated under reduced pressure to give the title compound as an orange oil. LC-MS-conditions 01: $t_R$=0.31 min; [M+H]$^+$=185.01.

(2-Bromo-thiazol-5-yl)methanamine

In a flame dried round-bottomed flask equipped with a magnetic stir bar and under inert atmosphere (N$_2$), a solution of (2-bromo-thiazol-5-yl)-methanol (621 mg, 3.20 mmol) in dry CH$_2$Cl$_2$ (10 mL) was treated at 0° C. with Et$_3$N (0.60 mL, 4.23 mmol) followed by DMAP (39 mg, 0.32 mmol) and Ms-Cl (0.33 mL, 4.15 mmol). After stirring at 0° C. for 1 h, the reaction was quenched with water (10 mL). The org. layer was dried over MgSO$_4$, filtered, and the solvents were removed under reduced pressure to give crude (2-bromothiazol-5-yl)methyl methanesulfonate as a colorless oil. The crude material was dissolved in dry DMF (15 mL) and treated with NaN$_3$ (223 mg, 3.40 mmol) at 80° C. until completion of the reaction. The reaction mixture was then cooled down to rt and partitioned between EA and water. The layers were separated and the org. layer washed with water (2×), dried over MgSO$_4$, filtered and concentrated under reduced pressure to give crude 5-(azidomethyl)-2-bromothiazole as a yellow oil. To a solution of the crude azide in THF (12 mL) were added polymer-supported Ph$_3$P (1.2 eq.) and water (4 mL). The reaction mixture was stirred at 55° C. until completion of the reaction, cooled down to rt and filtered. The filtrate was partitioned between EA and aq. 1N NaOH/aq. sat. NaHCO$_3$ and the layers separated. The aq. layer was extracted with EA and the combined org. extracts dried over MgSO$_4$, filtered and concentrated under reduced pressure to give the title compound as a yellow oil. LC-MS-conditions 01: $t_R$=0.16 min; [M+CH$_3$CN+H]$^+$=233.91.

(E)-2-Styryl-oxazole-4-carboxylic acid ethyl ester

In a flame dried round-bottomed flask equipped with a magnetic stir bar and under inert atmosphere (N$_2$), a suspension of 3-phenyl-acrylamide (10.31 g, 67.95 mmol) and NaHCO$_3$ (28.47 g, 339.73 mmol) in THF (260 mL) was treated with 3-bromo-2-oxo-propionic acid ethyl ester (13.04 mL, 88.33 mmol) and the reaction mixture was heated at reflux for 15 h. 3-Bromo-2-oxo-propionic acid ethyl ester (13.04 mL, 88.33 mmol) was added again and the reaction mixture was stirred at reflux for 15 h. The reaction mixture was then filtered over celite and the solvents were evaporated under reduced pressure. The residue was dissolved in THF (30 mL) and treated at 0° C., dropwise, with trifluoroacetic anhydride (30.0 mL, 215.83 mmol). The reaction mixture was then stirred at rt overnight. Sat. aq. Na$_2$CO$_3$ was added and the mixture was extracted with EA (3×150 mL), dried over MgSO$_4$, filtered, and the solvent was removed under reduced pressure. Purification of the residue by FC (1:9 EA-Hept) gave the title compound as a yellow solid. TLC:rf (1:9 EA-Hept)=0.1. LC-MS-conditions 02: $t_R$=1.01 min; [M+H]$^+$=244.48.

2-Formyl-oxazole-4-carboxylic acid ethyl ester

In a flame dried round-bottomed flask equipped with a magnetic stir bar and under inert atmosphere (N$_2$), a solution of NaIO$_4$ (3.21 g, 15.00 mmol) in water (26.0) mL was slowly added to a vigorously stirred suspension of silica gel (15.0 g) in acetone (60.0 mL). The mixture was then concentrated under reduced pressure and the lumpy solid slurried in CH$_2$Cl$_2$ and the solvent was evaporated under reduced pressure. CH$_2$Cl$_2$ (40.0 mL) was added and the reaction mixture was treated at rt with (E)-2-styryl-oxazole-4-carboxylic acid ethyl ester (1.22 g, 5.00 mmol) and RuCl$_3$ hydrate (82 mg, 0.15 mmol). The reaction mixture was stirred at rt in the dark for 30 min, filtered and concentrated under reduced pressure. Purification of the residue by FC (1:9 to 1:2 EA-Hept) gave the title compound as a yellow solid. TLC:rf (3:2 EA-Hept)= 0.21. LC-MS-conditions 02: $t_R$=0.51 min; [M+H$_2$O+H]$^+$= 188.50.

2-Hydroxymethyl-oxazole-4-carboxylic acid ethyl ester

In a flame dried round-bottomed flask equipped with a magnetic stir bar and under inert atmosphere (N$_2$), 2-formyl-oxazole-4-carboxylic acid ethyl ester (272 mg, 1.61 mmol) was dissolved in EtOH (5.0 mL). NaBH$_4$ (112 mg, 2.84 mmol) was added portionwise at 0° C. and the reaction mixture stirred at 0° C. for 1 h. Sat. aq. NH$_4$Cl was added and the mixture extracted with EA (5×10 mL). The combined org. extracts were dried over Na$_2$SO$_4$, filtered, and the solvents were removed under reduced pressure to give the title compound as a yellow oil. TLC: rf (EA)=0.50. LC-MS-conditions 02: $t_R$=0.58 min; [M+H]$^+$=172.03.

2-(tert-Butyl-dimethyl-silanyloxymethyl)-oxazole-4-carboxylic acid ethyl ester

In a flame dried round-bottomed flask equipped with a magnetic stir bar and under inert atmosphere (N$_2$), 2-hydroxymethyl-oxazole-4-carboxylic acid ethyl ester (275 mg, 1.61 mmol) was dissolved in dry $CH_2Cl_2$ (5.0 mL). tert-Butyldimethylsilyl chloride (510 mg, 3.22 mmol) was added at rt followed by imidazole (221 mg, 3.22 mmol). The reaction mixture was stirred at rt for 30 min. Water was added, the layers were separated and the org. layer was dried over $Na_2SO_4$, filtered, and the solvent removed under reduced pressure. Purification of the residue by FC (1:20 to 1:9 EA-Hept) gave the title compound as a colorless oil. TLC:rf (9:1 hept-EA)=0.15. LC-MS-conditions 02: $t_R$=1.10 min; $[M+H]^+$=286.38.

2-(tert-Butyl-dimethyl-silanyloxymethyl)-oxazole-4-carbaldehyde

In a flame dried round-bottomed flask equipped with a magnetic stir bar and under inert atmosphere ($N_2$), a solution of 2-(tert-butyl-dimethyl-silanyloxymethyl)-oxazole-4-carboxylic acid ethyl ester (283 mg, 0.99 mmol) in $CH_2Cl_2$ (5.0 mL) was treated at $-78°$ C. with DiBAL (1.85 mL of a 1M sol in toluene, 1.85 mmol) and the reaction mixture was stirred for 1 h at $-78°$ C. MeOH (70 µL) and $H_2O$ (100 µL) were added and the reaction mixture was allowed to warm to rt. The reaction mixture was filtered, and the solvent removed under reduced pressure to give the title compound as a colorless oil. TLC:rf (1:1 hept-EA)=0.61. LC-MS-conditions 02: $t_R$=1.03 min; $[M+H_2O+H]^+$=260.50.

1-[2-(tert-Butyl-dimethyl-silanyloxymethyl)-oxazol-4-yl]-ethanol

In a flame dried round-bottomed flask equipped with a magnetic stir bar and under inert atmosphere ($N_2$), a solution of 2-(tert-butyl-dimethyl-silanyloxymethyl)-oxazole-4-carbaldehyde (223 mg, 0.92 mmol) in $CH_2Cl_2$ (8.0 mL) was treated at 0° C. with trimethylaluminum (2.50 mL of a 2M solution in toluene, 5.00 mmol). The reaction mixture was then stirred at 0° C. for 45 min. Sat. aq. $NH_4Cl$ was then added and the aq. layer was extracted twice with $CH_2Cl_2$ and twice with EA. The combined org. extracts were dried over $Na_2SO_4$, filtered, and the solvents were removed under reduced pressure to give the title compound as a colorless oil. TLC:rf (1:1 hept-EA)=0.32. LC-MS-conditions 02: $t_R$=0.97 min, $[M+H]^+$=258.30.

1-[2-(tert-Butyl-dimethyl-silanyloxymethyl)-oxazol-4-yl]-ethanone

In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanol (193 mg, 0.75 mmol) in AcCN (5.0 mL) was treated at rt with $MnO_2$ (362 mg, 3.75 mmol). The reaction mixture was stirred for 16 h at rt before being filtered through Celite. The solvent was removed under reduced pressure to give the title compound as a white solid. TLC:rf (1:1 hept-EA)=0.69. LC-MS-conditions 02: $t_R$=1.04 min, $[M+H]^+$=255.84.

2-{[(tert-Butyldimethylsilyl)oxy]methyl}-4-(2-methyl-[1,3]dioxolan-2-yl)oxazole In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanone (3.82 g, 14.96 mmol) in ethylene glycol (16 mL) was treated with trimethylorthoformate (3.35 mL, 30.51 mmol) followed by $LiBF_4$ (0.29 g, 2.99 mmol). The reaction mixture was heated at 95° C. until completion of the reaction. Aq. 0.5 M $Na_2CO_3$ was added and the mixture was extracted with $Et_2O$. The org. layer was washed with aq. 0.5 M $Na_2CO_3$ (2×), dried over $Na_2SO_4$, filtered, and the solvent was removed under reduced pressure to give the title compound as a brown oil. LC-MS-conditions 01: $t_R$=1.03 min; $[M+H]^+$=300.08.

(4-(2-Methyl-[1,3]dioxolan-2-yl)-oxazol-2-yl)-methanol

In a flame dried round-bottomed flask equipped with a magnetic stir bar and under inert atmosphere ($N_2$), a solution of 2-{[(tert-butyldimethylsilyl)oxy]methyl}-4-(2-methyl-[1,3]dioxolan-2-yl)oxazole (3.50 g, 11.69 mmol) in dry THF (70 mL) was treated at 0° C. with TBAF (15.2 mL of a 1M solution in THF, 15.20 mmol). The reaction mixture was stirred at 0° C. for 1 h. Sat. aq. $NH_4Cl$ was added, the layers separated and the aq. layer extracted with EA. The combined org. extracts were dried over $Na_2SO_4$, filtered and concentrated under reduced pressure. Purification of the residue by FC (2:3 to 1:0 EA-Hept) gave the title compound as a pale yellow oil. TLC: rf (EA)=0.20. LC-MS-conditions 01: $t_R$=0.45 min, $[M+H]^+$=186.00.

(4-(2-Methyl-[1,3]dioxolan-2-yl)-oxazol-2-yl)methanamine

In a flame dried round-bottomed flask equipped with a magnetic stir bar and under inert atmosphere ($N_2$), a solution of (4-(2-methyl-[1,3]dioxolan-2-yl)-oxazol-2-yl)-methanol (230 mg, 1.24 mmol) in dry $CH_2Cl_2$ (10 mL) was treated at 0° C. with $Et_3N$ (0.23 mL, 1.64 mmol) followed by DMAP (15 mg, 0.12 mmol) and Ms-Cl (0.13 mL, 1.61 mmol). After stirring at 0° C. for 1 h, the reaction was quenched with water (10 mL). The org. layer was dried over $MgSO_4$, filtered, and the solvents were removed under reduced pressure to give crude (4-(2-methyl-[1,3]dioxolan-2-yl)oxazol-2-yl)methyl methanesulfonate as a colorless oil. The crude material was dissolved in dry DMF (6 mL) and treated with $NaN_3$ (93 mg, 1.41 mmol) at 80° C. until completion of the reaction. The reaction mixture was then cooled down to rt and partitioned between EA and water. The layers were separated and the org. layer dried over $MgSO_4$, filtered and concentrated under reduced pressure to give crude 2-(azidomethyl)-4-(2-methyl-[1,3]dioxolan-2-yl)oxazole as a colorless oil. To a solution of the crude azide in THF (9 mL) were added polymer-supported $Ph_3P$ (1.4 eq.) and water (3 mL). The reaction mixture was stirred at 55° C. until completion of the reaction, cooled down to rt and filtered. The filtrate was partitioned between EA and aq. sat. $NaHCO_3$ and the layers separated. The aq. layer was concentrated under reduced pressure, the residue triturated in EtOH and the solid filtered off. The filtrate was dried over $Na_2SO_4$, filtered and concentrated under reduced pressure to give the title compound as an orange oil. LC-MS-conditions 01: $t_R$=0.22 min; $[M+H]^+$=185.00.

4-Chloromethyl-thiazole-2-carboxylic acid ethyl ester

In a flame dried round-bottomed flask equipped with a magnetic stir bar and under inert atmosphere ($N_2$), a solution of amino-thioxo-acetic acid ethyl ester (7.29 g, 54.74 mmol) in toluene (58 mL) was treated with 1,3-dichloroacetone (8.41 g, 62.95 mmol). The resulting mixture was stirred at reflux for 2 h. EA (60 mL) was added and the org. layer was washed with sat. aq. NaHCO$_3$, brine, dried over MgSO$_4$, filtered, and the solvents were removed under reduced pressure. Purification of the residue by FC (70:30 hept-EA) gave the title compound as an orange oil. TLC:rf (4:1 hept-EA)= 0.26. LC-MS-conditions 02: $t_R$=0.89 min; [M+H]$^+$=206.45.

(4-Chloromethyl-thiazol-2-yl)-methanol

In a flame dried round-bottomed flask equipped with a magnetic stir bar and under inert atmosphere (N$_2$), a solution of 4-chloromethyl-thiazole-2-carboxylic acid ethyl ester (8.51 g, 41.38 mmol) in THF (413 mL) was treated at −78° C. with DiBAL (124 mL of a 1M sol in THF, 124 mmol) and the reaction mixture was stirred for 1 h at −78° C. The mixture was then allowed to warm up to rt and poured into a Rochelle's salt solution. After stirring for 1 h, the layers were separated and the aq. layer extracted with EA. The combined org. extracts were washed with brine, dried over MgSO$_4$, filtered and concentrated under reduced pressure. Purification by FC (hept-EA) gave the title compound as a yellow oil. TLC:rf (1:1 hept-EA)=0.29. LC-MS-conditions 02: $t_R$=0.59 min; [M+H]$^+$=164.08.

(4-Chloromethyl-thiazol-2-yl)-carbaldehyde

In a flame dried round-bottomed flask equipped with a magnetic stir bar and under inert atmosphere (N$_2$), a solution of (4-chloromethyl-thiazol-2-yl)-methanol (4.20 g, 25.67 mmol) in CH$_3$CN (257 mL) was treated at rt with MnO$_2$ (18.60 g, 192.55 mmol). The reaction mixture was stirred at rt until completion of the reaction, and then filtered through Celite. The solvent was removed under reduced pressure to give the title compound as a pale yellow oil after purification by FC (hept-EA 4:1). TLC:rf (4:1 hept-EA)=0.37. LC-MS-conditions 02: $t_R$=0.77 min, [M+H$_2$O+H]$^+$=180.56.

1-(4-Chloromethyl-thiazol-2-yl)-ethanol

In a flame dried round-bottomed flask equipped with a magnetic stir bar and under inert atmosphere (N$_2$), a solution of (4-chloromethyl-thiazol-2-yl)-carbaldehyde (2.00 g, 12.37 mmol) in CH$_2$Cl$_2$ (124 mL) was treated at 0° C. with trimethylaluminum (62 mL of a 1M solution in heptane, 62.00 mmol). The reaction mixture was then stirred at 0° C. for 45 min. Sat. aq. NH$_4$Cl and aq. 1N HCl were then added and the aq. layer was extracted twice with CH$_2$Cl$_2$. The combined org. extracts were dried over MgSO$_4$, filtered, and the solvents were removed under reduced pressure to give the title compound as a yellow oil. LC-MS-conditions 02: $t_R$=0.66 min, [M+H]$^+$=178.54.

1-(4-Chloromethyl-thiazol-2-yl)-ethanone

In a flame dried round-bottomed flask equipped with a magnetic stir bar and under inert atmosphere (N$_2$), a solution of 1-(4-chloromethyl-thiazol-2-yl)-ethanol (2.19 g, 12.31 mmol) in CH$_3$CN (122 mL) was treated at rt with MnO$_2$ (5.94 g, 61.52 mmol). The reaction mixture was stirred at rt until completion of the reaction, and then filtered through Celite. The solvent was removed under reduced pressure to give the title compound as a yellow oil. LC-MS-conditions 02: $t_R$=0.84 min.

(2-Acetyl-thiazol-4-yl)-methanamine

In a flame dried round-bottomed flask equipped with a magnetic stir bar and under inert atmosphere (N$_2$), a solution of 1-(4-chloromethyl-thiazol-2-yl)-ethanone (1.08 g, 6.13 mmol) in dry DMF (21 mL) and treated with NaN$_3$ (1.20 g, 18.39 mmol) at 65° C. until completion of the reaction. The reaction mixture was then cooled down to rt and partitioned between EA and water. The layers were separated and the org. layer dried over MgSO$_4$, filtered and concentrated under reduced pressure to give crude 1-(4-(azidomethyl)-thiazol-2-yl)-ethanone as a yellow oil. To a solution of the crude azide (200 mg, 1.10 mmol) in THF (6 mL) were added polymer-supported Ph$_3$P (2.0 eq.) and water (2 mL). The reaction mixture was stirred at 60° C. until completion of the reaction, cooled down to rt and filtered. The filtrate was partitioned between EA and aq. sat. NaHCO$_3$ and the layers separated. The org. layer was dried over MgSO$_4$, filtered and concentrated under reduced pressure to give the title compound as a brown oil after purification by FC (CH$_2$Cl$_2$-MeOH-Et$_3$N). LC-MS-conditions 01: $t_R$=0.26 min; [M+H]$^+$=157.04.

2-(3-Bromo-phenyl)-2-methyl-[1,3]dioxolane

In a flame dried round-bottomed flask equipped with a magnetic stir bar and under inert atmosphere (N$_2$), a solution of 3-bromo-acetophenone (2.11 g, 10.60 mmol) in ethylene glycol (12 mL) was treated with trimethylorthoformate (2.3 mL, 21.02 mmol) followed by LiBF$_4$ (204 mg, 2.13 mmol). The reaction mixture was heated at 95° C. for 18 h. Sat. aq. Na$_2$CO$_3$ was added and the mixture was extracted twice with ether and the combined organic extracts were dried over Na$_2$SO$_4$, filtered, and the solvent was removed under reduced pressure. Purification of the residue by FC (20:1 hept-EA) gave the title compound as a pale yellow oil. TLC:rf (9:1 hept-EA)=0.41. LC-MS-conditions 02: $t_R$=1.01 min.

3-(2-Methyl-[1,3]dioxolan-2-yl)-benzaldehyde

In a flame dried round-bottomed flask equipped with a magnetic stir bar and under inert atmosphere (N$_2$), to a solution of 2-(3-bromo-phenyl)-2-methyl-[1,3]dioxolane (2.37 g, 9.74 mmol) in THF (20.0 mL) at −78° C. was added dropwise n-BuLi (4 mL of a 2.5M solution in hexane, 10.00 mmol). The reaction mixture was then stirred for 30 min at −78° C. before DMF (1.0 mL, 12.92 mmol) was added dropwise. The reaction mixture was allowed to warm to rt over 1 h. Sat. aq. NH$_4$Cl was added and the mixture was extracted three times with Et$_2$O. The combined org. extracts were dried over NaSO$_4$, filtered, and the solvent was removed under reduced pressure to give the crude title compound as a pale yellow oil. LC-MS-conditions 02: $t_R$=0.87 min.

[3-(2-Methyl-[1,3]dioxolan-2-yl)-phenyl]-methanol

In a flame dried round-bottomed flask equipped with a magnetic stir bar and under inert atmosphere (N$_2$), to a ice-cold solution of 3-(2-methyl-[1,3]dioxolan-2-yl)benzaldehyde (1.84 g, 9.59 mmol) in MeOH (20 mL) was added NaBH$_4$ (456 mg, 12.05 mmol in four portions). The reaction mixture was then stirred for 1 h at 0° C. Water was added and the mixture was extracted twice with EA. The combined org. extracts were washed with brine, dried over Na$_2$SO$_4$, filtered, and the solvent was removed under reduced pressure to give the title compound as a pale yellow oil. TLC:rf (4:1 hept-EA)=0.12. LC-MS-conditions 02: $t_R$=0.74 min.

(3-(2-Methyl-[1,3]dioxolan-2-yl)-phenyl)methanamine

In a flame dried round-bottomed flask equipped with a magnetic stir bar and under inert atmosphere (N$_2$), a solution of [3-(2-methyl-[1,3]dioxolan-2-yl)-phenyl]-methanol (1.68 g, 8.65 mmol) in dry $CH_2Cl_2$ (20 mL) was treated at 0° C. with $Et_3N$ (1.60 mL, 11.38 mmol) followed by DMAP (109 mg, 0.88 mmol) and Ms-Cl (0.80 mL, 10.13 mmol). After stirring at 0° C. for 0.5 h, the reaction was quenched with water (10 mL). The org. layer was dried over $MgSO_4$, filtered, and the solvents were removed under reduced pressure. The crude residue was purified by FC (hept-EA 9:1 to 0:1) to give pure (3-(2-methyl-[1,3]dioxolan-2-yl)-phenyl)methyl methanesulfonate as a white solid. Part of this material (300 mg, 1.10 mmol) was dissolved in dry DMF (5 mL) and treated with $NaN_3$ (220 mg, 3.35 mmol) at 80° C. until completion of the reaction. The reaction mixture was then cooled down to rt and partitioned between EA and water. The layers were separated and the org. layer dried over $MgSO_4$, filtered and concentrated under reduced pressure to give crude 3-(azidomethyl)-(2-methyl-[1,3]dioxolan-2-yl)benzene as a yellow oil. LC-MS-conditions 02: $t_R$=0.99 min.

A mixture of the crude azide (194 mg, 0.88 mmol) in MeOH (5 mL) was hydrogenated in the presence of Pd/C (10%) at rt until completion of the reaction. The reaction mixture was filtered and concentrated under reduced pressure to give the title compound as a pale yellow solid. LC-MS-conditions 02: $t_R$=0.59 min; $[M+H]^+$=194.64.

(4-Bromo-2,6-difluorophenyl)-methanamine

In a flame dried round-bottomed flask equipped with a magnetic stir bar and under inert atmosphere ($N_2$), a solution of 4-bromo-2,6-difluorobenzyl alcohol (1.00 g, 4.48 mmol) in dry $CH_2Cl_2$ (20 mL) was treated at 0° C. with $Et_3N$ (0.81 mL, 5.79 mmol) followed by DMAP (55 mg, 0.45 mmol) and Ms-Cl (0.37 mL, 4.71 mmol). After stirring at 0° C. for 0.5 h and at rt for 1 h, the reaction was quenched with water (10 mL). The org. layer was dried over $MgSO_4$, filtered, and the solvents were removed under reduced pressure to give crude (4-bromo-2,6-difluorophenyl)methyl methanesulfonate as a yellow oil. This material was dissolved in dry DMF (6 mL) and treated with $NaN_3$ (93 mg, 1.41 mmol) at 80° C. until completion of the reaction. The reaction mixture was then cooled down to rt and partitioned between EA and water. The layers were separated and the org. layer dried over $MgSO_4$, filtered and concentrated under reduced pressure to give crude 1-(azidomethyl)-4-bromo-2,6-difluorobenzene as a yellow oil. LC-MS-conditions 01: $t_R$=1.00 min.

To a mixture of the crude azide (330 mg, 1.33 mmol) in THF (12 mL) were added polymer-supported $Ph_3P$ (2.0 eq.) and water (2 mL). The reaction mixture was stirred at 55° C. until completion of the reaction, cooled down to rt and filtered. The filtrate was partitioned between EA and aq. sat. $NaHCO_3$ and the layers separated. The aq. layer was extracted with EA and the combined org. extracts dried over $MgSO_4$, filtered and concentrated under reduced pressure to give the title compound as a yellow solid. LC-MS-conditions 02: $t_R$=0.54 min; $[M+CH_3CN+H]^+$=263.45.

4-Bromo-3-fluorobenzylamine

In a flame dried round-bottomed flask equipped with a magnetic stir bar and under inert atmosphere ($N_2$), a solution of 4-bromo-3-fluorobenzoic acid (250 mg, 1.14 mmol) in dry THF (5 mL) was treated at 0° C. with $Et_3N$ (0.16 mL, 1.14 mmol) and ethyl chloroformate (0.11 mL, 1.14 mmol). The reaction mixture was stirred at 0° C. for 15 min then aq. $NH_3$ (3 mL) was added. The reaction mixture was vigorously stirred at 0° C. for 30 min and at rt for 2 h and then concentrated under reduced pressure. The residue was partitioned between water and $CH_2Cl_2$, the layers separated and the aq. layer extracted with $CH_2Cl_2$ (2×). The combined org. extracts were dried ($MgSO_4$), filtered and concentrated under reduced pressure. The crude residue was purified by FC (EA-MeOH 1:0 to 10:1) and the corresponding carboxamide obtained as a white solid. TLC:rf (9:1 EA-MeOH)=0.40. LC-MS-conditions 01: $t_R$=0.73 min; $[M+H]^+$=217.83.

Part of this material (150 mg, 0.69 mmol) was dissolved in dry THF (5 mL) and treated with $BH_3 \cdot Me_2S$ complex (1.0 M in THF, 1.6 mL, 1.60 mmol) at 0° C. The reaction mixture was then warmed to 50° C. and stirred at this temperature until completion of the reaction. The mixture was cooled to 0° C. and water was added followed by EA. The layers were separated and the aq. layer extracted with EA (3×). The combined org. extracts were washed with brine, dried over $MgSO_4$, filtered and concentrated under reduced pressure to give the title compound as a white solid. LC-MS-conditions 07: $t_R$=0.33 min; $[M+CH_3CN+H]^+$=245.12.

1,4-Dibromo-2,3-difluorobenzene

In a flame dried round-bottomed flask equipped with a magnetic stir bar and under inert atmosphere ($N_2$), to a solution of lithium diisopropylamide (11.25 mmol) in dry THF (8 mL) was added a mixture of 1,3-difluorobenzene (600 mg, 5.26 mmol) and $Me_3SiCl$ (1.48 mL, 11.57 mmol) at −78° C. After stirring at −78° C. for 75 min, the reaction was quenched by the addition of aq. 1M $H_2SO_4$. The mixture was warmed to rt, diluted with TBME and saturated with solid NaCl. The layers were separated and the aq. layer extracted with TBME. The combined org. extracts were dried over $MgSO_4$, filtered, and the solvents were removed under reduced pressure to give crude (2,3-difluoro-1,4-phenylene)-bis(trimethylsilane) as a white solid. This material (1.33 g, 5.15 mmol) was treated with bromine (1.06 mL, 20.58 mmol) at 0° C. The reaction mixture was then warmed to 58° C. and stirred at this temperature until completion of the reaction. The reaction mixture was then cooled down to 0° C. and an ice-cold sat. $NaHCO_3$ solution was carefully added. The mixture was then extracted with TBME (2×) and the combined org. extracts dried over $MgSO_4$, filtered and concentrated under reduced pressure to give 1,4-dibromo-2,3-difluorobenzene as a colorless oil after distillation (0.05 mbar, 90° C.). LC-MS-conditions 07: $t_R$=0.93 min.

4-Bromo-2,3-difluorobenzyl alcohol

In a flame dried round-bottomed flask equipped with a magnetic stir bar and under inert atmosphere ($N_2$), a solution of 1,4-dibromo-2,3-difluorobenzene (490 mg, 1.80 mmol) in dry $Et_2O$ (6 mL) was added to a n-BuLi (0.72 mL of a 2.5M solution in hexanes, 1.80 mmol) at −78° C. The reaction mixture was stirred at −78° C. for 2 h before solid $CO_2$ was added. The reaction mixture was stirred at −78° C. for 10 min and then allowed to warm up to rt. The mixture was then diluted with EA and aq. 1N HCl was added. The layers separated and the org. layer dried over $MgSO_4$, filtered, and the solvents were removed under reduced pressure to give the crude carboxylic acid as a pale yellow solid. The crude material (360 mg, 1.52 mmol) was dissolved in dry THF (7 mL) and treated with $BH_3 \cdot Me_2S$ complex (1.0 M in THF, 3.0 mL, 3.00 mmol) at 0° C. The reaction mixture was then warmed to 50° C. and stirred at this temperature until completion of the reaction. The mixture was cooled to 0° C. and water was added followed by EA. The layers were separated and the aq. layer extracted with EA (3×). The combined org. extracts were washed with brine, dried over $MgSO_4$, filtered and concentrated under reduced pressure. The crude residue was purified by FC (hept-EA 9:1 to 2:1) to give the title compound as a colorless oil. TLC:rf (1:1 EA-hept)=0.50.

4-Bromo-2,3-difluorobenzylamine

In a flame dried round-bottomed flask equipped with a magnetic stir bar and under inert atmosphere ($N_2$), a solution of 4-bromo-2,3-difluorobenzyl alcohol (175 mg, 0.70 mmol) in dry $CH_2Cl_2$ (2 mL) was treated at 0° C. with $Et_3N$ (0.14 mL, 1.01 mmol) followed by DMAP (10 mg, 0.08 mmol) and Ms-Cl (0.06 mL, 0.82 mmol). After stirring at 0° C. for 0.5 h and at rt for 1 h, the reaction was quenched with water (2 mL). The org. layer was dried over $MgSO_4$, filtered, and the solvents were removed under reduced pressure to give crude (4-bromo-2,3-difluorophenyl)methyl methanesulfonate as a yellow oil. This material was dissolved in dry DMF (3 mL) and treated with $NaN_3$ (46 mg, 0.71 mmol) at 80° C. until completion of the reaction. The reaction mixture was then cooled down to rt and partitioned between EA and water. The layers were separated and the org. layer dried over $MgSO_4$, filtered and concentrated under reduced pressure to give crude 1-(azidomethyl)-4-bromo-2,3-difluorobenzene as a colorless oil. LC-MS-conditions 07: $t_R$=0.89 min.

To a mixture of the crude azide (164 mg, 0.60 mmol) in THF (3 mL) were added polymer-supported $Ph_3P$ (2.0 eq.) and water (1 mL). The reaction mixture was stirred at 55° C. until completion of the reaction, cooled down to rt and filtered. The filtrate was partitioned between EA and aq. sat. $NaHCO_3$ and the layers separated. The aq. layer was extracted with EA and the combined org. extracts dried over $MgSO_4$, filtered and concentrated under reduced pressure to give the title compound as a yellow oil. LC-MS-conditions 07: $t_R$=0.42 min; $[M+CH_3CN+H]^+$=263.15.

4-Bromo-3,5-difluorobenzyl alcohol

In a flame dried round-bottomed flask equipped with a magnetic stir bar and under inert atmosphere ($N_2$), a solution of 4-bromo-3,5-difluoroiodobenzene (790 mg, 2.48 mmol) in dry $Et_2O$ (12 mL) was added to a n-BuLi (0.98 mL of a 2.5M solution in hexanes, 2.45 mmol) at −78° C. The reaction mixture was stirred at −78° C. for 2 h before solid $CO_2$ was added. The reaction mixture was stirred at −78° C. for 10 min and then allowed to warm up to rt. The mixture was then diluted with EA and aq. 1N HCl was added. The layers separated and the org. layer dried over $MgSO_4$, filtered, and the solvents were removed under reduced pressure to give the crude carboxylic acid as a pale yellow solid. The crude material (270 mg, 1.14 mmol) was dissolved in dry THF (6 mL) and treated with $BH_3.Me_2S$ complex (1.0 M in THF, 2.3 mL, 2.30 mmol) at 0° C. The reaction mixture was then warmed to 50° C. and stirred at this temperature until completion of the reaction. The mixture was cooled to 0° C. and water was added followed by EA. The layers were separated and the aq. layer extracted with EA (3×). The combined org. extracts were washed with brine, dried over $MgSO_4$, filtered and concentrated under reduced pressure. The crude residue was purified by FC (hept-EA 9:1 to 2:1) to give the title compound as a white solid. TLC:rf (1:1 EA-hept)=0.53.

4-Bromo-3,5-difluorobenzylamine

In a flame dried round-bottomed flask equipped with a magnetic stir bar and under inert atmosphere ($N_2$), a solution of 4-bromo-3,5-difluorobenzyl alcohol (100 mg, 0.45 mmol) in dry $CH_2Cl_2$ (3 mL) was treated at 0° C. with $Et_3N$ (0.081 mL, 0.58 mmol) followed by DMAP (5 mg, 0.045 mmol) and Ms-Cl (0.037 mL, 0.47 mmol). After stirring at 0° C. for 0.5 h and at rt for 0.5 h, the reaction was quenched with water (2 mL). The org. layer was dried over $MgSO_4$, filtered, and the solvents were removed under reduced pressure to give crude (4-bromo-3,5-difluorophenyl)methyl methanesulfonate as a yellow oil. This material was dissolved in dry DMF (3 mL) and treated with $NaN_3$ (29 mg, 0.45 mmol) at 80° C. until completion of the reaction. The reaction mixture was then cooled down to rt and partitioned between EA and water. The layers were separated and the org. layer dried over $MgSO_4$, filtered and concentrated under reduced pressure to give crude 1-(azidomethyl)-4-bromo-3,5-difluorobenzene as a yellow oil. LC-MS-conditions 07: $t_R$=0.90 min.

To a mixture of the crude azide (70 mg, 0.28 mmol) in THF (4 mL) were added polymer-supported $Ph_3P$ (3.0 eq.) and water (1 mL). The reaction mixture was stirred at 55° C. until completion of the reaction, cooled down to rt and filtered. The filtrate was partitioned between EA and aq. sat. $NaHCO_3$ and the layers separated. The aq. layer was extracted with EA and the combined org. extracts dried over $MgSO_4$, filtered and concentrated under reduced pressure to give the title compound as a yellow oil. LC-MS-conditions 07: $t_R$=0.37 min; $[M+CH_3CN+H]^+$=263.15.

4-Bromo-2,5-difluorobenzyl alcohol

In a flame dried round-bottomed flask equipped with a magnetic stir bar and under inert atmosphere ($N_2$), a solution of 1,4-dibromo-2,5-difluorobenzene (600 mg, 2.21 mmol) in dry $Et_2O$ (8 mL) was added to a n-BuLi (0.88 mL of a 2.5M solution in hexanes, 2.20 mmol) at −78° C. The reaction mixture was stirred at −78° C. for 2 h before solid $CO_2$ was added. The reaction mixture was stirred at −78° C. for 10 min and then allowed to warm up to rt. The mixture was then diluted with EA and aq. 1N HCl was added. The layers separated and the org. layer dried over $MgSO_4$, filtered, and the solvents were removed under reduced pressure to give the crude carboxylic acid as a pale yellow solid. The crude material (530 mg, 2.24 mmol) was dissolved in dry THF (20 mL) and treated with $BH_3.Me_2S$ complex (1.0 M in THF, 4.5 mL, 4.50 mmol) at 0° C. The reaction mixture was then warmed to 50° C. and stirred at this temperature until completion of the reaction. The mixture was cooled to 0° C. and water was added followed by EA. The layers were separated and the aq. layer extracted with EA (3×). The combined org. extracts were washed with brine, dried over $MgSO_4$, filtered and concentrated under reduced pressure. The crude residue was purified by FC (hept-EA 3:1 to 1:1) to give the title compound as a white solid. TLC:rf (1:1 EA-hept)=0.53.

4-Bromo-2,5-difluorobenzylamine

In a flame dried round-bottomed flask equipped with a magnetic stir bar and under inert atmosphere ($N_2$), a solution of 4-bromo-2,5-difluorobenzyl alcohol (160 mg, 0.72 mmol) in dry $CH_2Cl_2$ (4 mL) was treated at 0° C. with $Et_3N$ (0.13 mL, 0.93 mmol) followed by DMAP (9 mg, 0.07 mmol) and Ms-Cl (0.06 mL, 0.75 mmol). After stirring at 0° C. for 0.5 h and at rt for 1 h, the reaction was quenched with water (3 mL). The org. layer was dried over $MgSO_4$, filtered, and the solvents were removed under reduced pressure to give crude (4-bromo-2,5-difluorophenyl)methyl methanesulfonate as a yellow oil. This material was dissolved in dry DMF (3 mL) and treated with $NaN_3$ (51 mg, 0.78 mmol) at 80° C. until completion of the reaction. The reaction mixture was then cooled down to rt and partitioned between EA and water. The layers were separated and the org. layer dried over MgSO$_4$, filtered and concentrated under reduced pressure to give crude 1-(azidomethyl)-4-bromo-2,5-difluorobenzene as a yellow oil. LC-MS-conditions 07: t$_R$=0.89 min.

To a mixture of the crude azide (110 mg, 0.44 mmol) in THF (3 mL) were added polymer-supported Ph$_3$P (3.0 eq.) and water (1.5 mL). The reaction mixture was stirred at 55° C. until completion of the reaction, cooled down to rt and filtered. The filtrate was partitioned between EA and aq. sat. NaHCO$_3$ and the layers separated. The aq. layer was extracted with EA and the combined org. extracts dried over MgSO$_4$, filtered and concentrated under reduced pressure to give the title compound as a yellow oil. LC-MS-conditions 07: t$_R$=0.40 min; [M+CH$_3$CN+H]$^+$=263.14.

5-Amino-2-bromo-3-fluoropyridine

In a flame dried round-bottomed flask equipped with a magnetic stir bar and under inert atmosphere (N$_2$), a solution of 3-amino-5-fluoropyridine (900 mg, 8.03 mmol) in dry DMF (13 mL) was treated at 0° C. with N-bromo-succinimide (1.43 g, 8.03 mmol). The reaction mixture was stirred at rt until completion of the reaction. The mixture was then partitioned between Et$_2$O and water. The layers were separated and the org. layer successively washed with water, sat. aq. NaHCO$_3$ and brine, dried over MgSO$_4$, filtered and concentrated under reduced pressure. The crude residue was purified by FC (hept-EA 9:1 to 1:1) and the title compound obtained as an orange solid. LC-MS-conditions 07: t$_R$=0.52 min; [M+H]$^+$=191.30.

4-(Azetidin-1-yl)butan-1-amine

In a flame dried round-bottomed flask equipped with a magnetic stir bar and under inert atmosphere (N$_2$), to a solution of trimethylene imine (300 mg, 5.25 mmol) and DBU (0.79 mL, 5.23 mmol) in dry Et$_2$O (4 mL) was added 4-bromobutyronitrile (0.54 mL, 5.27 mmol) at 0° C. The reaction mixture was stirred at rt until completion of the reaction. The mixture was filtered and concentrated under reduced pressure. The crude nitrile was redissolved in dry THF (4 mL) and treated with LiALH$_4$ (230 mg, 6.06 mmol) at 0° C. The reaction mixture was warmed up to rt and stirred at this temperature until completion of the reaction. Aq. 1N NaOH (2 mL) was then added, the layers separated and the aq. layer extracted with EA (3×). The combined organic extracts were washed with brine, dried over Na$_2$SO$_4$, filtered, and the solvents were removed under reduced pressure to give crude 4-(azetidin-1-yl)butan-1-amine as a pale yellow oil. GC-MS-conditions 01: t$_R$=1.35 min; [M+H]$^+$=129.00.

2-(2-(Pyrrolidin-1-yl)ethoxy)ethanamine hydrochloride

In a flame dried round-bottomed flask equipped with a magnetic stir bar and under inert atmosphere (N$_2$), to a solution of 2-(2-aminoethoxy)ethanol (536 mg, 5.00 mmol) in THF (3 mL) was added aq. 2M NaOH (2.6 mL, 5.20 mmol) at 0° C. The reaction mixture was stirred at 0° C. for 10 min and a solution of di-tert-butyl dicarbonate (1.16 g, 5.20 mmol) in THF (3 mL) was then added dropwise. The reaction mixture was warmed to rt and stirred at this temperature until completion of the reaction. The mixture was diluted with CH$_2$Cl$_2$, filtered and the layers separated. The organic layer was dried over Na$_2$SO$_4$, filtered, and the solvents were removed under reduced pressure. The crude alcohol was redissolved in dry CH$_2$Cl$_2$ (20 mL) and treated with triphenylphoshine on polystyrene (5.63 mmol) and imidazole (190 mg, 2.76 mmol). To this mixture cooled to 0° C. was added iodine (808 mg, 3.15 mmol). The reaction mixture was warmed to rt and stirred at this temperature until completion of the reaction. The mixture was then filtered, CH$_2$Cl$_2$ removed under reduced pressure. The residue was redissolved in EA, successively washed with 10% aq. Na$_2$SO$_3$ and brine, dried over Na$_2$SO$_4$, filtered and concentrated under reduced pressure. The crude iodide was redissolved in CH$_3$CN (15 mL) and treated with pyrrolidine (0.17 mL, 1.99 mmol) and K$_2$CO$_3$ (465 mg, 3.36 mmol). The reaction mixture was stirred at rt until completion of the reaction, filtered and concentrated under reduced pressure. The amine was purified by FC (hept-EA-acetone, 1:0:0->0: 0:1) and then the Boc group was removed by treatment with HCl (4.0 M in dioxane, 10 eq.) in dry CH$_2$Cl$_2$ (3 mL). The title compound was obtained after trituration in hot EA/acetone/ MeOH as a beige solid. LC-MS-conditions 01: t$_R$=0.13 min; [M+H]$^+$=159.11.

(3R,6S)-6-(Pyrrolidin-1-ylmethyl)tetrahydro-2H-pyran-3-amine hydrochloride

In a flame dried round-bottomed flask equipped with a magnetic stir bar and under inert atmosphere (N$_2$), to an ice-cold solution of (3R,6S)-6-hydroxymethyl-tetrahydro-2H-pyran-3-yl carbamic acid tert-butyl ester (328 mg, 1.40 mmol, H. S. Overkleeft et al. *Eur. J. Org. Chem.* 2003, 2418), triphenylphoshine on polystyrene (6.16 mmol) and imidazole (203 mg, 2.95 mmol) in dry CH$_2$Cl$_2$ (14 mL) was added iodine (891 mg, 3.48 mmol). The reaction mixture was warmed to rt and stirred at this temperature until completion of the reaction. The mixture was then filtered, CH$_2$Cl$_2$ removed under reduced pressure. The residue was redissolved in EA, successively washed with 10% aq. Na$_2$SO$_3$ and brine, dried over Na$_2$SO$_4$, filtered and concentrated under reduced pressure. After purification by FC, the iodide was redissolved in CH$_3$CN (15 mL) and treated with pyrrolidine (1.13 mL, 13.57 mmol) and K$_2$CO$_3$ (750 mg, 5.43 mmol). The reaction mixture was stirred at 85° C. until completion of the reaction, filtered and concentrated under reduced pressure. The amine was purified by FC (hept-EA-acetone, 1:0:0->0: 0:1) and then the Boc group was removed by treatment with HCl (4.0 M in dioxane, 9 eq.) in dry CH$_2$Cl$_2$ (2 mL). The title compound was obtained after trituration in hot EA/acetone/ MeOH as an off-white solid. LC-MS-conditions 01: t$_R$=0.15 min; [M+H]$^+$=185.06.

1-(4-(4-Aminobutyl)piperazin-1-yl)ethanone

In a flame dried round-bottomed flask equipped with a magnetic stir bar and under inert atmosphere (N$_2$), to a solution of 1-acetylpiperazine (256 mg, 2.00 mmol) and DBU (0.30 mL, 2.00 mmol) in dry Et$_2$O (2 mL) was added 4-bromobutyronitrile (0.21 mL, 2.00 mmol) at 0° C. The reaction mixture was stirred at rt until completion of the reaction. The mixture was filtered and concentrated under reduced pressure. A 0.087 mol/L solution of the crude nitrile in EtOH (10 mL) was hydrogenated at 50° C. using the H-Cube® (1 mL/min) with a Raney Nickel cartridge (30 mm) under 50 bar until completion of the reaction. The solution was then concentrated under reduced pressure to give crude 1-(4-(4-aminobutyl)piperazin-1-yl)ethanone as a colorless oil. GC-MS-conditions 01: t$_R$=2.94 min; [M+H]$^+$=200.40.

cis-4-Benzyloxycarbonylaminocyclohexane-methanol

In a flame dried round-bottomed flask equipped with a magnetic stir bar and under inert atmosphere (N$_2$), to a solution of cis-4-benzyloxycarbonylaminocyclohexanecarboxylic acid (417 mg, 1.50 mmol) in THF (15 mL) was added BH$_3$.Me$_2$S complex (2.0 M in THF, 1.5 mL, 3.00 mmol) at 0° C. The reaction mixture was stirred at 0° C. for 1 h30. More BH₃.Me₂S complex (2.0 M in THF, 1.0 mL, 2.00 mmol) was added at 0° C. followed by NaBH₄ (12 mg, 0.30 mmol). The reaction mixture was warmed to rt and stirred at this temperature until completion of the reaction. MeOH was carefully added to quench the reaction, the volatiles were removed under reduced pressure and the residue co-evaporated with MeOH (2×). Purification by FC (hept-EA, 1:0->3:2) gave pure cis-4-benzyloxycarbonylaminocyclohexane-methanol as a colorless oil. TLC:rf (1:2 hept-EA)=0.45. LC-MS-conditions 01: $t_R$=0.82 min; [M+H]⁺=264.07.

cis-4-(Pyrrolidin-1-ylmethyl)cyclohexanamine

In a flame dried round-bottomed flask equipped with a magnetic stir bar and under inert atmosphere (N₂), to an ice-cold solution of cis-4-benzyloxycarbonylaminocyclohexane-methanol (267 mg, 1.01 mmol), triphenylphoshine on polystyrene (3.20 mmol) and imidazole (97 mg, 1.42 mmol) in dry CH₂Cl₂ (40 mL) was added iodine (416 mg, 1.62 mmol). The reaction mixture was warmed to rt and stirred at this temperature until completion of the reaction. The mixture was then filtered, successively washed with 10% aq. Na₂SO₃ and brine, dried over Na₂SO₄, filtered and concentrated under reduced pressure. The crude iodide was redissolved in CH₃CN (15 mL) and treated with pyrrolidine (0.32 mL, 3.86 mmol) and K₂CO₃ (533 mg, 3.86 mmol). The reaction mixture was refluxed until completion of the reaction, filtered and concentrated under reduced pressure. The amine was purified by FC (hept-EA, 1:0->1:1) and then the Cbz group was removed by treatment with 10% Pd/C (116 mg) in EtOH (20 mL) under a H₂ atmosphere. The title compound was obtained as a white solid. LC-MS-conditions 04: $t_R$=0.99 min; [M+H]⁺=183.35.

trans-4-Benzyloxycarbonylaminocyclohexane-methanol

In a flame dried round-bottomed flask equipped with a magnetic stir bar and under inert atmosphere (N₂), to a solution of trans-4-benzyloxycarbonylaminocyclohexanecarboxylic acid (417 mg, 1.50 mmol) in THF (15 mL) was added BH₃.Me₂S complex (2.0 M in THF, 1.5 mL, 3.00 mmol) at 0° C. The reaction mixture was stirred at 0° C. for 1 h30. More BH₃.Me₂S complex (2.0 M in THF, 1.0 mL, 2.00 mmol) was added at 0° C. followed by NaBH₄ (12 mg, 0.30 mmol). The reaction mixture was warmed to rt and stirred at this temperature until completion of the reaction. MeOH was carefully added to quench the reaction, the volatiles were removed under reduced pressure and the residue co-evaporated with MeOH (2×). Purification by FC (hept-EA, 1:0->3:2) gave pure trans-4-benzyloxycarbonylaminocyclohexane-methanol as a white solid. TLC:rf (1:2 hept-EA)=0.35. LC-MS-conditions 01: $t_R$=0.82 min; [M+H]⁺=264.05.

trans-4-(Pyrrolidi n-1-ylmethyl)cyclohexanamine

In a flame dried round-bottomed flask equipped with a magnetic stir bar and under inert atmosphere (N₂), to an ice-cold solution of trans-4-benzyloxycarbonylaminocyclohexane-methanol (292 mg, 1.11 mmol), triphenylphoshine on polystyrene (3.52 mmol) and imidazole (107 mg, 1.55 mmol) in dry CH₂Cl₂ (40 mL) was added iodine (455 mg, 1.77 mmol). The reaction mixture was warmed to rt and stirred at this temperature until completion of the reaction. The mixture was then filtered, successively washed with 10% aq. Na₂SO₃ and brine, dried over Na₂SO₄, filtered and concentrated under reduced pressure. The crude iodide was redissolved in CH₃CN (15 mL) and treated with pyrrolidine (0.34 mL, 4.09 mmol) and K₂CO₃ (566 mg, 4.09 mmol). The reaction mixture was refluxed until completion of the reaction, filtered and concentrated under reduced pressure. The amine was purified by FC (hept-EA, 1:0->1:1) and then the Cbz group was removed by treatment with 10% Pd/C (147 mg) in MeOH (10 mL) under a H₂ atmosphere. The title compound was obtained as a colorless oil. LC-MS-conditions 07d: $t_R$=0.97 min; [M+H]⁺=183.37.

(R)-4-(3-Fluoropyrrolidin-1-yl)butan-1-amine

In a flame dried round-bottomed flask equipped with a magnetic stir bar and under inert atmosphere (N₂), to a solution of (R)-3-fluoropyrrolidine hydrochloride (400 mg, 3.09 mmol) and 4-bromobutyronitrile (0.32 mL, 3.09 mmol) in dry CH₃CN (16 mL) was added K₂CO₃ (2.35 g, 16.99 mmol) at rt followed by KI (51 mg, 0.31 mmol). The reaction mixture was stirred at rt for 15 h. The mixture was filtered and the filtrate partitioned between water and CH₂Cl₂. The layers were separated and the aq. layer extracted with CH₂Cl₂ (3×). The combined org. extracts were dried over MgSO₄, filtered and concentrated under reduced pressure. The crude nitrile was redissolved in dry THF (23 mL) and treated with LiAlH₄ (214 mg, 5.47 mmol) at 0° C. The reaction mixture was warmed up to rt and stirred at this temperature until completion of the reaction. Aq. 1N NaOH (7 mL) was then added, the layers separated and the aq. layer extracted with EA (3×). The combined organic extracts were washed with brine, dried over Na₂SO₄, filtered, and the solvents were removed under reduced pressure to give crude (R)-4-(3-fluoropyrrolidin-1-yl)butan-1-amine as a colorless oil. GC-MS-conditions 01: $t_R$=1.71 min; [M+H]⁺=161.10.

(S)-4-(3-Fluoropyrrolidin-1-yl)butan-1-amine

In a flame dried round-bottomed flask equipped with a magnetic stir bar and under inert atmosphere (N₂), to a solution of (S)-3-fluoropyrrolidine hydrochloride (200 mg, 1.54 mmol) and 4-bromobutyronitrile (0.16 mL, 1.54 mmol) in dry CH₃CN (8 mL) was added K₂CO₃ (1.17 g, 8.50 mmol) at rt followed by KI (26 mg, 0.15 mmol). The reaction mixture was stirred at rt for 15 h. The mixture was filtered and the filtrate partitioned between water and CH₂Cl₂. The layers were separated and the aq. layer extracted with CH₂Cl₂ (3×). The combined org. extracts were dried over MgSO₄, filtered and concentrated under reduced pressure. The crude nitrile was redissolved in dry THF (10 mL) and treated with LiAlH₄ (92 mg, 2.35 mmol) at 0° C. The reaction mixture was warmed up to rt and stirred at this temperature until completion of the reaction. Aq. 1N NaOH (3 mL) was then added, the layers separated and the aq. layer extracted with EA (3×). The combined organic extracts were washed with brine, dried over Na₂SO₄, filtered, and the solvents were removed under reduced pressure to give crude (S)-4-(3-fluoropyrrolidin-1-yl)butan-1-amine as a yellow oil. GC-MS-conditions 01: $t_R$=1.70 min; [M+H]⁺=161.10.

5-(Pyrrolidin-1-yl)pentan-1-amine

In a flame dried round-bottomed flask equipped with a magnetic stir bar and under inert atmosphere (N₂), a mixture of 5-bromovaleronitrile (0.21 mL, 1.80 mmol), pyrrolidine (0.15 mL, 1.81 mmol), K₂CO₃ (498 mg, 3.60 mmol) and KI (60 mg, 0.36 mmol) in dry CH₃CN (15 mL) was refluxed for 1 h. The mixture was filtered and concentrated under reduced pressure. A 0.05 mol/L solution of the crude nitrile (59 mg, 0.39 mmol) in EtOH (8 mL) was hydrogenated at rt using the H-Cube® (1 mL/min) with a Raney Nickel cartridge (30 mm) under 50 bar until completion of the reaction. The solution was then concentrated under reduced pressure to give crude 5-(pyrrolidin-1-yl)pentan-1-amine as a colorless oil. LC-MS-conditions 01: $t_R$=0.16 min; [M+H]$^+$=157.19.

4-(2,5-Dimethylpyrrolidin-1-yl)butan-1-amine

In a flame dried round-bottomed flask equipped with a magnetic stir bar and under inert atmosphere ($N_2$), to a solution of 2,5-dimethylpyrrolidine (250 mg, 2.34 mmol) and 4-bromobutyronitrile (0.24 mL, 2.34 mmol) in dry $CH_3CN$ (12 mL) was added $K_2CO_3$ (1.78 g, 12.89 mmol) at rt followed by KI (39 mg, 0.23 mmol). The reaction mixture was stirred at rt for 15 h. The mixture was filtered and the filtrate partitioned between water and $CH_2Cl_2$. The layers were separated and the aq. layer extracted with $CH_2Cl_2$ (3×). The combined org. extracts were dried over $MgSO_4$, filtered and concentrated under reduced pressure. The crude nitrile was redissolved in dry THF (19 mL) and treated with LiALH$_4$ (176 mg, 4.50 mmol) at 0° C. The reaction mixture was warmed up to rt and stirred at this temperature until completion of the reaction. Aq. 1N NaOH (7 mL) was then added, the layers separated and the aq. layer extracted with EA (3×). The combined organic extracts were washed with brine, dried over $MgSO_4$, filtered, and the solvents were removed under reduced pressure to give crude 4-(2,5-dimethylpyrrolidin-1-yl)butan-1-amine as a yellow oil. GC-MS-conditions 01: $t_R$=1.75 and 1.83 min; [M+H]$^+$=171.30.

tert-Butyl (4-oxopentyl)carbamate

In a flame dried round-bottomed flask equipped with a magnetic stir bar and under inert atmosphere ($N_2$), to a solution of 4-(tert-butoxycarbonyl-amino)butyric acid (1.00 g, 4.77 mmol) in dry $CH_3CN$ (24 mL) were added N,O-dimethyl-hydroxylamine hydrochloride (475 mg, 4.77 mmol), EDC.HCl (934 mg, 4.77 mmol), HOBt (658 mg, 4.77 mmol) and N-methylmorpholine (2.68 mL, 23.86 mmol) at rt. The reaction mixture was stirred at rt until completion of the reaction. The mixture was then concentrated under reduced pressure. The residue was redissolved in EA, successively washed with water, 10% aq. $KHSO_4$, sat. aq. $NaHCO_3$ and brine, dried over $MgSO_4$, filtered and concentrated under reduced pressure. The crude material was dissolved in dry THF (20 mL) and treated with MeMgBr (3.0M solution in $Et_2O$, 3.25 mL, 9.75 mmol) at 0° C. The reaction mixture was stirred at 0° C. until completion of the reaction. 10% Aq. $KHSO_4$ was then carefully added, the layers separated and the aq. layer extracted with EA (3×). The combined org. extracts were successively washed with aq. sat. $NaHCO_3$ and brine, dried over $MgSO_4$, filtered and concentrated under reduced pressure. The crude residue was purified by FC (hept-EA 3:2) to give the title compound as a colorless oil. TLC:rf (3:2 hept-EA)=0.38.

4-(Pyrrolidin-1-yl)pentan-1-amine hydrochloride

In a flame dried round-bottomed flask equipped with a magnetic stir bar and under inert atmosphere ($N_2$), to a solution of pyrrolidine (79 mg, 1.11 mmol) in dry $CH_3CN$ (6 mL) was added tert-butyl (4-oxopentyl)carbamate (291 mg, 1.44 mmol) followed by Na(OAc)$_3$BH (680 mg, 2.88 mmol) at rt. The reaction mixture was stirred at rt until completion of the reaction. Sat. aq. $NaHCO_3$ was then added and the mixture extracted with EA (3×). The combined org. extracts were dried over $MgSO_4$, filtered and concentrated under reduced pressure. The crude residue was purified by FC($CH_2Cl_2$-MeOH—$NH_3$) to give pure N-tert-butoxycarbonyl-4-(pyrrolidin-1-yl)pentan-1-amine as a colorless oil. LC-MS-conditions 05c: $t_R$=0.53 min; [M+H]$^+$=257.41. The title compound was obtained after Boc deprotection using 4N HCl in dioxane (10.0 eq.) in $CH_2Cl_2$ at rt as a colorless oil.

tert-Butyl (2-(oxiran-2-yl)ethyl)carbamate

In a flame dried round-bottomed flask equipped with a magnetic stir bar and under inert atmosphere ($N_2$), to a solution of 4-amino-1-butene (2.00 g, 25.31 mmol) in dry $CH_2Cl_2$ (100 mL) were added di-tert-butyl dicarbonate (8.45 g, 37.96 mmol) and DIPEA (8.66 mL, 50.62 mmol) at 0° C. The reaction mixture was stirred at rt until completion of the reaction. Water was added, the layers separated and the aq. layer extracted with $CH_2Cl_2$ (3×). The combined org. extracts were washed with sat. aq. $NaHCO_3$, dried over $MgSO_4$, filtered and concentrated under reduced pressure. The crude residue was purified by FC(hept-EA) and 4-(N-tert-butoxycarbonyl-amino)-1-butene was obtained as a colorless oil, which was redissolved in dry $CH_2Cl_2$ (175 mL) and treated with m-chloroperbenzoic acid (1.4 eq.) at rt. The reaction mixture was stirred at rt until completion of the reaction. Aq. 1N NaOH was then added, the layers separated and the aq. layer extracted with $CH_2Cl_2$ (3×). The combined org. extracts were dried over $MgSO_4$, filtered and concentrated under reduced pressure. The crude residue was purified by FC (hept-EA 3:2) and the title compound obtained as a colorless oil. TLC:rf (3:2 hept-EA)=0.33.

3-Fluoro-4-(pyrrolidin-1-yl)butan-1-amine hydrochloride

In a flame dried round-bottomed flask equipped with a magnetic stir bar and under inert atmosphere ($N_2$), a solution of tert-butyl (2-(oxiran-2-yl)ethyl)carbamate (1.50 g, 8.01 mmol) in pyrrolidine (2 mL) was heated at 85° C. until completion of the reaction. The reaction mixture was evaporated to dryness to give a yellow oil. Part of this crude material (300 mg, 1.16 mmol) was dissolved in dry $CH_2Cl_2$ (34 mL) and treated with (diethylamino)sulphur trifluoride (0.18 mL, 1.37 mmol) at 0° C. The reaction mixture was stirred at 0° C. until completion of the reaction. Sat. aq. $NaHCO_3$ was then added, the layers separated and the aq. layer extracted with $CH_2Cl_2$ (3×). The combined org. extracts were dried over $MgSO_4$, filtered and concentrated under reduced pressure. The crude residue was then redissolved in dry $CH_2Cl_2$ (1 mL) and treated with 4N HCl in dioxane (1 mL) at rt. The reaction mixture was stirred at rt until completion of the reaction, and the solvents removed under reduced pressure to give the title compound as a yellow oil. LC-MS-conditions 07b: $t_R$=0.14 min; [M+H]$^+$=161.18.

4-(2-(Methoxymethyl)pyrrolidin-1-yl)butan-1-amine

In a flame dried round-bottomed flask equipped with a magnetic stir bar and under inert atmosphere ($N_2$), to a solution of 2-(methoxymethyl)pyrrolidine (300 mg, 2.61 mmol) and 4-bromobutyronitrile (0.31 mL, 2.99 mmol) in dry $CH_3CN$ (13 mL) was added $K_2CO_3$ (1.51 g, 10.94 mmol) at rt followed by KI (43 mg, 0.26 mmol). The reaction mixture was stirred at rt for 15 h. The mixture was filtered and the filtrate partitioned between water and $CH_2Cl_2$. The layers were separated and the aq. layer extracted with $CH_2Cl_2$ (3×). The combined org. extracts were dried over $MgSO_4$, filtered and concentrated under reduced pressure. The crude nitrile was redissolved in dry THF (21 mL) and treated with LiALH$_4$ (192 mg, 5.07 mmol) at 0° C. The reaction mixture was warmed up to rt and stirred at this temperature until completion of the reaction. Sat. aq. Rochelle's salt solution and EA were then added, the layers separated and the aq. layer extracted with EA (3×). The combined organic extracts were washed with brine, dried over MgSO$_4$, filtered, and the solvents were removed under reduced pressure to give crude 4-(2-(methoxymethyl)pyrrolidin-1-yl)butan-1-amine as a pale yellow oil. GC-MS-conditions 01: $t_R$=2.1 min; [M+H]$^+$=187.20.

4-(3,3-Difluoropyrrolidin-1-yl)butan-1-amine

In a flame dried round-bottomed flask equipped with a magnetic stir bar and under inert atmosphere (N$_2$), to a solution of 3,3-difluoropyrrolidine hydrochloride (250 mg, 1.69 mmol) and 4-bromobutyronitrile (0.17 mL, 1.69 mmol) in dry CH$_3$CN (9 mL) was added K$_2$CO$_3$ (1.28 g, 9.29 mmol) at rt followed by KI (28 mg, 0.17 mmol). The reaction mixture was stirred at rt for 15 h. The mixture was filtered and the filtrate partitioned between water and CH$_2$Cl$_2$. The layers were separated and the aq. layer extracted with CH$_2$Cl$_2$ (3×). The combined org. extracts were dried over MgSO$_4$, filtered and concentrated under reduced pressure. The crude nitrile was redissolved in dry THF (8 mL) and treated with LiALH$_4$ (75 mg, 1.92 mmol) at 0° C. The reaction mixture was warmed up to rt and stirred at this temperature until completion of the reaction. Sat. aq. Rochelle's salt solution and EA were then added, the layers separated and the aq. layer extracted with EA (3×). The combined organic extracts were washed with brine, dried over MgSO$_4$, filtered, and the solvents were removed under reduced pressure to give crude 4-(3,3-difluoropyrrolidin-1-yl)butan-1-amine as a colorless oil. GC-MS-conditions 01: $t_R$=1.56 min; [M+H]$^+$=179.10.

(trans-4-Aminocyclohexyl)methanol

In a flame dried round-bottomed flask equipped with a magnetic stir bar and under inert atmosphere (N$_2$), a solution of trans-4-benzyloxycarbonylaminocyclohexane-methanol (110 mg, 0.42 mmol) in MeOH (5 mL) was hydrogenated in the presence of Pd/C (10%) at rt until completion of the reaction. The mixture was then filtered and concentrated under reduced pressure. The title compound was obtained as a light brown solid. LC-MS-conditions 07: $t_R$=0.11 min; [M+H]$^+$=130.24.

(cis-4-Aminocyclohexyl)methanol

In a flame dried round-bottomed flask equipped with a magnetic stir bar and under inert atmosphere (N$_2$), a solution of cis-4-benzyloxycarbonylaminocyclohexane-methanol (235 mg, 0.89 mmol) in MeOH (5 mL) was hydrogenated in the presence of Pd/C (10%) at rt until completion of the reaction. The mixture was then filtered and concentrated under reduced pressure. The title compound was obtained as a colorless oil. LC-MS-conditions 07: $t_R$=0.12 min; [M+H]$^+$=130.26.

tert-Butyl ((cis-4-aminocyclohexyl)methyl)carbamate

In a flame dried round-bottomed flask equipped with a magnetic stir bar and under inert atmosphere (N$_2$), to an ice-cold solution of cis-4-benzyloxycarbonylaminocyclohexane-methanol (1.53 g, 5.81 mmol), triphenylphoshine on polystyrene (17.43 mmol) and imidazole (559 mg, 8.13 mmol) in dry CH$_2$Cl$_2$ (150 mL) was added iodine (2.38 g, 9.30 mmol). The reaction mixture was warmed to rt and stirred at this temperature until completion of the reaction. The mixture was then filtered, successively washed with 10% aq. Na$_2$SO$_3$ and brine, dried over Na$_2$SO$_4$, filtered and concentrated under reduced pressure. The crude iodide (1.94 g, 5.20 mmol) was redissolved in DMF (15 mL) and treated with sodium azide (358 mg, 5.46 mmol). The reaction mixture was heated to 80° C. until completion of the reaction. The mixture was then diluted with EA, washed with brine (3×), dried over MgSO$_4$, filtered and concentrated under reduced pressure. To a mixture of the crude azide (1.50 g, 5.20 mmol) in THF (27 mL) were added polymer-supported Ph$_3$P (2.0 eq.) and water (9 mL). The reaction mixture was stirred at 55° C. until completion of the reaction, cooled down to rt and filtered. The filtrate was partitioned between EA and aq. 0.5M Na$_2$CO$_3$ and the layers separated. The aq. layer was extracted with EA (2×) and the combined org. extracts dried over MgSO$_4$, filtered and concentrated under reduced pressure to give benzyl (cis-4-(aminomethyl)cyclohexyl)carbamate as a yellow oil. LC-MS-conditions 07b: $t_R$=0.57 min; [M+H]$^+$=263.46.

To a solution of the crude amine (467 mg, 1.78 mmol) in THF (4 mL) was added aq. 1M NaOH (1.85 mL, 1.85 mmol) at 0° C. The reaction mixture was stirred at 0° C. for 10 min and a solution of di-tert-butyl dicarbonate (412 mg, 1.85 mmol) in THF (3 mL) was then added dropwise. The reaction mixture was warmed to rt and stirred at this temperature until completion of the reaction. The mixture was diluted with CH$_2$Cl$_2$, filtered and the layers separated. The organic layer was dried over Na$_2$SO$_4$, filtered, and the solvents were removed under reduced pressure. The crude residue was purified by FC (hept-EA, 1:0->7:3) and then the Cbz group was removed by treatment with 10% Pd/C (150 mg) in EA/MeOH 1:1 (10 mL) under a H$_2$ atmosphere. The title compound was obtained as a colorless oil. LC-MS-conditions 07b: $t_R$=0.52 min; [M+H]$^+$=229.46.

tert-Butyl ((trans-4-aminocyclohexyl)methyl)carbamate

In a flame dried round-bottomed flask equipped with a magnetic stir bar and under inert atmosphere (N$_2$), to an ice-cold solution of trans-4-benzyloxycarbonylaminocyclohexane-methanol (1.32 g, 5.01 mmol), triphenylphoshine on polystyrene (15.04 mmol) and imidazole (483 mg, 7.02 mmol) in dry CH$_2$Cl$_2$ (150 mL) was added iodine (2.06 g, 8.02 mmol). The reaction mixture was warmed to rt and stirred at this temperature until completion of the reaction. The mixture was then filtered, successively washed with 10% aq. Na$_2$SO$_3$ and brine, dried over Na$_2$SO$_4$, filtered and concentrated under reduced pressure. The crude iodide (1.64 g, 4.39 mmol) was redissolved in DMF (15 mL) and treated with sodium azide (303 mg, 4.61 mmol). The reaction mixture was heated to 80° C. until completion of the reaction. The mixture was then diluted with EA, washed with brine (3×), dried over MgSO$_4$, filtered and concentrated under reduced pressure. To a mixture of the crude azide (1.27 g, 4.40 mmol) in THF (21 mL) were added polymer-supported Ph$_3$P (2.0 eq.) and water (7 mL). The reaction mixture was stirred at 55° C. until completion of the reaction, cooled down to rt and filtered. The filtrate was partitioned between EA and aq. 0.5M Na$_2$CO$_3$ and the layers separated. The aq. layer was extracted with EA (2×) and the combined org. extracts dried over MgSO$_4$, filtered and concentrated under reduced pressure to give benzyl (trans-4-(aminomethyl)cyclohexyl)carbamate as a white solid. LC-MS-conditions 07b: $t_R$=0.57 min; [M+H]$^+$=263.46.

To a solution of the crude amine (466 mg, 1.78 mmol) in THF (4 mL) was added aq. 1M NaOH (1.85 mL, 1.85 mmol) at 0° C. The reaction mixture was stirred at 0° C. for 10 min and a solution of di-tert-butyl dicarbonate (412 mg, 1.85 mmol) in THF (3 mL) was then added dropwise. The reaction mixture was warmed to rt and stirred at this temperature until completion of the reaction. The mixture was diluted with $CH_2Cl_2$, filtered and the layers separated. The organic layer was dried over $Na_2SO_4$, filtered, and the solvents were removed under reduced pressure. The crude residue was purified by FC (hept-EA, 1:0->7:3) and then the Cbz group was removed by treatment with 10% Pd/C (120 mg) in EA/MeOH 1:1 (10 mL) under a $H_2$ atmosphere. The title compound was obtained as a white solid. LC-MS-conditions 07b: $t_R$=0.51 min; [M+H]$^+$=229.47.

Amide coupling (with 2-[1-(tert-butyl-dimethyl-silanyloxy)-ethyl]-oxazol-5-yl-methylamine)—formation of (5R*)—N$^5$-(2-[1-(tert-butyl-dimethyl-silanyloxy)-ethyl]-oxazol-5-yl -methyl)-(6R*)—N$^6$-(4-pyrrolidin-1-yl -butyl)-(4S*,7R*)-[4,7-ethenylene-spiro[2.4]heptane]-5,6-dicarboxamide In a flame dried round-bottomed flask equipped with a magnetic stir bar and under inert atmosphere ($N_2$), to a solution of (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide (150 mg, 0.45 mmol) in dry $CH_2Cl_2$ (5 mL) were added HOBt (73 mg, 0.54 mmol), EDC.HCl (216 mg, 1.13 mmol), DMAP (14 mg, 0.11 mmol) and DIPEA (0.31 mL, 1.81 mmol). The reaction mixture was stirred at rt for 30 minutes, then a solution of 2-[1-(tert-butyl-dimethyl-silanyloxy)-ethyl]-oxazol-5-yl-methylamine (116 mg, 0.45 mmol) in dry $CH_2Cl_2$ (4 mL) was added. The reaction mixture was stirred at rt until reaction completion. Water was added, the layers separated, and the org. layer dried over $MgSO_4$, filtered, and concentrated under reduced pressure. The crude residue was purified by FC (9:1 $CH_2Cl_2$-MeOH+1% $NH_4OH$) to give the title compound as a yellow oil. LC-MS-conditions 01: $t_R$=0.88 min; [M+H]$^+$=571.24.

Amide coupling (with 2-amino-5-methyl-thiazole)—formation of (5R*)—N$^5$-(5-methyl-thiazol-2-yl)-(6R*)-6-ethoxycarbonyl -(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (6R*)-6-ethoxycarbonyl-(4S*,7R*)-[4,7-ethenylene-spiro[2.4]heptane]-(5R*)-5-carboxylic acid (400 mg, 1.69 mmol) in dry $CH_2Cl_2$ (9 mL) were added EDC.HCl (828 mg, 4.23 mmol), DMAP (53 mg, 0.42 mmol) and DIPEA (1.45 mL, 8.46 mmol). The reaction mixture was stirred at rt for 30 minutes, then 2-amino-5-methyl-thiazole (197 mg, 1.69 mmol) was added. The reaction mixture was stirred at rt for 2 days. Water was added, the layers separated, and the aq. layer extracted with $CH_2Cl_2$ (3×). The combined org. extracts were dried over $MgSO_4$, filtered, and concentrated under reduced pressure. The crude residue was purified by FC (1:1 hept-EA) to give the title compound as a white solid. TLC:rf (1:1 hept-EA)=0.37. LC-MS-conditions 02: $t_R$=0.99 min; [M+H]$^+$=333.41.

Amide coupling (with 4-bromo-benzylamine)—formation of (5R*)—N$^5$-(4-bromophenyl-methyl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (6R*)-6-ethoxycarbonyl-(4S*,7R*)-[4,7-ethenylene-spiro[2.4]heptane]-(5R*)-5-carboxylic acid (2.50 g, 10.58 mmol) in dry $CH_2Cl_2$ (53 mL) were added EDC.HCl (5.17 g, 26.45 mmol), DMAP (330 mg, 2.64 mmol) and DIPEA (9.1 mL, 52.91 mmol). The reaction mixture was stirred at rt for 30 minutes, then 4-bromo-benzylamine hydrochloride (2.40 g, 10.58 mmol) was added. The reaction mixture was stirred at rt for 2 days. Water was added, the layers separated, and the aq. layer extracted with $CH_2Cl_2$ (3×). The combined org. extracts were dried over $MgSO_4$, filtered, and concentrated under reduced pressure. The crude residue was purified by FC (3:2 hept-EA) to give the title compound as a yellow oil. TLC:rf (3:2 hept-EA)=0.45. LC-MS-conditions 02: $t_R$=1.06 min; [M+H]$^+$=404.00.

Saponification—formation of (5R*)—N$^5$-(4-bromophenyl-methyl)-(6R*)-6-hydroxycarbonyl-(4S*,7R*)-[4,7-ethenylene-spiro[2.4]heptane]-5-carboxamide A mixture of (5R*)—N$^5$-(4-bromophenyl-methyl)-(6R*)-6-ethoxycarbonyl-(4S*,7R*)-[4,7-ethenylene-spiro[2.4]heptane]-5-carboxamide (3.43 g, 8.48 mmol) in EtOH (85 mL) and 1N NaOH (85 mL) was stirred at rt until completion of the reaction. EtOH was removed under reduced pressure and the residue partitioned between 1N HCl and EA. The layers were separated and the aq. layer extracted with EA (3×). The combined org. extracts were washed with brine, dried over $MgSO_4$, filtered, and concentrated under reduced pressure to give the title compound as a yellow oil. LC-MS-conditions 02: $t_R$=0.94 min; [M+H]$^+$=376.10.

Amide coupling (with 2-amino-5-bromo-thiazole)—formation of (5R*)—N$^5$-(5-bromo-thiazol-2-yl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere ($N_2$), to a solution of (6R*)-6-ethoxycarbonyl-(4S*,7R*)-[4,7-ethenylene-spiro[2.4]heptane]-(5R*)-5-carboxylic acid (500 mg, 2.12 mmol) in dry $CH_2Cl_2$ (5 mL) were added a few drops of DMF and oxalyl chloride (0.20 mL, 2.33 mmol). The reaction mixture was stirred at rt for 30 minutes. To the solution of the resulting acyl chloride was added a solution of 2-amino-5-bromo-thiazole hydrobromide (851 mg, 3.17 mmol) and DIPEA (1.45 mL, 8.47 mmol) in dry $CH_2Cl_2$ (2.5 mL). The reaction mixture was stirred at rt for 2 h. 1N HCl was added, the layers separated, and the aq. layer extracted with EA (2×). The combined org. extracts were successively washed with aq. sat. $Na_2CO_3$, brine, dried over $MgSO_4$, filtered, and concentrated under reduced pressure. The crude residue was purified by FC (7:3 hept-EA) to give the title compound as a white foam. TLC:rf (7:3 hept-EA)=0.30. LC-MS-conditions 02: $t_R$=1.05 min; [M+H]$^+$=397.25.

Saponification—formation of (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide A mixture of (5R*)—N$^5$-(5-bromo-thiazol-2-yl)-(6R*)-6-ethoxycarbonyl-(4S*,7R*)-[4,7-ethenylene-spiro[2.4]heptane]-5-carboxamide (1.13 g, 2.86 mmol) in EtOH (29 mL) and 1N NaOH (29 mL) was stirred at rt until completion of the reaction. EtOH was removed under reduced pressure and the residue partitioned between 1N HCl and EA. The layers were separated and the aq. layer extracted with EA (3×). The combined org. extracts were washed with brine, dried over MgSO$_4$, filtered, and concentrated under reduced pressure to give the title compound as a beige solid. LC-MS-conditions 02: t$_R$=0.93 min; [M+H]$^+$=369.21.

Amide coupling (with (4-(2-methyl-[1,3]dioxolan-2-yl)thiazol-2-yl)methanamine)—formation of (5R*)—N$^5$-(4-(2-methyl-[1,3]dioxolan-2-yl)-thiazol-2-yl-methyl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere (N$_2$), to a solution of (6R*)-6-ethoxycarbonyl-(4S*,7R*)-[4,7-ethenylene-spiro[2.4]heptane]-(5R*)-5-carboxylic acid (970 mg, 4.11 mmol) in dry CH$_2$Cl$_2$ (15 mL) were added EDC.HCl (1.97 g, 10.26 mmol), DMAP (125 mg, 1.02 mmol) and DIPEA (2.81 mL, 16.42 mmol). The reaction mixture was stirred at rt for 30 minutes, then (4-(2-methyl-[1,3]dioxolan-2-yl)thiazol-2-yl)methanamine (822 mg, 4.11 mmol) in dry CH$_2$Cl$_2$ (15 mL) was added. The reaction mixture was stirred at rt until completion of the reaction. Water was added, the layers separated, and the org. layer dried over MgSO$_4$, filtered, and concentrated under reduced pressure. The crude residue was purified by FC (5:1->1:4 hept-EA) to give the title compound as a yellow oil. LC-MS-conditions 02: t$_R$=0.93 min; [M+H]$^+$=419.02.

Saponification/Acetal deprotection—formation of (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide A mixture of (5R*)—N$^5$-(4-(2-methyl-[1,3]dioxolan-2-yl)-thiazol-2-yl-methyl)-(6R*)-6-ethoxycarbonyl-(4S*,7R*)-[4,7-ethenylene-spiro[2.4]heptane]-5-carboxamide (1.50 g, 3.58 mmol) in EtOH (35 mL) and 1N NaOH (35 mL) was stirred at rt until completion of the reaction. EtOH was removed under reduced pressure and the residue partitioned between 2N HCl and EA. The layers were separated and the aq. layer extracted with EA (3×). The combined org. extracts were washed with brine, dried over MgSO$_4$, filtered, and concentrated under reduced pressure to give the crude carboxylic acid as a yellow solid. Part of this crude material (800 mg, 2.05 mmol) was dissolved in THF (10 mL) and treated with aq. 1N HCl (6 mL) at rt. The reaction mixture was stirred at rt until completion of the reaction. Water was added and the product extracted with EA (3×). The combined org. extracts were washed with brine, dried over MgSO$_4$, filtered, and concentrated under reduced pressure to give the title compound as a yellow solid. LC-MS-conditions 02: t$_R$=0.77 min; [M+H]$^+$=347.07.

Amide coupling (with 2-amino-4-acetyl-thiazole)—formation of (5R*)—N$^5$-(4-acetyl-thiazol-2-yl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere (N$_2$), to a solution of (6R*)-6-ethoxycarbonyl-(4S*,7R*)-[4,7-ethenylene-spiro[2.4]heptane]-(5R*)-5-carboxylic acid (250 mg, 1.06 mmol) in dry CH$_2$Cl$_2$ (5 mL) were added EDC.HCl (517 mg, 2.64 mmol), DMAP (33 mg, 0.26 mmol) and DIPEA (0.91 mL, 5.29 mmol). The reaction mixture was stirred at rt for 30 minutes, then 2-amino-4-acetyl-thiazole hydrobromide (236 mg, 1.06 mmol) was added. The reaction mixture was stirred at rt until completion of the reaction. Water was added, the layers separated, and the aq. layer extracted with CH$_2$Cl$_2$ (3×). The combined org. extracts were dried over MgSO$_4$, filtered, and concentrated under reduced pressure. The crude residue was purified by FC (hept-EA 1:1) to give the title compound as a pale pink solid. TLC:rf (1:1 hept-EA)=0.41. LC-MS-conditions 02: t$_R$=0.97 min; [M+H]$^+$=361.27.

Saponification—formation of (5R*)—N$^5$-(4-acetyl-thiazol-2-yl)-(6R*)-6-hydroxycarbonyl-(4S*,7R*)-[4,7-ethenylene-spiro[2.4]heptane]-5-carboxamide A mixture of (5R*)—N$^5$-(4-acetyl-thiazol-2-yl)-(6R*)-6-ethoxycarbonyl-(4S*,7R*)-[4,7-ethenylene-spiro[2.4]heptane]-5-carboxamide (80 mg, 0.22 mmol) in EtOH (2.2 mL) and 1N NaOH (2.2 mL) was stirred at rt until completion of the reaction. EtOH was removed under reduced pressure and the residue partitioned between 2N HCl and EA. The layers were separated and the aq. layer extracted with EA (3×). The combined org. extracts were washed with brine, dried over MgSO$_4$, filtered, and concentrated under reduced pressure to give the title compound as an off-white foam. LC-MS-conditions 02: t$_R$=0.84 min; [M+H]$^+$=333.29.

Amide coupling (with 4-methyl-1,3-oxazol-2-amine)—formation of (5R*)—N$^5$-(4-methyl-oxazol-2-yl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere (N$_2$), to a solution of (6R*)-6-ethoxycarbonyl-(4S*,7R*)-[4,7-ethenylene-spiro[2.4]heptane]-(5R*)-5-carboxylic acid (300 mg, 1.27 mmol) in dry CH$_2$Cl$_2$ (6.5 mL) were added EDC.HCl (621 mg, 3.17 mmol), DMAP (40 mg, 0.32 mmol) and DIPEA (1.09 mL, 6.35 mmol). The reaction mixture was stirred at rt for 30 minutes, then 4-methyl-1,3-oxazol-2-amine (138 mg, 1.27 mmol) was added. The reaction mixture was stirred at rt for 36 h. Water was added, the layers separated, and the aq. layer extracted with CH$_2$Cl$_2$ (3×). The combined org. extracts were dried over MgSO$_4$, filtered, and concentrated under reduced pressure. The crude residue was purified by FC (1:4 hept-EA) to give the title compound as a colorless oil. TLC:rf (1:4 hept-EA)=0.53. LC-MS-conditions 02: t$_R$=0.88 min; [M+H]$^+$=317.50.

Amide coupling (with 2-amino-4,5-dimethyl-thiazole)—formation of (5R*)—N$^5$-(4,5-dimethyl-thiazol-2-yl)-(6R*)-6-ethoxycarbonyl-(4S*,7R*)-[4,7-ethenylene-spiro[2.4]heptane]-5-carboxamide In a flame dried round-bottomed flask equipped with a magnetic stir bar and under inert atmosphere (N$_2$), to a solution of (6R*)-6-ethoxycarbonyl-(4S*,7R*)-[4,7-ethenylene-spiro[2.4]heptane]-(5R*)-5-carboxylic acid (238 mg, 1.01 mmol) in dry CH$_2$Cl$_2$ (5 mL) were added EDC.HCl (493 mg, 2.52 mmol), DMAP (31 mg, 0.25 mmol) and DIPEA (0.86 mL, 5.04 mmol). The reaction mixture was stirred at rt for 30 minutes, then 2-amino-4,5-dimethyl-thiazole hydrochloride (169 mg, 1.01 mmol) was added. The reaction mixture was stirred at rt for 36 h. Water was added, the layers separated, and the aq. layer extracted with CH$_2$Cl$_2$ (3×). The combined org. extracts were dried over MgSO$_4$, filtered, and concentrated under reduced pressure. The crude residue was purified by FC (3:2 hept-EA) to give the title compound as a colorless oil. TLC:rf (3:2 hept-EA)=0.25. LC-MS-conditions 02: $t_R$=1.00 min; [M+H]$^+$=347.51.

Diels Alder reaction—formation of (5R,6R)-5,6-bis-[(1-(1S)-ethoxycarbonyl)-ethoxy-carbonyl]-(4S,7R)-[4,7-ethenylene-spiro[2.4]heptane]

In a flame dried round-bottomed flask equipped with a magnetic stir bar and under inert atmosphere (N$_2$), to a solution of (E)-1,2-bis-[((1S)-1-ethoxycarbonyl)-ethoxy-carbonyl]-ethene (7.40 g, 22.7 mmol) in n-hexane (76 mL) was added spiro[2.4]hepta-4,6-diene (3.14 g, 34.0 mmol) at rt. The reaction mixture was stirred at this temperature overnight. The mixture was concentrated under reduced pressure and the crude residue purified by FC (hept/EA, 9:1). The title compound was obtained as a pale yellow oil. TLC:rf (9:1 hept-EA) =0.25. LC-MS-conditions 02: $t_R$=1.12 min; [M+H]$^+$=409.00. $^1$H NMR (400 MHz, CDCl$_3$) δ 6.44 (dd, J=5.5, 3.0 Hz, 1 H), 6.32 (dd, J=5.5, 2.8 Hz, 1 H), 5.12 (q, J=7.1 Hz, 1 H), 5.06 (q, J=7.1 Hz, 1 H), 4.28-4.14 (m, 4 H), 3.76 (app. t, J=4.0 Hz, 1 H), 2.92 (d, J=4.8 Hz, 1 H), 2.86 (m, 1 H), 2.80 (m, 1 H), 1.55-1.47 (m, 6 H), 1.29 (t, J=7.3 Hz, 3 H), 1.29 (t, J=7.3 Hz, 3 H), 0.70 (m, 1 H), 0.56-0.44 (m, 3 H).

Saponification—formation of (4S,7R)-[4,7-ethenylene-spiro[2.4]heptane]-(5R,6R)-5,6-bis-carboxylic acid To a solution of (5R,6R)-5,6-bis-[(1-(1S)-ethoxycarbonyl)-ethoxy-carbonyl]-(4S,7R)-[4,7-ethenylene-spiro[2.4]heptane] (9.51 g, 23.28 mmol) in THF/H$_2$O (1:1, 232 mL) was added LiOH (3.91 g, 93.13 mmol). The reaction mixture was stirred at rt overnight. 1N HCl was added in order to adjust the pH of the reaction mixture to pH=3, the layers separated and the aq. layer extracted with EA (3×). The combined org. extracts were dried over MgSO$_4$, filtered, and concentrated under reduced pressure. The crude residue was purified by FC (CH$_2$Cl$_2$/MeOH, 9:1) to give the title compound as a colorless oil. TLC:rf (9:1 CH$_2$Cl$_2$/MeOH)=0.31. LC-MS-conditions 02: $t_R$=0.72 min; [M+AcCN+H]$^+$=250.18.

Iodolactonization—formation of enantiopure iodolactone 2

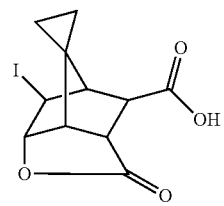 [SMILES: O=C(O)C1C2C(=O)OC3C(I)C1C1(CC1)C32]

To a solution of (4S,7R)-[4,7-ethenylene-spiro[2.4]heptane]-(5R,6R)-5,6-bis-carboxylic acid (5.60 g, 22.32 mmol) in CH$_2$Cl$_2$ (33 mL) were added NaHCO$_3$ (2.06 g, 24.56 mmol), water (100 mL), KI (1.37 g, 82.60 mmol) and I$_2$ (6.80 g, 26.79 mmol). The reaction mixture was stirred at rt for 3 h. The reaction was quenched by the addition of sat. aq. Na$_2$S$_2$O$_3$. The layers were separated and the aq. layer extracted with CH$_2$Cl$_2$ (3×). The combined org. extracts were dried over MgSO$_4$, filtered, and concentrated under reduced pressure. The crude foam was purified by FC (EA) to give enantiopure iodolactone 2 as a white solid. TLC: rf (EA)=0.33.

Esterification—formation of enantiopure iodolactone 1 (R$^{10}$=Me)

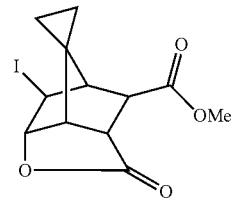 [SMILES: COC(=O)C1C2C(=O)OC3C(I)C1C1(CC1)C32]

In a flame dried round-bottomed flasked equipped with a magnetic stir bar and under inert atmosphere (N$_2$), to a solution of enantiopure iodolactone 2 (5.00 g, 14.96 mmol) in dry MeOH (75 mL) was added TMSCH$_2$N$_2$ (2.0 M in hexanes, 37.0 mL, 74.83 mmol). The reaction mixture was stirred at rt overnight, concentrated under reduced pressure and purified by FC (hept-EA, 4:1) to give enantiopure iodolactone 1 (R$^{10}$=Me) as a white solid. TLC:rf (4:1 hept-EA)=0.18.

Retro-iodolactonization—formation of (6R)-6-methoxycarbonyl-(4S,7R)-[4,7-ethenylene-spiro[2.4]heptane]-(5R)-5-carboxylic acid In a flame dried round-bottomed flask equipped with a magnetic stir bar and under inert atmosphere (N$_2$), to a solution of enantiopure iodolactone 1 (R$^{10}$=Me) (2.86 g, 8.21 mmol) in acetic acid (29 mL) was added zinc powder (8.06 g, 123.23 mmol). The reaction mixture was stirred at 65° C. for 4 h, cooled down to rt, filtered and partitioned between water and EA. The layers were separated and the aq. layer extracted with EA (3×). The combined org. extracts were washed with brine, dried over MgSO$_4$, filtered, and concentrated under reduced pressure. The crude residue was purified by FC (hept-EA, 1:1) and the title compound was obtained as a colorless oil. TLC:rf (1:1 hept-EA)=0.41.

Amide coupling (with 4-bromo-aniline)—formation of (5R)—N$^5$-(4-bromo-phenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (80 mg, 0.36 mmol) in dry toluene (2 mL) were added a few drops of DMF and oxalyl chloride (0.048 mL, 0.54 mmol). The reaction mixture was stirred at reflux for 40 minutes, cooled down to rt, concentrated under reduced pressure and the residue dried under high vacuum.

To a solution of this acyl chloride in dry CH$_2$Cl$_2$ (2 mL) were added 4-bromoaniline (96 mg, 0.54 mmol) and DIPEA (0.18 mL, 1.08 mmol). The reaction mixture was stirred at rt for 1 h. 1N HCl was added, the layers separated, and the aq. layer extracted with CH$_2$Cl$_2$ (3×). The combined org. extracts were washed with brine, dried over MgSO$_4$, filtered, and concentrated under reduced pressure. The crude residue was purified by FC (3:2 hept-EA) to give the title compound as an orange solid. TLC:rf (3:2 hept-EA)=0.50. LC-MS-conditions 02: $t_R$=1.06 min; [M+H]$^+$=376.20.

Amide coupling (with 1-(5-aminomethyl-furan-2-yl)-ethanone)—formation of (5R)—N$^5$-(5-acetyl-furan-2-yl-methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (200 mg, 0.90 mmol) in dry CH$_2$Cl$_2$ (3 mL) were added EDC.HCl (440 mg, 2.25 mmol), DMAP (28 mg, 0.22 mmol) and DIPEA (0.46 mL, 2.70 mmol). The reaction mixture was stirred at rt for 30 minutes, then 1-(5-aminomethyl-furan-2-yl)-ethanone (125 mg, 0.90 mmol) was added. The reaction mixture was stirred at rt for 16 h. Water was added, the layers separated, and the aq. layer extracted with CH$_2$Cl$_2$ (3×). The combined org. extracts were dried over MgSO$_4$, filtered, and concentrated under reduced pressure. The crude residue was purified by FC (4:6 hept-EA) to give the title compound as a colorless oil. TLC:rf (4:6 hept-EA)=0.21. LC-MS-conditions 02: $t_R$=0.89 min; [M+H]$^+$=344.49.

(5R)—N$^5$-(5-Acetyl-furan-2-yl-methyl)-(6R)-6-hydroxycarbonyl-(4S,7R)-[4,7-ethenylene-spiro[2.4]heptane]-5-carboxamide To a solution of (5R)—N$^5$-(5-acetyl-furan-2-yl-methyl)-(6R)-6-methoxycarbonyl-(4S,7R)-[4,7-ethenylene-spiro[2.4]heptane]-5-carboxamide (210 mg, 0.61 mmol) in EtOH (6.1 mL) was added aq. 1N NaOH (6.1 mL, 6.10 mmol). The reaction mixture was stirred at rt overnight and concentrated under reduced pressure. The residue was partitioned between 1N HCl and EA, the layers separated and the aq. layer extracted with EA (3×). The combined org. extracts were dried over MgSO$_4$, filtered, and concentrated under reduced pressure to give the title compound as a yellow foam. TLC:rf (9:1 CH$_2$Cl$_2$/MeOH)=0.38. LC-MS-conditions 02: $t_R$=0.79 min; [M+H]$^+$=329.94.

(5R)—N$^5$-(4-Bromo-phenyl)-(6R)-6-hydroxycarbonyl-(4S,7R)-[4,7-ethenylene-spiro[2.4]heptane]-5-carboxamide A mixture of (5R)—N$^5$-(4-bromo-phenyl)-(6R)-6-ethoxycarbonyl-(4S,7R)-[4,7-ethylene-spiro[2.4]heptane]-5-carboxamide (prepared from the racemic compound using chiral HPLC, 500 mg, 1.28 mmol) and 1N aq. NaOH (13 mL) in EtOH (13 mL) was stirred at rt overnight. The reaction mixture was then concentrated under reduced pressure and partitioned between 2M HCl and EA. The layers were separated and the aq. layer extracted with EA (3×). The combined organic extracts were washed with brine, dried over MgSO$_4$, filtered and concentrated under reduced pressure to give the title compound as a white solid. LC-MS-conditions 02: $t_R$=0.97 min; [M+H]$^+$=362.20.

Double bond reduction—formation of (6R)-6-methoxycarbonyl-(4S,7R)-[4,7-ethylene-spiro[2.4]heptane]-(5R)-5-carboxylic acid In a flame dried round-bottomed flask equipped with a magnetic stir bar and under inert atmosphere (N$_2$), a deoxygenated suspension of (6R)-6-methoxycarbonyl-(4S,7R)-[4,7-ethenylene-spiro[2.4]heptane]-(5R)-5-carboxylic acid (220 mg, 0.99 mmol), Pd/C 10% (44 mg) and cyclohexene (0.20 mL, 1.98 mmol) in dry THF (2.5 mL) was stirred at reflux for 2 h. The reaction mixture was filtered through celite and the filter cake washed with THF. The filtrate was concentrated under reduced pressure and the title compound obtained as a white solid. TLC:rf (2:3 hept-EA)=0.48.

Amide coupling (with 4-bromo-aniline)—formation of (5R)—N$^5$-(4-bromo-phenyl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (220 mg, 0.98 mmol) in dry toluene (5 mL) were added a few drops of DMF and oxalyl chloride (0.13 mL, 1.47 mmol). The reaction mixture was stirred at reflux for 40 minutes, cooled down to rt, concentrated under reduced pressure and the residue dried under high vacuum.

To a solution of this acyl chloride in dry CH$_2$Cl$_2$ (5 mL) were added 4-bromoaniline (261 mg, 1.47 mmol) and DIPEA (0.50 mL, 2.94 mmol). The reaction mixture was stirred at rt for 1 h. 1N HCl was added, the layers separated, and the aq. layer extracted with CH$_2$Cl$_2$ (3×). The combined org. extracts were washed with brine, dried over MgSO$_4$, filtered, and concentrated under reduced pressure. The crude residue was purified by FC (hept-EA, 4:1) and the title compound obtained as a white foam. TLC:rf (4:1 hept-EA)=0.35. LC-MS-conditions 02: $t_R$=1.10 min; [M+H]$^+$=378.22.

Amide coupling (with 1-(5-aminomethyl-furan-2-yl)-ethanone)—formation of (5R)—N$^5$-(5-acetyl-furan-2-yl-methyl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (200 mg, 0.89 mmol) in dry CH$_2$Cl$_2$ (3 mL) were added EDC.HCl (436 mg, 2.23 mmol), DMAP (28 mg, 0.22 mmol) and DIPEA (0.46 mL, 2.68 mmol). The reaction mixture was stirred at rt for 30 minutes, then 1-(5-aminomethyl-furan-2-yl)-ethanone (124 mg, 0.89 mmol) was added. The reaction mixture was stirred at rt for 16 h. Water was added, the layers separated, and the aq. layer extracted with CH$_2$Cl$_2$ (3×). The combined org. extracts were dried over MgSO$_4$, filtered, and concentrated under reduced pressure. The crude residue was purified by FC (4:6 hept-EA) to give the title compound as a colorless oil. TLC:rf (4:6 hept-EA)=0.35. LC-MS-conditions 01: $t_R$=0.88 min; [M+H]$^+$=346.05.

(5R)—N$^5$-(5-Acetyl-furan-2-yl-methyl)-(6R)-6-hydroxycarbonyl-(4S,7R)-[4,7-ethylene-spiro[2.4]heptane]-5-carboxamide To a solution of (5R)—N$^5$-(5-acetyl-furan-2-yl-methyl)-(6R)-6-methoxycarbonyl-(4S,7R)-[4,7-ethylene-spiro[2.4]heptane]-5-carboxamide (110 mg, 0.32 mmol) in EtOH (3.2 mL) was added aq. 1N NaOH (3.2 mL, 3.20 mmol). The reaction mixture was stirred at rt overnight and concentrated under reduced pressure. The residue was partitioned between 1N HCl and EA, the layers separated and the aq. layer extracted with EA (3×). The combined org. extracts were dried over MgSO$_4$, filtered, and concentrated under reduced pressure to give the title compound as a yellow foam. TLC:rf (9:1 CH$_2$Cl$_2$/MeOH)=0.38. LC-MS-conditions 02: t$_R$=0.82 min; [M+H]$^+$=332.37.

Amide coupling (with 2-amino-5-bromo-thiazole)—formation of (5R)—N$^5$-(5-bromo-thiazol-2-yl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (1.11 g, 5.00 mmol) in dry CH$_2$Cl$_2$ (20 mL) were added a few drops of DMF and oxalyl chloride (0.48 mL, 5.50 mmol). The reaction mixture was stirred at rt for 30 minutes, concentrated under reduced pressure and the residue dried under high vacuum.

To a suspension of 2-amino-5-bromo-thiazole monohydrobromide (1.34 g, 5.00 mmol) in dry THF (10 mL) was added a solution of the acyl chloride in dry THF (10 mL) followed by Et$_3$N (1.4 mL, 10.0 mmol). The reaction mixture was stirred at rt for 1 h, diluted with EA and washed with brine. The layers were separated and the aq. layer extracted with EA (3×). The combined org. extracts were dried over MgSO$_4$, filtered, and concentrated under reduced pressure. The crude residue was purified by FC (hept-EA, 5:1) and the title compound obtained as a pale yellow oil. TLC:rf (1:1 hept-EA)=0.60. LC-MS-conditions 01: t$_R$=0.98 min; [M+H]$^+$=382.92.

(5R)—N$^5$-(5-Bromo-thiazol-2-yl)-(6R)-6-hydroxycarbonyl-(4S,7R)-[4,7-ethenylene-spiro[2.4]heptane]-5-carboxamide To a solution of (5R)—N$^5$-(5-bromo-thiazol-2-yl)-(6R)-6-methoxycarbonyl-(4S,7R)-[4,7-ethenylene-spiro[2.4]heptane]-5-carboxamide (2.14 g, 5.58 mmol) in THF (30 mL) was added aq. 2N NaOH (11 mL, 22.00 mmol). The reaction mixture was stirred at rt until completion of the reaction. The mixture was then washed with Et$_2$O, the aq. layer acidified and extracted with EA (3×). The combined org. extracts were washed with brine, dried over MgSO$_4$, filtered, and concentrated under reduced pressure to give the title compound as a pale yellow solid. LC-MS-conditions 01: t$_R$=0.88 min; [M+H]$^+$=368.87.

Amide coupling (with 5-amino-2-bromo-pyridine)—formation of (5R)—N$^5$-(2-bromo-pyrid-5-yl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (222 mg, 1.00 mmol) in dry CH$_2$Cl$_2$ (4 mL) were added a few drops of DMF and oxalyl chloride (0.10 mL, 1.13 mmol). The reaction mixture was stirred at rt for 30 minutes and a solution of 5-amino-2-bromo-pyridine (265 mg, 1.50 mmol) and DIPEA (0.70 mL, 4.00 mmol) in dry CH$_2$Cl$_2$ (2 mL). The reaction mixture was stirred at rt for 20 minutes, diluted with EA and washed with aq. 1N HCl. The layers were separated and the aq. layer extracted with EA (2×). The combined org. extracts were dried over MgSO$_4$, filtered, and concentrated under reduced pressure. The crude residue was purified by FC (hept-EA, 5:1->3:1) and the title compound obtained as a colorless oil. LC-MS-conditions 01: t$_R$=0.95 min; [M+H]$^+$=376.97.

(5R)—N$^5$-(2-Bromo-pyrid-5-yl)-(6R)-6-hydroxycarbonyl-(4S,7R)-[4,7-ethenylene-spiro[2.4]heptane]-5-carboxamide To a solution of (5R)—N$^5$-(2-bromo-pyrid-5-yl)-(6R)-6-methoxycarbonyl-(4S,7R)-[4,7-ethenylene-spiro[2.4]heptane]-5-carboxamide (323 mg, 0.86 mmol) in THF (4 mL) was added aq. 2N NaOH (1.7 mL, 3.40 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a pale yellow foam. LC-MS-conditions 02: t$_R$=0.87 min; [M+H]$^+$=362.93.

Amide coupling (with 4-bromo-3-fluoroaniline)—formation of (5R)—N$^5$-(4-bromo-3-fluorophenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 4-bromo-3-fluoroaniline (95 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a colorless solid. TLC:rf (1:1 hept-EA)=0.55. LC-MS-conditions 02: t$_R$=1.07 min; [M+H]$^+$=393.86.

Amide coupling (with 4-bromo-2-fluoroaniline)—formation of (5R)—N$^5$-(4-bromo-2-fluorophenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (59 mg, 0.26 mmol) in dry CH$_2$Cl$_2$ (2 mL) were added EDC.HCl (129 mg, 0.66 mmol) and DMAP (6 mg, 0.05 mmol). The mixture was cooled to 0° C. and a solution of 4-bromo-2-fluoroaniline (50 mg, 0.26 mmol) in dry CH$_2$Cl$_2$ (1 mL) was added followed by DIPEA (0.18 mL, 1.05 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a yellow oil. LC-MS-conditions 02: t$_R$=1.07 min; [M+H]$^+$=393.65.

(5R)—N$^5$-(4-Bromo-2-fluorophenyl)-(6R)-6-hydroxycarbonyl-(4S,7R)-[4,7-ethenylene-spiro[2.4]heptane]-5-carboxamide To a solution of (5R)—N$^5$-(4-bromo-2-fluorophenyl)-(6R)-6-methoxycarbonyl-(4S,7R)-[4,7-ethenylene-spiro

[2.4]heptane]-5-carboxamide (20 mg, 0.05 mmol) in EtOH (1 mL) was added aq. 1N NaOH (0.5 mL, 0.50 mmol). The reaction mixture was stirred at rt until completion of the reaction. The mixture was then concentrated under reduced pressure, the residue partitioned between 2N HCl and EA. The layers were separated and the aq. layer extracted with EA (3×). The combined org. extracts were washed with brine, dried over MgSO$_4$, filtered, and concentrated under reduced pressure to give the title compound as a yellow oil. LC-MS-conditions 02: $t_R$=0.97 min; [M+H]$^+$=380.22.

Amide coupling (with 4-bromo-2-methylaniline)—
formation of (5R)—N$^5$-(4-bromo-2-methyl phenyl)-
(6R)-6-methoxycarbonyl -(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 4-bromo-2-methylaniline (93 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a yellow oil. LC-MS-conditions 02: $t_R$=1.06 min; [M+H]$^+$=389.98.

(5R)—N$^5$-(4-Bromo-2-methylphenyl)-(6R)-6-hydroxycarbonyl-(4S,7R)-[4,7-ethenylene-spiro[2.4]heptane]-5-carboxamide To a solution of (5R)—N$^5$-(4-bromo-2-methylphenyl)-(6R)-6-methoxycarbonyl-(4S,7R)-[4,7-ethenylene-spiro[2.4]heptane]-5-carboxamide (93 mg, 0.24 mmol) in EtOH (2 mL) was added aq. 1N NaOH (1.0 mL, 1.00 mmol). The reaction mixture was stirred at rt until completion of the reaction. The mixture was then concentrated under reduced pressure, the residue partitioned between 2N HCl and EA. The layers were separated and the aq. layer extracted with EA (3×). The combined org. extracts were washed with brine, dried over MgSO$_4$, filtered, and concentrated under reduced pressure to give the title compound as a pale brown foam. LC-MS-conditions 02: $t_R$=0.97 min; [M+H]$^+$=376.26.

Amide coupling (with 5-amino-2-chloropyridine)—
formation of (5R)—N$^5$-(2-chloro-pyridin-5-yl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 4-bromo-3-fluoroaniline (66 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a white foam. LC-MS-conditions 02: $t_R$=0.96 min; [M+H]$^+$=333.27.

Amide coupling (with 2-amino-5-bromopyridine)—
formation of (5R)—N$^5$-(5-bromo-pyridin-2-yl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 2-amino-5-bromopyridine (86 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a yellow oil. LC-MS-conditions 02: $t_R$=1.03 min; [M+H]$^+$=376.72.

(5R)—N$^5$-(5-Bromo-pyridin-2-yl)-(6R)-6-hydroxycarbonyl-(4S,7R)-[4,7-ethenylene-spiro[2.4]heptane]-5-carboxamide To a solution of (5R)—N$^5$-(5-bromo-pyridin-2-yl)-(6R)-6-methoxycarbonyl-(4S,7R)-[4,7-ethenylene-spiro[2.4]heptane]-5-carboxamide (29 mg, 0.08 mmol) in EtOH (1 mL) was added aq. 1N NaOH (0.5 mL, 0.50 mmol). The reaction mixture was stirred at rt until completion of the reaction. The mixture was then concentrated under reduced pressure, the residue partitioned between 2N HCl and EA. The layers were separated and the aq. layer extracted with EA (3×). The combined org. extracts were washed with brine, dried over MgSO$_4$, filtered, and concentrated under reduced pressure to give the title compound as a pale yellow solid. LC-MS-conditions 02: $t_R$=0.94 min.

Amide coupling (with 2-amino-5-methylpyridine)—
formation of (5R)—N$^5$-(5-methyl-pyridin-2-yl)-
(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (222 mg, 1.00 mmol) in dry CH$_2$Cl$_2$ (4 mL) were added 2-amino-5-methylpyridine (109 mg, 1.00 mmol), EDC.HCl (489 mg, 2.50 mmol) and DMAP (25 mg, 0.20 mmol). The mixture was cooled to 0° C. and DIPEA (0.70 mL, 4.00 mmol) was added. The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 2:1) and the title compound obtained as a yellow oil. TLC:rf (2:1 hept-EA)=0.43. LC-MS-conditions 02: $t_R$=0.79 min; $[M+H]^+$=313.40.

(5R)—$N^5$-(5-Methyl-pyridin-2-yl)-(6R)-6-hydroxycarbonyl-(4S,7R)-[4,7-ethenylene-spiro[2.4]heptane]-5-carboxamide To a solution of (5R)—$N^5$-(5-methyl-pyridin-2-yl)-(6R)-6-methoxycarbonyl-(4S,7R)-[4,7-ethenylene-spiro[2.4]heptane]-5-carboxamide (56 mg, 0.18 mmol) in THF (1 mL) was added aq. 2N NaOH (0.4 mL, 0.80 mmol). The reaction mixture was stirred at rt until completion of the reaction. The mixture was then poured into aq. 1N HCl and extracted with EA (3×). The combined org. extracts were washed with brine, dried over $MgSO_4$, filtered, and concentrated under reduced pressure to give the title compound as a pale yellow solid. LC-MS-conditions 02: $t_R$=0.71 min; $[M+H]^+$=298.61.

Amide coupling (with 4-bromo-2,5-difluoroaniline)—formation of (5R)—$N^5$-(4-bromo-2,5-difluorophenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry $CH_2Cl_2$ (2 mL) were added EDC.HCl (244 mg, 1.25 mmol) and DMAP (12 mg, 0.10 mmol). The mixture was cooled to 0° C. and a solution of 4-bromo-2,5-difluoroaniline (104 mg, 0.50 mmol) in dry $CH_2Cl_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over $MgSO_4$, filtered, and concentrated under reduced pressure. The crude residue was purified by FC (hept-EA, 5:1 to 3:1) and the title compound obtained as a yellow oil. LC-MS-conditions 02: $t_R$=1.09 min; $[M+H]^+$=412.39.

(5R)—$N^5$-(4-Bromo-2,5-difluorophenyl)-(6R)-6-hydroxycarbonyl -(4S,7R)-[4,7-ethenylene-spiro[2.4]heptane]-5-carboxamide To a solution of (5R)—$N^5$-(4-bromo-2,5-difluorophenyl)-(6R)-6-methoxycarbonyl-(4S,7R)-[4,7-ethenylene-spiro[2.4]heptane]-5-carboxamide (170 mg, 0.41 mmol) in THF (2 mL) was added aq. 1N NaOH (0.8 mL, 0.80 mmol). The reaction mixture was stirred at rt until completion of the reaction. The mixture was then poured into aq. 1N HCl and extracted with EA (3×). The combined org. extracts were washed with brine, dried over $MgSO_4$, filtered, and concentrated under reduced pressure. Purification by FC($CH_2Cl_2$-MeOH—$NH_4OH$) gave the title compound as a pale yellow oil. LC-MS-conditions 02: $t_R$=1.00 min; $[M+H]^+$=398.40.

Amide coupling (with 4-bromo-2,6-difluoroaniline)—formation of (5R)—$N^5$-(4-bromo-2,6-difluorophenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethenylene-spiro[2.4]heptane]-(5R)-5-carboxylic acid (200 mg, 0.90 mmol) in dry $CH_2Cl_2$ (4 mL) were added 3 drops of DMF and oxalyl chloride (0.09 mL, 1.02 mmol). The reaction mixture was stirred at rt for 60 minutes and concentrated under reduced pressure.

To a suspension of 4-bromo-2,6-difluoroaniline (187 mg, 0.90 mmol) in pyridine (1.1 mL) was added a solution of the acyl chloride in acetone (5 mL). The reaction mixture was stirred at rt for 2 h, diluted with EA and successively washed with aq. 1N HCl, sat. aq. $NaHCO_3$ and brine. The org. layer was dried over $MgSO_4$, filtered, and concentrated under reduced pressure. The crude residue was purified by FC (hept-EA, 5:1 to 3:1) and the title compound obtained as a colorless oil. TLC:rf (2:3 hept-EA)=0.40. LC-MS-conditions 02: $t_R$=1.03 min; $[M+H]^+$=411.86.

(5R)—$N^5$-(4-Bromo-2,6-difluorophenyl)-(6R)-6-hydroxycarbonyl-(4S,7R)-[4,7-ethenylene-spiro[2.4]heptane]-5-carboxamide To a solution of (5R)—$N^5$-(4-bromo-2,6-difluorophenyl)-(6R)-6-methoxycarbonyl-(4S,7R)-[4,7-ethenylene-spiro[2.4]heptane]-5-carboxamide (240 mg, 0.58 mmol) in THF (2 mL) was added aq. 1N NaOH (1.1 mL, 1.10 mmol). The reaction mixture was stirred at rt until completion of the reaction. The mixture was then poured into aq. 1N HCl and extracted with EA (3×). The combined org. extracts were washed with brine, dried over $MgSO_4$, filtered, and concentrated under reduced pressure to give the title compound as a white foam. LC-MS-conditions 02: $t_R$=0.94 min; $[M+H]^+$=398.02.

Amide coupling (with 4-bromo-2,3-difluoroaniline)—formation of (5R)—$N^5$-(4-bromo-2,3-difluorophenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethenylene-spiro[2.4]heptane]-(5R)-5-carboxylic acid (150 mg, 0.67 mmol) in dry $CH_2Cl_2$ (4 mL) were added 3 drops of DMF and oxalyl chloride (0.07 mL, 0.77 mmol). The reaction mixture was stirred at rt for 60 minutes and concentrated under reduced pressure.

To a suspension of 4-bromo-2,3-difluoroaniline (140 mg, 0.67 mmol) in pyridine (0.8 mL) was added a solution of the acyl chloride in acetone (4 mL). The reaction mixture was stirred at rt for 1 h, diluted with EA and successively washed with aq. 1N HCl, sat. aq. $NaHCO_3$ and brine. The org. layer was dried over $MgSO_4$, filtered, and concentrated under reduced pressure to give the title compound obtained as a yellow oil. TLC:rf (1:1 hept-EA)=0.63. LC-MS-conditions 02: $t_R$=1.08 min; $[M+H]^+$=411.93.

(5R)—$N^5$-(4-Bromo-2,3-difluorophenyl)-(6R)-6-hydroxycarbonyl-(4S,7R)-[4,7-ethenylene-spiro[2.4]heptane]-5-carboxamide To a solution of (5R)—$N^5$-(4-bromo-2,3-difluorophenyl)-(6R)-6-methoxycarbonyl-(4S,7R)-[4,7-ethenylene-spiro[2.4]heptane]-5-carboxamide (260 mg, 0.63 mmol) in THF (2.5 mL) was added aq. 1N NaOH (1.2 mL, 1.20 mmol). The reaction mixture was stirred at rt until completion of the reaction. The mixture was then poured into aq. 1N HCl and extracted with EA (3×). The combined org. extracts were washed with brine, dried over $MgSO_4$, filtered, and concentrated under reduced pressure to give the title compound as a white foam. LC-MS-conditions 02: $t_R$=0.99 min; [M+H]$^+$=398.38.

Amide coupling (with 4-bromo-3,5-difluoroaniline)—formation of (5R)—N$^5$-(4-bromo-3,5-difluorophenyl)-(6R)-6-methoxycarbonyl -(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 4-bromo-3,5-difluoroaniline (109 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a yellow oil. LC-MS-conditions 01: $t_R$=1.06 min; [M+H]$^+$=411.90.

Amide coupling (with 4-bromo-3-(trifluoromethyl) aniline)—formation of (5R)—N$^5$-(4-bromo-3-trifluoromethylphenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (111 mg, 0.50 mmol) in dry CH$_2$Cl$_2$ (2 mL) were added EDC.HCl (244 mg, 1.25 mmol) and DMAP (12 mg, 0.10 mmol). The mixture was cooled to 0° C. and a solution of 4-bromo-3-(trifluoromethyl) aniline (120 mg, 0.50 mmol) in dry CH$_2$Cl$_2$ (1 mL) was added followed by DIPEA (0.35 mL, 2.00 mmol). The reaction mixture was stirred at rt until completion of the reaction. Water was added, the layers separated and the org. layer washed with aq. 1N HCl, dried over MgSO$_4$, filtered, and concentrated under reduced pressure. The crude residue was purified by FC (hept-EA, 5:1 to 1:1) and the title compound obtained as a colorless oil. LC-MS-conditions 02: $t_R$=1.11 min; [M+H]$^+$=443.88.

Amide coupling (with 4-bromo-2-fluorobenzylamine)—formation of (5R)—N$^5$-(4-bromo-2-fluorophenyl -methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (150 mg, 0.67 mmol) in dry CH$_2$Cl$_2$ (4 mL) were added 3 drops of DMF and oxalyl chloride (0.07 mL, 0.77 mmol). The reaction mixture was stirred at rt for 60 minutes and concentrated under reduced pressure.

To a suspension of 4-bromo-2-fluorobenzylamine hydrochloride (162 mg, 0.67 mmol) in pyridine (0.80 mL) was added a solution of the acyl chloride in acetone (4 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure to give the title compound obtained as a yellow oil. LC-MS-conditions 01: $t_R$=0.99 min; [M+H]$^+$=407.94.

(5R)—N$^5$-(4-Bromo-2-fluorophenyl-methyl)-(6R)-6-hydroxycarbonyl-(4S,7R)-[4,7-ethenylene-spiro[2.4]heptane]-5-carboxamide To a solution of (5R)—N$^5$-(4-bromo-2-fluorophenyl-methyl)-(6R)-6-methoxycarbonyl-(4S,7R)-[4,7-ethenylene-spiro[2.4]heptane]-5-carboxamide (250 mg, 0.61 mmol) in THF (5 mL) was added aq. 1N NaOH (2.9 mL, 2.90 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a white foam. LC-MS-conditions 02: $t_R$=0.94 min; [M+H]$^+$=394.00.

Amide coupling (with 4-bromo-3-fluorobenzylamine)—formation of (5R)—N$^5$-(4-bromo-3-fluorophenyl -methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (80 mg, 0.36 mmol) in dry CH$_2$Cl$_2$ (4 mL) were added 3 drops of DMF and oxalyl chloride (0.04 mL, 0.41 mmol). The reaction mixture was stirred at rt for 60 minutes and concentrated under reduced pressure.

To a suspension of 4-bromo-3-fluorobenzylamine (90 mg, 0.44 mmol) in pyridine (0.43 mL) was added a solution of the acyl chloride in acetone (4 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure. Purification by FC (hept-EA 1:1 to 1:2) gave the title compound as a colorless oil. LC-MS-conditions 07: $t_R$=0.84 min; [M+H]$^+$=408.01.

Amide coupling (with 4-bromo-2,3-difluorobenzylamine)—formation of (5R)—N$^5$-(4-bromo-2,3-difluorophenyl-methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (120 mg, 0.54 mmol) in dry CH$_2$Cl$_2$ (4 mL) were added 3 drops of DMF and oxalyl chloride (0.05 mL, 0.62 mmol). The reaction mixture was stirred at rt for 60 minutes and concentrated under reduced pressure.

To a suspension of 4-bromo-2,3-difluorobenzylamine (120 mg, 0.54 mmol) in pyridine (0.64 mL) was added a solution of the acyl chloride in acetone (4 mL). The reaction mixture was stirred at rt for 2 h, diluted with EA and successively washed with aq. 1N HCl, sat. aq. NaHCO$_3$ and brine. The org. layer was dried over MgSO$_4$, filtered, and concentrated under reduced pressure. Purification by FC (hept-EA 9:1 to 1:1)

gave the title compound as a yellow oil. TLC:rf (1:1 hept-EA)=0.65. LC-MS-conditions 07: $t_R$=0.86 min; [M+H]$^+$=426.05.

(5R)—N$^5$-(4-Bromo-2,3-difluorophenyl-methyl)-(6R)-6-hydroxycarbonyl-(4S,7R)-[4,7-ethenylene-spiro[2.4]heptane]-5-carboxamide To a solution of (5R)—N$^5$-(4-bromo-2,3-difluorophenyl-methyl)-(6R)-6-methoxycarbonyl-(4S,7R)-[4,7-ethenylene-spiro[2.4]heptane]-5-carboxamide (120 mg, 0.28 mmol) in THF (4 mL) was added aq. 1N NaOH (1.3 mL, 1.30 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a white foam. LC-MS-conditions 07: $t_R$=0.77 min; [M+H]$^+$=411.93.

Amide coupling (with 4-bromo-3,5-difluorobenzy-lamine)—formation of (5R)—N$^5$-(4-bromo-3,5-dif-luorophenyl-methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (55 mg, 0.25 mmol) in dry CH$_2$Cl$_2$ (4 mL) were added 2 drops of DMF and oxalyl chloride (0.025 mL, 0.28 mmol). The reaction mixture was stirred at rt for 60 minutes and concentrated under reduced pressure.

To a suspension of 4-bromo-3,5-difluorobenzylamine (55 mg, 0.25 mmol) in pyridine (0.24 mL) was added a solution of the acyl chloride in acetone (4 mL). The reaction mixture was stirred at rt for 2 h, diluted with EA and successively washed with aq. 1N HCl, sat. aq. NaHCO$_3$ and brine. The org. layer was dried over MgSO$_4$, filtered, and concentrated under reduced pressure to give the title compound as a yellow oil. TLC:rf (1:1 hept-EA)=0.65. LC-MS-conditions 07: $t_R$=0.85 min; [M+H]$^+$=426.08.

(5R)—N$^5$-(4-Bromo-3,5-difluorophenyl-methyl)-(6R)-6-hydroxycarbonyl-(4S,7R)-[4,7-ethenylene-spiro[2.4]heptane]-5-carboxamide To a solution of (5R)—N$^5$-(4-bromo-3,5-difluorophenyl-methyl)-(6R)-6-methoxycarbonyl-(4S,7R)-[4,7-ethenylene-spiro[2.4]heptane]-5-carboxamide (80 mg, 0.19 mmol) in THF (2 mL) was added aq. 1N NaOH (1.5 mL, 1.50 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a brown foam. LC-MS-conditions 07: $t_R$=0.75 min; [M+H]$^+$=412.08.

Amide coupling (with 4-bromo-2,5-difluorobenzy-lamine)—formation of (5R)—N$^5$-(4-bromo-2,5-dif-luorophenyl-methyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (90 mg, 0.40 mmol) in dry CH$_2$Cl$_2$ (4 mL) were added 2 drops of DMF and oxalyl chloride (0.04 mL, 0.46 mmol). The reaction mixture was stirred at rt for 60 minutes and concentrated under reduced pressure.

To a suspension of 4-bromo-2,5-difluorobenzylamine (90 mg, 0.40 mmol) in pyridine (0.39 mL) was added a solution of the acyl chloride in acetone (4 mL). The reaction mixture was stirred at rt for 2 h, diluted with EA and successively washed with aq. 1N HCl, sat. aq. NaHCO$_3$ and brine. The org. layer was dried over MgSO$_4$, filtered, and concentrated under reduced pressure to give the title compound as a yellow oil. TLC:rf (1:1 hept-EA)=0.65. LC-MS-conditions 07: $t_R$=0.86 min; [M+H]$^+$=426.08.

(5R)—N$^5$-(4-Bromo-2,5-difluorophenyl-methyl)-(6R)-6-hydroxycarbonyl-(4S,7R)-[4,7-ethenylene-spiro[2.4]heptane]-5-carboxamide To a solution of (5R)—N$^5$-(4-bromo-2,5-difluorophenyl-methyl)-(6R)-6-methoxycarbonyl-(4S,7R)-[4,7-ethenylene-spiro[2.4]heptane]-5-carboxamide (170 mg, 0.40 mmol) in THF (4 mL) was added aq. 1N NaOH (1.6 mL, 1.60 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a brown foam. LC-MS-conditions 07: $t_R$=0.76 min; [M+H]$^+$=412.08.

Amide coupling (with 5-amino-2-bromo-3-fluoropy-ridine)—formation of (5R)—N$^5$-(2-bromo-3-fluoro-pyridin-5-yl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (120 mg, 0.54 mmol) in dry CH$_2$Cl$_2$ (2 mL) were added 2 drops of DMF and oxalyl chloride (0.054 mL, 0.61 mmol). The reaction mixture was stirred at rt for 60 minutes and concentrated under reduced pressure.

To a suspension of 5-amino-2-bromo-3-fluoropyridine (103 mg, 0.54 mmol) in pyridine (0.64 mL) was added a solution of the acyl chloride in acetone (3 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure. Purification by FC (hept-EA 9:1 to 4:1) gave the title compound as a white foam. TLC:rf (2:3 hept-EA)=0.51. LC-MS-conditions 07: $t_R$=0.86 min; [M+H]$^+$=395.30.

Amide coupling (with 2-(4-chlorophenyl)ethy-lamine)—formation of (5R)—N$^5$-(2-(4-chlorophe-nyl)ethyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (800 mg, 3.60 mmol) in dry CH$_2$Cl$_2$ (10 mL) were added a few drops of DMF and oxalyl chloride (0.33 mL, 3.96 mmol). The reaction mixture was stirred at rt for 30 minutes and a solution of 2-(4-chlorophenyl)ethylamine (857 mg, 5.40 mmol) and DIPEA (2.5 mL, 14.40 mmol) in dry $CH_2Cl_2$ (5 mL) was added. The reaction mixture was stirred at rt for 10 min, diluted with $CH_2Cl_2$ and washed with aq. 1N HCl. The layers were separated and the aq. layer extracted with $CH_2Cl_2$ (2×). The combined org. extracts were successively washed with aq. $Na_2CO_3$ and brine, dried over $MgSO_4$, filtered, and concentrated under reduced pressure. The crude residue was purified by FC (hept-EA, 4:1 to 1:1) and the title compound obtained as a yellow oil. TLC:rf (1:1 hept-EA)=0.55. LC-MS-conditions 01: $t_R$=1.00 min; $[M+H]^+$=360.03.

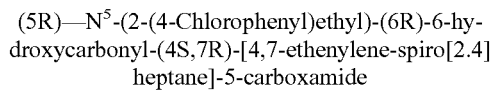
(5R)—$N^5$-(2-(4-Chlorophenyl)ethyl)-(6R)-6-hydroxycarbonyl-(4S,7R)-[4,7-ethenylene-spiro[2.4]heptane]-5-carboxamide To a solution of (5R)-N-5-(2-(4-chlorophenyl)ethyl)-(6R)-6-methoxycarbonyl-(4S,7R)-[4,7-ethenylene-spiro[2.4]heptane]-5-carboxamide (550 mg, 1.53 mmol) in EtOH (15 mL) was added aq. 1N NaOH (7.5 mL, 7.50 mmol). The reaction mixture was stirred at rt until completion of the reaction. The mixture was then concentrated under reduced pressure and the residue partitioned between EA and aq. 2N HCl. The layers were separated and the aq. layer extracted with EA (3×). The combined org. extracts were washed with brine, dried over $MgSO_4$, filtered, and concentrated under reduced pressure to give the title compound as a pale yellow solid. LC-MS-conditions 01: $t_R$=0.91 min; $[M+H]^+$=346.00.

Amide coupling (with 2-(2,4-dichlorophenyl)ethylamine)—formation of (5R)—$N^5$-(2-(2,4-dichlorophenyl)ethyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethenylene-spiro[2.4]heptane]-(5R)-5-carboxylic acid (110 mg, 0.50 mmol) in dry DMF (5 mL) were added HATU (188 mg, 0.50 mmol) and DIPEA (0.13 mL, 0.75 mmol) at rt. The reaction mixture was stirred at rt for 1 h and a solution of 2-(2,4-dichlorophenyl)ethylamine (94 mg, 0.50 mmol) in dry DMF (2.5 mL) was added. The reaction mixture was stirred at rt for 30 min, diluted with EA and washed with water. The layers were separated and the org. layer was dried over $MgSO_4$, filtered, and concentrated under reduced pressure. The crude residue was purified by FC (hept-EA, 5:1 to 3:2) and the title compound obtained as a colorless oil. LC-MS-conditions 01: $t_R$=1.03 min; $[M+H]^+$=394.02.

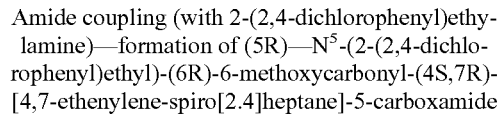
(5R)—$N^5$-(2-(2,4-Dichlorophenyl)ethyl)-(6R)-6-hydroxycarbonyl-(4S,7R)-[4,7-ethenylene-spiro[2.4]heptane]-5-carboxamide To a solution of (5R)—$N^5$-(2-(2,4-dichlorophenyl)ethyl)-(6R)-6-methoxycarbonyl-(4S,7R)-[4,7-ethenylene-spiro[2.4]heptane]-5-carboxamide (170 mg, 0.43 mmol) in EtOH (4 mL) was added aq. 1N NaOH (2 mL, 2.00 mmol). The reaction mixture was stirred at rt until completion of the reaction. The mixture was then concentrated under reduced pressure and the residue partitioned between EA and aq. 2N HCl. The layers were separated and the aq. layer extracted with EA (3×). The combined org. extracts were washed with brine, dried over $MgSO_4$, filtered, and concentrated under reduced pressure to give the title compound as a white foam. LC-MS-conditions 02: $t_R$=0.97 min; $[M+H]^+$=380.36.

Amide coupling (with 4-bromo-2-fluorobenzylamine)—formation of (5R)—$N^5$-(4-bromo-2-fluorophenyl-methyl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethylene-spiro[2.4]heptane]-(5R)-5-carboxylic acid (160 mg, 0.71 mmol) in dry $CH_2Cl_2$ (4 mL) were added 3 drops of DMF and oxalyl chloride (0.07 mL, 0.81 mmol). The reaction mixture was stirred at rt for 60 minutes and concentrated under reduced pressure.

To a suspension of 4-bromo-2-fluorobenzylamine hydrochloride (171 mg, 0.71 mmol) in pyridine (0.84 mL) was added a solution of the acyl chloride in acetone (4 mL). The reaction mixture was stirred at rt for 1 h, diluted with EA and successively washed with aq. 1N HCl, sat. aq. $NaHCO_3$ and brine. The org. layer was dried over $MgSO_4$, filtered, and concentrated under reduced pressure to give the title compound obtained as a yellow oil. LC-MS-conditions 02: $t_R$=1.06 min; $[M+H]^+$=410.67.

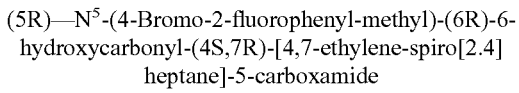
(5R)—$N^5$-(4-Bromo-2-fluorophenyl-methyl)-(6R)-6-hydroxycarbonyl-(4S,7R)-[4,7-ethylene-spiro[2.4]heptane]-5-carboxamide To a solution of (5R)—$N^5$-(4-bromo-2-fluorophenyl-methyl)-(6R)-6-methoxycarbonyl-(4S,7R)-[4,7-ethylene-spiro[2.4]heptane]-5-carboxamide (290 mg, 0.71 mmol) in THF (5 mL) was added aq. 1N NaOH (2.8 mL, 2.80 mmol). The reaction mixture was stirred at rt until completion of the reaction. The mixture was then poured into aq. 1N HCl and extracted with EA (3×). The combined org. extracts were washed with brine, dried over $MgSO_4$, filtered, and concentrated under reduced pressure to give the title compound as a white foam. LC-MS-conditions 01: $t_R$=0.93 min; $[M+H]^+$=395.95.

Amide coupling (with 2-amino-5-bromo-thiazole)—formation of (5R)—$N^5$-(5-bromo-thiazol-2-yl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere ($N_2$), to a solution of (6R)-6-methoxycarbonyl-(4S,7R)-[4,7-ethylene-spiro[2.4]heptane]-(5R)-5-carboxylic acid (4.70 g, 20.9 mmol) in dry $CH_2Cl_2$ (80 mL) were added 10 drops of DMF and oxalyl chloride (2.2 mL, 25.1 mmol). The reaction mixture was stirred at rt for 60 minutes and concentrated under reduced pressure. To a suspension of 2-amino-5-bromo-thiazole monohydrobromide (5.67 g, 21.1 mmol) in pyridine (5 mL) was added a solution of the acyl chloride in acetone (80 mL). The reaction mixture was stirred at rt for 1 h, diluted with EA and successively washed with aq. 1N HCl, sat. aq. $NaHCO_3$ and brine. The org. layer was dried over $MgSO_4$, filtered, and concentrated under reduced pressure. The crude residue was purified by FC (hept-EA, 5:1) and the title compound obtained as a pale yellow solid. TLC:rf (2:1 hept-EA)=0.38. LC-MS-conditions 07c: $t_R$=0.98 min; $[M+H]^+$=385.12.

(5R)—N⁵-(5-Bromo-thiazol-2-yl)-(6R)-6-hydroxy-carbonyl-(4S,7R)-[4,7-ethylene-spiro[2.4]heptane]-5-carboxamide To a solution of (5R)—N⁵-(5-bromo-thiazol-2-yl)-(6R)-6-methoxycarbonyl-(4S,7R)-[4,7-ethylene-spiro[2.4]heptane]-5-carboxamide (2.90 g, 7.53 mmol) in THF (60 mL) was added aq. 2N NaOH (15 mL, 30.00 mmol). The reaction mixture was stirred at rt until completion of the reaction. The mixture was then washed with Et₂O, the aq. layer acidified and extracted with EA (3×). The combined org. extracts were washed with brine, dried over MgSO₄, filtered, and concentrated under reduced pressure to give the title compound as a light brown solid. LC-MS-conditions 07c: $t_R$=0.84 min; [M+H]⁺=371.11.

Amide coupling (with 5-amino-2-bromo-pyridine)—formation of (5R)—N⁵-(2-bromo-pyrid-5-yl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N₂), to a solution of (6R)-6-methoxycarbonyl-(4S,7R)-[4,7-ethylene-spiro[2.4]heptane]-(5R)-5-carboxylic acid (2.55 g, 11.37 mmol) in dry CH₂Cl₂ (60 mL) were added 10 drops of DMF and oxalyl chloride (1.20 mL, 13.65 mmol). The reaction mixture was stirred at rt for 60 minutes and concentrated under reduced pressure.

To a suspension of 5-amino-2-bromo-pyridine (1.97 g, 11.37 mmol) in pyridine (2.75 mL) was added a solution of the acyl chloride in acetone (60 mL). The reaction mixture was stirred at rt for 30 minutes, diluted with EA and successively washed with aq. 1N HCl, sat. aq. NaHCO₃ and brine. The org. layer was dried over MgSO₄, filtered, and concentrated under reduced pressure. The crude residue was purified by FC (hept-EA, 1:0->1:1) and the title compound obtained as a white solid. TLC:rf (2:1 hept-EA)=0.44. LC-MS-conditions 07: $t_R$=0.84 min; [M+H]⁺=379.04.

(5R)—N⁵-(2-Bromo-pyrid-5-yl)-(6R)-6-hydroxycarbonyl-(4S,7R)-[4,7-ethylene-spiro[2.4]heptane]-5-carboxamide To a solution of (5R)—N⁵-(2-bromo-pyrid-5-yl)-(6R)-6-methoxycarbonyl-(4S,7R)-[4,7-ethylene-spiro[2.4]heptane]-5-carboxamide (3.81 g, 10.05 mmol) in THF (100 mL) was added aq. 2N NaOH (20 mL, 40.00 mmol). The reaction mixture was stirred at rt until completion of the reaction. The mixture was then poured into aq. 1N HCl and extracted with EA (3×). The combined org. extracts were washed with brine, dried over MgSO₄, filtered, and concentrated under reduced pressure to give the title compound as a white solid. LC-MS-conditions 07: $t_R$=0.72 min; [M+H]⁺=365.22.

Amide coupling (with 5-amino-2-bromo-3-fluoropyridine)—formation of (5R)—N⁵-(2-bromo-3-fluoro-pyridin-5-yl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N₂), to a solution of (6R)-6-methoxycarbonyl-(4S,7R)-[4,7-ethylene-spiro[2.4]heptane]-(5R)-5-carboxylic acid (121 mg, 0.54 mmol) in dry CH₂Cl₂ (2 mL) were added 2 drops of DMF and oxalyl chloride (0.054 mL, 0.61 mmol). The reaction mixture was stirred at rt for 60 minutes and concentrated under reduced pressure.

To a suspension of 5-amino-2-bromo-3-fluoropyridine (103 mg, 0.54 mmol) in pyridine (0.64 mL) was added a solution of the acyl chloride in acetone (3 mL). The reaction mixture was stirred at rt for 1 h, diluted with EA and successively washed with aq. 1N HCl, sat. aq. NaHCO₃ and brine. The org. layer was dried over MgSO₄, filtered, and concentrated under reduced pressure. Purification by FC (hept-EA 9:1 to 4:1) gave the title compound as a white foam. TLC:rf (2:3 hept-EA)=0.52. LC-MS-conditions 07: $t_R$=0.91 min; [M+H]⁺=397.18.

Amide coupling (with beta-alanine methyl ester hydrochloride)—formation of enantiopure iodolactone 3 (R²=2-methoxycarbonyl-ethyl and R³=H)

In a flame dried round-bottomed flask equipped with a magnetic stir bar and under inert atmosphere (N₂), to a solution of enantiopure iodolactone 2 (3.40 g, 10.18 mmol) in dry toluene (32 mL) were added a few drops of DMF and oxalyl chloride (1.11 mL, 12.58 mmol). The reaction mixture was stirred at rt for 60 min, concentrated under reduced pressure and the residue co-evaporated with toluene (2×). The residue was then redissolved in CH₂Cl₂ (32 mL) and beta-alanine methyl ester hydrochloride (1.59 g, 11.19 mmol) and DIPEA (5.37 mL, 30.53 mmol) were added at rt. The reaction mixture was stirred at rt for 25 minutes, diluted with CH₂Cl₂ and washed with sat. aq. NH₄Cl. The layers were separated, and the aq. layer extracted with CH₂Cl₂ (3×). The combined org. extracts were washed with brine, dried over MgSO₄, filtered, and concentrated under reduced pressure. The crude residue was purified by FC (hept-EA, 5:1->1:1) and the title compound obtained as a pale yellow foam. TLC:rf (95:5 hept-EA)=0.38. LC-MS-conditions 02: $t_R$=0.87 min; [M+H]⁺=420.00.

Retro-iodolactonization—formation of (5R)-5-hydroxycarbonyl-(6R)—N⁶-(2-methoxycarbonyl-ethyl)-(4S,7R)-[4,7-ethenylene-spiro[2.4]heptane]-6-carboxamide In a flame dried round-bottomed flask equipped with a magnetic stir bar and under inert atmosphere (N₂), to a solution of enantiopure iodolactone 3 (R²=2-methoxycarbonyl-ethyl and R³=H) (3.21 g, 7.66 mmol) in acetic acid (15 mL) was added zinc powder (0.60 g, 9.20 mmol). The reaction mixture was stirred at 65° C. for 2 h, cooled down to rt, filtered and the filter cake rinsed with EA. The filtrate was washed with water, dried over MgSO₄, filtered and concentrated under reduced pressure. The crude residue was purified by FC (hept-EA, 1:1->1:2) and the title compound was obtained as a colorless oil. TLC: rf (EA)=0.27. LC-MS-conditions 02: $t_R$=0.71 min; [M+H]⁺=294.00.

Amide coupling (with 4-pyrrolidin-1-yl-butylamine)—formation of enantiopure iodolactone 3 (R²=4-pyrrolidin-1-yl-butyl and R³=H)

In a flame dried round-bottomed flask equipped with a magnetic stir bar and under inert atmosphere (N₂), to a solution of enantiopure iodolactone 2 (1.59 g, 4.76 mmol) in dry CH₂Cl₂ (30 mL) were added a few drops of DMF and oxalyl chloride (0.45 mL, 5.23 mmol). The reaction mixture was stirred at rt for 2 h, after which 4-(1-pyrrolidino)-butylamine (0.69 g, 4.76 mmol) and DIPEA (0.81 mL, 4.76 mmol) were added. The reaction mixture was stirred at rt for 30 minutes, diluted with CH$_2$Cl$_2$ and washed with sat. aq. NH$_4$Cl. The layers were separated, and the aq. layer extracted with CH$_2$Cl$_2$ (3×). The combined org. extracts were washed with brine, dried over Na$_2$SO$_4$, filtered, and concentrated under reduced pressure. The crude residue was purified by FC (CH$_2$Cl$_2$/MeOH, 9:1) and the title compound obtained as a pale yellow oil. TLC:rf (9:1 CH$_2$Cl$_2$/MeOH)=0.22. LC-MS-conditions 01: $t_R$=0.68 min; [M+H]$^+$=458.65.

Retro-iodolactonization—formation of (5R)-5-hydroxycarbonyl-(6R)—N$^6$-(4-pyrrolidin-1-yl-butyl)-(4S,7R)-[4,7-ethenylene-spiro[2.4]heptane]-6-carboxamide In a flame dried round-bottomed flask equipped with a magnetic stir bar and under inert atmosphere (N$_2$), to a solution of enantiopure iodolactone 3 (R$^2$=4-pyrrolidin-1-yl-butyl and R$^3$=H) (1.29 g, 2.81 mmol) in acetic acid (5 mL) was added zinc powder (276 mg, 4.22 mmol). The reaction mixture was stirred at 65° C. for 0.5 h, cooled down to rt, filtered, washed with EA and the filtrate concentrated under reduced pressure. The crude residue was purified by FC(C-18 reverse phase silica, H$_2$O/MeOH, 1:0 then 0:1) and the title compound was obtained as a white foam. LC-MS-conditions 02: $t_R$=0.64 min; [M+H]$^+$=333.54.

Double bond reduction—formation of (5R)-5-hydroxycarbonyl-(6R)—N$^6$-(2-methoxycarbonyl-ethyl)-(4S,7R)-[4,7-ethylene-spiro[2.4]heptane]-6-carboxamide In a flame dried round-bottomed flask equipped with a magnetic stir bar and under inert atmosphere (N$_2$), a deoxygenated suspension of (5R)-5-hydroxycarbonyl-(6R)—N$^6$-(2-methoxycarbonyl-ethyl)-(4S,7R)-[4,7-ethenylene-spiro[2.4]heptane]-6-carboxamide (500 mg, 1.70 mmol), Pd/C 10% (181 mg) and cyclohexene (0.80 mL, 7.80 mmol) in dry THF (15 mL) was stirred at reflux for 16 h. The reaction mixture was filtered through celite and the filter cake washed with THF. The filtrate was concentrated under reduced pressure and the title compound obtained as a colorless oil. TLC:rf (EA)=0.37. LC-MS-conditions 02: $t_R$=0.77 min; [M+H]$^+$=296.26.

Amide coupling (with 4-bromo-benzylamine)—formation of (5R)—N$^5$-(4-bromophenyl-methyl)-(6R)—N$^6$-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N$_2$), to a solution of (5R)-5-hydroxycarbonyl-(6R)—N$^6$-(2-methoxycarbonyl-ethyl)-(4S,7R)-[4,7-ethenylene-spiro[2.4]heptane]-6-carboxamide (59 mg, 0.20 mmol) in dry CH$_2$Cl$_2$ (2 mL) was added 4-bromo-benzylamine (39 mg, 0.20 mmol) in dry CH$_2$Cl$_2$ (0.5 mL) at rt followed by EDC.HCl (98 mg, 0.50 mmol) and DMAP (5 mg, 0.04 mmol). DIPEA (0.14 mL, 0.80 mmol) was then added dropwise at 0° C. The reaction mixture was stirred at rt until completion of the reaction. Water was added, the layers separated, and the org. layer successively washed with aq. 1N HCl (2×), brine, dried over MgSO$_4$, filtered, and concentrated under reduced pressure to give the title compound as a pale brown oil. TLC:rf (1:2 hept-EA)=0.31. LC-MS-conditions 02: $t_R$=0.92 min; [M+H]$^+$=461.08.

Amide coupling (with 2-amino-5-bromopyridine)—formation of (5R)—N$^5$-(5-bromopyrid-2-yl)-(6R)—N$^6$-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N$_2$), to a solution of (5R)-5-hydroxycarbonyl-(6R)—N$^6$-(2-methoxycarbonyl-ethyl)-(4S,7R)-[4,7-ethenylene-spiro[2.4]heptane]-6-carboxamide (88 mg, 0.30 mmol) in dry CH$_2$Cl$_2$ (2 mL) was added 2-amino-5-bromopyridine (58 mg, 0.33 mmol) in dry CH$_2$Cl$_2$ (0.5 mL) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO$_4$, filtered, and concentrated under reduced pressure to give the title compound as a yellow oil. TLC:rf (1:1 hept-EA)=0.37. LC-MS-conditions 02: $t_R$=0.96 min; [M+H]$^+$=448.40.

Amide coupling (with 5-amino-2-chloropyridine)—formation of (5R)—N$^5$-(2-chloropyrid-5-yl)-(6R)—N$^6$-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N$_2$), to a solution of (5R)-5-hydroxycarbonyl-(6R)—N$^6$-(2-methoxycarbonyl-ethyl)-(4S,7R)-[4,7-ethenylene-spiro[2.4]heptane]-6-carboxamide (88 mg, 0.30 mmol) in dry CH$_2$Cl$_2$ (2 mL) was added 5-amino-2-chloropyridine (44 mg, 0.33 mmol) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO$_4$, filtered, and concentrated under reduced pressure to give the title compound as a yellow solid. TLC:rf (1:1 hept-EA)=0.13. LC-MS-conditions 02: $t_R$=0.88 min; [M+H]$^+$=404.06.

Amide coupling (with 4-bromo-2-fluoro-benzylamine hydrochloride)—formation of (5R)—N$^5$-(4-bromo-2-fluorophenyl-methyl)-(6R)—N$^6$-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N$_2$), to a solution of (5R)-5-hydroxycarbonyl-(6R)—N$^6$-(2-methoxycarbonyl-ethyl)-(4S,7R)-[4,7-ethenylene-spiro[2.4]heptane]-6-carboxamide (88 mg, 0.30 mmol) in dry CH$_2$Cl$_2$ (3 mL) was added 4-bromo-2-fluoro-benzylamine hydrochloride (72 mg, 0.30 mmol) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO$_4$, filtered, and concentrated under reduced pressure to give the title compound as a pale yellow oil. TLC:rf (1:2 hept-EA)=0.42. LC-MS-conditions 02: $t_R$=0.96 min; [M+H]$^+$=479.10.

Amide coupling (with (2-bromothiazol-5-yl)methylamine)—formation of (5R)—N$^5$-[(2-bromothiazol-5-yl)methyl]-(6R)—N$^6$-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N$_2$), to a solution of (5R)-5-hydroxycarbonyl-(6R)—N⁶-(2-methoxycarbonyl-ethyl)-(4S,7R)-[4,7-ethenylene-spiro[2.4]heptane]-6-carboxamide (88 mg, 0.30 mmol) in dry CH₂Cl₂ (2 mL) was added (2-bromo-thiazol-5-yl)methanamine (58 mg, 0.30 mmol) in dry CH₂Cl₂ (0.5 mL) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as a brown oil. TLC:rf (1:2 hept-EA)=0.21. LC-MS-conditions 02: $t_R$=0.85 min; [M+H]⁺=467.57.

Amide coupling (with 4-methoxy-aniline)—formation of (5R)—N⁵-(4-methoxy-phenyl)-(6R)—N⁶-(2-methoxycarbonyl-ethyl)-(4S,7R)-[4,7-ethenylene-spiro[2.4]heptane]-5,6-dicarboxamide In a flame dried round-bottomed flask equipped with a magnetic stir bar and under inert atmosphere (N₂), to a solution of (5R)-5-hydroxycarbonyl-(6R)—N⁶-(2-methoxycarbonyl-ethyl)-(4S,7R)-[4,7-ethylene-spiro[2.4]heptane]-6-carboxamide (88 mg, 0.30 mmol) in dry CH₂Cl₂ (2 mL) was added 4-methoxy-aniline (41 mg, 0.33 mmol) in dry CH₂Cl₂ (0.5 mL) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as a yellow oil. TLC:rf (1:2 hept-EA)=0.37. LC-MS-conditions 02: $t_R$=0.90 min; [M+H]⁺=399.02.

Amide coupling (with 4-bromo-benzylamine)—formation of (5R)—N⁵-(4-bromophenyl-methyl)-(6R)—N⁶-(2-methoxycarbonyl -ethyl)-(4S,7R)-[4,7-ethylene-spiro[2.4]heptane]-5,6-dicarboxamide In a flame dried round-bottomed flask equipped with a magnetic stir bar and under inert atmosphere (N₂), to a solution of (5R)-5-hydroxycarbonyl-(6R)—N⁶-(2-methoxycarbonyl-ethyl)-(4S,7R)-[4,7-ethylene-spiro[2.4]heptane]-6-carboxamide (88 mg, 0.30 mmol) in dry CH₂Cl₂ (2 mL) was added 4-bromo-benzylamine (64 mg, 0.33 mmol) in dry CH₂Cl₂ (0.5 mL) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as a pale yellow solid. TLC:rf (1:2 hept-EA)=0.39. LC-MS-conditions 02: $t_R$=0.97 min; [M+H]⁺=462.80.

Amide coupling (with 5-amino-2-chloropyridine)—formation of (5R)—N⁵-(2-chloropyrid-5-yl)-(6R)—N⁶-(2-methoxycarbonyl-ethyl)-(4S,7R)-[4,7-ethylene-spiro[2.4]heptane]-5,6-dicarboxamide In a flame dried round-bottomed flask equipped with a magnetic stir bar and under inert atmosphere (N₂), to a solution of (5R)-5-hydroxycarbonyl-(6R)—N⁶-(2-methoxycarbonyl-ethyl)-(4S,7R)-[4,7-ethylene-spiro[2.4]heptane]-6-carboxamide (88 mg, 0.30 mmol) in dry CH₂Cl₂ (2 mL) was added 5-amino-2-chloropyridine (44 mg, 0.33 mmol) in dry CH₂Cl₂ (1 mL) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as a light brown solid. LC-MS-conditions 02: $t_R$=0.92 min; [M+H]⁺=406.25.

Amide coupling (with 4-bromo-2-fluoro-benzylamine hydrochloride)—formation of (5R)—N⁵-(4-bromo-2-fluorophenyl-methyl)-(6R)—N⁶-(2-methoxycarbonyl-ethyl)-(4S,7R)-[4,7-ethylene-spiro[2.4]heptane]-5,6-dicarboxamide In a flame dried round-bottomed flask equipped with a magnetic stir bar and under inert atmosphere (N₂), to a solution of (5R)-5-hydroxycarbonyl-(6R)—N⁶-(2-methoxycarbonyl-ethyl)-(4S,7R)-[4,7-ethylene-spiro[2.4]heptane]-6-carboxamide (88 mg, 0.30 mmol) in dry CH₂Cl₂ (3 mL) was added 4-bromo-2-fluoro-benzylamine hydrochloride (80 mg, 0.33 mmol) at rt followed by EDC.HCl (147 mg, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as a white solid. TLC:rf (1:2 hept-EA)=0.45. LC-MS-conditions 02: $t_R$=0.98 min; [M+H]⁺=481.00.

Amide coupling (with 4-methoxy-aniline)—formation of (5R)—N⁵-(4-methoxy-phenyl)-(6R)—N⁶-(2-methoxycarbonyl -ethyl)-(4S,7R)-[4,7-ethylene-spiro[2.4]heptane]-5,6-dicarboxamide In a flame dried round-bottomed flask equipped with a magnetic stir bar and under inert atmosphere (N₂), to a solution of (5R)-5-hydroxycarbonyl-(6R)—N⁶-(2-methoxycarbonyl-ethyl)-(4S,7R)-[4,7-ethylene-spiro[2.4]heptane]-6-carboxamide (88 mg, 0.30 mmol) in dry CH₂Cl₂ (3 mL) was added 4-methoxy-aniline (41 mg, 0.33 mmol) at rt followed by EDC.HCl (147 R)—N$^{l\ mg}$, 0.75 mmol) and DMAP (7 mg, 0.06 mmol). DIPEA (0.21 mL, 1.20 mmol) was then added dropwise at 0° C. The reaction mixture was stirred at rt until completion of the reaction. Water was added, the layers separated, and the org. layer successively washed with aq. 1N HCl (2×), brine, dried over MgSO₄, filtered, and concentrated under reduced pressure to give the title compound as an orange oil. TLC:rf (1:2 hept-EA)=0.45. LC-MS-conditions 02: $t_R$=0.93 min; [M+H]⁺=401.28.

PREPARATION OF EXAMPLES

Example 1

(5R*)—N⁵-(4-Bromophenyl)-(6R*)—N⁶-(5-aminopentyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 5-(tert-butoxycarbonyl-amino)-pentylamine.
LC-MS-conditions 05c: $t_R$=0.55 min; [M+H]⁺=446.12.

Example 2

(5R)—N⁵-(4-Bromophenyl)-(6R)—N⁶-(4-pyrrolidin-1-yl-butyl)-(4S,7R)-[4,7-ethenylene-spiro[2.4]heptane]-5,6-dicarboxamide Following general procedure F, starting from (5R)—N⁵-(4-bromo-phenyl)-(6R)-6-methoxycarbonyl-(4S,7R)-[4,7-ethenylene-spiro[2.4]heptane]-5-carboxamide and 4-(1-pyrrolidino)-butylamine.
LC-MS-conditions 02: $t_R$=0.85 min; [M+H]⁺=486.21.

Example 3

(5R*)—N⁵-(4-Bromophenyl)-(6R*)—N⁶-(piperidin-4-yl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-(4-amino)-piperidine.
LC-MS-conditions 05c: $t_R$=0.54 min; [M+H]⁺=444.00.

Example 4

(5R*)—N⁵-(4-Bromophenyl)-(6R*)—N⁶-(3-isobutyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and isobutylamine.
LC-MS-conditions 05c: $t_R$=0.84 min; [M+H]⁺=417.18.

Example 5

(5R*)—N⁵-(4-Bromophenyl)-(6R*)—N⁶-(4-amino-butyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-(tert-butoxycarbonyl-amino)-butylamine.
LC-MS-conditions 05c: $t_R$=0.54 min; [M+H]⁺=432.05.

Example 6

(5R)—N⁵-(4-Bromophenyl)-(6R)—N⁶-(2-N,N-dimethyl-amino-ethyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 2-(dimethylamino)-ethylamine.
LC-MS-conditions 02: $t_R$=0.82 min; [M+H]⁺=432.24.

Example 7

(5R*)—N⁵-(4-Bromophenyl)-(6R*)—N⁶-((3-aminomethyl-phenyl)-methyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-(tert-butoxycarbonyl-aminomethyl)-benzylamine.
LC-MS-conditions 05c: $t_R$=0.58 min; [M+H]⁺=479.90.

Example 8

(5R*)—N⁵-(4-Bromophenyl)-(6R*)—N⁶-(4-piperidinyl-methyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-4-(amino-methyl)-piperidine.
LC-MS-conditions 05c: $t_R$=0.55 min; [M+H]⁺=458.00.

Example 9

(5R*)—N⁵-(4-Bromophenyl)-(6R*)—N⁶-(pyrrolidin-3-yl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and (±)-1-tert-butoxycarbonyl-3-amino-pyrrolidine.
LC-MS-conditions 05c: $t_R$=0.54 min; [M+H]⁺=429.97.

Example 10

(5R*)—N⁵-(4-Bromophenyl)-(6R*)—N⁶-(2,2-dimethyl-3-amino-propyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-3-amino-2,2-dimethyl-propylamine.
LC-MS-conditions 05c: $t_R$=0.57 min; [M+H]⁺=446.08.

Example 11

(5R*)—N⁵-(4-Bromophenyl)-(6R*)—N⁶-(4-(N,N-diethyl-amino)-butyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-(diethylamino)-butylamine.
LC-MS-conditions 05b: $t_R$=0.56 min; [M+H]⁺=488.28.

Example 12

(5R)—N⁵-(4-Bromophenyl)-(6R)—N⁶-(3-hydroxy-propyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 3-amino-1-propanol.
LC-MS-conditions 02: $t_R$=0.92 min; [M+H]⁺=418.92.

Example 13

(5R)—N⁵-(4-Bromophenyl)-(6R)—N⁶-(2-carbamoyl-ethyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and beta-alaninamide hydrochloride.
LC-MS-conditions 02: $t_R$=0.88 min; [M+H]⁺=432.20.

Example 14

(5R*)—N⁵-(4-Bromophenyl)-(6R*)—N⁶-(N-tert-butoxycarbonyl-pyrrolidin-3-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and (±)-3-amino-N-tert-butoxycarbonyl-pyrrolidine.
LC-MS-conditions 05c: $t_R$=0.78 min; [M+H]⁺=530.03.

Example 15

(5R*)—N⁵-(4-Bromophenyl)-(6R*)—N⁶-(cyclopentyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and cyclopentylamine.
LC-MS-conditions 05b: $t_R$=0.85 min; [M+H]⁺=429.15.

Example 16

(5R*)—N⁵-(4-Bromophenyl)-(6R*)—N⁶-(3-amino-propyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-3-amino-propylamine.
LC-MS-conditions 05c: $t_R$=0.53 min; [M+H]⁺=417.99.

Example 17

(5R*)—N⁵-(4-Bromophenyl)-(6R*)—N⁶-(3-ethoxy-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-ethoxypropylamine.
LC-MS-conditions 05b: $t_R$=0.79 min; [M+H]⁺=447.17.

Example 18

(5R*)—N⁵-(4-Bromophenyl)-(6R*)—N⁶-(2-pyrrolidinyl-methyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 1-tert-butoxycarbonyl-2-(amino-methyl)-pyrrolidine.
LC-MS-conditions 05c: $t_R$=0.55 min; [M+H]⁺=444.06.

Example 19

(5R*)—N⁵-(4-Bromophenyl)-(6R*)—N⁶-(2,2,2-trifluoro-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2,2,2-trifluoro-ethylamine.
LC-MS-conditions 05b: $t_R$=0.80 min; [M+H]⁺=443.07.

Example 20

(5R*)—N⁵-(4-Bromophenyl)-(6R*)—N⁶-(2-fluoro-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-fluoro-ethylamine.
LC-MS-conditions 05b: $t_R$=0.73 min; [M+H]⁺=407.10.

Example 21

(5R*)—N⁵-(4-Bromophenyl)-(6R*)—N⁶-(2-(N-methyl-amino)-ethyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-N-methyl-2-amino-ethylamine.
LC-MS-conditions 05c: $t_R$=0.54 min; [M+H]⁺=418.17.

Example 22

(5R*)—N⁵-(4-Bromophenyl)-(6R*)—N⁶-(2-tetrahydrofuranyl-methyl)-(4S*,7R*)-[4,7-ethenylene-spiro[2.4]heptane]-5,6-dicarboxamide:

Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-tetrahydrofuranyl-methylamine.
LC-MS-conditions 05b: $t_R$=1.10 min; [M+H]⁺=445.31.

Example 23

(5R*)—N⁵-(4-Bromophenyl)-(6R*)—N⁶-(4-hydroxy-cyclohexyl)-(4S*,7R*)-[4,7-ethenylene-spiro[2.4]heptane]-5,6-dicarboxamide Following general procedure E, starting from (5R*)—N⁵-(4-bromo-phenyl)-(6R*)-6-hydroxycarbonyl-(4S*,7R*)-[4,7-ethenylene-spiro[2.4]heptane]-5-carboxamide and trans-4-amino-cyclohexanol hydrochloride.
LC-MS-conditions 05: $t_R$=0.83 min; [M+H]⁺=459.20.

Example 24

(5R*)—N$^5$-(4-Bromophenyl)-(6R*)—N$^6$-(2-ethyl-sulfanyl-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-ethylsulfanyl-ethylamine.

LC-MS-conditions 05b: $t_R$=0.83 min; [M+H]$^+$=449.20.

Example 25

(5R*)—N$^5$-(4-Bromophenyl)-(6R*)—N$^6$-(5-(N,N-diethyl-amino)-pent-2-yl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 4-(N,N-diethyl-amino)-1-methyl-butylamine.

LC-MS-conditions 05b: $t_R$=0.92 min; [M+H]$^+$=502.11.

Example 26

(5R*)—N$^5$-(4-Bromophenyl)-(6R*)—N$^6$-(piperidin-3-yl)-(4S*,7R*)-[4,7-ethenylene-spiro[2.4]heptane]-5,6-dicarboxamide Following general procedures A then H, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (±)-N-tert-butoxycarbonyl-(3-amino)-piperidine.

LC-MS-conditions 05c: $t_R$=0.55 min; [M+H]$^+$=444.01.

Example 27

(5R*)—N$^5$-(4-Bromophenyl)-(6R*)—N$^6$-(2-tert-butoxycarbonyl-amino-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-tert-butoxycarbonyl-amino-ethylamine.

LC-MS-conditions 05c: $t_R$=0.75 min; [M+H]$^+$=504.02.

Example 28

(5R*)—N$^5$-(4-Bromophenyl)-(6R*)—N$^6$-(1-hydroxy-prop-2-yl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and D,L-2-amino-1-propanol.

LC-MS-conditions 05: $t_R$=0.81 min; [M+H]$^+$=419.07.

Example 29

(5R*)—N$^5$-(4-Bromophenyl)-(6R*)—N$^6$-(2-imidazolidin-2-on-1-yl-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-imidazolidin-2-on-1-yl-ethylamine.

LC-MS-conditions 05b: $t_R$=0.96 min; [M+H]$^+$=472.98.

Example 30

(5R*)—N$^5$-(4-Bromophenyl)-(6R*)—N$^6$-(3-pyrrolidin-1-yl-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-(1-pyrrolidino)-propylamine.

LC-MS-conditions 05b: $t_R$=0.86 min; [M+H]$^+$=472.10.

Example 31

(5R)—N$^5$-(4-Bromophenyl)-(6R)—N$^6$-(2-methoxy-ethyl)-(4S,7R)-[4,7-ethenylene-spiro[2.4]heptane]-5,6-dicarboxamide Following general procedure E, starting from (5R)—N$^5$-(4-bromo-phenyl)-(6R)-6-hydroxycarbonyl-(4S,7R)-[4,7-ethenylene-spiro[2.4]heptane]-5-carboxamide and 2-methoxy-ethylamine.

LC-MS-conditions 02: $t_R$=0.98 min; [M+H]$^+$=418.98.

Example 32

(5R*)—N$^5$-(4-Bromophenyl)-(6R*)—N$^6$-(3-(1H-benzoimidazol-2-yl)-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-(1H-benzoimidazol-2-yl)-propylamine.

LC-MS-conditions 05b: $t_R$=0.59 min; [M+H]$^+$=519.28.

Example 33

(5R*)—N$^5$-(4-Bromophenyl)-(6R*)—N$^6$-(2-(1-methyl-pyrrolidin-2-yl)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-(1-methyl-pyrrolidin-2-yl)-ethylamine.

LC-MS-conditions 05b: $t_R$=0.85 min; [M+H]$^+$=472.17.

Example 34

(5R*)—N$^5$-(4-Bromophenyl)-(6R*)—N$^6$-(2-hydroxy-ethyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-amino-ethanol.

LC-MS-conditions 02: $t_R$=0.90 min; [M+H]$^+$=405.26.

Example 35

(5R*)—N⁵-(4-Bromophenyl)-(6R*)—N⁶,N⁶-bis-(2-methoxy-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and bis-(2-methoxy-ethyl)-amine.
LC-MS-conditions 05b: $t_R$=0.78 min; [M+H]⁺=477.20.

Example 36

(5R*)—N⁵-(4-Bromophenyl)-(6R*)—N⁶-(cyano-methyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and amino-acetonitrile.
LC-MS-conditions 05b: $t_R$=0.70 min; [M+H]⁺=400.09.

Example 37

(5R*)—N⁵-(4-Bromophenyl)-(6R*)—N⁶-(3-1H-pyrazol-1-yl-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-1H-pyrazol-1-yl-propylamine.
LC-MS-conditions 05b: $t_R$=0.73 min; [M+H]⁺=469.15.

Example 38

(5R*)—N⁵-(4-Bromophenyl)-(6R*)—N⁶-[(4-aminomethyl-phenyl)-methyl]-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-(tert-butoxycarbonyl-aminomethyl)-benzylamine.
LC-MS-conditions 05c: $t_R$=0.57 min; [M+H]⁺=480.04.

Example 39

(5R*)—N⁵-(4-Bromophenyl)-(6R*)—N⁶-ethyl-N⁶-(2-diethylamino-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-ethyl-2-(N,N-diethyl-amino)-ethylamine.
LC-MS-conditions 05b: $t_R$=0.60 min; [M+H]⁺=488.21.

Example 40

(5R*)—N⁵-(4-Bromophenyl)-(6R*)—N⁶-(3-1H-imidazol-1-yl-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-(1H-imidazol-1-yl)-propylamine.
LC-MS-conditions 05b: $t_R$=0.54 min; [M+H]⁺=469.20.

Example 41

(5R*)—N⁵-(4-Bromophenyl)-(6R*)—N⁶-([1,4]-dioxan-2-yl-methyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and [1,4]-dioxan-2-yl-methylamine.
LC-MS-conditions 05b: $t_R$=1.06 min; [M+H]⁺=460.97.

Example 42

(5R*)—N⁵-(4-Bromophenyl)-(6R*)—N⁶-(4-hydroxy-butyl)-(4S*,7R*)-[4,7-ethenylene-spiro[2.4]heptane]-5,6-dicarboxamide Following general procedure E, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-amino-butanol.
LC-MS-conditions 05: $t_R$=0.81 min; [M+H]⁺=433.21.

Example 43

(5R*)—N⁵-(4-Bromophenyl)-(6R*)—N⁶-(3-(4-methyl-piperazin-1-yl)-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-(4-methyl-piperazin-1-yl)-propylamine.
LC-MS-conditions 05b: $t_R$=0.74 min; [M+H]⁺=501.10.

Example 44

(5R*)—N⁵-(4-Bromophenyl)-(6R*)—N⁶-(2-amino-ethyl)-(4S*,7R*)-[4,7-ethenylene-spiro[2.4]heptane]-5,6-dicarboxamide Following general procedures A then H, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-2-amino-ethylamine.
LC-MS-conditions 05c: $t_R$=0.53 min; [M+H]⁺=404.06.

Example 45

(5R*)—N⁵-(4-Bromophenyl)-(6R*)—N⁶-methyl-N⁶-(2-dimethylamino-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-methyl-2-(N,N-dimethyl-amino)-ethylamine.
LC-MS-conditions 05b: $t_R$=0.55 min; [M+H]⁺=446.17.

Example 46

(5R*)—N⁵-(4-Bromophenyl)-(6R*)—N⁶-(4-tert-butoxycarbonyl-amino-butyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-tert-butoxycarbonyl-amino-butylamine.
LC-MS-conditions 05c: $t_R$=0.78 min; [M+H]⁺=532.07.

Example 47

(5R*)—N$^5$-(4-Bromophenyl)-(6R*)—N$^6$-(2-(methyl-tert-butoxycarbonyl-amino)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-N-methyl-2-amino-ethylamine.

LC-MS-conditions 05c: $t_R$=0.78 min; [M+H]$^+$=517.63.

Example 48

(5R*)—N$^5$-(4-Bromophenyl)-(6R*)—N$^6$-(2-pyrrolidin-1-yl-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-pyrrolidino-ethylamine.

LC-MS-conditions 05b: $t_R$=0.54 min; [M+H]$^+$=458.14.

Example 49

(5R*)—N$^5$-(4-Bromophenyl)-(6R*)—N$^6$-(2-1H-[1,2,4]-triazol-1-yl-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-1H-[1,2,4]-triazol-1-yl-ethylamine.

LC-MS-conditions 05: $t_R$=0.78 min; [M+H]$^+$=456.13.

Example 50

(5R*)—N$^5$-(4-Bromophenyl)-(6R*)—N$^6$-(furan-3-yl-methyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and furan-3-yl-methylamine.

LC-MS-conditions 05b: $t_R$=0.79 min; [M+H]$^+$=441.18.

Example 51

(5R*)—N$^5$-(4-Bromophenyl)-(6R*)—N$^6$-(5-dimethyl-amino-pentyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 5-dimethyl-amino-pentylamine.

LC-MS-conditions 02: $t_R$=0.84 min; [M+H]$^+$=474.32.

Example 52

(5R*)—N$^5$-(4-Bromophenyl)-(6R*)—N$^6$-(3-dimethyl-amino-propyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-dimethyl-amino-propylamine.

LC-MS-conditions 02: $t_R$=0.82 min; [M+H]$^+$=446.09.

Example 53

(5R*)—N$^5$-(4-Bromophenyl)-(6R*)—N$^6$-(3-methoxy-propyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-methoxy-propylamine.

LC-MS-conditions 02: $t_R$=1.00 min; [M+H]$^+$=432.99.

Example 54

(5R*)—N$^5$-(4-Bromophenyl)-(6R*)—N$^6$-[(1-ethyl-pyrrolidin-2-yl)-methyl]-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (1-ethyl-pyrrolidin-2-yl)-methylamine.

LC-MS-conditions 05b: $t_R$=0.88 min; [M+H]$^+$=472.12.

Example 55

(5R*)—N$^5$-(4-Bromophenyl)-(6R*)—N$^6$-(3-1H-[1,2,4]-triazol-1-yl-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-1H-[1,2,4]-triazol-1-yl-propylamine.

LC-MS-conditions 05b: $t_R$=0.63 min; [M+H]$^+$=470.22.

Example 56

(5R*)—N$^5$-(4-Bromophenyl)-(6R*)—N$^6$-(N-tert-butoxycarbonyl-piperidin-3-yl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (±)-3-amino-N-tert-butoxycarbonyl-piperidine.

LC-MS-conditions 05c: $t_R$=0.81 min; [M+H]$^+$=544.06.

Example 57

(5R*)—N$^5$-(4-Bromophenyl)-(6R*)—N$^6$-(3-(N-tert-butoxycarbonyl-amino)-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4, 7-ethenylene-spiro[2.4]heptane]-5-carboxamide and 3-tert-butoxycarbonyl-amino-propylamine.

LC-MS-conditions 05c: $t_R$=0.77 min; [M+H]$^+$=517.58.

Example 58

(5R*)—N$^5$-(4-Bromophenyl)-(6R*)—N$^6$-(3-methyl-butyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-methyl-butylamine.

LC-MS-conditions 05b: $t_R$=0.89 min; [M+H]$^+$=431.13.

Example 59

(5R*)—N$^5$-(4-Bromophenyl)-(6R*)—N$^6$-[(2S)-1-hydroxy-4-methyl-pent-2-yl]-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (2S)-2-amino-4-methyl-pentan-1-ol.

LC-MS-conditions 05: $t_R$=0.93 min; [M+H]$^+$=461.21.

Example 60

(5R*)—N$^5$-(4-Bromophenyl)-(6R*)—N$^6$-(2-(methoxy-carbonyl)-ethyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and beta-alanine methylester hydrochloride.

LC-MS-conditions 02: $t_R$=0.99 min; [M+H]$^+$=446.94.

Example 61

(5R*)—N$^5$-(4-Bromophenyl)-(6R*)—N$^6$-(2-(4-aminosulfonyl-phenyl)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-(4-aminosulfonyl-phenyl)-ethylamine.

LC-MS-conditions 05b: $t_R$=1.06 min; [M+H]$^+$=544.03.

Example 62

(5R*)—N$^5$-(4-Bromophenyl)-(6R*)—N$^6$-(2-(1-ethyl-5-methyl-1H-pyrazol-3-yl)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-(1-ethyl-5-methyl-1H-pyrazol-3-yl)-ethylamine.

LC-MS-conditions 05: $t_R$=0.87 min; [M+H]$^+$=497.14.

Example 63

(5R)—N$^5$-(4-Bromophenyl)-(6R)—N$^6$,N$^6$-bis-(2-methoxy-ethyl)-(4S,7R)-[4,7-ethenylene-spiro[2.4]heptane]-5,6-dicarboxamide Following general procedure E, starting from (5R)—N$^5$-(4-bromo-phenyl)-(6R)-6-hydroxycarbonyl-(4S,7R)-[4,7-ethenylene-spiro[2.4]heptane]-5-carboxamide and bis-(2-methoxy-ethyl)-amine. LC-MS-conditions 02: $t_R$=1.02 min; [M+H]$^+$=477.24.

Example 64

(5R*)—N$^5$-(4-Bromophenyl)-(6R*)—N$^6$-(2-(4,5-dimethyl-1H-imidazol-2-yl)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-(4,5-dimethyl-1H-imidazol-2-yl)-ethylamine.

LC-MS-conditions 05b: $t_R$=0.88 min; [M+H]$^+$=483.00.

Example 65

(5R*)—N$^5$-(4-Bromophenyl)-(6R*)—N$^6$-[(1S)-1-carbamoyl-ethyl]-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (2S)-2-amino-propionamide.

LC-MS-conditions 02: $t_R$=0.89 min; [M+H]$^+$=431.92.

Example 66

(5R*)—N$^5$-(4-Bromophenyl)-(6R*)—N$^6$-(2-diethyl-amino-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-diethyl-amino-ethylamine.

LC-MS-conditions 05b: $t_R$=0.86 min; [M+H]$^+$=460.09.

Example 67

(5R*)—N$^5$-(4-Bromophenyl)-(6R*)—N$^6$-(pentyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and pentylamine.

LC-MS-conditions 05b: $t_R$=0.89 min; [M+H]$^+$=431.10.

Example 68

(5R*)—N$^5$-(4-Bromophenyl)-(6R*)—N$^6$-(5-tert-butoxycarbonyl-amino-pentyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4, 7-ethenylene-spiro[2.4]heptane]-5-carboxamide and 5-tert-butoxycarbonyl-amino-pentylamine.

LC-MS-conditions 05c: $t_R$=0.80 min; [M+H]$^+$=546.04.

Example 69

(5R*)—N$^5$-(4-Bromophenyl)-(6R*)—N$^6$—(N-(3-methyl-butyl)-piperidin-4-yl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 4-amino-1-isopentyl-piperidine.

LC-MS-conditions 05b: $t_R$=0.96 min; [M+H]$^+$=514.10.

Example 70

(5R*)—N$^5$-(4-Bromophenyl)-(6R*)—N$^6$-(2-pyridin-2-yl-ethyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-pyridin-2-yl-ethylamine.

LC-MS-conditions 02: $t_R$=0.83 min; [M+H]$^+$=465.93.

Example 71

(5R*)—N$^5$-(4-Bromophenyl)-(6R*)—N$^6$-(2,2-dimethyl-3-N-tert-butoxycarbonyl-amino-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2,2-dimethyl-3-tert-butoxycarbonyl-amino-propylamine.

LC-MS-conditions 05c: $t_R$=0.84 min; [M+H]$^+$=546.02.

Example 72

(5R*)—N$^5$-(4-Bromophenyl)-(6R*)—N$^6$-(1-phenyl-1H-pyrazol-5-yl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-phenyl-2H-pyrazol-3-ylamine. LC-MS-conditions 05b: $t_R$=1.15 min; [M+H]$^+$=503.04.

Example 73

(5R*)—N$^5$-(4-Bromophenyl)-(6R*)—N$^6$-(cyclopropyl)-(4S*,7R*)-[4,7-ethenylene-spiro[2.4]heptane]-5,6-dicarboxamide In a flame dried round-bottomed flask equipped with a magnetic stir bar and under inert atmosphere (N$_2$), to a solution of (5R*)—N$^5$-(4-bromo-phenyl)-(6R*)-6-hydroxycarbonyl-(4S*,7R*)-[4,7-ethenylene-spiro[2.4]heptane]-5-carboxamide (1.0 eq.) in DMF (0.2 M) were added cyclopropylamine (1.5 eq.), PyBOP (1.5 eq.) and DIPEA (3.0 eq.). The reaction mixture was stirred at rt until completion of the reaction. The reaction mixture was then partitioned between water and EA. The layers were separated and the aq. layer extracted with EA (3×). The combined org. extracts were dried over MgSO$_4$, filtered, and the solvents were removed under reduced pressure. Purification of the residue by FC or HPLC gave the desired compound.

LC-MS-conditions 02: $t_R$=1.00 min; [M+H]$^+$=401.13.

Example 74

(5R*)—N$^5$-(4-Bromophenyl)-(6R*)—N$^6$-(butyl)-(4S*,7R*)-[4,7-ethenylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and butylamine.

LC-MS-conditions 02: $t_R$=1.07 min; [M+H]$^+$=416.25.

Example 75

(5R*)—N$^5$-(4-Bromophenyl)-(6R*)—N$^6$-(hexyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and hexylamine.

LC-MS-conditions 05b: $t_R$=1.25 min; [M+H]$^+$=445.11.

Example 76

(5R*)—N$^5$-(4-Bromophenyl)-(6R*)—N$^6$-(2-(1-ethyl-3-methyl-1H-pyrazol-5-yl)-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-(1-ethyl-3-methyl-1H-pyrazol-5-yl)-ethylamine.

LC-MS-conditions 05b: $t_R$=1.04 min; [M+H]$^+$=497.09.

Example 77

(5R*)—N$^5$-(4-Bromophenyl)-(6R*)—N$^6$-(2-phenyl-2-morpholino-ethyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 2-phenyl-2-morpholino-ethylamine.

LC-MS-conditions 05b: $t_R$=0.94 min; [M+H]$^+$=550.09.

Example 78

(5R*)—N$^5$-(4-Bromophenyl)-(6R*)—N$^6$-(3-diethyl-amino-propyl)-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and 3-diethylamino-propylamine.

LC-MS-conditions 05b: $t_R$=0.88 min; [M+H]$^+$=474.07.

Example 79

(5R*)—N⁵-(4-Bromophenyl)-(6R*)—N⁶—(N-tert-butoxycarbonyl-pyrrolidin-2-yl-methyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-pyrrolidin-2-yl-methylamine.

LC-MS-conditions 05c: $t_R$=0.83 min; [M+H]⁺=544.06.

Example 80

(5R*)—N⁵-(4-Bromophenyl)-(6R*)—N⁶-(2-morpholino-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-morpholino-ethylamine.

LC-MS-conditions 05b: $t_R$=0.83 min; [M+H]⁺=474.05.

Example 81

(5R*)—N⁵-(4-Bromophenyl)-(6R*)—N⁶-(2-carbamoyl-cyclohexyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and cis-2-amino-cyclohexane-carboxylic acid amide.

LC-MS-conditions 05b: $t_R$=1.05 min; [M+H]⁺=486.06.

Example 82

(5R*)—N⁵-(4-Bromophenyl)-(6R*)—N⁶-(1-piperidin-1-yl-propan-1-on-2-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-amino-1-piperidin-1-yl-propan-1-one.

LC-MS-conditions 05b: $t_R$=1.13 min; [M+H]⁺=500.08.

Example 83

(5R*)—N⁵-(4-Bromophenyl)-(6R*)—N⁶—(N-benzyl-piperidin-4-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-amino-N-benzyl-piperidine.

LC-MS-conditions 05b: $t_R$=0.60 min; [M+H]⁺=534.24.

Example 84

(5R*)—N⁵-(4-Bromophenyl)-(6R*)—N⁶-methyl-N⁶-hexyl-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-methyl-hexylamine.

LC-MS-conditions 05b: $t_R$=0.97 min; [M+H]⁺=459.15.

Example 85

(5R*)—N⁵-(4-Bromophenyl)-(6R*)—N⁶-(3,3-dimethyl-butyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3,3-dimethyl-butylamine.

LC-MS-conditions 05b: $t_R$=0.93 min; [M+H]⁺=445.13.

Example 86

(5R*)—N⁵-(4-Bromophenyl)-(6R*)—N⁶—(N-methyl-piperidin-4-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-amino-N-methyl-piperidine.

LC-MS-conditions 05b: $t_R$=0.83 min; [M+H]⁺=458.11.

Example 87

(5R*)—N⁵-(4-Bromophenyl)-(6R*)—N⁶-(3-morpholino-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-morpholino-propylamine.

LC-MS-conditions 05b: $t_R$=0.84 min; [M+H]⁺=488.15.

Example 88

(5R*)—N⁵-(4-Bromophenyl)-(6R*)—N⁶-(3-(5-methyl-1H-pyrazol-4-yl)-propyl)-(4S*,7R*)-[4,7-ethenylene-spiro[2.4]heptane]-5,6-dicarboxamide:

Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-(5-methyl-1H-pyrazol-4-yl)-propylamine.

LC-MS-conditions 05b: $t_R$=0.97 min; [M+H]⁺=483.05.

Example 89

(5R*)—N⁵-(4-Bromophenyl)-(6R*)—N⁶-(3-tert-butoxycarbonyl-propyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-tert-butoxycarbonyl-propylamine.

LC-MS-conditions 05b: $t_R$=1.21 min; [M+H]⁺=503.06.

Example 90

(5R*)—N⁵-(4-Bromophenyl)-(6R*)—N⁶-{[(3-N-tert-butoxycarbonyl-aminomethyl)-phenyl]-methyl}-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-(tert-butoxycarbonyl-aminomethyl)-benzylamine.
LC-MS-conditions 05c: $t_R$=0.82 min; [M+H]⁺=580.00.

Example 91

(5R*)—N⁵-(4-Bromophenyl)-(6R*)—N⁶-propyl-N⁶-(cyclopropylmethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-(cyclopropyl-methyl)-propylamine.
LC-MS-conditions 05b: $t_R$=0.93 min; [M+H]⁺=457.16.

Example 92

(5R*)—N⁵-(4-Bromophenyl)-(6R*)—N⁶—(N-tert-butoxycarbonyl-piperidin-4-yl-methyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and N-tert-butoxycarbonyl-4-(amino-methyl)-piperidine.
LC-MS-conditions 05c: $t_R$=0.81 min; [M+H]⁺=558.03.

Example 93

(5R*)—N⁵-(4-Bromophenyl)-(6R*)—N⁶-(cyclohexyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and cyclohexylamine.
LC-MS-conditions 05b: $t_R$=1.22 min; [M+H]⁺=443.05.

Example 94

(5R*)—N⁵-(4-Bromophenyl)-(6R*)—N⁶—(N-tert-butoxycarbonyl-piperidin-4-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-amino-N-tert-butoxycarbonyl-piperidine.
LC-MS-conditions 05c: $t_R$=0.80 min; [M+H]⁺=544.04.

Example 95

(5R*)—N⁵-(4-Bromophenyl)-(6R*)—N⁶-[(1S)-1-carbamoyl-2-phenyl-ethyl]-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and (2S)-2-amino-3-phenyl-propionamide.
LC-MS-conditions 05b: $t_R$=1.08 min; [M+H]⁺=508.04.

Example 96

(5R*)—N⁵-(4-Bromophenyl)-(6R*)—N⁶—[(2S)-3,3-dimethyl-1-(methylamino)-1-oxobutan-2-yl]-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and (2S)-2-amino-3,3,N-trimethyl-butyramide.
LC-MS-conditions 05b: $t_R$=1.11 min; [M+H]⁺=488.11.

Example 97

(5R*)—N⁵-(4-Bromophenyl)-(6R*)—N⁶-[(4-N-tert-butoxycarbonyl-aminomethyl-phenyl)-methyl]-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-(tert-butoxycarbonyl-aminomethyl)-benzylamine.
LC-MS-conditions 05c: $t_R$=0.82 min; [M+H]⁺=580.03.

Example 98

(5R*)—N⁵-(4-Bromophenyl)-(6R*)—N⁶—(N-tert-butoxycarbonyl-azetidin-3-yl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-amino-N-tert-butoxycarbonyl-azetidine.
LC-MS-conditions 05c: $t_R$=0.77 min; [M+H]⁺=516.07.

Example 99

(5R*)—N⁵-(4-Bromophenyl)-(6R*)—N⁶-(2-(N-tert-butoxycarbonyl-piperidin-3-yl)-ethyl)-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-(N-tert-butoxycarbonyl-piperidin-3-yl)-ethylamine.
LC-MS-conditions 05b: $t_R$=1.25 min; [M+H]⁺=572.15.

Example 100

(5R*)—N⁵-(4-Bromophenyl)-(6R*)—N⁶-[(1S)-2-methoxy-1-benzyl-ethyl]-(4S*,7R*)-[4,7-ethenylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethenylene-spiro[2.4]heptane]-5-carboxamide and (1S)-1-benzyl-2-methoxy-ethylamine.
LC-MS-conditions 05b: $t_R$=1.19 min; [M+H]⁺=509.01.

Example 101

(5R*)—N$^5$-(4-Bromophenyl)-(6R*)—N$^6$-[(5-methyl-3-phenyl-isoxazol-4-yl)-methyl]-(4S*,7R*)-[4,7-ethenylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethenylene-spiro[2.4]heptane]-5-carboxamide and (5-methyl-3-phenyl-isoxazol-4-yl)-methylamine.
LC-MS-conditions 05b: $t_R$=0.86 min; [M+H]$^+$=531.77.

Example 102

(5R*)—N$^5$-(4-Bromophenyl)-(6R*)—N$^6$-(2-carbamoyl-ethyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 3-aminopropionamide.
LC-MS-conditions 05b: $t_R$=0.63 min; [M+H]$^+$=433.63.

Example 103

(5R*)—N$^5$-(4-Bromophenyl)-(6R*)—N$^6$-(3-methoxy-propyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 3-methoxy-propylamine.
LC-MS-conditions 05b: $t_R$=0.77 min; [M+H]$^+$=435.12.

Example 104

(5R*)—N$^5$-(4-Bromophenyl)-(6R*)—N$^6$-(tetrahydrofuran-2-yl-methyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and tetrahydrofuran-2-yl-methylamine.
LC-MS-conditions 05b: $t_R$=0.78 min; [M+H]$^+$=447.12.

Example 105

(5R*)—N$^5$-(4-Bromophenyl)-(6R*)—N$^6$-[(2-imidazolidin-2-on-1-yl)-ethyl]-(4S*,7R*)-[4,7-ethylene-spiro[2.4]heptane]-5,6-dicarboxamide:

Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 2-imidazolidin-2-on-1-yl-ethylamine.
LC-MS-conditions 05b: $t_R$=0.65 min; [M+H]$^+$=475.14.

Example 106

(5R*)—N$^5$-(4-Bromophenyl)-(6R*)—N$^6$-(cyclopropyl)-(4S*,7R*)-[4,7-ethylene-spiro[2.4]heptane]-5,6-dicarboxamide In a flame dried round-bottomed flask equipped with a magnetic stir bar and under inert atmosphere (N$_2$), to a solution of (5R*)—N$^5$-(4-bromo-phenyl)-(6R*)-6-hydroxycarbonyl-(4S*,7R*)-[4,7-ethylene-spiro[2.4]heptane]-5-carboxamide (1.0 eq.) in DMF (0.1 M) were added cyclopropylamine (1.0 eq.), HATU (1.5 eq.), DMAP (0.25 eq.) and DIPEA (5.0 eq.). The reaction mixture was stirred at rt until completion of the reaction. The reaction mixture was then partitioned between sat. aq. NH$_4$C$_1$ and CH$_2$Cl$_2$. The layers were separated and the aq. layer extracted with CH$_2$Cl$_2$ (3×). The combined org. extracts were dried over MgSO$_4$, filtered, and the solvents were removed under reduced pressure. Purification of the residue by FC or HPLC gave the desired compound.
LC-MS-conditions 02: $t_R$=1.03 min; [M+H]$^+$=403.00.

Example 107

(5R*)—N$^5$-(4-Bromophenyl)-(6R*)—N$^6$-(3-hydroxy-propyl)-(4S*,7R*)-[4,7-ethylene-spiro[2.4]heptane]-5,6-dicarboxamide Following general procedure E, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 3-aminopropanol.
LC-MS-conditions 05: $t_R$=0.84 min; [M+H]$^+$=421.07.

Example 108

(5R*)—N$^5$-(4-Bromophenyl)-(6R*)—N$^6$-(3-(1H-imidazol-1-yl)-propyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 3-(1H-imidazol-1-yl)-propylamine.
LC-MS-conditions 05b: $t_R$=0.57 min; [M+H]$^+$=471.18.

Example 109

(5R*)—N$^5$-(4-Bromophenyl)-(6R*)—N$^6$-(5-(dimethyl-amino)-pentyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 5-dimethyl-amino-pentylamine.
LC-MS-conditions 05b: $t_R$=0.58 min; [M+H]$^+$=476.20.

Example 110

(5R*)—N$^5$-(4-Bromophenyl)-(6R*)—N$^6$-(3-pyrrolidin-1-yl-propyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,7-ethylene-spiro[2.4]heptane]-5-carboxamide and 3-pyrrolidino-propylamine.
LC-MS-conditions 05b: $t_R$=0.58 min; [M+H]$^+$=474.20.

Example 111

(5R*)—N$^5$-(4-Bromophenyl)-(6R*)—N$^6$-(3-(4-methyl-piperazin-1-yl)-propyl)-(4S*,7R*)-[4,7-ethylene-spiro[2.4]heptane]-5,6-dicarboxamide Following general procedure A, starting from (5R*)—N$^5$-(4-bromo-phenyl)-(6R*)-6-hydroxycarbonyl-(4S*,7R*)-[4,

Example 112

(5R*)—N⁵-(4-Bromophenyl)-(6R*)—N⁶-(2-(4,5-dimethyl-1H-imidazol-2-yl)-ethyl)-(4S*,7R*)-[4,7-ethylene-spiro[2.4]heptane]-5,6-dicarboxamide Following general procedure A, starting from (5R*)—N⁵-(4-bromo-phenyl)-(6R*)-6-hydroxycarbonyl-(4S*,7R*)-[4,7-ethylene-spiro[2.4]heptane]-5-carboxamide and 2-(4,5-dimethyl-1H-imidazol-2-yl)-ethylamine.

LC-MS-conditions 05b: $t_R$=0.59 min; [M+H]⁺=485.20.

Example 113

(5R)—N⁵-(4-Bromophenyl)-(6R)—N⁶-(4-pyrrolidin-1-yl-butyl)-(4S,7R)-[4,7-ethylene-spiro[2.4]heptane]-5,6-dicarboxamide Following general procedure F, starting from (5R)—N⁵-(4-bromo-phenyl)-(6R)-6-methoxycarbonyl-(4S,7R)-[4,7-ethylene-spiro[2.4]heptane]-5-carboxamide and 4-(1-pyrrolidino)-butylamine.

LC-MS-conditions 02: $t_R$=0.87 min; [M+H]⁺=487.96.

Example 114

(5R*)—N⁵-(2-Bromopyridin-5-yl)-(6R*)—N⁶-(4-pyrrolidin-1-yl-butyl)-(4S*,7R*)-[4,7-ethylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-2-bromo-pyridine.

LC-MS-conditions 05: $t_R$=0.68 min; [M+H]⁺=487.04.

Example 115

(5R*)—N⁵-(4-Methoxyphenyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-methoxy-phenylamine.

LC-MS-conditions 05c: $t_R$=0.55 min; [M+H]⁺=438.29.

Example 116

(5R*)—N⁵-(2-Chloro-pyridin-5-yl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-2-chloro-pyridine.

LC-MS-conditions 05: $t_R$=0.66 min; [M+H]⁺=443.15.

Example 117

(5R*)—N⁵-(Benzothiazol-5-yl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-benzothiazole.

LC-MS-conditions 05: $t_R$=0.65 min; [M+H]⁺=465.18.

Example 118

(5R*)—N⁵-(4-Bromophenyl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure E, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and p-bromo-benzylamine hydrochloride.

LC-MS-conditions 05: $t_R$=0.72 min; [M+H]⁺=500.17.

Example 119

(5R*)—N⁵-(5-Bromo-pyridin-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-bromo-pyridine.

LC-MS-conditions 05: $t_R$=0.69 min; [M+H]⁺=487.16.

Example 120

(5R*)—N⁵-(5-Bromo-thiazol-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-bromo-thiazole.

LC-MS-conditions 05: $t_R$=0.73 min; [M+H]⁺=493.03.

Example 121

(5R*)—N⁵-(5-Methyl-pyridin-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-methyl-pyridine.

LC-MS-conditions 05c: $t_R$=0.40 min; [M+H]⁺=423.32.

Example 122

(5R*)—N⁵-Pentyl-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and pentylamine.
LC-MS-conditions 05c: $t_R$=0.56 min; [M+H]⁺=401.96.

Example 123

(5R*)—N⁵-[(4-Methyl-phenyl)-methyl]-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-methyl-benzylamine.
LC-MS-conditions 05: $t_R$=0.72 min; [M+H]⁺=435.88.

Example 124

(5R*)—N⁵-(2-Methoxycarbonyl-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-methoxycarbonyl-ethylamine.
LC-MS-conditions 05c: $t_R$=0.45 min; [M+H]⁺=417.83.

Example 125

(5R*)—N⁵-(Cyclohexyl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and cyclohexyl-methylamine.
LC-MS-conditions 05c: $t_R$=0.56 min; [M+H]⁺=428.38.

Example 126

(5R*)—N⁵-(4-Methyl-cyclohex-1-yl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-methyl-cyclohexylamine.
LC-MS-conditions 05c: $t_R$=0.57 min; [M+H]⁺=428.39.

Example 127

(5R*)—N⁵-(5-oxo-hexyl)-(6R*)—N⁶-(4-pyrrolidin-1-yl-butyl)-(4S*,7R*)-[4,7-ethenylene-spiro[2.4]heptane]-5,6-dicarboxamide Following general procedures E then G, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-(2-methyl-[1,3]dioxolan-2-yl)butylamine.
LC-MS-conditions 02: $t_R$=0.70 min; [M+H]⁺=430.02.

Example 128

(5R*)—N⁵-(5-Nitro-thiazol-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure C, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-nitro-thiazole.
LC-MS-conditions 05: $t_R$=0.66 min; [M+H]⁺=460.09.

Example 129

(5R*)—N⁵-(5-Chloro-thiazol-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure C, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-chloro-thiazole.
LC-MS-conditions 05: $t_R$=0.68 min; [M+H]⁺=449.13.

Example 130

(5R*)—N⁵-(5-Cyano-thiazol-2-yl)-(6R*)—N⁶-(4-pyrrolidin-1-yl-butyl)-(4S*,7R*)-[4,7-ethenylene-spiro[2.4]heptane]-5,6-dicarboxamide Following general procedure C, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-amino-5-cyano-thiazole.
LC-MS-conditions 05: $t_R$=0.63 min; [M+H]⁺=440.23.

Example 131

(5R*)—N⁵-(Furan-2-yl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and furan-2-yl-methylamine.
LC-MS-conditions 05c: $t_R$=0.47 min; [M+H]⁺=412.32.

Example 132

(5R*)—N⁵-(1-(4-Bromophenyl)-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure E, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 1-(4-Bromophenyl)-ethylamine.
LC-MS-conditions 05: $t_R$=0.77 min; [M+H]⁺=513.73.

Example 133

(5R*)—N⁵-(4-Trifluoromethoxyphenyl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-trifluoromethoxy-aniline.
LC-MS-conditions 05: $t_R$=0.81 min; [M+H]⁺=492.15.

Example 134

(5R*)—N⁵-(2-Phenoxy-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-phenoxy-ethylamine.
LC-MS-conditions 05c: $t_R$=0.53 min; [M+H]⁺=452.30.

Example 135

(5R*)—N⁵-(3-Methyl-butyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and isopentylamine.
LC-MS-conditions 05c: $t_R$=0.52 min; [M+H]⁺=401.97.

Example 136

(5R*)—N⁵-Butyl-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and butylamine.
LC-MS-conditions 05c: $t_R$=0.52 min; [M+H]⁺=388.38.

Example 137

(5R*)—N⁵-(5-Methyl-furan-2-yl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (5-methyl-furan-2-yl)-methylamine.
LC-MS-conditions 05c: $t_R$=0.50 min; [M+H]⁺=426.33.

Example 138

(5R*)—N⁵-(2-Methyl-benzothiazol-5-yl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-2-methyl-benzothiazole.
LC-MS-conditions 05: $t_R$=0.68 min; [M+H]⁺=479.17.

Example 139

(5R*)—N⁵-(2-Phenyl-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-phenyl-ethylamine.
LC-MS-conditions 05c: $t_R$=0.53 min; [M+H]⁺=436.32.

Example 140

(5R*)—N⁵-(4-oxo-pentyl)-(6R*)—N⁶-(4-pyrrolidin-1-yl-butyl)-(4S*,7R*)-[4,7-ethenylene-spiro[2.4]heptane]-5,6-dicarboxamide Following general procedures E then G, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-(2-methyl-[1,3]dioxolan-2-yl)-propylamine.
LC-MS-conditions 02: $t_R$=0.68 min; [M+H]⁺=416.47.

Example 141

(5R*)—N⁵-(3-(1H-Imidazol-1-yl)-propyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-1H-imidazol-1-yl-propylamine.
LC-MS-conditions 05c: $t_R$=0.32 min; [M+H]⁺=440.36.

Example 142

(5R*)—N⁵-(2-Chloro-pyrimidin-5-yl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-2-chloro-pyrimidine.
LC-MS-conditions 05: $t_R$=0.63 min; [M+H]⁺=444.13.

Example 143

(5R*)—N⁵-(3-Bromophenyl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-bromo-benzylamine.
LC-MS-conditions 05: $t_R$=0.74 min; [M+H]⁺=499.62.

Example 144

(5R\*)—N5-(Benzothiazol-2-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-amino-benzothiazole.
LC-MS-conditions 05: $t_R$=0.74 min; [M+H]$^+$=465.18.

Example 145

(5R\*)—N5-(5-tert-Butyl-isoxazol-3-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 3-amino-5-tert-butyl-isoxazole.
LC-MS-conditions 05: $t_R$=0.76 min; [M+H]$^+$=455.21.

Example 146

(5R\*)—N5-(3-Methyl-benzo[d]isothiazol-5-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 5-amino-3-methyl-benzoisothiazole.
LC-MS-conditions 05: $t_R$=0.71 min; [M+H]$^+$=479.19.

Example 147

(5R\*)—N5-(1H-Indol-5-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 5-amino-1H-indole.
LC-MS-conditions 05: $t_R$=0.65 min; [M+H]$^+$=447.17.

Example 148

(5R\*)—N5-(6-Fluoro-benzothiazol-2-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-amino-6-fluoro-benzothiazole.
LC-MS-conditions 05: $t_R$=0.76 min; [M+H]$^+$=483.10.

Example 149

(5R\*)—N5-(2-Ethyl-butyl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-ethyl-butylamine.
LC-MS-conditions 05: $t_R$=0.75 min; [M+H]$^+$=416.28.

Example 150

(5R\*)—N5-(4-(4-Chlorophenyl)-thiazol-2-yl)-(6R\*)—N6-(4-pyrrolidin-1-yl-butyl)-(4S\*,7R\*)-[4,7-ethenylene-spiro[2.4]heptane]-5,6-dicarboxamide:

Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-amino-4-(4-chlorophenyl)-thiazole.
LC-MS-conditions 05: $t_R$=0.86 min; [M+H]$^+$=525.10.

Example 151

(5R\*)—N5-(Benzo[2,1,3]oxadiazol-4-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 4-amino-benzo[2,1,3]oxadiazole.
LC-MS-conditions 05: $t_R$=0.73 min; [M+H]$^+$=450.19.

Example 152

(5R\*)—N5-(4-tert-Butyl-thiazol-2-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-amino-4-tert-butyl-thiazole.
LC-MS-conditions 05: $t_R$=0.81 min; [M+H]$^+$=471.19.

Example 153

(5R\*)—N5-(3-Phenyl-[1,2,4]thiadiazol-5-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 5-amino-3-phenyl-[1,2,4]thiadiazole.
LC-MS-conditions 05: $t_R$=0.80 min; [M+H]$^+$=492.17.

Example 154

(5R\*)—N5-(6-Chloro-benzothiazol-2-yl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 2-amino-6-chloro-benzothiazole.
LC-MS-conditions 05: $t_R$=0.82 min; [M+H]$^+$=499.01.

Example 155

(5R\*)—N5-(3-(2-Methyl-1H-indol-1-yl)-propyl)-(6R\*)—N6-(4-pyrrolidin-1-yl-butyl)-(4S\*,7R\*)-[4,7-ethenylene-spiro[2.4]heptane]-5,6-dicarboxamide Following general procedure B, starting from (5R\*)-5-hydroxycarbonyl-(6R\*)—N6-(4-pyrrolidin-1-yl-butyl)-(4S\*,7R\*)-[4,7-ethenylene-spiro[2.4]heptane]-6-carboxamide and 3-(2-methyl-1H-indol-1-yl)-propylamine.
LC-MS-conditions 05: $t_R$=0.79 min; [M+H]$^+$=503.30.

Example 156

(5R*)—N⁵-(2-(1-Methyl-1H-benzoimidazol-2-yl)-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(1-methyl-1H-benzimidazol-2-yl)-ethylamine.

LC-MS-conditions 05: $t_R$=0.48 min; [M+H]⁺=490.19.

Example 157

(5R*)—N⁵-(2-(1H-Indol-1-yl)-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(1H-indol-1-yl)-ethylamine.

LC-MS-conditions 05: $t_R$=0.70 min; [M+H]⁺=475.19.

Example 158

(5R*)—N⁵-(2-(2-Methoxy-phenyl)-ethyl)-(6R*)—N⁶-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(2-methoxy-phenyl)-ethylamine.

LC-MS-conditions 05: $t_R$=0.72 min; [M+H]⁺=466.22.

Example 159

(5R*)—N⁵-(4-Bromo-phenyl)-(6R*)-6-[(3-(3,5-dimethyl-pyrazol-1-yl)-propionylamino)-methyl]-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and 3-(3,5-dimethyl-pyrazol-1-yl)-propionic acid.

LC-MS-conditions 05: $t_R$=0.84 min; [M+H]⁺=497.18.

Example 160

(5R*)—N⁵-(4-Bromo-phenyl)-(6R*)-6-{[(5-phenyl-isoxazole-4-carbonyl)-amino]-methyl}-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and 5-phenyl-isoxazole-4-carboxylic acid.

LC-MS-conditions 05: $t_R$=1.09 min; [M+H]⁺=518.11.

Example 161

(5R*)—N⁵-(4-Bromo-phenyl)-(6R*)-6-[(4-(2-oxo-pyrrolidin-1-yl)-butyryl amino)-methyl]-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and 4-(2-oxo-pyrrolidin-1-yl)-butyric acid.

LC-MS-conditions 05: $t_R$=0.80 min; [M+H]⁺=499.65.

Example 162

(5R*)—N⁵-(4-Bromo-phenyl)-(6R*)-6-[(2-(2-chloro-phenyl)-acetylamino)-methyl]-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and (2-chloro-phenyl)-acetic acid.

LC-MS-conditions 05: $t_R$=1.00 min; [M+H]⁺=499.18.

Example 163

(5R*)—N⁵-(4-Bromo-phenyl)-(6R*)-6-[(3-methoxy-propionylamino)-methyl]-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and 3-methoxy-propionic acid.

LC-MS-conditions 05: $t_R$=0.85 min; [M+H]⁺=433.13.

Example 164

(5R*)—N⁵-(4-Bromo-phenyl)-(6R*)-6-[(3-(N,N-dimethyl-aminocarbonyl)-propionyl-amino)-methyl]-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and N,N-dimethyl-succinamic acid.

LC-MS-conditions 05: $t_R$=0.81 min; [M+H]⁺=474.17.

Example 165

(5R*)—N⁵-(4-Bromo-phenyl)-(6R*)-6-{[(2,2-dichloro-1-methyl-cyclopropylcarbonyl)-amino]-methyl}-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7-ethenylene-spiro[2.4]heptane]-5-carboxamide and 2,2-dichloro-1-methyl-cyclopropanecarboxylic acid.

LC-MS-conditions 05: $t_R$=1.00 min; [M+H]⁺=497.04.

Example 166

(5R*)—N⁵-(4-Bromo-phenyl)-(6R*)-6-{[(4-methoxycarbonyl-butanoyl)-amino]-methyl}-(4S*,7R*)-[4,7-ethenylene-spiro[2.4]heptane]-5-carboxamide Following general procedure D, starting from (5R*)—N⁵-(4-bromo-phenyl)-6-(6R*)-(amino-methyl)-(4S*,7R*)-[4,7- ethenylene-spiro[2.4]heptane]-5-carboxamide and pentanedioic acid monomethyl ester.
LC-MS-conditions 05: $t_R$=0.88 min; [M+H]$^+$=475.14.

Example 167

(5R*)—N$^5$-(4-Bromo-phenyl)-(6R*)-6-(pentanoyl-amino-methyl)-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and pentanoic acid.
LC-MS-conditions 05: $t_R$=0.96 min; [M+H]$^+$=431.20.

Example 168

(5R*)—N$^5$-(4-Bromo-phenyl)-(6R*)-6-[2-(2,5-dimethyl-thiazol-4-yl)-acetylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and (2,5-dimethyl-thiazol-4-yl)-acetic acid.
LC-MS-conditions 05: $t_R$=0.89 min; [M+H]$^+$=499.54.

Example 169

(5R*)—N$^5$-(4-Bromo-phenyl)-(6R*)-6-{[(1-phenyl-1H-pyrazole-5-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 2-phenyl-2H-pyrazole-3-carboxylic acid.
LC-MS-conditions 05: $t_R$=0.97 min; [M+H]$^+$=517.14.

Example 170

(5R*)—N$^5$-(4-Bromo-phenyl)-(6R*)-6-{[(3-aminocarbonyl-propionyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and succinamic acid.
LC-MS-conditions 05: $t_R$=0.75 min; [M+H]$^+$=446.14.

Example 171

(5R*)—N$^5$-(4-Bromo-phenyl)-(6R*)-6-{[(4-methyl-pyridine-3-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 4-methyl-nicotinic acid.
LC-MS-conditions 05: $t_R$=0.75 min; [M+H]$^+$=466.20.

Example 172

(5R*)—N$^5$-(4-Bromo-phenyl)-(6R*)-6-[(isobutyrylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and isobutyric acid.
LC-MS-conditions 05: $t_R$=0.92 min; [M+H]$^+$=417.18.

Example 173

(5R*)—N$^5$-(4-Bromo-phenyl)-(6R*)-6-{[(N-ethyl-piperidine-4-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 1-ethyl-piperidine-4-carboxylic acid.
LC-MS-conditions 05: $t_R$=0.72 min; [M+H]$^+$=486.20.

Example 174

(5R*)—N$^5$-(4-Bromo-phenyl)-(6R*)-6-[(3-pyridin-3-yl-propionylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 3-pyridin-3-yl-propionic acid.
LC-MS-conditions 05: $t_R$=0.71 min; [M+H]$^+$=480.16.

Example 175

(5R*)—N$^5$-(4-Bromo-phenyl)-(6R*)-6-{[N-(3-methoxy-propionyl)-N-methyl-amino]-methyl}-(4S*,7R*)-[4,7-ethenylene-spiro[2.4]heptane]-5-carboxamide Following general procedure D, starting from (5R*)—N$^5$-(4-bromo-phenyl)-(6R*)-6-[(methyl-amino)-methyl]-(4S*,7R*)-[4,7-ethenylene-spiro[2.4]heptane]-5-carboxamide and 3-methoxy-propionic acid.
LC-MS-conditions 05: $t_R$=0.90 min; [M+H]$^+$=447.15.

Example 176

(5R*)—N$^5$-(4-Bromo-phenyl)-(6R*)-6-{[(2-chloro-3-fluoro-phenyl-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 2-chloro-3-fluoro-benzoic acid.
LC-MS-conditions 05: $t_R$=0.98 min; [M+H]$^+$=503.04.

Example 177

(5R*)—N$^5$-(4-Bromo-phenyl)-(6R*)-6-[(4-pyrrolidin-1-yl-butanoylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 4-pyrrolidin-1-yl-butyric acid.
LC-MS-conditions 05: $t_R$=0.73 min; [M+H]$^+$=486.23.

Example 178

(5R*)—N$^5$-(4-Bromo-phenyl)-(6R*)-6-{[(1,5-dimethyl-1H-pyrazole-3-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 1,5-dimethyl-1H-pyrazole-3-carboxylic acid.
LC-MS-conditions 05: $t_R$=0.93 min; [M+H]$^+$=468.91.

Example 179

(5R*)—N$^5$-(4-Bromo-phenyl)-(6R*)-6-{[(cyclopentyl-carbonyl)-amino]-methyl}-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and cyclopentanecarboxylic acid.
LC-MS-conditions 05: $t_R$=0.97 min; [M+H]$^+$=443.15.

Example 180

(5R*)—N$^5$-(4-Bromo-phenyl)-(6R*)-6-[(2-(2-methyl-thiazol-4-yl)-acetylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and (2-methyl-thiazol-4-yl)-acetic acid.
LC-MS-conditions 05: $t_R$=0.89 min; [M+H]$^+$=485.96.

Example 181

(5R*)—N$^5$-(4-Bromo-phenyl)-(6R*)-6-[(2-(N,N-dimethyl-amino)-acetylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and dimethylamino-acetic acid.
LC-MS-conditions 05: $t_R$=0.75 min; [M+H]$^+$=432.13.

Example 182

(5R*)—N$^5$-(4-Bromo-phenyl)-(6R*)-6-{[N-(2-(2-chloro-phenyl)-acetyl)-N-methyl-amino]-methyl}-(4S*,7R*)-[4,7-ethenylene-spiro[2.4]heptane]-5-carboxamide Following general procedure D, starting from (5R*)—N$^5$-(4-bromo-phenyl)-(6R*)-6-[(methyl-amino)-methyl]-(4S*,7R*)-[4,7-ethenylene-spiro[2.4]heptane]-5-carboxamide and (2-chloro-phenyl)-acetic acid.
LC-MS-conditions 05: $t_R$=1.06 min; [M+H]$^+$=513.13.

Example 183

(5R*)—N$^5$-(4-Bromo-phenyl)-(6R*)-6-{[N-(1,5-dimethyl-1H-pyrazole-3-carbonyl)-N-methyl-amino]-methyl}-(4S*,7R*)-[4,7-ethenylene-spiro[2.4]heptane]-5-carboxamide Following general procedure D, starting from (5R*)—N$^5$-(4-bromo-phenyl)-(6R*)-6-[(methyl-amino)-methyl]-(4S*,7R*)-[4,7-ethenylene-spiro[2.4]heptane]-5-carboxamide and 1,5-dimethyl-1H-pyrazole-3-carboxylic acid.
LC-MS-conditions 05: $t_R$=0.91 min; [M+H]$^+$=483.27.

Example 184

(5R*)—N$^5$-(4-Bromo-phenyl)-(6R*)-6-[(2-cyclopropyl-acetylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and cyclopropyl-acetic acid.
LC-MS-conditions 05: $t_R$=0.92 min; [M+H]$^+$=429.20.

Example 185

(5R*)—N$^5$-(4-Bromo-phenyl)-(6R*)-6-[(3-(1-methyl-1H-benzoimidazol-2-yl)-propionylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 3-(1-methyl-1H-benzoimidazol-2-yl)-propionic acid.
LC-MS-conditions 05: $t_R$=0.78 min; [M+H]$^+$=533.12.

Example 186

(5R*)—N$^5$-(4-Bromo-phenyl)-(6R*)-6-[(3-1H-indol-3-yl-propionylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and 3-(1H-indol-3-yl)-propionic acid.
LC-MS-conditions 05: $t_R$=0.96 min; [M+H]$^+$=518.20.

Example 187

(5R*)—N$^5$-(4-Bromo-phenyl)-(6R*)-6-[(butanoylamino)-methyl]-(4S*,7R*)-[4,7-ethenylene-spiro[2.4]heptane]-5-carboxamide Following general procedure D, starting from (5R*)—N$^5$-(4-bromo-phenyl)-6-(6R*)-(amino-methyl)-(4S*,7R*)-[4,7-ethenylene-spiro[2.4]heptane]-5-carboxamide and butyric acid.
LC-MS-conditions 02: $t_R$=1.02 min; [M+H]$^+$=417.45.

Example 188

(5R*)—N^5-(4-Bromo-phenyl)-(6R*)-6-[(3-(4-fluoro-phenyl)-propionylamino)-methyl]-(4S*,7R*)-[4,7-ethenylene-spiro[2.4]heptane]-5-carboxamide Following general procedure D, starting from (5R*)—N^5-(4-bromo-phenyl)-6-(6R*)-(amino-methyl)-(4S*,7R*)-[4,7-ethenylene-spiro[2.4]heptane]-5-carboxamide and 3-(4-fluoro-phenyl)-propionic acid.
LC-MS-conditions 05: $t_R$=0.99 min; $[M+H]^+$=497.16.

Example 189

(5R*)—N^5-(4-Bromo-phenyl)-(6R*)-6-[(3-phenyl-acryloylamino)-methyl]-(4S*,7R*)-[4,7-ethenylene-spiro[2.4]heptane]-5-carboxamide Following general procedure D, starting from (5R*)—N^5-(4-bromo-phenyl)-6-(6R*)-(amino-methyl)-(4S*,7R*)-[4,7-ethenylene-spiro[2.4]heptane]-5-carboxamide and 3-phenyl-acrylic acid.
LC-MS-conditions 05: $t_R$=0.99 min; $[M+H]^+$=477.13.

Example 190

(5R*)—N^5-(4-Bromo-phenyl)-(6R*)-6-{[(5-chloro-1,3-dimethyl-1H-pyrazole-4-carbonyl)-amino]-methyl}-(4S*,7R*)-[4,7-ethenylene-spiro[2.4]heptane]-5-carboxamide Following general procedure D, starting from (5R*)—N^5-(4-bromo-phenyl)-6-(6R*)-(amino-methyl)-(4S*,7R*)-[4,7-ethenylene-spiro[2.4]heptane]-5-carboxamide and 5-chloro-1,3-dimethyl-1H-pyrazole-4-carboxylic acid.
LC-MS-conditions 05: $t_R$=0.95 min; $[M+H]^+$=502.99.

Example 191

(5R*)—N^5-(4-Acetyl-thiazol-2-yl-methyl)-(6R*)—N^6-(4-pyrrolidin-1-yl-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N^6-(4-pyrrolidin-1-yl-butyl)-(4S*,7R*)-[4,7-ethenylene-spiro[2.4]heptane]-6-carboxamide and [4-(2-methyl-[1,3]dioxolan-2-yl)-thiazol-2-yl]-methylamine.
LC-MS-conditions 01: $t_R$=0.66 min; $[M+H]^+$=471.17.

Example 192

(5R*)—N^5-(4-Acetyl-phenyl)-(6R*)—N^6-(4-pyrrolidin-1-yl-butyl)-(4S*,7R*)-[4,7-ethenylene-spiro[2.4]heptane]-5,6-dicarboxamide Following general procedure B, starting from (5R*)-5-hydroxycarbonyl-(6R*)—N^6-(4-pyrrolidin-1-yl-butyl)-(4S*,7R*)-[4,7-ethenylene-spiro[2.4]heptane]-6-carboxamide and 1-(4-amino-phenyl)-ethanone.
LC-MS-conditions 02: $t_R$=0.78 min; $[M+H]^+$=450.55.

Example 193

(5R*)—N^5-(5-Methyl-thiazol-2-yl)-(6R*)—N^6-(4-pyrrolidin-1-yl-butyl)-(4S*,7R*)-[4,7-ethenylene-spiro[2.4]heptane]-5,6-dicarboxamide Following general procedure F, starting from (5R*)—N^5-(5-methyl-thiazol-2-yl)-(6R*)-6-ethoxycarbonyl-(4S*,7R*)-[4,7-ethenylene-spiro[2.4]heptane]-5-carboxamide and 4-(1-pyrrolidino)-butylamine.
LC-MS-conditions 02: $t_R$=0.77 min; $[M+H]^+$=429.17.

Example 194

(5R*)—N^5-(5-Acetyl-thiophen-2-yl-methyl)-(6R*)—N^6-(4-pyrrolidin-1-yl-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N^6-(4-pyrrolidin-1-yl-butyl)-(4S*,7R*)-[4,7-ethenylene-spiro[2.4]heptane]-6-carboxamide and [5-(2-methyl-[1,3]dioxolan-2-yl)-thiophen-2-yl]-methylamine.
LC-MS-conditions 02: $t_R$=0.74 min; $[M+H]^+$=470.48.

Example 195

(5R)—N^5-(5-Acetyl-furan-2-yl-methyl)-(6R)—N^6-(4-pyrrolidin-1-yl-butyl)-(4S,7R)-[4,7-ethenylene-spiro[2.4]heptane]-5,6-dicarboxamide Following general procedure J, starting from (5R)—N^5-(5-acetyl-furan-2-yl-methyl)-(6R)-6-hydroxycarbonyl-(4S,7R)-[4,7-ethenylene-spiro[2.4]heptane]-5-carboxamide and 4-(1-pyrrolidino)-butylamine.
LC-MS-conditions 02: $t_R$=0.71 min; $[M+H]^+$=454.27.

Example 196

(5R)—N^5-(5-Acetyl-furan-2-yl-methyl)-(6R)—N^6-(4-pyrrolidin-1-yl-butyl)-(4S,7R)-[4,7-ethylene-spiro[2.4]heptane]-5,6-dicarboxamide Following general procedure J, starting from (5R)—N^5-(5-acetyl-furan-2-yl-methyl)-(6R)-6-hydroxycarbonyl-(4S,7R)-[4,7-ethylene-spiro[2.4]heptane]-5-carboxamide and 4-(1-pyrrolidino)-butylamine.
LC-MS-conditions 02: $t_R$=0.73 min; $[M+H]^+$=456.18.

Example 197

(5R*)—N^5-(4-Trifluoromethyl-phenyl)-(6R*)—N^6-(4-pyrrolidin-1-yl-butyl)-(4S*,7R*)-[4,7-ethenylene-spiro[2.4]heptane]-5,6-dicarboxamide Following general procedure I, starting from (5R*)-5-hydroxycarbonyl-(6R*)—N^6-(4-pyrrolidin-1-yl-butyl)-(4S*,7R*)-[4,7-ethenylene-spiro[2.4]heptane]-6-carboxamide and 4-aminobenzotrifluoride.
LC-MS-conditions 01: $t_R$=0.85 min; $[M+H]^+$=476.13.

Example 198

(5R*)—N^5-(2-Acetyl-oxazol-5-yl-methyl)-(6R*)—N^6-(4-pyrrolidin-1-yl-butyl)-(4S*,7R*)-[4,7-ethenylene-spiro[2.4]heptane]-5,6-dicarboxamide In a flame dried round-bottomed flask equipped with a magnetic stir bar and under inert atmosphere ($N_2$), to a solution of (5R*)—N^5-(2-[1-(tert-butyl-dimethyl-silanyloxy)-ethyl]-oxazol-5-yl-methyl)-(6R*)—N^6-(4-pyrrolidin-1-yl-butyl)-(4S*,7R*)-[4,7-ethenylene-spiro[2.4]heptane]-5,6-dicarboxamide (1.0 eq.) in THF (0.05 M) was added a 1 M solution of TBAF in THF (1.5 eq.) at 0° C. The reaction mixture was stirred at rt until completion of the reaction. The reaction mixture was diluted with EA, washed with brine (3×), dried over $MgSO_4$, filtered, and the solvents were removed under reduced pressure in order to give (5R*)—N⁵-(2-(1-hydroxy-ethyl)-oxazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide. The crude material was dissolved in AcCN (0.06 M) and treated with MnO₂ (5.5 eq.) at 50° C. Once the reaction was completed, the mixture was filtered and concentrated under reduced pressure. Purification by HPLC gave the title compound.

LC-MS-conditions 01: $t_R$=0.66 min; [M+H]⁺=455.23.

Example 199

(5R*)—N⁵-(2-(4,5-Dimethyl-1H-imidazol-2-yl)-ethyl)-(6R*)—N⁶-(4-bromophenyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-bromo-phenyl)-(4S*,7R*)-[4,7-ethenylene-spiro[2.4]heptane]-6-carboxamide and 2-(4,5-dimethyl-1H-imidazol-2-yl)-ethylamine.

LC-MS-conditions 05c: $t_R$=0.59 min; [M+H]⁺=483.20.

Example 200

(5R*)—N⁵-(4-Iodophenyl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-iodo-benzylamine hydrochloride.

LC-MS-conditions 06: $t_R$=0.68 min; [M+H]⁺=547.75.

Example 201

(5R*)—N⁵-(5-(iso-Butyl)-isoxazol-3-yl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 1-(5-isobutyl-isoxazol-3-yl)-methylamine.

LC-MS-conditions 06: $t_R$=0.64 min; [M+H]⁺=468.89.

Example 202

(5R*)—N⁵-(2-Bromo-thiophen-4-yl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-bromothiophen-4-yl)-methylamine.

LC-MS-conditions 06: $t_R$=0.67 min; [M+H]⁺=506.49.

Example 203

(5R*)—N⁵-(2-Fluoro-4-bromophenyl-methyl)-(6R*)—N⁶-(4-pyrrolidin-1-yl-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-bromo-2-fluorobenzylamine hydrochloride.

LC-MS-conditions 06: $t_R$=0.69 min; [M+H]⁺=517.75.

Example 204

(5R*)—N⁵-(4-Bromophenyl)-(6R*)—N⁶-(3-dimethylamino-3-oxopropyl)-(4S*,7R*)-[4,7-ethenylene-spiro[2.4]heptane]-5,6-dicarboxamide Following general procedure J, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-amino-N,N-dimethylpropanamide.

LC-MS-conditions FA: $t_R$=0.94 min; [M+H]⁺=460.11.

Example 205

(5R*)—N⁵-(4-Bromophenyl)-(6R*)—N⁶-(4-amino-4-oxobutyl)-(4S*,7R*)-[4,7-ethenylene-spiro[2.4]heptane]-5,6-dicarboxamide, formate salt Following general procedure J, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 4-aminobutanamide hydrochloride.

LC-MS-conditions FA: $t_R$=0.87 min; [M+H]⁺=446.08.

Example 206

(5R*)—N⁵-(4-Bromophenyl)-(6R*)—N⁶-(3-pyrrolidino-3-oxopropyl)-(4S*,7R*)-[4,7-ethenylene-spiro[2.4]heptane]-5,6-dicarboxamide Following general procedure J, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 3-amino-1-(pyrrolidin-1-yl)propan-1-one hydrochloride.

LC-MS-conditions FA: $t_R$=0.98 min; [M+H]⁺=486.11.

Example 207

(5R*)—N⁵-(4-Bromophenyl)-(6R*)—N⁶-(2-amino-2-oxoethyl)-(4S*,7R*)-[4,7-ethenylene-spiro[2.4]heptane]-5,6-dicarboxamide Following general procedure J, starting from (5R*)—N⁵-(4-bromo-phenyl)-(6R*)-6-hydroxycarbonyl-(4S*,7R*)-[4,7-ethenylene-spiro[2.4]heptane]-5-carboxamide and 2-aminoacetamide hydrochloride.

LC-MS-conditions FA: $t_R$=0.84 min; [M+H]⁺=418.04.

Example 208

(5R)—N⁵-(4-Bromophenyl)-(6R)—N⁶-(4-(4-ethyl-piperazin-1-yl)-butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 4-(4-ethylpiperazin-1-yl)butan-1-amine.

LC-MS-conditions TFA: $t_R$=0.57 min; [M+H]⁺=529.20.

Example 209

(5R)—N⁵-(4-Bromophenyl)-(6R)—N⁶-(4-piperidino-butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 4-(piperidin-1-yl)butan-1-amine.
LC-MS-conditions TFA: $t_R$=0.67 min; [M+H]⁺=500.14.

Example 210

(5R)—N⁵-(4-Bromophenyl)-(6R)—N⁶-(4-(azetidin-1-yl)butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 4-(azetidin-1-yl)butan-1-amine.
LC-MS-conditions TFA: $t_R$=0.64 min; [M+H]⁺=472.12.

Example 211

(5R)—N⁵-(4-Bromophenyl)-(6R)—N⁶-(4-morpholino-butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 4-morpholinobutan-1-amine.
LC-MS-conditions TFA: $t_R$=0.63 min; [M+H]⁺=502.19.

Example 212

(5R)—N⁵-(4-Bromophenyl)-(6R)—N⁶-(4-(4-methyl-1,4-diazepan-1-yl)butyl)-(4S,7R)-[4,7-ethenylene-spiro[2.4]heptane]-5,6-dicarboxamide Following general procedure K, starting from (5R)—N⁵-(4-bromo-phenyl)-(6R)-6-hydroxycarbonyl-(4S,7R)-[4,7-ethenylene-spiro[2.4]heptane]-5-carboxamide and 4-(4-methyl-1,4-diazepan-1-yl)butan-1-amine.
LC-MS-conditions TFA: $t_R$=0.56 min; [M+H]⁺=529.19.

Example 213

(5R)—N⁵-(4-Bromophenyl)-(6R)—N⁶-(4-(4-methylpiperazin-1-yl)butyl)-(4S,7R)-[4,7-ethenylene-spiro[2.4]heptane]-5,6-dicarboxamide Following general procedure K, starting from (5R)—N⁵-(4-bromo-phenyl)-(6R)-6-hydroxycarbonyl-(4S,7R)-[4,7-ethenylene-spiro[2.4]heptane]-5-carboxamide and 4-(4-methylpiperazin-1-yl)butan-1-amine.
LC-MS-conditions TFA: $t_R$=0.58 min; [M+H]⁺=515.17.

Example 214

(5R)—N⁵-(4-Bromophenyl)-(6R)—N⁶-(4-pyrrolidino-4-oxobutyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and 4-amino-1-(pyrrolidin-1-yl)butan-1-one hydrochloride.
LC-MS-conditions FA: $t_R$=1.00 min; [M+H]⁺=500.13.

Example 215

(5R)—N⁵-(4-Bromophenyl)-(6R)—N⁶-(2-(2-(pyrrolidin-1-yl)ethoxy)ethyl)-(4S,7R)-[4,7-ethenylene-spiro[2.4]heptane]-5,6-dicarboxamide Following general procedure K, starting from (5R)—N⁵-(4-bromo-phenyl)-(6R)-6-hydroxycarbonyl-(4S,7R)-[4,7-ethenylene-spiro[2.4]heptane]-5-carboxamide and 2-(2-(pyrrolidin-1-yl)ethoxy)ethanamine hydrochloride.
LC-MS-conditions TFA: $t_R$=0.66 min; [M+H]⁺=502.15.

Example 216

(5R)—N⁵-(4-Bromophenyl)-(6R)—N⁶-((3R,6S)-6-(pyrrolidin-1-ylmethyl)tetrahydro-2H-pyran-3-yl)-(4S,7R)-[4,7-ethenylene-spiro[2.4]heptane]-5,6-dicarboxamide Following general procedure K, starting from (5R)—N⁵-(4-bromo-phenyl)-(6R)-6-hydroxycarbonyl-(4S,7R)-[4,7-ethenylene-spiro[2.4]heptane]-5-carboxamide and (3R,6S)-6-(pyrrolidin-1-ylmethyl)tetrahydro-2H-pyran-3-amine hydrochloride.
LC-MS-conditions TFA: $t_R$=0.68 min; [M+H]⁺=528.20.

Example 217

(5R)—N⁵-(4-Bromophenyl)-(6R)—N⁶-(4-(4-acetylpiperazin-1-yl)butyl)-(4S,7R)-[4,7-ethenylene-spiro[2.4]heptane]-5,6-dicarboxamide Following general procedure I, starting from (5R)—N⁵-(4-bromo-phenyl)-(6R)-6-hydroxycarbonyl-(4S,7R)-[4,7-ethenylene-spiro[2.4]heptane]-5-carboxamide and 1-(4-(4-aminobutyl)piperazin-1-yl)ethanone.
LC-MS-conditions TFA: $t_R$=0.62 min; [M+H]⁺=543.15.

Example 218

(5R)—N⁵-(4-Bromophenyl)-(6R)—N⁶-(cis-4-(pyrrolidin-1-yl-methyl)-cyclohexyl)-(4S,7R)-[4,7-ethenylene-spiro[2.4]heptane]-5,6-dicarboxamide Following general procedure L, starting from (5R)—N⁵-(4-bromo-phenyl)-(6R)-6-hydroxycarbonyl-(4S,7R)-[4,7-ethenylene-spiro[2.4]heptane]-5-carboxamide and cis-4-(pyrrolidin-1-ylmethyl)cyclohexanamine.
LC-MS-conditions TFA: $t_R$=0.68 min; [M+H]⁺=526.25.

Example 219

(5R)—N⁵-(4-Bromophenyl)-(6R)—N⁶-(4((3R)-fluoropyrrolidino)butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and (R)-4-(3-fluoropyrrolidin-1-yl)butan-1-amine.
LC-MS-conditions TFA: $t_R$=0.66 min; [M+H]⁺=504.18.

Example 220

(5R)—N⁵-(4-Bromophenyl)-(6R)—N⁶-(4-((3S)-fluoropyrrolidino)butyl)-(4S,7R)-[4,7-ethenylene-spiro[2.4]heptane]-5,6-dicarboxamide Following general procedure E, starting from (5R)—N⁵-(4-bromo-phenyl)-(6R)-6-hydroxycarbonyl-(4S,7R)-[4,7-ethenylene-spiro[2.4]heptane]-5-carboxamide and (S)-4-(3-fluoropyrrolidin-1-yl)butan-1-amine.

LC-MS-conditions TFA: $t_R$=0.65 min; [M+H]⁺=504.16.

Example 221

(5R)—N⁵-(4-Bromophenyl)-(6R)—N⁶-(5-pyrrolidino-pentyl)-(4S,7R)-[4,7-ethenylene-spiro[2.4]heptane]-5,6-dicarboxamide Following general procedure K, starting from (5R)—N⁵-(4-bromo-phenyl)-(6R)-6-hydroxycarbonyl-(4S,7R)-[4,7-ethenylene-spiro[2.4]heptane]-5-carboxamide and 5-(pyrrolidin-1-yl)pentan-1-amine.

LC-MS-conditions TFA: $t_R$=0.67 min; [M+H]⁺=500.14.

Example 222

(5R)—N⁵-(4-Bromophenyl)-(6R)—N⁶-(trans-4-(pyrrolidin-1-yl-methyl)-cyclohexyl)-(4S,7R)-[4,7-ethenylene-spiro[2.4]heptane]-5,6-dicarboxamide Following general procedure L, starting from (5R)—N⁵-(4-bromo-phenyl)-(6R)-6-hydroxycarbonyl-(4S,7R)-[4,7-ethenylene-spiro[2.4]heptane]-5-carboxamide and trans-4-(pyrrolidin-1-ylmethyl)cyclohexanamine.

LC-MS-conditions TFA: $t_R$=0.69 min; [M+H]⁺=526.19.

Example 223

(5R*)—N⁵-(4-Bromophenyl)-(6R*)—N⁶-(3-methylamino-3-oxopropyl)-(4S*,7R*)-[4,7-ethenylene-spiro[2.4]heptane]-5,6-dicarboxamide Following general procedure N, starting from (5R*)—N⁵-(4-bromo-phenyl)-(6R*)—N⁶-(2-methoxycarbonyl-ethyl)-(4S*,7R*)-[4,7-ethenylene-spiro[2.4]heptane]-5,6-dicarboxamide and methylamine.

LC-MS-conditions FA: $t_R$=0.88 min; [M+H]⁺=446.10.

Example 224

(5R*)—N⁵-(2-Acetyl-thiazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-(2-methyl-[1,3]dioxolan-2-yl)thiazol-5-yl)methanamine.

LC-MS-conditions TFA: $t_R$=0.48 min; [M+H]⁺=471.25.

Example 225

(5R)—N⁵-(5-Bromo-thiazol-2-yl)-(6R)—N⁶-(4-pyrrolidin-1-yl-butyl)-(4S,7R)-[4,7-ethenylene-spiro[2.4]heptane]-5,6-dicarboxamide Following general procedure K, starting from (5R)—N⁵-(5-bromo-thiazol-2-yl)-(6R)-6-hydroxycarbonyl-(4S,7R)-[4,7-ethenylene-spiro[2.4]heptane]-5-carboxamide and 4-pyrrolidin-1-yl-butylamine.

LC-MS-conditions TFA: $t_R$=0.61 min; [M+H]⁺=493.09.

Example 226

(5R*)—N⁵-(2,6-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,6-difluoro-4-methoxybenzylamine.

LC-MS-conditions TFA: $t_R$=0.59 min; [M+H]⁺=488.26.

Example 227

(5R*)—N⁵-(2,3-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,3-difluoro-4-methoxybenzylamine.

LC-MS-conditions FA: $t_R$=0.73 min; [M+H]⁺=488.28.

Example 228

(5R*)—N⁵-(3-Fluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-fluoro-4-methoxybenzylamine.

LC-MS-conditions TFA: $t_R$=0.56 min; [M+H]⁺=470.28.

Example 229

(5R*)—N⁵-(3,5-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3,5-difluoro-4-methoxybenzylamine.

LC-MS-conditions FA: $t_R$=0.74 min; [M+H]⁺=488.29.

Example 230

(5R*)—N$^5$-(4-Chloro-phenyl-methyl)-(6R*)—N$^6$-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-chlorobenzylamine.
LC-MS-conditions FA: $t_R$=0.77 min; [M+H]$^+$=456.24.

Example 231

(5R*)—N$^5$-(4-Fluoro-phenyl-methyl)-(6R*)—N$^6$-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-fluorobenzylamine.
LC-MS-conditions FA: $t_R$=0.70 min; [M+H]$^+$=440.27.

Example 232

(5R*)—N$^5$-(4-Trifluoromethoxy-phenyl-methyl)-(6R*)—N$^6$-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-trifluoromethoxybenzylamine.
LC-MS-conditions FA: $t_R$=0.86 min; [M+H]$^+$=506.26.

Example 233

(5R*)—N$^5$-(4-Isopropoxy-phenyl-methyl)-(6R*)—N$^6$-(4-pyrrolidin-1-yl-butyl)-(4S*,7R*)-[4,7-ethenylene-spiro[2.4]heptane]-5,6-dicarboxamide, formate salt Following general procedure I, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-isopropoxybenzylamine.
LC-MS-conditions FA: $t_R$=0.81 min; [M+H]$^+$=480.33.

Example 234

(5R*)—N$^5$-(4-Bromo-thiazol-2-yl-methyl)-(6R*)—N$^6$-(4-pyrrolidin-1-yl-butyl)-(4S*,7R*)-[4,7-ethenylene-spiro[2.4]heptane]-5,6-dicarboxamide Following general procedure I, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and (4-bromothiazol-2-yl)methanamine.
LC-MS-conditions TFA: $t_R$=0.52 min; [M+H]$^+$=507.12.

Example 235

(5R*)—N$^5$-(2-Acetyl-oxazol-4-yl-methyl)-(6R*)—N$^6$-(4-pyrrolidin-1-yl-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and (2-(2-methyl-[1,3]dioxolan-2-yl)oxazol-4-yl)methanamine.
LC-MS-conditions TFA: $t_R$=0.47 min; [M+H]$^+$=455.33.

Example 236

(5R*)—N$^5$-(4-Bromo-phenyl-methyl)-(6R*)—N$^6$-(3-pyrrolidin-1-yl-propyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and 3-(pyrrolidin-1-yl)propan-1-amine.
LC-MS-conditions TFA: $t_R$=0.62 min; [M+H]$^+$=486.17.

Example 237

(5R*)—N$^5$-(5-Bromo-thiazol-2-yl)-(6R*)—N$^6$-(3-pyrrolidin-1-yl-propyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 3-(pyrrolidin-1-yl)propan-1-amine.
LC-MS-conditions TFA: $t_R$=0.60 min; [M+H]$^+$=479.09.

Example 238

(5R)—N$^5$-(5-Bromo-thiazol-2-yl)-(6R)—N$^6$-(4-pyrrolidin-1-yl-butyl)-(4S,7R)-[4,7-ethylene-spiro[2.4]heptane]-5,6-dicarboxamide Following general procedure F, starting from (5R)—N$^5$-(5-bromo-thiazol-2-yl)-(6R)-6-methoxycarbonyl-(4S,7R)-[4,7-ethylene-spiro[2.4]heptane]-5-carboxamide and 4-(pyrrolidin-1-yl)butan-1-amine.
LC-MS-conditions TFA: $t_R$=0.65 min; [M+H]$^+$=495.19.

Example 239

(5R)—N$^5$-(5-Bromo-thiazol-2-yl)-(6R)—N$^6$-(3-amino-3-oxopropyl)-(4S,7R)-[4,7-ethylene-spiro[2.4]heptane]-5,6-dicarboxamide Following general procedure E, starting from (5R)—N$^5$-(5-bromo-thiazol-2-yl)-(6R)-6-hydroxycarbonyl-(4S,7R)-[4,7-ethylene-spiro[2.4]heptane]-5-carboxamide and 3-aminopropanamide hydrochloride.
LC-MS-conditions FA: $t_R$=0.84 min; [M+H]$^+$=441.06.

Example 240

(5R)—N$^5$-(5-Bromo-thiazol-2-yl)-(6R)—N$^6$-(3-amino-3-oxopropyl)-(4S,7R)-[4,7-ethylene-spiro[2.4]heptane]-5,6-dicarboxamide Following general procedure E, starting from (5R)—N$^5$-(5-bromo-thiazol-2-yl)-(6R)-6-hydroxycarbonyl-(4S,7R)-[4,7-ethylene-spiro[2.4]heptane]-5-carboxamide and 3-aminopropanamide hydrochloride.
LC-MS-conditions FA: $t_R$=0.79 min; [M+H]$^+$=439.04.

Example 241

(5R)—N$^5$-(4-Bromo-phenyl-methyl)-(6R)—N$^6$-(3-amino-3-oxopropyl)-(4S,7R)-[4,7-ethenylene-spiro[2.4]heptane]-5,6-dicarboxamide Following general procedure M, starting from (5R)—N$^5$-(4-bromophenyl-methyl)-(6R)—N$^6$-(2-methoxycarbonyl-ethyl)-(4S,7R)-[4,7-ethenylene-spiro[2.4]heptane]-5,6-dicarboxamide and NH$_4$OH.

LC-MS-conditions FA: t$_R$=0.81 min; [M+H]$^+$=446.11.

Example 242

(5R)—N$^5$-(2-Bromo-pyrid-5-yl)-(6R)—N$^6$-(3-amino-3-oxopropyl)-(4S,7R)-[4,7-ethenylene-spiro[2.4]heptane]-5,6-dicarboxamide Following general procedure E, starting from (5R)—N$^5$-(2-bromo-pyrid-5-yl)-(6R)-6-hydroxycarbonyl-(4S,7R)-[4,7-ethenylene-spiro[2.4]heptane]-5-carboxamide and 3-aminopropanamide hydrochloride.

LC-MS-conditions FA: t$_R$=0.70 min; [M+H]$^+$=433.07.

Example 243

(5R*)—N$^5$-(4-Acetyl-oxazol-2-yl-methyl)-(6R*)—N$^6$-(4-pyrrolidin-1-yl-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and (4-(2-methyl-[1,3]dioxolan-2-yl)-oxazol-2-yl)methanamine.

LC-MS-conditions TFA: t$_R$=0.43 min; [M+H]$^+$=455.23.

Example 244

(5R*)—N$^5$-(4-Acetyl-thiazol-2-yl-methyl)-(6R*)—N$^6$-(isobutyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and isobutylamine.

LC-MS-conditions FA: t$_R$=0.83 min; [M+H]$^+$=402.18.

Example 245

(5R*)—N$^5$-(5-Bromo-thiazol-2-yl)-(6R*)—N$^6$-(isobutyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and isobutylamine.

LC-MS-conditions FA: t$_R$=1.10 min; [M+H]$^+$=424.06.

Example 246

(5R*)—N$^5$-(4-Bromo-phenyl-methyl)-(6R*)—N$^6$-(isobutyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and isobutylamine.

LC-MS-conditions FA: t$_R$=1.10 min; [M+H]$^+$=431.12.

Example 247

(5R*)—N$^5$-(4-Acetyl-thiazol-2-yl-methyl)-(6R*)—N$^6$-(3-(1H-benzoimidazol-2-yl)-propyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 3-(1H-benzo[d]imidazol-2-yl)propan-1-amine.

LC-MS-conditions FA: t$_R$=0.63 min; [M+H]$^+$=504.18.

Example 248

(5R*)—N$^5$-(5-Bromo-thiazol-2-yl)-(6R*)—N$^6$-(3-(1H-benzoimidazol-2-yl)-propyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 3-(1H-benzo[d]imidazol-2-yl)propan-1-amine.

LC-MS-conditions FA: t$_R$=0.83 min; [M+H]$^+$=526.05.

Example 249

(5R*)—N$^5$-(4-Bromo-phenyl-methyl)-(6R*)—N$^6$-(3-(1H-benzoimidazol-2-yl)-propyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and 3-(1H-benzo[d]imidazol-2-yl)propan-1-amine.

LC-MS-conditions FA: t$_R$=0.86 min; [M+H]$^+$=533.15.

Example 250

(5R*)—N$^5$-(2-Methoxy-pyrid-5-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride:

Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 6-methoxypyridin-3-amine.

LC-MS-conditions TFA: t$_R$=0.48 min; [M+H]$^+$=439.27.

Example 251

(5R*)—N$^5$-(2-Bromo-pyrazin-5-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-

(4S*,7R*)-[4,7-ethenylene-spiro[2.4]heptane]-6-carboxamide and 5-bromopyrazin-2-amine.
LC-MS-conditions TFA: $t_R$=0.58 min; [M+H]$^+$=488.15.

Example 252

(5R*)—N$^5$-(5-Trifluoromethyl-pyridin-2-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 5-(trifluoromethyl)pyridin-2-amine.
LC-MS-conditions TFA: $t_R$=0.66 min; [M+H]$^+$=477.26.

Example 253

(5R*)—N$^5$-(2-Methyl-pyridin-5-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 6-methylpyridin-3-amine.
LC-MS-conditions TFA: $t_R$=0.40 min; [M+H]$^+$=423.28.

Example 254

(5R*)—N$^5$-(Benzo[d]oxazol-6-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and benzo[d]oxazol-6-amine.
LC-MS-conditions TFA: $t_R$=0.51 min; [M+H]$^+$=449.26.

Example 255

(5R*)—N$^5$-(5-Methyl-isoxazol-3-yl-methyl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and (5-methylisoxazol-3-yl)methanamine.
LC-MS-conditions TFA: $t_R$=0.47 min; [M+H]$^+$=427.25.

Example 256

(5R*)—N$^5$-(4-Methyl-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-methylthiazol-2-amine.
LC-MS-conditions TFA: $t_R$=0.52 min; [M+H]$^+$=429.24.

Example 257

(5R*)—N$^5$-(5-Trifluoromethyl-1,3,4-thiadiazol-2-yl)-(6R*)—N$^6$-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 5-(trifluoromethyl)-1,3,4-thiadiazol-2-amine.
LC-MS-conditions TFA: $t_R$=0.62 min; [M+H]$^+$=484.21.

Example 258

(5R)—N$^5$-(2-Bromo-pyridin-5-yl)-(6R)—N$^6$-(4-pyrrolidin-1-yl-butyl)-(4S,7R)-[4,7-ethenylene-spiro[2.4]heptane]-5,6-dicarboxamide Following general procedure E, starting from (5R)—N$^5$-(2-bromo-pyrid-5-yl)-(6R)-6-hydroxycarbonyl-(4S,7R)-[4,7-ethenylene-spiro[2.4]heptane]-5-carboxamide and 4-pyrrolidino-butylamine.
LC-MS-conditions TFA: $t_R$=0.56 min; [M+H]$^+$=487.20.

Example 259

(5R*)—N$^5$-(5-Bromo-thiazol-2-yl)-(6R*)—N$^6$-(2-fluoro-ethyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 2-fluoroethanamine.
LC-MS-conditions FA: $t_R$=0.94 min; [M+H]$^+$=414.02.

Example 260

(5R*)—N$^5$-(5-Bromo-thiazol-2-yl)-(6R*)—N$^6$-((2-imidazolidin-2-on)-1-yl-ethyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 1-(2-aminoethyl)imidazolidin-2-one.
LC-MS-conditions FA: $t_R$=0.82 min; [M+H]$^+$=480.05.

Example 261

(5R*)—N$^5$-(4-Acetyl-thiazol-2-yl-methyl)-(6R*)—N$^6$-(3-amino-3-oxopropyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 3-aminopropanamide hydrochloride.
LC-MS-conditions FA: $t_R$=0.54 min; [M+H]$^+$=417.14.

Example 262

(5R*)—N$^5$-(4-Acetyl-thiazol-2-yl-methyl)-(6R*)—N$^6$-(4-diethylamino-butyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl- (4S*,7R*)-[4,7-ethenylene-spiro[2.4]heptane]-5-carboxamide and 4-(diethylamino)butylamine.

LC-MS-conditions TFA: $t_R$=0.46 min; [M+H]$^+$=473.30.

Example 263

(5R*)—N$^5$-(4-Bromophenyl-methyl)-(6R*)—N$^6$-(3-ethoxy-propyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and 3-ethoxy-propylamine.

LC-MS-conditions FA: $t_R$=1.03 min; [M+H]$^+$=461.12.

Example 264

(5R*)—N$^5$-(4-Acetyl-thiazol-2-yl-methyl)-(6R*)—N$^6$-(3-pyrrolidino-propyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 1-(3-aminopropyl)pyrrolidine.

LC-MS-conditions TFA: $t_R$=0.44 min; [M+H]$^+$=457.22.

Example 265

(5R*)—N$^5$-(5-Bromothiazol-2-yl)-(6R*)—N$^6$-(3-(4-methyl piperazin-1-yl)-propyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 1-(3-aminopropyl)-4-methylpiperazine.

LC-MS-conditions TFA: $t_R$=0.53 min; [M+H]$^+$=508.14.

Example 266

(5R*)—N$^5$-(4-Acetyl-thiazol-2-yl-methyl)-(6R*)—N$^6$-(2-dimethylamino-ethyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 2-dimethylamino-ethylamine.

LC-MS-conditions TFA: $t_R$=0.43 min; [M+H]$^+$=417.18.

Example 267

(5R*)—N$^5$-(4-Acetyl-thiazol-2-yl-methyl)-(6R*)—N$^6$-(3-dimethylamino-propyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 3-dimethylamino-1-propylamine.

LC-MS-conditions TFA: $t_R$=0.43 min; [M+H]$^+$=431.24.

Example 268

(5R*)—N$^5$-(4-Acetyl-thiazol-2-yl-methyl)-(6R*)—N$^6$-(3-(4-methylpiperazin-1-yl)-propyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 1-(3-aminopropyl)-4-methyl-piperazine.

LC-MS-conditions TFA: $t_R$=0.40 min; [M+H]$^+$=486.22.

Example 269

(5R*)—N$^5$-(4-Acetyl-thiazol-2-yl-methyl)-(6R*)—N$^6$-((2-imidazolidin-2-on)-1-yl-ethyl)-(4S*,7R*)-[4,7-ethenylene-spiro[2.4]heptane]-5,6-dicarboxamide Following general procedure B, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 1-(2-aminoethyl)imidazolidin-2-one.

LC-MS-conditions FA: $t_R$=0.58 min; [M+H]$^+$=458.19.

Example 270

(5R*)—N$^5$-(5-Bromothiazol-2-yl)-(6R*)—N$^6$-(4-diethylamino-butyl)-(4S*,7R*)-[4,7-ethenylene-spiro[2.4]heptane]-5,6-dicarboxamide Following general procedure B, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 4-(diethylamino)butylamine.

LC-MS-conditions TFA: $t_R$=0.62 min; [M+H]$^+$=495.13.

Example 271

(5R*)—N$^5$-(4-Bromophenyl-methyl)-(6R*)—N$^6$-(2-fluoroethyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and 2-fluoroethylamine hydrochloride.

LC-MS-conditions FA: $t_R$=0.95 min; [M+H]$^+$=421.08.

Example 272

(5R*)—N$^5$-(4-Bromophenyl-methyl)-(6R*)—N$^6$-(4-diethylamino-butyl)-(4S*,7R*)-[4,7-ethenylene-spiro[2.4]heptane]-5,6-dicarboxamide Following general procedure B, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and 4-(diethylamino)butylamine.

LC-MS-conditions TFA: $t_R$=0.64 min; [M+H]$^+$=502.16.

Example 273

(5R*)—$N^5$-(4-Bromophenyl-methyl)-(6R*)—$N^6$-(3-(4-methylpiperazin-1-yl)-propyl)-(4S*,7R*)-[4,7-ethenylene-spiro[2.4]heptane]-5,6-dicarboxamide Following general procedure B, starting from (5R*)—$N^5$-(4-bromophenyl-methyl)-(6R*)-6-hydroxycarbonyl-(4S*,7R*)-[4,7-ethenylene-spiro[2.4]heptane]-5-carboxamide and 1-(3-aminopropyl)-4-methyl-piperazine.
LC-MS-conditions TFA: $t_R$=0.55 min; [M+H]$^+$=515.21.

Example 274

(5R*)—$N^5$-(4-Bromophenyl-methyl)-(6R*)—$N^6$-(2-dimethylamino-ethyl)-(4S*,7R*)-[4,7-ethenylene-spiro[2.4]heptane]-5,6-dicarboxamide Following general procedure B, starting from (5R*)—$N^5$-(4-bromophenyl-methyl)-(6R*)-6-hydroxycarbonyl-(4S*,7R*)-[4,7-ethenylene-spiro[2.4]heptane]-5-carboxamide and 2-dimethylamino-ethylamine.
LC-MS-conditions TFA: $t_R$=0.60 min; [M+H]$^+$=446.16.

Example 275

(5R*)—$N^5$-(4-Bromophenyl-methyl)-(6R*)—$N^6$-((2-imidazolidin-2-on)-1-yl-ethyl)-(4S*,7R*)-[4,7-ethenylene-spiro[2.4]heptane]-5,6-dicarboxamide Following general procedure B, starting from (5R*)—$N^5$-(4-bromophenyl-methyl)-(6R*)-6-hydroxycarbonyl-(4S*,7R*)-[4,7-ethenylene-spiro[2.4]heptane]-5-carboxamide and 1-(2-aminoethyl)imidazolidin-2-one.
LC-MS-conditions FA: $t_R$=0.84 min; [M+H]$^+$=487.12.

Example 276

(5R*)—$N^5$-(5-Bromothiazol-2-yl)-(6R*)—$N^6$-(2-methoxy-ethyl)-(4S*,7R*)-[4,7-ethenylene-spiro[2.4]heptane]-5,6-dicarboxamide Following general procedure B, starting from (5R*)—$N^5$-(5-bromo-thiazol-2-yl)-(6R*)-6-hydroxycarbonyl-(4S*,7R*)-[4,7-ethenylene-spiro[2.4]heptane]-5-carboxamide and 2-methoxy-ethylamine.
LC-MS-conditions FA: $t_R$=0.93 min; [M+H]$^+$=426.04.

Example 277

(5R*)—$N^5$-(5-Bromothiazol-2-yl)-(6R*)—$N^6$-(3-dimethylamino-propyl)-(4S*,7R*)-[4,7-ethenylene-spiro[2.4]heptane]-5,6-dicarboxamide Following general procedure B, starting from (5R*)—$N^5$-(5-bromo-thiazol-2-yl)-(6R*)-6-hydroxycarbonyl-(4S*,7R*)-[4,7-ethenylene-spiro[2.4]heptane]-5-carboxamide and 3-dimethylamino-1-propylamine.
LC-MS-conditions TFA: $t_R$=0.58 min; [M+H]$^+$=453.10.

Example 278

(5R)—$N^5$-(2-Bromopyrid-5-yl)-(6R)—$N^6$-(3-amino-3-oxopropyl)-(4S,7R)-[4,7-ethylene-spiro[2.4]heptane]-5,6-dicarboxamide Following general procedure E, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 3-aminopropanamide hydrochloride.
LC-MS-conditions FA: $t_R$=0.76 min; [M+H]$^+$=435.10.

Example 279

(5R)—$N^5$-(2-Bromopyrid-5-yl)-(6R)—$N^6$-(4-pyrrolidino-butyl)-(4S,7R)-[4,7-ethylene-spiro[2.4]heptane]-5,6-dicarboxamide Following general procedure E, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 4-(1-pyrrolidino)butylamine.
LC-MS-conditions TFA: $t_R$=0.60 min; [M+H]$^+$=489.17.

Example 280

(5R)—$N^5$-(5-Bromopyrid-2-yl)-(6R)—$N^6$-(3-amino-3-oxopropyl)-(4S,7R)-[4,7-ethenylene-spiro[2.4]heptane]-5,6-dicarboxamide Following general procedure M, starting from (5R)—$N^5$-(5-bromopyrid-2-yl)-(6R)—$N^6$-(2-methoxycarbonyl-ethyl)-(4S,7R)-[4,7-ethenylene-spiro[2.4]heptane]-5,6-dicarboxamide and NH$_4$OH.
LC-MS-conditions FA: $t_R$=0.79 min; [M+H]$^+$=433.08.

Example 281

(5R)—$N^5$-(2-Chloropyrid-5-yl)-(6R)—$N^6$-(3-amino-3-oxopropyl)-(4S,7R)-[4,7-ethenylene-spiro[2.4]heptane]-5,6-dicarboxamide Following general procedure M, starting from (5R)—$N^5$-(2-chloropyrid-5-yl)-(6R)—$N^6$-(2-methoxycarbonyl-ethyl)-(4S,7R)-[4,7-ethenylene-spiro[2.4]heptane]-5,6-dicarboxamide and NH$_4$OH.
LC-MS-conditions FA: $t_R$=0.68 min; [M+H]$^+$=389.14.

Example 282

(5R)—$N^5$-(4-Bromo-2-fluorophenyl-methyl)-(6R)—$N^6$-(3-amino-3-oxopropyl)-(4S,7R)-[4,7-ethenylene-spiro[2.4]heptane]-5,6-dicarboxamide Following general procedure M, starting from (5R)—$N^5$-(4-bromo-2-fluorophenyl-methyl)-(6R)—$N^6$-(2-methoxycarbonyl-ethyl)-(4S,7R)-[4,7-ethenylene-spiro[2.4]heptane]-5,6-dicarboxamide and NH$_4$OH.
LC-MS-conditions FA: $t_R$=0.83 min; [M+H]$^+$=464.06.

Example 283

(5R)—$N^5$-(2-Bromothiazol-5-yl-methyl)-(6R)—$N^6$-(3-amino-3-oxopropyl)-(4S,7R)-[4,7-ethenylene-spiro[2.4]heptane]-5,6-dicarboxamide Following general procedure M, starting from (5R)—$N^5$-[(2-bromothiazol-5-yl)methyl]-(6R)—$N^6$-(2-methoxycarbonyl-ethyl)-(4S,7R)-[4,7-ethenylene-spiro[2.4]heptane]-5,6-dicarboxamide and NH$_4$OH.
LC-MS-conditions FA: $t_R$=0.64 min; [M+H]$^+$=453.01.

Example 284

(5R)—$N^5$-(4-Bromo-2-fluorophenyl-methyl)-(6R)—$N^6$-(4-pyrrolidino-butyl)-(4S,7R)-[4,7-ethenylene-spiro[2.4]heptane]-5,6-dicarboxamide Following general procedure I, starting from (5R)-5-hydroxycarbonyl-(6R)—$N^6$-(4-pyrrolidin-1-yl-butyl)-(4S,7R)-[4,7-ethenylene-spiro[2.4]heptane]-6-carboxamide and 4-bromo-2-fluorobenzylamine hydrochloride.
LC-MS-conditions TFA: $t_R$=0.64 min; [M+H]$^+$=518.13.

Example 285

(5R)—N⁵-(4-Methoxyphenyl)-(6R)—N⁶-(4-pyrrolidino-butyl)-(4S,7R)-[4,7-ethenylene-spiro[2.4]heptane]-5,6-dicarboxamide Following general procedure I, starting from (5R)-5-hydroxycarbonyl-(6R)—N⁶-(4-pyrrolidin-1-yl-butyl)-(4S,7R)-[4,7-ethenylene-spiro[2.4]heptane]-6-carboxamide and 4-amino-anisole.

LC-MS-conditions TFA: $t_R$=0.56 min; [M+H]⁺=438.25.

Example 286

(5R)—N⁵-(4-Bromophenyl-methyl)-(6R)—N⁶-(4-pyrrolidino-butyl)-(4S,7R)-[4,7-ethenylene-spiro[2.4]heptane]-5,6-dicarboxamide Following general procedure I, starting from (5R)-5-hydroxycarbonyl-(6R)—N⁶-(4-pyrrolidin-1-yl-butyl)-(4S,7R)-[4,7-ethenylene-spiro[2.4]heptane]-6-carboxamide and 4-bromo-benzylamine.

LC-MS-conditions TFA: $t_R$=0.63 min; [M+H]⁺=500.10.

Example 287

(5R)—N⁵-(4-Methoxyphenyl)-(6R)—N⁶-(3-hydroxyl-3-oxopropyl)-(4S,7R)-[4,7-ethenylene-spiro[2.4]heptane]-5,6-dicarboxamide A solution of (5R)—N⁵-(4-methoxy-phenyl)-(6R)—N⁶-(2-methoxycarbonyl-ethyl)-(4S,7R)-[4,7-ethenylene-spiro[2.4]heptane]-5,6-dicarboxamide in THF (0.09 M) was treated with aq. 1N NaOH (4.0 eq.) at rt until completion of the reaction. The reaction mixture was poured into aq. 2N HCl and extracted with EA (3×). The combined organic extracts were dried over MgSO₄, filtered, and the solvents were removed under reduced pressure to give the title compound as a brown oil.

LC-MS-conditions FA: $t_R$=0.75 min; [M+H]⁺=385.15.

Example 288

(5R)—N⁵-(4-Bromo-3-fluorophenyl)-(6R)—N⁶-(4-pyrrolidino-butyl)-(4S,7R)-[4,7-ethenylene-spiro[2.4]heptane]-5,6-dicarboxamide Following general procedure F, starting from (5R)—N⁵-(4-bromo-3-fluorophenyl)-(6R)-6-methoxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.68 min; [M+H]⁺=504.13.

Example 289

(5R)—N⁵-(2-Chloro-pyridin-5-yl)-(6R)—N⁶-(4-pyrrolidino-butyl)-(4S,7R)-[4,7-ethenylene-spiro[2.4]heptane]-5,6-dicarboxamide Following general procedure F, starting from (5R)—N⁵-(2-chloro-pyridin-5-yl)-(6R)-6-methoxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.54 min; [M+H]⁺=443.21.

Example 290

(5R)—N⁵-(4-Methoxyphenyl)-(6R)—N⁶-(3-amino-3-oxopropyl)-(4S,7R)-[4,7-ethenylene-spiro[2.4]heptane]-5,6-dicarboxamide Following general procedure M, starting from (5R)—N⁵-(4-methoxy-phenyl)-(6R)—N⁶-(2-methoxycarbonyl-ethyl)-(4S,7R)-[4,7-ethenylene-spiro[2.4]heptane]-5,6-dicarboxamide and NH₄OH.

LC-MS-conditions FA: $t_R$=0.69 min; [M+H]⁺=384.19.

Example 291

(5R)—N⁵-(4-Bromophenyl-methyl)-(6R)—N⁶-(3-amino-3-oxopropyl)-(4S,7R)-[4,7-ethylene-spiro[2.4]heptane]-5,6-dicarboxamide Following general procedure M, starting from (5R)—N⁵-(4-bromophenyl-methyl)-(6R)—N⁶-(2-methoxycarbonyl-ethyl)-(4S,7R)-[4,7-ethenylene-spiro[2.4]heptane]-5,6-dicarboxamide and NH₄OH.

LC-MS-conditions FA: $t_R$=0.86 min; [M+H]⁺=448.11.

Example 292

(5R)—N⁵-(4-Bromo-2-fluorophenyl-methyl)-(6R)—N⁶-(3-amino-3-oxopropyl)-(4S,7R)-[4,7-ethylene-spiro[2.4]heptane]-5,6-dicarboxamide Following general procedure M, starting from (5R)—N⁵-(4-bromo-2-fluorophenyl-methyl)-(6R)—N⁶-(2-methoxycarbonyl-ethyl)-(4S,7R)-[4,7-ethenylene-spiro[2.4]heptane]-5,6-dicarboxamide and NH₄OH.

LC-MS-conditions FA: $t_R$=0.88 min; [M+H]⁺=466.10.

Example 293

(5R)—N⁵-(4-Methoxyphenyl)-(6R)—N⁶-(3-amino-3-oxopropyl)-(4S,7R)-[4,7-ethenylene-spiro[2.4]heptane]-5,6-dicarboxamide Following general procedure M, starting from (5R)—N⁵-(4-methoxy-phenyl)-(6R)—N⁶-(2-methoxycarbonyl-ethyl)-(4S,7R)-[4,7-ethenylene-spiro[2.4]heptane]-5,6-dicarboxamide and NH₄OH.

LC-MS-conditions FA: $t_R$=0.76 min; [M+H]⁺=386.20.

Example 294

(5R)—N⁵-(5-Bromo-pyridin-2-yl)-(6R)—N⁶-(4-pyrrolidino-butyl)-(4S,7R)-[4,7-ethenylene-spiro[2.4]heptane]-5,6-dicarboxamide Following general procedure I, starting from (5R)—N⁵-(5-bromo-pyridin-2-yl)-(6R)-6-hydroxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.63 min; [M+H]⁺=487.16.

Example 295

(5R)—N⁵-(4-Bromo-2-fluorophenyl)-(6R)—N⁶-(4-pyrrolidino-butyl)-(4S,7R)-[4,7-ethenylene-spiro[2.4]heptane]-5,6-dicarboxamide Following general procedure I, starting from (5R)—N⁵-(4-bromo-2-fluorophenyl)-(6R)-6-hydroxycarbonyl-(4S,7R)-

[4,7-ethenylene-spiro[2.4]heptane]-5-carboxamide and 4-(pyrrolidin-1-yl)butan-1-amine.

LC-MS-conditions TFA: $t_R$=0.67 min; [M+H]$^+$=504.16.

Example 296

(5R)—N$^5$-(4-Bromo-2-methylphenyl)-(6R)—N$^6$-(4-pyrrolidino-butyl)-(4S,7R)-[4,7-ethenylene-spiro[2.4]heptane]-5,6-dicarboxamide Following general procedure E, starting from (5R)—N$^5$-(4-bromo-2-methylphenyl)-(6R)-6-hydroxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.67 min; [M+H]$^+$=500.14.

Example 297

(5R)—N$^5$-(4-Bromo-3-chlorophenyl)-(6R)—N$^6$-(4-pyrrolidino-butyl)-(4S,7R)-[4,7-ethenylene-spiro[2.4]heptane]-5,6-dicarboxamide Following general procedure L, starting from (5R)-5-hydroxycarbonyl-(6R)—N$^6$-(4-pyrrolidin-1-yl-butyl)-(4S,7R)-[4,7-ethenylene-spiro[2.4]heptane]-6-carboxamide and 4-bromo-3-chloroaniline.

LC-MS-conditions TFA: $t_R$=0.72 min; [M+H]$^+$=520.16.

Example 298

(5R)—N$^5$-(2-Chloro-pyridin-5-yl)-(6R)—N$^6$-(3-amino-3-oxopropyl)-(4S,7R)-[4,7-ethylene-spiro[2.4]heptane]-5,6-dicarboxamide Following general procedure M, starting from (5R)—N$^5$-(2-chloropyrid-5-yl)-(6R)—N$^6$-(2-methoxycarbonyl-ethyl)-(4S,7R)-[4,7-ethylene-spiro[2.4]heptane]-5,6-dicarboxamide and NH$_4$OH.

LC-MS-conditions FA: $t_R$=0.74 min; [M+H]$^+$=391.15.

Example 299

(5R*)—N$^5$-(4-Acetyl-thiazol-2-yl-methyl)-(6R*)—N$^6$-(3-amino-propyl)-(4S*,7R*)-[4,7-ethenylene-spiro[2.4]heptane]-5,6-dicarboxamide Following general procedures B then H, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and N-tert-butoxycarbonyl-1,3-propanediamine.

LC-MS-conditions TFA: $t_R$=0.41 min; [M+H]$^+$=403.18.

Example 300

(5R*)—N$^5$-(4-Acetyl-thiazol-2-yl-methyl)-(6R*)—N$^6$-(piperidin-4-yl-methyl)-(4S*,7R*)-[4,7-ethenylene-spiro[2.4]heptane]-5,6-dicarboxamide Following general procedures B then H, starting from (5R*)—N$^5$-(4-acetyl-thiazol-2-yl-methyl)-(6R*)-6-hydroxycarbonyl-(4S*,7R*)-[4,7-ethenylene-spiro[2.4]heptane]-5-carboxamide and 1-tert-butoxycarbonyl-4-(aminomethyl)piperidine.

LC-MS-conditions TFA: $t_R$=0.45 min; [M+H]$^+$=443.20.

Example 301

(5R*)—N$^5$-(5-Bromo-thiazol-2-yl)-(6R*)—N$^6$-(2-methylamino-ethyl)-(4S*,7R*)-[4,7-ethenylene-spiro[2.4]heptane]-5,6-dicarboxamide Following general procedures B then H, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and N-tert-butoxycarbonyl-N-methylethylenediamine.

LC-MS-conditions TFA: $t_R$=0.56 min; [M+H]$^+$=425.03.

Example 302

(5R*)—N$^5$-(5-Bromo-thiazol-2-yl)-(6R*)—N$^6$-(5-amino-pentyl)-(4S*,7R*)-[4,7-ethenylene-spiro[2.4]heptane]-5,6-dicarboxamide Following general procedure A, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-bromo-2-fluorobenzylamine hydrochloride.

LC-MS-conditions TFA: $t_R$=0.60 min; [M+H]$^+$=453.04.

Example 303

(5R*)—N$^5$-(5-Bromo-thiazol-2-yl)-(6R*)—N$^6$-(4-(aminomethyl)phenyl-methyl)-(4S*,7R*)-[4,7-ethenylene-spiro[2.4]heptane]-5,6-dicarboxamide Following general procedures B then H, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 1-(N-tert-butoxycarbonyl-aminomethyl)-4-(aminomethyl)benzene.

LC-MS-conditions TFA: $t_R$=0.61 min; [M+H]$^+$=487.09.

Example 304

(5R*)—N$^5$-(5-Bromo-thiazol-2-yl)-(6R*)—N$^6$-(2,2-dimethyl-3-amino-propyl)-(4S*,7R*)-[4,7-ethenylene-spiro[2.4]heptane]-5,6-dicarboxamide Following general procedures B then H, starting from (5R*)—N$^5$-(5-bromo-thiazol-2-yl)-(6R*)-6-hydroxycarbonyl-(4S*,7R*)-[4,7-ethenylene-spiro[2.4]heptane]-5-carboxamide and 3-(tert-butoxycarbonyl-amino)-2,2-dimethyl-propylamine.

LC-MS-conditions TFA: $t_R$=0.61 min; [M+H]$^+$=453.09.

Example 305

(5R*)—N$^5$-(4-Bromophenyl-methyl)-(6R*)—N$^6$-(2-methylamino-ethyl)-(4S*,7R*)-[4,7-ethenylene-spiro[2.4]heptane]-5,6-dicarboxamide Following general procedures B then H, starting from (5R*)—N$^5$-(4-bromophenyl-methyl)-(6R*)-6-hydroxycarbonyl-(4S*,7R*)-[4,7-ethenylene-spiro[2.4]heptane]-5-carboxamide and N-tert-butoxycarbonyl-N-methylethylenediamine.

LC-MS-conditions TFA: $t_R$=0.59 min; [M+H]$^+$=432.18.

Example 306

(5R*)—N⁵-(4-Bromophenyl-methyl)-(6R*)—N⁶-(piperidin-4-yl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and N-tert-butoxycarbonyl-4-aminopiperidine.
LC-MS-conditions TFA: $t_R$=0.60 min; [M+H]⁺=458.17.

Example 307

(5R*)—N⁵-(4-Bromophenyl-methyl)-(6R*)—N⁶-(3-amino-propyl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and N-tert-butoxycarbonyl-1,3-propanediamine.
LC-MS-conditions TFA: $t_R$=0.59 min; [M+H]⁺=432.06.

Example 308

(5R*)—N⁵-(4-Bromophenyl-methyl)-(6R*)—N⁶-(3-(aminomethyl)phenyl-methyl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and 1-(N-tert-butoxycarbonyl-aminomethyl)-3-(aminomethyl)benzene.
LC-MS-conditions TFA: $t_R$=0.64 min; [M+H]⁺=494.17.

Example 309

(5R*)—N⁵-(4-Bromophenyl-methyl)-(6R*)—N⁶-(4-(aminomethyl)phenyl-methyl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and 1-(N-tert-butoxycarbonyl-aminomethyl)-4-(aminomethyl)benzene.
LC-MS-conditions TFA: $t_R$=0.63 min; [M+H]⁺=494.12.

Example 310

(5R*)—N⁵-(4-Bromophenyl-methyl)-(6R*)—N⁶-(2,2-dimethyl-3-amino-propyl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and 3-(tert-butoxycarbonyl-amino)-2,2-dimethyl-propylamine.
LC-MS-conditions TFA: $t_R$=0.63 min; [M+H]⁺=460.13.

Example 311

(5R*)—N⁵-(4-Bromophenyl-methyl)-(6R*)—N⁶-(piperidin-4-yl-methyl)-(4S*,7R*)-[4,7-ethenylene-spiro[2.4]heptane]-5,6-dicarboxamide Following general procedures B then H, starting from (5R*)—N⁵-(4-bromophenyl-methyl)-(6R*)-6-hydroxycarbonyl-(4S*,7R*)-[4,7-ethenylene-spiro[2.4]heptane]-5-carboxamide and 1-tert-butoxycarbonyl-4-(aminomethyl)piperidine.
LC-MS-conditions TFA: $t_R$=0.60 min; [M+H]⁺=472.16.

Example 312

(5R)—N⁵-(2-Bromo-thiazol-5-yl-methyl)-(6R)—N⁶-(4-pyrrolidino-butyl)-(4S,7R)-[4,7-ethenylene-spiro[2.4]heptane]-5,6-dicarboxamide Following general procedure I, starting from (5R)-5-hydroxycarbonyl-(6R)—N⁶-(4-pyrrolidin-1-yl-butyl)-(4S,7R)-[4,7-ethenylene-spiro[2.4]heptane]-6-carboxamide and (2-bromo-thiazol-5-yl)methanamine.
LC-MS-conditions TFA: $t_R$=0.52 min; [M+H]⁺=507.13.

Example 313

(5R)—N⁵-(5-Methyl-pyridin-2-yl)-(6R)—N⁶-(3-amino-3-oxopropyl)-(4S,7R)-[4,7-ethenylene-spiro[2.4]heptane]-5,6-dicarboxamide Following general procedure E, starting from (5R)—N⁵-(5-methyl-pyridin-2-yl)-(6R)-6-hydroxycarbonyl-(4S,7R)-[4,7-ethenylene-spiro[2.4]heptane]-5-carboxamide and 3-aminopropanamide hydrochloride.
LC-MS-conditions FA: $t_R$=0.56 min; [M+H]⁺=369.19.

Example 314

(5R)—N⁵-(4-Bromo-2,5-difluorophenyl)-(6R)—N⁶-(4-pyrrolidino-butyl)-(4S,7R)-[4,7-ethenylene-spiro[2.4]heptane]-5,6-dicarboxamide Following general procedure E, starting from (5R)—N⁵-(4-bromo-2,5-difluorophenyl)-(6R)-6-hydroxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.70 min; [M+H]⁺=522.17.

Example 315

(5R)—N⁵-(4-Bromo-2,6-difluorophenyl)-(6R)—N⁶-(4-pyrrolidino-butyl)-(4S,7R)-[4,7-ethenylene-spiro[2.4]heptane]-5,6-dicarboxamide Following general procedure E, starting from (5R)—N⁵-(4-bromo-2,6-difluorophenyl)-(6R)-6-hydroxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.62 min; [M+H]⁺=522.17.

Example 316

(5R)—N⁵-(4-Bromo-2,3-difluorophenyl)-(6R)—N⁶-(4-pyrrolidino-butyl)-(4S,7R)-[4,7-ethenylene-spiro[2.4]heptane]-5,6-dicarboxamide Following general procedure E, starting from (5R)—N⁵-(4-bromo-2,3-difluorophenyl)-(6R)-6-hydroxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.69 min; [M+H]⁺=522.14.

Example 317

(5R)—N⁵-(4-Bromo-2,6-difluorophenyl-methyl)-(6R)—N⁶-(4-pyrrolidin-1-yl-butyl)-(4S,7R)-[4,7-ethenylene-spiro[2.4]heptane]-5,6-dicarboxamide Following general procedure E, starting from (5R)-5-hydroxycarbonyl-(6R)—N⁶-(4-pyrrolidin-1-yl-butyl)-(4S,7R)-[4,7-ethenylene-spiro[2.4]heptane]-6-carboxamide and (4-bromo-2,6-difluorophenyl)-methanamine.
LC-MS-conditions TFA: $t_R$=0.64 min; [M+H]⁺=536.12.

Example 318

(5R)—N⁵-(4-Bromo-2-fluorophenyl-methyl)-(6R)—N⁶-(4-pyrrolidino-butyl)-(4S,7R)-[4,7-ethylene-spiro[2.4]heptane]-5,6-dicarboxamide Following general procedure I, starting from (5R)—N⁵-(4-bromo-2-fluorophenyl-methyl)-(6R)-6-hydroxycarbonyl-(4S,7R)-[4,7-ethylene-spiro[2.4]heptane]-5-carboxamide and 4-(pyrrolidin-1-yl)butan-1-amine.
LC-MS-conditions TFA: $t_R$=0.68 min; [M+H]⁺=520.20.

Example 319

(5R)—N⁵-(4-Bromo-2-fluorophenyl-methyl)-(6R)—N⁶-(5-amino-pentyl)-(4S,7R)-[4,7-ethenylene-spiro[2.4]heptane]-5,6-dicarboxamide Following general procedures I then H, starting from (5R)—N⁵-(4-bromo-2-fluorophenyl-methyl)-(6R)-6-hydroxycarbonyl-(4S,7R)-[4,7-ethenylene-spiro[2.4]heptane]-5-carboxamide and N-tert-butoxycarbonyl-1,5-pentanediamine.
LC-MS-conditions TFA: $t_R$=0.62 min; [M+H]⁺=478.13.

Example 320

(5R)—N⁵-(4-Bromo-2-fluorophenyl-methyl)-(6R)—N⁶-(4-amino-butyl)-(4S,7R)-[4,7-ethenylene-spiro[2.4]heptane]-5,6-dicarboxamide Following general procedures I then H, starting from (5R)—N⁵-(4-bromo-2-fluorophenyl-methyl)-(6R)-6-hydroxycarbonyl-(4S,7R)-[4,7-ethenylene-spiro[2.4]heptane]-5-carboxamide and N-tert-butoxycarbonyl-1,4-butanediamine.
LC-MS-conditions TFA: $t_R$=0.61 min; [M+H]⁺=464.12.

Example 321

(5R)—N⁵-(4-Bromo-3-fluorophenyl-methyl)-(6R)—N⁶-(4-pyrrolidino-butyl)-(4S,7R)-[4,7-ethenylene-spiro[2.4]heptane]-5,6-dicarboxamide Following general procedure F, starting from (5R)—N⁵-(4-bromo-3-fluorophenyl-methyl)-(6R)-6-methoxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.65 min; [M+H]⁺=518.16.

Example 322

(5R)—N⁵-(5-Bromo-thiazol-2-yl)-(6R)—N⁶-(5-amino-pentyl)-(4S,7R)-[4,7-ethenylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethenylene-spiro[2.4]heptane]-5-carboxamide and N-tert-butoxycarbonyl-1,5-pentanediamine.
LC-MS-conditions TFA: $t_R$=0.61 min; [M+H]⁺=453.05.

Example 323

(5R)—N⁵-(5-Bromo-thiazol-2-yl)-(6R)—N⁶-(piperidin-4-yl)-(4S,7R)-[4,7-ethenylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethenylene-spiro[2.4]heptane]-5-carboxamide and 4-amino-1-tert-butoxycarbonyl-piperidine.
LC-MS-conditions TFA: $t_R$=0.57 min; [M+H]⁺=451.10.

Example 324

(5R)—N⁵-(5-Bromo-thiazol-2-yl)-(6R)—N⁶-(piperidin-4-yl-methyl)-(4S,7R)-[4,7-ethenylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethenylene-spiro[2.4]heptane]-5-carboxamide and 4-(aminomethyl)-1-tert-butoxycarbonyl-piperidine.
LC-MS-conditions TFA: $t_R$=0.58 min; [M+H]⁺=465.16.

Example 325

(5R)—N⁵-(5-Bromo-thiazol-2-yl)-(6R)—N⁶,N⁶-(3-(aminomethyl)pentane-1,5-diyl)-(4S,7R)-[4,7-ethenylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethenylene-spiro[2.4]heptane]-5-carboxamide and 4-(tert-butoxycarbonyl-aminomethyl)piperidine.
LC-MS-conditions TFA: $t_R$=0.57 min; [M+H]⁺=465.07.

Example 326

(5R)—N⁵-(4-Bromo-2-fluorophenyl-methyl)-(6R)—N⁶-(5-amino-pentyl)-(4S,7R)-[4,7-ethylene-spiro[2.4]heptane]-5,6-dicarboxamide Following general procedures I then H, starting from (5R)—N⁵-(4-bromo-2-fluorophenyl-methyl)-(6R)-6-hydroxycarbonyl-(4S,7R)-[4,7-ethylene-spiro[2.4]heptane]-5-carboxamide and N-tert-butoxycarbonyl-1,5-pentanediamine.
LC-MS-conditions TFA: $t_R$=0.64 min; [M+H]⁺=480.12.

Example 327

(5R)—N⁵-(4-Bromo-2,3-difluorophenyl-methyl)-(6R)—N⁶-(4-pyrrolidino-butyl)-(4S,7R)-[4,7-ethenylene-spiro[2.4]heptane]-5,6-dicarboxamide Following general procedure I, starting from (5R)—N⁵-(4-bromo-2,3-difluorophenyl-methyl)-(6R)-6-hydroxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.64 min; [M+H]⁺=536.17.

Example 328

(5R)—N⁵-(4-Bromo-3,5-difluorophenyl-methyl)-(6R)—N⁶-(4-pyrrolidino-butyl)-(4S,7R)-[4,7-ethenylene-spiro[2.4]heptane]-5,6-dicarboxamide Following general procedure I, starting from (5R)—N⁵-(4-bromo-3,5-difluorophenyl-methyl)-(6R)-6-hydroxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.64 min; [M+H]⁺=536.12.

Example 329

(5R)—N⁵-(4-Bromo-2,5-difluorophenyl-methyl)-(6R)—N⁶-(4-pyrrolidino-butyl)-(4S,7R)-[4,7-ethenylene-spiro[2.4]heptane]-5,6-dicarboxamide Following general procedure I, starting from (5R)—N⁵-(4-bromo-2,5-difluorophenyl-methyl)-(6R)-6-hydroxycarbonyl-(4S,7R)-[4,7-ethenylene-spiro[2.4]heptane]-5-carboxamide and 4-(pyrrolidin-1-yl)butan-1-amine.

LC-MS-conditions TFA: $t_R$=0.65 min; [M+H]⁺=536.22.

Example 330

(5R)—N⁵-(5-Bromo-thiazol-2-yl)-(6R)—N⁶-(piperidin-4-yl)-(4S,7R)-[4,7-ethylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethylene-spiro[2.4]heptane]-5-carboxamide and 4-amino-1-tert-butoxycarbonyl-piperidine.

LC-MS-conditions TFA: $t_R$=0.60 min; [M+H]⁺=453.04.

Example 331

(5R)—N⁵-(5-Bromo-thiazol-2-yl)-(6R)—N⁶-(isobutyl)-(4S,7R)-[4,7-ethylene-spiro[2.4]heptane]-5,6-dicarboxamide Following general procedure I, starting from (5R)—N⁵-(5-bromo-thiazol-2-yl)-(6R)-6-hydroxycarbonyl-(4S,7R)-[4,7-ethylene-spiro[2.4]heptane]-5-carboxamide and isobutylamine.

LC-MS-conditions FA: $t_R$=1.15 min; [M+H]⁺=426.08.

Example 332

(5R)—N⁵-(5-Bromo-thiazol-2-yl)-(6R)—N⁶-(4-tert-butoxycarbonyl-amino-butyl)-(4S,7R)-[4,7-ethylene-spiro[2.4]heptane]-5,6-dicarboxamide Following general procedure I, starting from (5R)—N⁵-(5-bromo-thiazol-2-yl)-(6R)-6-hydroxycarbonyl-(4S,7R)-[4,7-ethylene-spiro[2.4]heptane]-5-carboxamide and N-tert-butoxycarbonyl-1,4-butanediamine.

LC-MS-conditions FA: $t_R$=1.16 min; [M+H]⁺=541.09.

Example 333

(5R)—N⁵-(5-Bromo-thiazol-2-yl)-(6R)—N⁶-(5-tert-butoxycarbonyl-amino-pentyl)-(4S,7R)-[4,7-ethylene-spiro[2.4]heptane]-5,6-dicarboxamide Following general procedure I, starting from (5R)—N⁵-(5-bromo-thiazol-2-yl)-(6R)-6-hydroxycarbonyl-(4S,7R)-[4,7-ethylene-spiro[2.4]heptane]-5-carboxamide and N-tert-butoxycarbonyl-1,5-pentanediamine.

LC-MS-conditions FA: $t_R$=1.20 min; [M+H]⁺=555.12.

Example 334

(5R)—N⁵-(5-Bromo-thiazol-2-yl)-(6R)—N⁶-(5-amino-pentyl)-(4S,7R)-[4,7-ethylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethylene-spiro[2.4]heptane]-5-carboxamide and N-tert-butoxycarbonyl-1,5-pentanediamine.

LC-MS-conditions TFA: $t_R$=0.63 min; [M+H]⁺=455.11.

Example 335

(5R)—N⁵-(5-Bromo-thiazol-2-yl)-(6R)—N⁶-(4-amino-butyl)-(4S,7R)-[4,7-ethylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethylene-spiro[2.4]heptane]-5-carboxamide and N-tert-butoxycarbonyl-1,4-butanediamine.

LC-MS-conditions TFA: $t_R$=0.61 min; [M+H]⁺=441.10.

Example 336

(5R)—N⁵-(5-Bromo-thiazol-2-yl)-(6R)—N⁶,N⁶-(3-(aminomethyl)pentane-1,5-diyl)-(4S,7R)-[4,7-ethylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethylene-spiro[2.4]heptane]-5-carboxamide and 4-(tert-butoxycarbonyl-aminomethyl)piperidine.

LC-MS-conditions TFA: $t_R$=0.61 min; [M+H]⁺=467.15.

Example 337

(5R)—N⁵-(5-Bromo-thiazol-2-yl)-(6R)—N⁶-(piperidin-4-yl-methyl)-(4S,7R)-[4,7-ethylene-spiro[2.4]heptane]-5,6-dicarboxamide Following general procedures I then H, starting from (5R)—N⁵-(5-bromo-thiazol-2-yl)-(6R)-6-hydroxycarbonyl-(4S,7R)-[4,7-ethylene-spiro[2.4]heptane]-5-carboxamide and 1-tert-butoxycarbonyl-4-(aminomethyl)piperidine.

LC-MS-conditions TFA: $t_R$=0.62 min; [M+H]⁺=467.12.

Example 338

(5R)—N⁵-(2-Bromo-3-fluoro-pyridin-5-yl)-(6R)—
N⁶-(4-pyrrolidino-butyl)-(4S,7R)-[4,7-ethenylene-
spiro[2.4]heptane]-5,6-dicarboxamide Following general procedure F, starting from (5R)—N⁵-(2-bromo-3-fluoro-pyridin-5-yl)-(6R)-6-methoxycarbonyl-(4S,7R)-[4,7-ethylene-spiro[2.4]heptane]-5-carboxamide and 4-(pyrrolidin-1-yl)butan-1-amine.
LC-MS-conditions TFA: $t_R$=0.61 min; [M+H]⁺=505.12.

Example 339

(5R*)—N⁵-(4-Aminobutyl)-(6R*)—N⁶-(4-bromophe-
nyl)-(4S*,7R*)-[4,7-ethenylene-spiro[2.4]heptane]-5,6-di-
carboxamide Following general procedures A then H, starting from (5R*)-5-hydroxycarbonyl-(6R*)—N⁶-(4-bromo-phenyl)-(4S*,7R*)-[4,7-ethenylene-spiro[2.4]heptane]-6-carboxamide and N-tert-butoxycarbonyl-1,4-butanediamine.
LC-MS-conditions TFA: $t_R$=0.63 min; [M+H]⁺=432.12.

Example 340

(5R*)—N⁵-(5-Aminopentyl)-(6R*)—N⁶-(4-bro-
mophenyl)-(4S*,7R*)-[4,7-ethenylene-spiro[2.4]
heptane]-5,6-dicarboxamide Following general procedures A then H, starting from (5R*)-5-hydroxycarbonyl-(6R*)—N⁶-(4-bromo-phenyl)-(4S*,7R*)-[4,7-ethenylene-spiro[2.4]heptane]-6-carboxamide and N-tert-butoxycarbonyl-1,5-pentanediamine.
LC-MS-conditions TFA: $t_R$=0.65 min; [M+H]⁺=446.14.

Example 341

(5R*)—N⁵-(2-(Cyclohexen-1-yl)ethyl)-(6R*)—N⁶-
(4-pyrrolidino-butyl)-(4S*,7R*)-[4,7-ethenylene-
spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(1-cyclohexenyl)ethylamine.
LC-MS-conditions TFA: $t_R$=0.66 min; [M+H]⁺=440.36.

Example 342

(5R*)—N⁵-(4-tert-Butyl-cyclohexyl)-(6R*)—N⁶-(4-
pyrrolidino-butyl)-(4S*,7R*)-[4,7-ethenylene-spiro
[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-tert-butylcyclohexylamine.
LC-MS-conditions TFA: $t_R$=0.78 min; [M+H]⁺=470.39.

Example 343

(5R*)—N⁵-(2-(Pyridin-2-yl)ethyl)-(6R*)—N⁶-(4-
pyrrolidino-butyl)-(4S*,7R*)-[4,7-ethenylene-spiro
[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(2-aminoethyl)pyridine.
LC-MS-conditions TFA: $t_R$=0.35 min; [M+H]⁺=437.27.

Example 344

(5R*)—N⁵-(4-Acetyl-thiazol-2-yl)-(6R*)—N⁶-(4-
pyrrolidino-butyl)-(4S*,7R*)-[4,7-ethenylene-spiro
[2.4]heptane]-5,6-dicarboxamide Following general procedure E, starting from (5R*)—N⁵-(4-acetyl-thiazol-2-yl)-(6R*)-6-hydroxycarbonyl-(4S*,7R*)-[4,7-ethenylene-spiro[2.4]heptane]-5-carboxamide and 4-(pyrrolidin-1-yl)butan-1-amine.
LC-MS-conditions TFA: $t_R$=0.50 min; [M+H]⁺=457.26.

Example 345

(5R*)—N⁵-(4-Trifluoromethyl-thiazol-2-yl)-
(6R*)—N⁶-(4-pyrrolidino-butyl)-(4S*,7R*)-[4,7-
ethenylene-spiro[2.4]heptane]-5,6-dicarboxamide Following general procedure C, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-trifluoromethyl-thiazole-2-ylamine.
LC-MS-conditions TFA: $t_R$=0.64 min; [M+H]⁺=483.20.

Example 346

(5R*)—N⁵-(2,4,6-Trifluorophenyl-methyl)-(6R*)—
N⁶-(4-pyrrolidino-butyl)-(4S*,7R*)-[4,7-ethenylene-
spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,4,6-trifluorobenzylamine.
LC-MS-conditions TFA: $t_R$=0.58 min; [M+H]⁺=476.24.

Example 347

(5R*)—N⁵-(2,4-Dimethylphenyl-methyl)-(6R*)—
N⁶-(4-pyrrolidino-butyl)-(4S*,7R*)-[4,7-ethenylene-
spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,4-dimethylbenzylamine.
LC-MS-conditions TFA: $t_R$=0.649 min; [M+H]⁺=450.31.

Example 348

(5R*)—N⁵-[(2-Acetyl-thiazol-4-yl)methyl]-(6R*)—
N⁶-(4-pyrrolidino-butyl)-(4S*,7R*)-[4,7-ethenylene-
spiro[2.4]heptane]-5,6-dicarboxamide Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-acetyl-thiazol-4-yl)-methanamine.
LC-MS-conditions TFA: $t_R$=0.49 min; [M+H]⁺=471.23.

Example 349

(5R*)—N⁵-(3-Chloro-2-fluorophenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-chloro-2-fluorobenzylamine.
LC-MS-conditions TFA: $t_R$=0.62 min; [M+H]⁺=474.23.

Example 350

(5R*)—N⁵-(4-Methyl-oxazol-2-yl)-(6R*)—N⁶-(4-pyrrolidino-butyl)-(4S*,7R*)-[4,7-ethenylene-spiro[2.4]heptane]-5,6-dicarboxamide Following general procedure F, starting from (5R*)—N⁵-(4-methyl-oxazol-2-yl)-(6R*)-6-ethoxycarbonyl-(4S*,7R*)-[4,7-ethenylene-spiro[2.4]heptane]-5-carboxamide and 4-(pyrrolidin-1-yl)butan-1-amine.
LC-MS-conditions TFA: $t_R$=0.46 min; [M+H]⁺=413.25.

Example 351

(5R*)—N⁵-[(5-Acetyl-thiazol-2-yl)methyl]-(6R*)—N⁶-(4-pyrrolidino-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (5-(2-methyl-[1,3]dioxolan-2-yl)thiazol-2-yl)methanamine.
LC-MS-conditions TFA: $t_R$=0.46 min; [M+H]⁺=471.23.

Example 352

(5R*)—N⁵-(3-Acetylphenyl)-(6R*)—N⁶-(4-pyrrolidino-butyl)-(4S*,7R*)-[4,7-ethenylene-spiro[2.4]heptane]-5,6-dicarboxamide Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 1-(3-aminophenyl)ethanone.
LC-MS-conditions TFA: $t_R$=0.55 min; [M+H]⁺=450.28.

Example 353

(5R*)—N⁵-(2-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-bromo-4-fluorobenzylamine hydrochloride.
LC-MS-conditions TFA: $t_R$=0.63 min; [M+H]⁺=518.18.

Example 354

(5R*)—N⁵-(3-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-bromo-4-fluorobenzylamine hydrochloride.
LC-MS-conditions TFA: $t_R$=0.63 min; [M+H]⁺=518.21.

Example 355

(5R*)—N⁵-(2,3,5-Trifluorophenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,3,5-trifluorobenzylamine.
LC-MS-conditions TFA: $t_R$=0.60 min; [M+H]⁺=476.26.

Example 356

(5R*)—N⁵-[(4-Methyl-1,2,5-oxadiazol-3-yl)methyl]-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (4-methyl-1,2,5-oxadiazol-3-yl)methanamine hydrochloride.
LC-MS-conditions TFA: $t_R$=0.48 min; [M+H]⁺=428.26.

Example 357

(5R*)—N⁵-(2-Fluoro-3-trifluoromethyl phenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-fluoro-3-(trifluoromethyl)benzylamine.
LC-MS-conditions TFA: $t_R$=0.65 min; [M+H]⁺=508.25.

Example 358

(5R*)—N⁵-(3,5-Dimethylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3,5-dimethylbenzylamine.
LC-MS-conditions TFA: $t_R$=0.66 min; [M+H]⁺=450.31.

Example 359

(5R*)—N⁵-(3-Acetylphenyl-methyl)-(6R*)—N⁶-(4-pyrrolidino-butyl)-(4S*,7R*)-[4,7-ethenylene-spiro[2.4]heptane]-5,6-dicarboxamide Following general procedures I then G, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (3-(2-methyl-[1,3]dioxolan-2-yl)-phenyl)methanamine.
LC-MS-conditions TFA: $t_R$=0.52 min; [M+H]⁺=464.28.

Example 360

(5R*)—N⁵-(3-Difluoromethoxyphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-(difluoromethoxy)benzylamine.
LC-MS-conditions TFA: $t_R$=0.60 min; [M+H]⁺=488.27.

Example 361

(5R*)—N⁵-[(2-Methoxypyridin-4-yl)methyl]-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-methoxypyridin-4-yl)methanamine.
LC-MS-conditions TFA: $t_R$=0.40 min; [M+H]⁺=453.25.

Example 362

(5R*)—N⁵-(3-Fluoro-5-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-fluoro-5-(trifluoromethyl)benzylamine.
LC-MS-conditions TFA: $t_R$=0.66 min; [M+H]⁺=508.27.

Example 363

(5R*)—N⁵-(4-Acetylphenyl-methyl)-(6R*)—N⁶-(4-pyrrolidino-butyl)-(4S*,7R*)-[4,7-ethenylene-spiro[2.4]heptane]-5,6-dicarboxamide Following general procedure I, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 1-(4-(aminomethyl)phenyl)ethanone.
LC-MS-conditions TFA: $t_R$=0.51 min; [M+H]⁺=464.24.

Example 364

(5R*)—N⁵-(2-Chloro-5-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-chloro-5-(trifluoromethyl)benzylamine.
LC-MS-conditions TFA: $t_R$=0.68 min; [M+H]⁺=524.22.

Example 365

(5R*)—N⁵-(2-Fluoro-5-trifluoromethyl phenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-fluoro-5-(trifluoromethyl)benzylamine.
LC-MS-conditions TFA: $t_R$=0.65 min; [M+H]⁺=508.24.

Example 366

(5R*)—N⁵-(4-Fluoro-3-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-fluoro-3-(trifluoromethyl)benzylamine.
LC-MS-conditions TFA: $t_R$=0.66 min; [M+H]⁺=508.26.

Example 367

(5R*)—N⁵-[(2,6-Dichloropyridin-4-yl)methyl]-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2,6-dichloropyridin-4-yl)methanamine.
LC-MS-conditions TFA: $t_R$=0.58 min; [M+H]⁺=491.18.

Example 368

(5R*)—N⁵-(2,5-Dimethylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,5-dimethylbenzylamine.
LC-MS-conditions TFA: $t_R$=0.64 min; [M+H]⁺=450.30.

Example 369

(5R*)—N⁵-(4,5-Dimethyl-thiazol-2-yl)-(6R*)—N⁶-(4-pyrrolidino-butyl)-(4S*,7R*)-[4,7-ethenylene-spiro[2.4]heptane]-5,6-dicarboxamide Following general procedure F, starting from (5R*)—N⁵-(4,5-dimethyl-thiazol-2-yl)-(6R*)-6-ethoxycarbonyl-(4S*,7R*)-[4,7-ethenylene-spiro[2.4]heptane]-5-carboxamide and 4-(pyrrolidin-1-yl)butan-1-amine.
LC-MS-conditions TFA: $t_R$=0.55 min; [M+H]⁺=443.25.

Example 370

(5R*)—N⁵-(2-Methoxy-5-methylphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-methoxy-5-methylphenyl)methanamine hydrochloride.
LC-MS-conditions TFA: $t_R$=0.62 min; [M+H]⁺=466.32.

Example 371

(5R*)—N⁵-(2-Chloro-3,6-difluorophenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-chloro-3,6-difluorobenzylamine.
LC-MS-conditions TFA: $t_R$=0.61 min; [M+H]⁺=492.20.

Example 372

(5R*)—N⁵-(2-Isopropoxyphenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and (2-isopropoxyphenyl)methanamine.
LC-MS-conditions TFA: $t_R$=0.66 min; [M+H]⁺=480.31.

Example 373

(5R*)—N⁵-(2-Chloro-6-fluoro-3-methyl phenyl-methyl)-(6R*)—N⁶-(4-pyrrolidino-butyl)-(4S*,7R*)-[4,7-ethenylene-spiro[2.4]heptane]-5,6-dicarboxamide Following general procedure A, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-chloro-6-fluoro-3-methylbenzylamine.
LC-MS-conditions TFA: $t_R$=0.64 min; [M+H]⁺=488.27.

Example 374

(5R*)—N⁵-(3-Chloro-4-methoxyphenyl-methyl)-(6R*)—N⁶-(4-pyrrolidino-butyl)-(4S*,7R*)-[4,7-ethenylene-spiro[2.4]heptane]-5,6-dicarboxamide, formate salt:

Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3-chloro-4-methoxybenzylamine hydrochloride.
LC-MS-conditions FA: $t_R$=0.75 min; [M+H]⁺=486.24.

Example 375

(5R*)—N⁵-(3,4-Dimethoxyphenyl-methyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3,4-dimethoxybenzylamine.
LC-MS-conditions FA: $t_R$=0.64 min; [M+H]⁺=482.32.

Example 376

(5R*)—N⁵-(2,4-Dimethoxyphenyl-methyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2,4-dimethoxybenzylamine.
LC-MS-conditions FA: $t_R$=0.73 min; [M+H]⁺=482.30.

Example 377

(5R*)—N⁵-(2-(3,4-Dimethoxyphenyl)ethyl)-(6R*)—N⁶-(4-pyrrolidino-butyl)-(4S*,7R*)-[4,7-ethenylene-spiro[2.4]heptane]-5,6-dicarboxamide Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(3,4-dimethoxyphenyl)ethylamine.
LC-MS-conditions TFA: $t_R$=0.56 min; [M+H]⁺=496.30.

Example 378

(5R*)—N⁵-(2-(4-Methoxyphenyl)ethyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(4-methoxyphenyl)ethylamine.
LC-MS-conditions TFA: $t_R$=0.58 min; [M+H]⁺=466.32.

Example 379

(5R*)—N⁵-(2-(4-Bromophenyl)ethyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 4-bromophenethylamine.
LC-MS-conditions TFA: $t_R$=0.65 min; [M+H]⁺=514.23.

Example 380

(5R*)—N⁵-(2-(3,4-Dimethylphenyl)ethyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 3,4-Dimethylphenethylamine hydrochloride.
LC-MS-conditions TFA: $t_R$=0.67 min; [M+H]⁺=464.28.

Example 381

(5R*)—N⁵-(2-(4-Methylphenyl)ethyl)-(6R*)—N⁶-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 2-(p-tolyl)ethylamine.
LC-MS-conditions TFA: $t_R$=0.63 min; [M+H]⁺=450.33.

Example 382

(5R*)—N$^5$-(2-(4-Fluorophenyl)ethyl)-(6R*)—N$^6$-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-fluorophenethylamine.
LC-MS-conditions TFA: $t_R$=0.59 min; [M+H]$^+$=454.29.

Example 383

(5R*)—N$^5$-(2-(Benzo[d][1,3]dioxol-5-yl)ethyl)-(6R*)—N$^6$-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 3,4-methylenedioxyphenethylamine hydrochloride.
LC-MS-conditions TFA: $t_R$=0.57 min; [M+H]$^+$=480.28.

Example 384

(5R*)—N$^5$-(2-(3-Bromo-4-methoxyphenyl)ethyl)-(6R*)—N$^6$-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 3-bromo-4-methoxyphenethylamine.
LC-MS-conditions TFA: $t_R$=0.63 min; [M+H]$^+$=544.22.

Example 385

(5R*)—N$^5$-(2-(2,4-Dimethyl phenyl)ethyl)-(6R*)—N$^6$-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 2,4-dimethylphenethylamine.
LC-MS-conditions TFA: $t_R$=0.67 min; [M+H]$^+$=464.32.

Example 386

(5R*)—N$^5$-(4-Ethoxyphenyl-methyl)-(6R*)—N$^6$-(4-pyrrolidino-butyl)-(4S*,7R*)-[4,7-ethenylene-spiro[2.4]heptane]-5,6-dicarboxamide, formate salt Following general procedure N, starting from (5R*)-5-hydroxycarbonyl-(6R*)—N$^6$-(4-pyrrolidin-1-yl-butyl)-(4S*,7R*)-[4,7-ethenylene-spiro[2.4]heptane]-6-carboxamide and 4-ethoxybenzylamine.
LC-MS-conditions TFA: $t_R$=0.60 min; [M+H]$^+$=466.32.

Example 387

(5R)—N$^5$-(2-(4-Chlorophenyl)ethyl)-(6R)—N$^6$-(4-pyrrolidino-butyl)-(4S,7R)-[4,7-ethenylene-spiro[2.4]heptane]-5,6-dicarboxamide Following general procedure I, starting from (5R)—N$^5$-(2-(4-chlorophenyl)ethyl)-(6R)-6-hydroxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.64 min; [M+H]$^+$=470.25.

Example 388

(5R)—N$^5$-(2-(4-Chlorophenyl)ethyl)-(6R)—N$^6$-(2-dimethylamino-ethyl)-(4S,7R)-[4,7-ethenylene-spiro[2.4]heptane]-5,6-dicarboxamide Following general procedure D, starting from (5R)—N$^5$-(2-(4-chlorophenyl)ethyl)-(6R)-6-hydroxycarbonyl-(4S,7R)-[4,7-ethenylene-spiro[2.4]heptane]-5-carboxamide and 2-dimethylamino-ethylamine.
LC-MS-conditions TFA: $t_R$=0.61 min; [M+H]$^+$=416.21.

Example 389

(5R)—N$^5$-(2-(4-Chlorophenyl)ethyl)-(6R)—N$^6$-(2-(pyridin-2-yl)ethyl)-(4S,7R)-[4,7-ethenylene-spiro[2.4]heptane]-5,6-dicarboxamide Following general procedure D, starting from (5R)—N$^5$-(2-(4-chlorophenyl)ethyl)-(6R)-6-hydroxycarbonyl-(4S,7R)-[4,7-ethenylene-spiro[2.4]heptane]-5-carboxamide and 2-(2-aminoethyl)pyridine.
LC-MS-conditions FA: $t_R$=0.80 min; [M+H]$^+$=450.21.

Example 390

(5R)—N$^5$-(2-(4-Chlorophenyl)ethyl)-(6R)—N$^6$-(2-(4-aminosulfonyl-phenyl)-ethyl)-(4S,7R)-[4,7-ethenylene-spiro[2.4]heptane]-5,6-dicarboxamide Following general procedure D, starting from (5R)—N$^5$-(2-(4-chlorophenyl)ethyl)-(6R)-6-hydroxycarbonyl-(4S,7R)-[4,7-ethenylene-spiro[2.4]heptane]-5-carboxamide and 4-(2-aminoethyl)benzene sulfonamide.
LC-MS-conditions FA: $t_R$=0.95 min; [M+H]$^+$=528.16.

Example 391

(5R)—N$^5$-(2-(2,4-Dichlorophenyl)ethyl)-(6R)—N$^6$-(4-pyrrolidino-butyl)-(4S,7R)-[4,7-ethenylene-spiro[2.4]heptane]-5,6-dicarboxamide Following general procedure I, starting from (5R)—N$^5$-(2-(2,4-dichlorophenyl)ethyl)-(6R)-6-hydroxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.69 min; [M+H]$^+$=504.22.

Example 392

(5R)—N$^5$-(2-(4-Chlorophenyl)ethyl)-(6R)—N$^6$—(N-isopentyl-piperidin-4-yl)-(4S,7R)-[4,7-ethenylene-spiro[2.4]heptane]-5,6-dicarboxamide Following general procedure I, starting from (5R)—N$^5$-(2-(4-chlorophenyl)ethyl)-(6R)-6-hydroxycarbonyl-(4S,7R)-[4,7-ethenylene-spiro[2.4]heptane]-5-carboxamide and 1-(3-methyl-butyl)-piperidin-4-ylamine hydrochloride.
LC-MS-conditions TFA: $t_R$=0.70 min; [M+H]$^+$=498.30.

Example 393

(5R)—N⁵-(4-Bromo-3,5-difluorophenyl)-(6R)—N⁶-(4-pyrrolidino-butyl)-(4S,7R)-[4,7-ethenylene-spiro[2.4]heptane]-5,6-dicarboxamide Following general procedure F, starting from (5R)—N⁵-(4-bromo-3,5-difluorophenyl)-(6R)-6-methoxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.71 min; [M+H]⁺=522.13.

Example 394

(5R)—N⁵-(4-Bromo-thiazol-2-yl)-(6R)—N⁶-(4-pyrrolidino-butyl)-(4S,7R)-[4,7-ethenylene-spiro[2.4]heptane]-5,6-dicarboxamide In a flame dried round-bottomed flask equipped with a magnetic stir bar and under inert atmosphere (N₂), to a freshly prepared solution of lithium di-isopropylamide (3.4 eq.) in THF (0.3 M) was added a 0.1 M solution of (5R)—N⁵-(5-bromo-thiazol-2-yl)-(6R)—N⁶-(4-pyrrolidino-butyl)-(4S,7R)-[4,7-ethenylene-spiro[2.4]heptane]-5,6-dicarboxamide at 0° C. The reaction mixture was stirred at 0° C. until completion of the reaction. Water (3.0 eq.) was added and the mixture stirred at rt for 15 h, diluted with EA, washed with brine, dried over Na₂SO₄, filtered, and the solvents were removed under reduced pressure. Purification by FC gave the title compound.
LC-MS-conditions TFA: $t_R$=0.59 min; [M+H]⁺=493.15.

Example 395

(5R)—N⁵-(4-Bromo-3-trifluoromethyl phenyl)-(6R)—N⁶-(4-pyrrolidino-butyl)-(4S,7R)-[4,7-ethenylene-spiro[2.4]heptane]-5,6-dicarboxamide Following general procedure F, starting from (5R)—N⁵-(4-bromo-3-trifluoromethylphenyl)-(6R)-6-methoxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.75 min; [M+H]⁺=554.16.

Example 396

(5R*)—N⁵-[(4-Acetyl-thiazol-2-yl)methyl]-(6R*)—N⁶-(2-methyl amino-ethyl)-(4S*,7R*)-[4,7-ethenylene-spiro[2.4]heptane]-5,6-dicarboxamide Following general procedures B then H, starting from (5R*)—N⁵-[(4-acetyl-thiazol-2-yl)methyl]-(6R*)-6-hydroxycarbonyl-(4S*,7R*)-[4,7-ethenylene-spiro[2.4]heptane]-5-carboxamide and N-tert-butoxycarbonyl-N-methyl-ethylenediamine.
LC-MS-conditions TFA: $t_R$=0.42 min; [M+H]⁺=403.19.

Example 397

(5R)—N⁵-(4-Bromophenyl)-(6R)—N⁶-(4-(2,5-dimethylpyrrolidin-1-yl)butyl)-(4S,7R)-[4,7-ethenylene-spiro[2.4]heptane]-5,6-dicarboxamide Following general procedure E, starting from (5R)—N⁵-(4-bromophenyl)-(6R)-6-hydroxycarbonyl-(4S,7R)-[4,7-ethenylene-spiro[2.4]heptane]-5-carboxamide and 4-(2,5-dimethylpyrrolidin-1-yl)butan-1-amine.
LC-MS-conditions TFA: $t_R$=0.69 min; [M+H]⁺=514.19.

Example 398

(5R)—N⁵-(4-Bromophenyl)-(6R)—N⁶-(4-(pyrrolidin-1-yl)pentyl)-(4S,7R)-[4,7-ethenylene-spiro[2.4]heptane]-5,6-dicarboxamide, formate salt Following general procedure E, starting from (5R)—N⁵-(4-bromophenyl)-(6R)-6-hydroxycarbonyl-(4S,7R)-[4,7-ethenylene-spiro[2.4]heptane]-5-carboxamide and 4-(pyrrolidin-1-yl)pentan-1-amine hydrochloride.
LC-MS-conditions TFA: $t_R$=0.67 min; [M+H]⁺=500.16.

Example 399

(5R)—N⁵-(4-Bromophenyl)-(6R)—N⁶-(3-fluoro-4-(pyrrolidin-1-yl)butyl)-(4S,7R)-[4,7-ethenylene-spiro[2.4]heptane]-5,6-dicarboxamide, formate salt Following general procedure E, starting from (5R)—N⁵-(4-bromophenyl)-(6R)-6-hydroxycarbonyl-(4S,7R)-[4,7-ethenylene-spiro[2.4]heptane]-5-carboxamide and 3-fluoro-4-(pyrrolidin-1-yl)butan-1-amine hydrochloride.
LC-MS-conditions TFA: $t_R$=0.66 min; [M+H]⁺=504.15.

Example 400

(5R)—N⁵-(4-Bromophenyl)-(6R)—N⁶-(4-(2-(methoxymethyl)pyrrolidin-1-yl)butyl)-(4S,7R)-[4,7-ethenylene-spiro[2.4]heptane]-5,6-dicarboxamide, formate salt Following general procedure E, starting from (5R)—N⁵-(4-bromophenyl)-(6R)-6-hydroxycarbonyl-(4S,7R)-[4,7-ethenylene-spiro[2.4]heptane]-5-carboxamide and 4-(2-(methoxymethyl)pyrrolidin-1-yl)butan-1-amine.
LC-MS-conditions TFA: $t_R$=0.68 min; [M+H]⁺=530.20.

Example 401

(5R)—N⁵-(4-Bromophenyl)-(6R)—N⁶-(4-(3,3-difluoropyrrolidin-1-yl)butyl)-(4S,7R)-[4,7-ethenylene-spiro[2.4]heptane]-5,6-dicarboxamide, formate salt Following general procedure E, starting from (5R)—N⁵-(4-bromophenyl)-(6R)-6-hydroxycarbonyl-(4S,7R)-[4,7-ethenylene-spiro[2.4]heptane]-5-carboxamide and 4-(3,3-difluoropyrrolidin-1-yl)butan-1-amine.
LC-MS-conditions TFA: $t_R$=0.67 min; [M+H]⁺=522.14.

Example 402

(5R)—N⁵-(2-Bromo-3-fluoro-pyridin-5-yl)-(6R)—N⁶-(4-pyrrolidino-butyl)-(4S,7R)-[4,7-ethylene-spiro[2.4]heptane]-5,6-dicarboxamide Following general procedure F, starting from (5R)—N⁵-(2-bromo-3-fluoro-pyridin-5-yl)-(6R)-6-methoxycarbonyl-(4S,7R)-[4,7-ethenylene-spiro[2.4]heptane]-5-carboxamide and 4-(pyrrolidin-1-yl)butan-1-amine.
LC-MS-conditions TFA: $t_R$=0.65 min; [M+H]⁺=507.17.

Example 403

(5R)—N⁵-(5-Bromothiazol-2-yl)-(6R)—N⁶-(2-hydroxyethyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and ethanolamine.
LC-MS-conditions FA: $t_R$=0.87 min; [M+H]⁺=414.03.

Example 404

(5R)—N⁵-(5-Bromothiazol-2-yl)-(6R)—N⁶-(3-hydroxypropyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and 3-aminopropan-1-ol.
LC-MS-conditions FA: $t_R$=0.90 min; [M+H]⁺=428.03.

Example 405

(5R)—N⁵-(5-Bromothiazol-2-yl)-(6R)—N⁶-(4-hydroxybutyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and 4-aminobutan-1-ol.
LC-MS-conditions FA: $t_R$=0.92 min; [M+H]⁺=442.06.

Example 406

(5R)—N⁵-(5-Bromothiazol-2-yl)-(6R)—N⁶-(2-methyl-3-hydroxyprop-2-yl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and 2-amino-2-methylpropan-1-ol.
LC-MS-conditions FA: $t_R$=1.00 min; [M+H]⁺=442.06.

Example 407

(5R)—N⁵-(5-Bromothiazol-2-yl)-(6R)—N⁶-(2-(2-hydroxyethoxy)ethyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and 2-(2-aminoethoxy)ethanol.
LC-MS-conditions FA: $t_R$=0.88 min; [M+H]⁺=458.05.

Example 408

(5R)—N⁵-(5-Bromothiazol-2-yl)-(6R)—N⁶-(4-hydroxy-cyclohexyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and trans-4-amino-cyclohexanol hydrochloride.
LC-MS-conditions FA: $t_R$=0.96 min; [M+H]⁺=468.06.

Example 409

(5R)—N⁵-(5-Bromothiazol-2-yl)-(6R)—N⁶-[(1-hydroxy-cyclohexyl)methyl]-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and 1-aminomethyl-1-cyclohexanol hydrochloride.
LC-MS-conditions FA: $t_R$=1.08 min; [M+H]⁺=482.08.

Example 410

(5R)—N⁵-(5-Bromothiazol-2-yl)-(6R)—N⁶-(trans-4-(hydroxymethyl)-cyclohexyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and (trans-4-aminocyclohexyl)methanol.
LC-MS-conditions FA: $t_R$=1.01 min; [M+H]⁺=482.09.

Example 411

(5R)—N⁵-(5-Bromothiazol-2-yl)-(6R)—N⁶-(cis-4-(hydroxymethyl)-cyclohexyl)-(4S,7R)-[4,7-ethylene-spiro[2.4]heptane]-5,6-dicarboxamide Following general procedure I, starting from (5R)—N⁵-(5-bromothiazol-2-yl)-(6R)-6-hydroxycarbonyl-(4S,7R)-[4,7-ethylene-spiro[2.4]heptane]-5-carboxamide and (cis-4-aminocyclohexyl)methanol.
LC-MS-conditions FA: $t_R$=0.99 min; [M+H]⁺=482.08.

Example 412

(5R)—N⁵-(5-Bromothiazol-2-yl)-(6R)—N⁶-(pyrrolidin-3-yl)-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 3-amino-1-tert-butoxycarbonyl-pyrrolidine hydrochloride.
LC-MS-conditions 07: $t_R$=0.60 min; [M+H]⁺=439.41.

Example 413

(5R)—N⁵-(5-Bromothiazol-2-yl)-(6R)—N⁶-(2-(N-methyl amino)-ethyl)-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and N-tert-butoxycarbonyl-N-methylethylenediamine.
LC-MS-conditions 07: $t_R$=0.60 min; [M+H]⁺=427.16.

Example 414

(5R)—N⁵-(5-Bromothiazol-2-yl)-(6R)—N⁶-(3-(N-methylamino)-propyl)-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and N-(3-aminopropyl)-N-methylcarbamic acid tert-butyl ester.
LC-MS-conditions 07: $t_R$=0.61 min; [M+H]⁺=441.16.

Example 415

(5R)—N⁵-(5-Bromothiazol-2-yl)-(6R)—N⁶-(piperidin-3-yl)-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 3-amino-N-tert-butoxycarbonyl-piperidine.
LC-MS-conditions 07: $t_R$=0.61 min; [M+H]⁺=453.20.

Example 416

(5R)—N⁵-(5-Bromothiazol-2-yl)-(6R)—N⁶-[(pyrrolidin-2-yl)-methyl]-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 2-aminomethyl-N-tert-butoxycarbonyl-pyrrolidine.
LC-MS-conditions 07: $t_R$=0.62 min; [M+H]⁺=453.20.

Example 417

(5R)—N⁵-(5-Bromothiazol-2-yl)-(6R)—N⁶-[(piperidin-2-yl)-methyl]-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 2-aminomethyl-N-tert-butoxycarbonyl-piperidine.
LC-MS-conditions 07: $t_R$=0.63 min; [M+H]⁺=467.23.

Example 418

(5R)—N⁵-(5-Bromothiazol-2-yl)-(6R)—N⁶-[(piperidin-3-yl)-methyl]-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 3-aminomethyl-N-tert-butoxycarbonyl-piperidine.
LC-MS-conditions 07: $t_R$=0.62 min; [M+H]⁺=467.22.

Example 419

(5R)—N⁵-(5-Bromothiazol-2-yl)-(6R)—N⁶-(azetidin-3-yl)-(4S,7R)-[4,7-ethylene-spiro[2.4]heptane]-5,6-dicarboxamide Following general procedures I then H, starting from (5R)—N⁵-(5-bromothiazol-2-yl)-(6R)-6-hydroxycarbonyl-(4S,7R)-[4,7-ethylene-spiro[2.4]heptane]-5-carboxamide and 3-amino-N-tert-butoxycarbonyl-azetidine.
LC-MS-conditions 07: $t_R$=0.60 min; [M+H]⁺=425.15.

Example 420

(5R)—N⁵-(4-Bromophenyl)-(6R)—N⁶-(cis-4-(aminomethyl)-cyclohexyl)-(4S,7R)-[4,7-ethenylene-spiro[2.4]heptane]-5,6-dicarboxamide Following general procedures L then H, starting from (5R)—N⁵-(4-bromophenyl)-(6R)-6-hydroxycarbonyl-(4S,7R)-[4,7-ethenylene-spiro[2.4]heptane]-5-carboxamide and tert-butyl ((cis-4-aminocyclohexyl)methyl)carbamate.
LC-MS-conditions 07b: $t_R$=0.69 min; [M+H]⁺=472.07.

Example 421

(5R)—N⁵-(4-Bromophenyl)-(6R)—N⁶-(trans-4-(aminomethyl)-cyclohexyl)-(4S,7R)-[4,7-ethenylene-spiro[2.4]heptane]-5,6-dicarboxamide Following general procedures L then H, starting from (5R)—N⁵-(4-bromophenyl)-(6R)-6-hydroxycarbonyl-(4S,7R)-[4,7-ethenylene-spiro[2.4]heptane]-5-carboxamide and tert-butyl ((trans-4-aminocyclohexyl)methyl)carbamate.
LC-MS-conditions 07b: $t_R$=0.70 min; [M+H]⁺=472.09.

Example 422

(5R*)—N⁵-(2-Trifluoromethyl-pyridin-5-yl)-(6R*)—N⁶-(4-pyrrolidin-1-yl-butyl)-(4S*,7R*)-[4,7-ethenylene-spiro[2.4]heptane]-5,6-dicarboxamide, hydrochloride Following general procedure B, starting from (5R*)-5-hydroxycarbonyl-(6R*)—N⁶-(4-pyrrolidin-1-yl-butyl)-(4S*,7R*)-[4,7-ethenylene-spiro[2.4]heptane]-6-carboxamide and 5-amino-2-(trifluoromethyl)pyridine.
LC-MS-conditions TFA: $t_R$=0.60 min; [M+H]⁺=477.20.

II. Biological Assays

In Vitro Assay

The ALX receptor and FPRL2 agonistic activities of the compounds of formula (I) are determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 µM Fluo-4 (AM) (Invitrogen, F14202), and 20 mM HEPES (Gibco, 15630-056), the cells were washed and resuspended in AB. They were then seeded onto 384-well FLIPR assay plates (Greiner, 781091) at 50'000 cells in 70 µl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. FLIPR384 or FLIPR Tetra instruments (Molecular Devices) were operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Cells expressing recombinant human FPRL2 and the G-protein Gα16 (HEK293-hFPRL2-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 μM Fluo-4 (AM) (Invitrogen, F14202), and 20 mM HEPES (Gibco, 15630-056), the cells were washed and resuspended in AB. They were then seeded onto 384-well FLIPR assay plates (Greiner, 781091) at 50'000 cells in 70 μl per well and sedimented by centrifugation at 1,000 rpm for 1 min. Stock solutions of test compounds were made up at a concentration of 10 mM in DMSO, and serially diluted in AB to concentrations required for activation dose response curves. Gly14-Humanin (Humanin peptide with replacement of Serine by Glycine at position 14, Phoenix Peptides) was used as a reference agonist. FLIPR384 or FLIPR Tetra instruments (Molecular Devices) were operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (GLY14-Humanin compound, 100 nM final concentration) after subtraction of the base line value (AB addition).

Agonistic activities of exemplified compounds are displayed in Table 1.

TABLE 1

| Compound | ALX receptor $EC_{50}$ [nM] | FPRL2 $EC_{50}$ [nM] |
|---|---|---|
| Example 1 | 0.16 | 571 |
| Example 2 | 0.10 | 46 |
| Example 3 | 0.20 | 2000 |
| Example 4 | 0.24 | 5310 |
| Example 5 | 0.34 | 1160 |
| Example 6 | 0.41 | 1260 |
| Example 7 | 0.55 | 413 |
| Example 8 | 0.82 | 2600 |
| Example 9 | 0.94 | 1510 |
| Example 10 | 0.98 | 726 |
| Example 11 | 1.0 | 329 |
| Example 12 | 1.0 | 1300 |
| Example 13 | 1.1 | 4620 |
| Example 14 | 1.2 | 1690 |
| Example 15 | 1.3 | 4400 |
| Example 16 | 1.4 | 3920 |
| Example 17 | 1.8 | 2010 |
| Example 18 | 2.0 | 551 |
| Example 19 | 2.4 | 2480 |
| Example 20 | 2.7 | 2860 |
| Example 21 | 2.8 | 1690 |
| Example 22 | 3.2 | 4640 |
| Example 23 | 3.3 | >25000 |
| Example 24 | 3.7 | 4120 |
| Example 25 | 3.9 | 365 |
| Example 26 | 4.2 | 744 |
| Example 27 | 4.2 | 1960 |
| Example 28 | 4.5 | >25000 |
| Example 29 | 4.8 | 5584 |
| Example 30 | 4.9 | 405 |
| Example 31 | 5.0 | 1410 |
| Example 32 | 5.4 | 3280 |
| Example 33 | 5.8 | 4100 |
| Example 34 | 6.1 | 16100 |
| Example 35 | 6.1 | 1870 |
| Example 36 | 6.7 | 11500 |
| Example 37 | 7.1 | 1710 |
| Example 38 | 7.5 | 1550 |
| Example 39 | 7.6 | 1540 |
| Example 40 | 9.0 | 848 |
| Example 41 | 9.5 | 8510 |
| Example 42 | 9.6 | 7840 |
| Example 43 | 9.5 | 925 |
| Example 44 | 10 | 4910 |
| Example 45 | 11 | 4160 |
| Example 46 | 11 | 1600 |
| Example 47 | 12 | 1170 |
| Example 48 | 12 | 1380 |
| Example 49 | 12 | 1510 |
| Example 50 | 13 | 1080 |
| Example 51 | 8.2 | 1487 |
| Example 52 | 9.6 | 6357 |
| Example 53 | 16 | 5030 |
| Example 54 | 16 | 2587 |
| Example 55 | 18 | 6680 |
| Example 56 | 18 | 1750 |
| Example 57 | 17 | 1660 |
| Example 58 | 20 | 6190 |
| Example 59 | 21 | 8280 |
| Example 60 | 22 | 1481 |
| Example 61 | 23 | 2267 |
| Example 62 | 24 | 363 |
| Example 63 | 24 | 3950 |
| Example 64 | 19 | 68 |
| Example 65 | 26 | >25000 |
| Example 66 | 34 | 2219 |
| Example 67 | 34 | >25000 |
| Example 68 | 27 | 2170 |
| Example 69 | 58 | 708 |
| Example 70 | 61 | 4378 |
| Example 71 | 63 | 5550 |
| Example 72 | 70 | 1850 |
| Example 73 | 63 | 4615 |
| Example 74 | 72 | 18200 |
| Example 75 | 73 | 7976 |
| Example 76 | 77 | 2432 |
| Example 77 | 80 | 2277 |
| Example 78 | 80 | 5480 |
| Example 79 | 96 | 1300 |
| Example 80 | 97 | 7875 |
| Example 81 | 100 | 8734 |
| Example 82 | 118 | 6587 |
| Example 83 | 123 | 678 |
| Example 84 | 133 | 5500 |
| Example 85 | 146 | 8300 |
| Example 86 | 147 | 6942 |
| Example 87 | 156 | 2205 |
| Example 88 | 168 | 9420 |
| Example 89 | 191 | 2467 |
| Example 90 | 194 | 2260 |
| Example 91 | 200 | 2980 |
| Example 92 | 204 | 2670 |
| Example 93 | 216 | >25000 |
| Example 94 | 218 | 1040 |
| Example 95 | 223 | 1846 |
| Example 96 | 373 | 8045 |
| Example 97 | 391 | 1430 |
| Example 98 | 477 | 582 |
| Example 99 | 552 | 5488 |
| Example 100 | 735 | 6114 |

TABLE 1-continued

| Compound | ALX receptor EC$_{50}$ [nM] | FPRL2 EC$_{50}$ [nM] |
|---|---|---|
| Example 101 | 812 | 457 |
| Example 102 | 0.46 | >25000 |
| Example 103 | 4.8 | 6920 |
| Example 104 | 1.5 | 5250 |
| Example 105 | 2.4 | 3730 |
| Example 106 | 82 | 2935 |
| Example 107 | 1.8 | 2270 |
| Example 108 | 4.1 | 1480 |
| Example 109 | 0.7 | 666 |
| Example 110 | 16 | 307 |
| Example 111 | 1.3 | 71 |
| Example 112 | 8.3 | 57 |
| Example 113 | 0.35 | 15 |
| Example 114 | 1.4 | 532 |
| Example 115 | 2.0 | 204 |
| Example 116 | 7.8 | 891 |
| Example 117 | 10 | 359 |
| Example 118 | 47 | 140 |
| Example 119 | 17 | 404 |
| Example 120 | 17 | 363 |
| Example 121 | 95 | 454 |
| Example 122 | 79 | 496 |
| Example 123 | 46 | 332 |
| Example 124 | 52 | 1150 |
| Example 125 | 60 | 268 |
| Example 126 | 71 | 613 |
| Example 127 | 95 | 2740 |
| Example 128 | 120 | 3440 |
| Example 129 | 121 | 1190 |
| Example 130 | 166 | 6370 |
| Example 131 | 173 | 358 |
| Example 132 | 898 | 79 |
| Example 133 | 263 | 122 |
| Example 134 | 319 | 612 |
| Example 135 | 352 | 224 |
| Example 136 | 365 | 1180 |
| Example 137 | 556 | 192 |
| Example 138 | 570 | 332 |
| Example 139 | 731 | 152 |
| Example 140 | 748 | 1310 |
| Example 141 | 835 | 1600 |
| Example 142 | 1330 | 182 |
| Example 143 | 2060 | 94 |
| Example 144 | 2270 | 324 |
| Example 145 | 3650 | 647 |
| Example 146 | 4420 | 337 |
| Example 147 | 7410 | 837 |
| Example 148 | 7600 | 226 |
| Example 149 | 8090 | 691 |
| Example 150 | 8440 | 110 |
| Example 151 | 9120 | 714 |
| Example 152 | 9630 | 150 |
| Example 153 | 9890 | 91 |
| Example 154 | 10000 | 214 |
| Example 155 | >25000 | 91 |
| Example 156 | >25000 | 623 |
| Example 157 | >25000 | 136 |
| Example 158 | >25000 | 204 |
| Example 159 | 13 | 2370 |
| Example 160 | 37 | >25000 |
| Example 161 | 47 | 7920 |
| Example 162 | 61 | 1730 |
| Example 163 | 72 | 5680 |
| Example 164 | 80 | 6820 |
| Example 165 | 87 | 2600 |
| Example 166 | 88 | 4710 |
| Example 167 | 103 | 3690 |
| Example 168 | 71 | 862 |
| Example 169 | 112 | 1790 |
| Example 170 | 114 | >25000 |
| Example 171 | 118 | 3220 |
| Example 172 | 125 | 4610 |
| Example 173 | 131 | 1820 |
| Example 174 | 136 | 4810 |
| Example 175 | 155 | 7210 |
| Example 176 | 158 | 2230 |
| Example 177 | 160 | 446 |
| Example 178 | 115 | 4070 |
| Example 179 | 200 | 1380 |
| Example 180 | 252 | 888 |
| Example 181 | 265 | 2050 |
| Example 182 | 298 | 2020 |
| Example 183 | 303 | 8900 |
| Example 184 | 315 | >14505 |
| Example 185 | 336 | 709 |
| Example 186 | 463 | 8960 |
| Example 187 | 505 | 4270 |
| Example 188 | 529 | 1920 |
| Example 189 | 697 | 3240 |
| Example 190 | 963 | 1705 |
| Example 191 | 140 | 826 |
| Example 192 | 23 | 139 |
| Example 193 | 463 | 355 |
| Example 194 | 223 | 436 |
| Example 195 | 28 | 647 |
| Example 196 | 21 | 1080 |
| Example 197 | 5.4 | 105 |
| Example 198 | 92 | 462 |
| Example 199 | 77 | 7.4 |
| Example 200 | 42 | 236 |
| Example 201 | 93 | 1440 |
| Example 202 | 33 | 75 |
| Example 203 | 24 | 200 |
| Example 204 | 3.4 | 2080 |
| Example 205 | 7.3 | 4780 |
| Example 206 | 31 | 2980 |
| Example 207 | 6.5 | 7430 |
| Example 208 | 2.3 | 15 |
| Example 209 | 0.07 | 58 |
| Example 210 | 0.40 | 200 |
| Example 211 | 0.53 | 423 |
| Example 212 | 0.89 | 12 |
| Example 213 | 4.1 | 16 |
| Example 214 | 6.1 | 338 |
| Example 215 | 0.72 | 95 |
| Example 216 | 2.7 | 297 |
| Example 217 | 38 | 61 |
| Example 218 | 2.1 | 356 |
| Example 219 | 0.30 | 174 |
| Example 220 | 0.35 | 235 |
| Example 221 | 0.66 | 41 |
| Example 222 | 208 | 398 |
| Example 223 | 3.2 | 1210 |
| Example 224 | 994 | 1860 |
| Example 225 | 6.4 | 143 |
| Example 226 | 912 | 356 |
| Example 227 | 290 | 89 |
| Example 228 | 389 | 308 |
| Example 229 | 119 | 67 |
| Example 230 | 31 | 65 |
| Example 231 | 514 | 159 |
| Example 232 | 1260 | 112 |
| Example 233 | 7220 | 197 |
| Example 234 | 73 | 176 |
| Example 235 | 153 | 181 |
| Example 236 | 49 | 292 |
| Example 237 | 305 | 542 |
| Example 238 | 22 | 142 |
| Example 239 | 15 | >25000 |
| Example 240 | 8.1 | >25000 |
| Example 241 | 240 | >25000 |
| Example 242 | 5.9 | 6140 |
| Example 243 | 170 | 2300 |
| Example 244 | 369 | >25000 |
| Example 245 | 3.9 | 8240 |
| Example 246 | 191 | 5330 |
| Example 247 | 106 | 1080 |
| Example 248 | 174 | 3060 |
| Example 249 | 216 | 47 |
| Example 250 | 673 | 746 |
| Example 251 | 7.9 | 558 |
| Example 252 | 82 | 210 |
| Example 253 | 131 | 1770 |
| Example 254 | 492 | 67 |

TABLE 1-continued

| Compound | ALX receptor EC$_{50}$ [nM] | FPRL2 EC$_{50}$ [nM] |
|---|---|---|
| Example 255 | 40 | 489 |
| Example 256 | 6720 | 348 |
| Example 257 | 6010 | 167 |
| Example 258 | 1.1 | 173 |
| Example 259 | 354 | >25000 |
| Example 260 | 9.1 | 8730 |
| Example 261 | 297 | >25000 |
| Example 262 | 97 | 106 |
| Example 263 | 899 | 4460 |
| Example 264 | 140 | 835 |
| Example 265 | 49 | 462 |
| Example 266 | 65 | 1210 |
| Example 267 | 288 | 15300 |
| Example 268 | 477 | 22900 |
| Example 269 | 82 | 3550 |
| Example 270 | 54 | 396 |
| Example 271 | 673 | >25000 |
| Example 272 | 121 | 299 |
| Example 273 | 213 | 432 |
| Example 274 | 290 | 1170 |
| Example 275 | 181 | 7040 |
| Example 276 | 44 | >25000 |
| Example 277 | 61 | 2010 |
| Example 278 | 7.9 | >25000 |
| Example 279 | 1.3 | 62 |
| Example 280 | 258 | >25000 |
| Example 281 | 31 | >25000 |
| Example 282 | 146 | >25000 |
| Example 283 | 884 | >25000 |
| Example 284 | 13 | 264 |
| Example 285 | 9.0 | 224 |
| Example 286 | 32 | 32 |
| Example 287 | 516 | >25000 |
| Example 288 | 0.87 | 33 |
| Example 289 | 1.6 | 214 |
| Example 290 | 32 | 1440 |
| Example 291 | 113 | >25000 |
| Example 292 | 71 | 661 |
| Example 293 | 59 | 2370 |
| Example 294 | 2.9 | 187 |
| Example 295 | 1.3 | 116 |
| Example 296 | 275 | 193 |
| Example 297 | 367 | 28 |
| Example 298 | 24 | 4070 |
| Example 299 | 273 | 359 |
| Example 300 | 384 | 1820 |
| Example 301 | 98 | 2700 |
| Example 302 | 1.3 | 543 |
| Example 303 | 45 | 1340 |
| Example 304 | 12 | 1630 |
| Example 305 | 350 | 2050 |
| Example 306 | 23 | 2760 |
| Example 307 | 76 | 2640 |
| Example 308 | 59 | 493 |
| Example 309 | 367 | 1340 |
| Example 310 | 26 | 466 |
| Example 311 | 54 | 1170 |
| Example 312 | 213 | 208 |
| Example 313 | 330 | >25000 |
| Example 314 | 103 | 204 |
| Example 315 | 9.4 | 296 |
| Example 316 | 236 | 122 |
| Example 317 | 28 | 44 |
| Example 318 | 13 | 18 |
| Example 319 | 55 | 331 |
| Example 320 | 52 | 472 |
| Example 321 | 117 | 15 |
| Example 322 | 0.61 | 382 |
| Example 323 | 17 | 4690 |
| Example 324 | 5.7 | 1545 |
| Example 325 | 19 | >14120 |
| Example 326 | 22 | 930 |
| Example 327 | 40 | 27 |
| Example 328 | 46 | 60 |
| Example 329 | 301 | 64 |
| Example 330 | 24 | 4420 |
| Example 331 | 82 | 8250 |
| Example 332 | 467 | 3540 |
| Example 333 | 519 | 1240 |
| Example 334 | 0.45 | 230 |
| Example 335 | 0.50 | 1300 |
| Example 336 | 6.2 | 1490 |
| Example 337 | 7.3 | 1210 |
| Example 338 | 168 | 139 |
| Example 339 | 19 | 1480 |
| Example 340 | 30 | 255 |
| Example 341 | 1740 | 165 |
| Example 342 | >2390 | 100 |
| Example 343 | >2390 | 885 |
| Example 344 | 7850 | 414 |
| Example 345 | >25000 | 734 |
| Example 346 | 1540 | 508 |
| Example 347 | 1800 | 417 |
| Example 348 | 3230 | 219 |
| Example 349 | 4720 | 200 |
| Example 350 | 5730 | 444 |
| Example 351 | 6330 | 94 |
| Example 352 | 6700 | 958 |
| Example 353 | 6900 | 256 |
| Example 354 | 7410 | 223 |
| Example 355 | 7500 | 477 |
| Example 356 | 7710 | 948 |
| Example 357 | 7910 | 290 |
| Example 358 | 7980 | 176 |
| Example 359 | 8350 | 359 |
| Example 360 | 8700 | 530 |
| Example 361 | 8870 | 330 |
| Example 362 | 9090 | 306 |
| Example 363 | 9740 | 570 |
| Example 364 | 9970 | 372 |
| Example 365 | 9970 | 350 |
| Example 366 | 10000 | 366 |
| Example 367 | 10600 | 644 |
| Example 368 | 11100 | 255 |
| Example 369 | >25000 | 204 |
| Example 370 | >25000 | 180 |
| Example 371 | >25000 | 271 |
| Example 372 | >25000 | 389 |
| Example 373 | >25000 | 478 |
| Example 374 | 2620 | 237 |
| Example 375 | 9050 | 443 |
| Example 376 | 10300 | 334 |
| Example 377 | >25000 | 417 |
| Example 378 | 8610 | 74 |
| Example 379 | 8810 | 6.6 |
| Example 380 | >25000 | 103 |
| Example 381 | 3900 | 30 |
| Example 382 | 6360 | 52 |
| Example 383 | 7680 | 29 |
| Example 384 | 10300 | 72 |
| Example 385 | >25000 | 27 |
| Example 386 | 2910 | 254 |
| Example 387 | 8270 | 26 |
| Example 388 | >25000 | 623 |
| Example 389 | >25000 | 554 |
| Example 390 | >25000 | 576 |
| Example 391 | 9710 | 3.8 |
| Example 392 | 10400 | 20 |
| Example 393 | 1190 | 16 |
| Example 394 | 1550 | 166 |
| Example 395 | 3800 | 13 |
| Example 396 | 1040 | 872 |
| Example 397 | 2.1 | 149 |
| Example 398 | 1.8 | 7510 |
| Example 399 | 5.0 | 4770 |
| Example 400 | 1.4 | 7650 |
| Example 401 | 4.4 | 516 |
| Example 402 | 349 | 66 |
| Example 403 | 158 | 21400 |
| Example 404 | 96 | 10000 |
| Example 405 | 80 | 7840 |
| Example 406 | 333 | 15200 |
| Example 407 | 11 | 9230 |
| Example 408 | 69 | 16300 |

TABLE 1-continued

| Compound | ALX receptor EC$_{50}$ [nM] | FPRL2 EC$_{50}$ [nM] |
|---|---|---|
| Example 409 | 129 | 9190 |
| Example 410 | 855 | 18200 |
| Example 411 | 61 | 6520 |
| Example 412 | 8.9 | 1020 |
| Example 413 | 13 | 2110 |
| Example 414 | 14 | 773 |
| Example 415 | 9.1 | 354 |
| Example 416 | 8.3 | 479 |
| Example 417 | 2.1 | 262 |
| Example 418 | 0.45 | 339 |
| Example 419 | 57 | 2290 |
| Example 420 | 0.13 | 1150 |
| Example 421 | 13 | 1700 |
| Example 422 | 11 | 99 |

The invention claimed is:

1. A compound of the formula (I)

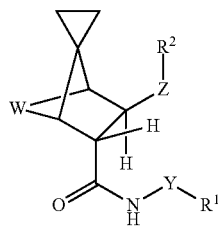

(I)

wherein
W represents —CH$_2$CH$_2$— or —CH=CH—;
Y represents a bond or a (C$_1$-C$_4$)alkandiyl group and R$^1$ represents:
  an aryl-group or a heteroaryl-group, wherein the groups are independently unsubstituted, mono-, di- or tri-substituted, and wherein the substituents are independently selected from halogen, (C$_1$-C$_4$)alkyl, (C$_1$-C$_4$)alkoxy, (C$_1$-C$_2$)alkyl-carbonyl, (C$_1$-C$_2$)fluoroalkyl, (C$_1$-C$_2$)fluoroalkoxy, nitro, cyano or phenyl, wherein the phenyl is unsubstituted or mono-substituted with halogen;
  benzo[d][1,3]dioxolyl;
  aryloxy;
  a cyclohexyl-group or a cyclohexenyl-group, wherein the groups are independently unsubstituted or mono-substituted with (C$_1$-C$_4$)alkyl;
  (C$_1$-C$_2$)alkyl-carbonyl; or
  (C$_1$-C$_4$)alkoxy-carbonyl; or
Y represents, together with R$^1$, a (C$_4$-C$_6$)alkyl group or an amino-(C$_4$-C$_6$)alkyl group;
Z represents —C(O)NR$^3$—* or —CH$_2$NR$^4$C(O)—*, wherein the asterisks indicate the bond which is linked to R$^2$;
R$^2$ represents:
  (C$_3$-C$_6$)cycloalkyl, which is unsubstituted or mono-substituted with hydroxy, hydroxy-methyl, R$^5$R$^6$N—CH$_2$—, heterocyclyl-methyl or —CONH$_2$;
  (C$_1$-C$_6$)alkyl, which is unsubstituted or mono-substituted with fluorine, trifluoromethyl, (C$_1$-C$_4$)alkylthio, (C$_1$-C$_4$)alkoxy-carbonyl, hydroxy, cyano, —NR$^5$R$^6$, —COOH, —C(O)NR$^7$R$^8$ or optionally mono-substituted (C$_1$-C$_4$)alkoxy, wherein the substituent is selected from hydroxy or heterocyclyl; or
  (C$_1$-C$_6$)alkyl, which is mono-substituted
    with (C$_3$-C$_6$)cycloalkyl, wherein the cycloalkyl is unsubstituted or mono- substituted with —NR$^5$R$^6$ or hydroxy;
    with heterocyclyl, wherein the heterocyclyl is unsubstituted or mono- substituted at a nitrogen atom with (C$_1$-C$_4$)alkyl, (C$_1$-C$_2$)alkyl-carbonyl or tert-butoxycarbonyl, and/or mono- or di-substituted at one or two of the carbon atoms with substituents independently selected from halogen, (C$_1$-C$_4$)alkyl or (C$_1$-C$_2$)alkoxy-(C$_1$-C$_2$)alkyl; or
    with an aryl-group or heteroaryl-group, wherein the groups are independently unsubstituted, mono-, di- or tri-substituted, and wherein the substituents are independently selected from halogen, (C$_1$-C$_4$)alkyl, —CH$_2$NHR$^9$, —SO$_2$NH$_2$ or phenyl;
  (C$_3$-C$_5$)fluoroalkyl, which is mono-substituted with heterocyclyl, wherein the heterocyclyl is unsubstituted or mono- or di-substituted at one or two of the carbon atoms with substituents independently selected from halogen or (C$_1$-C$_4$)alkyl;
  heterocyclyl, which is unsubstituted or mono-substituted at a nitrogen atom with (C$_1$-C$_6$)alkyl, benzyl or tert-butoxycarbonyl or mono-substituted at a carbon atom with pyrrolidin-1-yl-methyl;
  an aryl-group or a heteroaryl-group, wherein the groups are independently unsubstituted, mono-, di- or tri-substituted, and wherein the substituents are independently selected from halogen, (C$_1$-C$_4$)alkyl or phenyl; or
  a group selected from 1-carbamoyl-2-phenyl-ethyl, 1-methoxymethyl-2-phenyl-ethyl, 2-morpholino-2-phenyl-ethyl, 2-phenyl-vinyl, or 2,2-dichloro-1-methyl-cyclopropyl;
R$^3$ represents hydrogen, (C$_1$-C$_3$)alkyl or 2-methoxy-ethyl; or
R$^2$ and R$^3$ form, together with the nitrogen that carries them, a ring of 5 to 7 members, wherein the ring is substituted with amino-(C$_1$-C$_4$)alkyl;
R$^4$ represents hydrogen or methyl;
R$^5$ represents hydrogen, (C$_1$-C$_3$)alkyl or tert-butoxycarbonyl;
R$^6$ represents hydrogen or (C$_1$-C$_3$)alkyl;
R$^7$ and R$^8$ represent independently from each other hydrogen or methyl; or
R$^7$ and R$^8$ form, together with the nitrogen that carries them, a pyrrolidine or piperidine ring; and
R$^9$ represents hydrogen or tert-butoxycarbonyl;
or a salt thereof.

2. The compound according to claim 1, wherein
W represents —CH$_2$CH$_2$— or —CH=CH—;
Y represents a bond;
R$^1$ represents an aryl-group or a heteroaryl-group, wherein the groups are independently unsubstituted, mono-, di- or tri-substituted, and wherein the substituents are independently selected from halogen, (C$_1$-C$_4$)alkyl, (C$_1$-C$_4$)alkoxy, (C$_1$-C$_2$)alkyl-carbonyl, or (C$_1$-C$_2$)fluoroalkyl;
Z represents —C(O)NR$^3$—*, wherein the asterisk indicates the bond which is linked to R$^2$;
R$^2$ represents:
  (C$_3$-C$_6$)cycloalkyl, which is unsubstituted or mono-substituted with hydroxy or pyrrolidin-1-yl-methyl;
  (C$_3$-C$_6$)alkyl, which is unsubstituted or mono-substituted with fluorine, trifluoromethyl, (C$_1$-C$_4$)alkylthio, hydroxy, cyano, —NR$^5$R$^6$, —C(O)NH$_2$ or optionally mono-substituted (C$_1$-C$_4$)alkoxy, wherein the substituent is selected from hydroxy or heterocyclyl;

($C_1$-$C_5$)alkyl, which is mono-substituted
  with heterocyclyl, wherein the heterocyclyl is unsubstituted or mono-substituted at a nitrogen atom with methyl or ethyl, or mono- or di-substituted at one or two of the carbon atoms with substituents independently selected from fluorine, methyl or methoxy-methyl; or
  with an aryl-group or heteroaryl-group, wherein the groups are independently unsubstituted, mono- or di-substituted, and wherein the substituents are independently selected from ($C_1$-$C_4$)alkyl or —$CH_2NH_2$; or
($C_3$-$C_5$)fluoroalkyl, which is mono-substituted with heterocyclyl; or
heterocyclyl, which is unsubstituted or mono-substituted at a carbon atom with pyrrolidin-1-yl-methyl;
$R^3$ represents hydrogen, ($C_1$-$C_3$)alkyl or 2-methoxy-ethyl;
$R^5$ represents hydrogen, ($C_1$-$C_3$)alkyl or tert-butoxycarbonyl; and
$R^6$ represents hydrogen or ($C_1$-$C_3$)alkyl;
or a salt thereof.

3. The compound according to claim 1, wherein Y represents a bond; or a salt thereof.

4. The compound according to claim 1, wherein
$R^1$ represents an aryl-group or a heteroaryl-group, wherein the groups are independently unsubstituted or mono-substituted, and wherein the substituent is selected from halogen, ($C_1$-$C_4$)alkyl, ($C_1$-$C_4$)alkoxy, ($C_1$-$C_2$)alkyl-carbonyl or ($C_1$-$C_2$)fluoroalkyl; or a salt thereof.

5. The compound according to claim 1, wherein Z represents —C(O)NR$^3$—*, wherein the asterisk indicates the bond which is linked to $R^2$; or
a salt thereof.

6. The compound according to claim 1, wherein $R^2$ represents:
($C_3$-$C_6$)cycloalkyl, which is unsubstituted or mono-substituted with hydroxy or pyrrolidin-1-yl-methyl;
($C_1$-$C_6$)alkyl, which is unsubstituted or mono-substituted with fluorine, trifluoromethyl, ($C_1$-$C_4$)alkylthio, hydroxy, cyano, —NR$^5$R$^6$, —C(O)NH$_2$ or optionally mono-substituted ($C_1$-$C_4$)alkoxy, wherein the substituent is selected from hydroxy or heterocyclyl;
($C_1$-$C_5$)alkyl, which is mono-substituted with heterocyclyl, wherein the heterocyclyl is unsubstituted or mono-substituted at a nitrogen atom with methyl or ethyl, or mono- or di-substituted at one or two of the carbon atoms with substituents independently selected from fluorine, methyl or methoxy-methyl; or
($C_1$-$C_5$)alkyl, which is mono-substituted with an aryl-group or heteroaryl-group, wherein the groups are independently unsubstituted, mono- or di-substituted, and wherein the substituents are independently selected from ($C_1$-$C_4$)alkyl or —$CH_2NH_2$; or
($C_1$-$C_5$)fluoroalkyl, which is mono-substituted with heterocyclyl; or heterocyclyl, which is unsubstituted or mono-substituted at a carbon atom with pyrrolidin-1-yl-methyl;
or
a salt thereof.

7. The compound according to claim 1, wherein
$R^2$ represents ($C_1$-$C_6$)alkyl, which is unsubstituted or mono-substituted with fluorine, trifluoromethyl, ($C_1$-$C_4$)alkylthio, hydroxy, cyano, —NR$^5$R$^6$, —C(O)NR$^7$R$^8$ or optionally mono-substituted ($C_1$-$C_4$)alkoxy, wherein the substituent is selected from hydroxy or heterocyclyl;
or
a salt thereof.

8. The compound according to claim 1, wherein
$R^2$ represents ($C_1$-$C_5$)alkyl, which is mono-substituted with heterocyclyl, wherein the heterocyclyl is unsubstituted or mono-substituted at a nitrogen atom with methyl or ethyl, or mono- or di-substituted at one or two of the carbon atoms with substituents independently selected from fluorine, methyl or methoxy-methyl; or
a salt thereof.

9. The compound according to claim 1, wherein
$R^2$ represents ($C_1$-$C_4$)alkyl, which is mono-substituted with an aryl-group or heteroaryl-group, wherein the groups are independently unsubstituted, mono- or di-substituted, and wherein the substituents are independently selected from ($C_1$-$C_4$)alkyl or —$CH_2NH_2$; or
a salt thereof.

10. The compound according to claim 1, selected from:
(5R*)—N$^5$-(4-Bromophenyl)-(6R*)—N$^6$-(5-amino-pentyl)-(4S*,7R*)-[4,7-ethenylene-spiro[2.4]heptane]-5,6-dicarboxamide;
(5R)—N$^5$-(4-Bromophenyl)-(6R)—N$^6$-(4-pyrrolidin-1-yl-butyl)-(4S,7R)-[4,7-ethenylene-spiro[2.4]heptane]-5,6-dicarboxamide;
(5R*)—N$^5$-(4-Bromophenyl)-(6R*)—N$^6$-(piperidin-4-yl)-(4S*,7R*)-[4,7-ethenylene-spiro[2.4]heptane]-5,6-dicarboxamide;
(5R*)—N$^5$-(4-Bromophenyl)-(6R*)—N$^6$-(3-iso-butyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-amino-butyl)-(4S*,7R*)-[4,7-ethenylene-spiro[2.4]heptane]-5,6-dicarboxamide;
(5R)—N$^5$-(4-Bromophenyl)-(6R)—N$^6$-(2-N,N-dimethyl-amino-ethyl)-(4S,7R)-[4,7-ethenylene-spiro[2.4]heptane]-5,6-dicarboxamide;
(5R*)—N$^5$-(4-Bromophenyl)-(6R*)—N$^6$-((3-aminomethyl-phenyl)-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-piperidinyl-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(pyrrolidin-3-yl)-(4S*,7R*)-[4,7-ethenylene-spiro[2.4]heptane]-5,6-dicarboxamide;
(5R*)—N$^5$-(4-Bromophenyl)-(6R*)—N$^6$-(2,2-dimethyl-3-amino-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-(N,N-diethyl-amino)-butyl)-(4S*,7R*)-[4,7-ethenylene-spiro[2.4]heptane]-5,6-dicarboxamide;
(5R)—N$^5$-(4-Bromophenyl)-(6R)—N$^6$-(3-hydroxy-propyl)-(4S,7R)-[4,7-ethenylene-spiro[2.4]heptane]-5,6-dicarboxamide;
(5R)—N$^5$-(4-Bromophenyl)-(6R)—N$^6$-(2-carbamoyl-ethyl)-(4S,7R)-[4,7-ethenylene-spiro[2.4]heptane]-5,6-dicarboxamide;
(5R*)—N$^5$-(4-Bromophenyl)-(6R*)—N$^6$-(N-tert-butoxycarbonyl-pyrrolidin-3-yl)-(4S*,7R*)-[4,7-ethenylene-spiro[2.4]heptane]-5,6-dicarboxamide;
(5R*)—N$^5$-(4-Bromophenyl)-(6R*)—N$^6$-(cyclopentyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-amino-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-ethoxy-propyl)-(4S*,7R*)-[4,7-ethenylene-spiro[2.4]heptane]-5,6-dicarboxamide;

(5R*)—N$^5$-(4-Bromophenyl)-(6R*)—N$^6$-(2-pyrrolidi-nyl-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(2,2,2-trifluoro-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-fluoro-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-(N-methyl-amino)-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-tetrahydro-furanyl-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-hydroxy-cyclohexyl)-(4S*,7R*)-[4,7-ethenylene-spiro[2.4]heptane]-5,6-dicarboxamide;
(5R*)—N$^5$-(4-Bromophenyl)-(6R*)—N$^5$-(2-ethylsulfa-nyl-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(5-(N,N-di-ethyl-amino)-pent-2-yl)-(4S*,7R*)-[4,7-ethenylene-spiro[2.4]heptane]-5,6-dicarboxamide;
(5R*)—N$^5$-(4-Bromophenyl)-(6R*)—N$^6$-(piperidin-3-yl)-(4S*,7R*)-[4,7-ethenylene-spiro[2.4]heptane]-5,6-dicarboxamide;
(5R*)—N$^5$-(4-Bromophenyl)-(6R*)—N$^6$-(2-tert-butoxy-carbonyl-amino-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(1-hydroxy-prop-2-yl)-(4S*,7R*)-[4,7-ethenylene-spiro[2.4]heptane]-5,6-dicarboxamide;
(5R*)—N$^5$-(4-Bromophenyl)-(6R*)—N$^6$-(2-imidazoli-din-2-on-1-yl-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-pyrrolidin-1-yl-propyl)-(4S*,7R*)-[4,7-ethenylene-spiro[2.4]heptane]-5,6-dicarboxamide;
(5R)—N$^5$-(4-Bromophenyl)-(6R)—N$^6$-(2-methoxy-ethyl)-(4S,7R)-[4,7-ethenylene-spiro[2.4]heptane]-5,6-dicarboxamide;
(5R*)—N$^5$-(4-Bromophenyl)-(6R*)—N$^6$-(3-(1H-ben-zoimidazol-2-yl)-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-(1-methyl-pyrrolidin-2-yl)-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-hydroxy-ethyl)-(4S*,7R*)-[4,7-ethenylene-spiro[2.4]heptane]-5,6-dicarboxamide;
(5R*)—N$^5$-(4-Bromophenyl)-(6R*)—N$^6$,N$^6$-bis-(2-methoxy-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(cyano-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-1H-pyrazol-1-yl-propyl)-(4S*,7R*)-[4,7-ethenylene-spiro[2.4]heptane]-5,6-dicarboxamide;
(5R*)—N$^5$-(4-Bromophenyl)-(6R*)—N$^6$-[(4-aminom-ethyl-phenyl)-methyl]-(4S*,7R*)-[4,7-ethenylene-spiro[2.4]heptane]-5,6-dicarboxamide;
(5R*)—N$^5$-(4-Bromophenyl)-(6R*)—N$^6$-ethyl-N$^6$-(2-diethylamino-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-1H-imida-zol-1-yl-propyl)-(4S*,7R*)-[4,7-ethenylene-spiro[2.4]heptane]-5,6-dicarboxamide;
(5R*)—N$^5$-(4-Bromophenyl)-(6R*)—N$^6$-([1,4]-dioxan-2-yl-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-hydroxy-butyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-(4-methyl-piperazin-1-yl)-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-amino-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-methyl-N$^6$-(2-dimethylamino-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(4-tert-butoxy-carbonyl-amino-butyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-(methyl-tert-butoxycarbonyl-amino)-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-pyrrolidin-1-yl-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-1H-[1,2,4]-triazol-1-yl-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(furan-3-yl-methyl)-(4S*,7R*)-[4,7-ethenylene-spiro[2.4]heptane]-5,6-dicarboxamide;
(5R*)—N$^5$-(4-Bromophenyl)-(6R*)—N$^6$-(5-dimethyl-amino-pentyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-dimethyl-amino-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-methoxy-propyl)-(4S*,7R*)-[4,7-ethenylene-spiro[2.4]heptane]-5,6-dicarboxamide;
(5R*)—N$^5$-(4-Bromophenyl)-(6R*)—N$^6$-[(1-ethyl-pyr-rolidin-2-yl)-methyl]-(4S*,7R*)-[4,7-ethenylene-spiro[2.4]heptane]-5,6-dicarboxamide;
(5R*)—N$^5$-(4-Bromophenyl)-(6R*)—N$^6$-(3-1H-[1,2,4]-triazol-1-yl-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(N-tert-bu-toxycarbonyl-piperidin-3-yl)-(4S*,7R*)-[4,7-ethenylene-spiro[2.4]heptane]-5,6-dicarboxamide;
(5R*)—N$^5$-(4-Bromophenyl)-(6R*)—N$^6$-(3-(N-tert-butoxycarbonyl-amino)-propyl)-(4S*,7R*)-[4,7-ethenylene-spiro[2.4]heptane]-5,6-dicarboxamide;
(5R*)—N$^5$-(4-Bromophenyl)-(6R*)—N$^6$-(3-methyl-butyl)-(4S*,7R*)-[4,7-ethenylene-spiro[2.4]heptane]-5,6-dicarboxamide;
(5R*)—N$^5$-(4-Bromophenyl)-(6R*)—N$^6$-[(2S)-1-hy-droxy-4-methyl-pent-2-yl]-(4S*,7R*)-[4,7-ethenylene-spiro[2.4]heptane]-5,6-dicarboxamide;
(5R*)—N$^5$-(4-Bromophenyl)-(6R*)—N$^6$-(2-(methoxy-carbonyl)-ethyl)-(4S*,7R*)-[4,7-ethenylene-spiro[2.4]heptane]-5,6-dicarboxamide;
(5R*)—N$^5$-(4-Bromophenyl)-(6R*)—N$^6$-(2-(4-amino-sulfonyl-phenyl)-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-(2-(1-ethyl-5-methyl-1H-pyrazol-3-yl)-ethyl)-(4S*,7R*)-[4,7-ethenylene-spiro[2.4]heptane]-5,6-dicarboxamide;

(5R)—N$^5$-(4-Bromophenyl)-(6R)—N$^6$, N$^6$-bis-(2-methoxy-ethyl)-(4S,7R)-[4,7-ethenylene-spiro[2.4]heptane]-5,6-dicarboxamide;

(5R*)—N$^5$-(4-Bromophenyl)-(6R*)—N$^6$-(2-(4,5-dimethyl-1H-imidazol-2-yl)-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-[(1S)-1-carbamoyl-ethyl]-(4S*,7R*)-[4,7-ethenylene-spiro[2.4]heptane]-5,6-dicarboxamide;

(5R*)—N$^5$-(4-Bromophenyl)-(6R*)—N$^6$-(2-diethylamino-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-(pentyl)-(4S*,7R*)-[4,7-ethenylene-spiro[2.4]heptane]-5,6-dicarboxamide;

(5R*)—N$^5$-(4-Bromophenyl)-(6R*)—N$^6$-(5-tert-butoxycarbonyl-amino-pentyl)-(4S*,7R*)-[4,7-ethenylene-spiro[2.4]heptane]-5,6-dicarboxamide;

(5R*)—N$^5$-(4-Bromophenyl)-(6R*)—N$^6$-(N-(3-methyl-butyl)-piperidin-4-yl)-(4S*,7R*)-[4,7-ethenylene-spiro[2.4]heptane]-5,6-dicarboxamide;

(5R*)—N$^5$-(4-Bromophenyl)-(6R*)—N$^6$-(2-pyridin-2-yl-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-(2,2-dimethyl-3-N-tert-butoxycarbonyl-amino-propyl)-(4S*,7R*)-[4,7-ethenylene-spiro[2.4]heptane]-5,6-dicarboxamide;

(5R*)—N$^5$-(4-Bromophenyl)-(6R*)—N$^6$-(1-phenyl-1H-pyrazol-5-yl)-(4S*,7R*)-[4,7-ethenylene-spiro[2.4]heptane]-5,6-dicarboxamide;

(5R*)—N$^5$-(4-Bromophenyl)-(6R*)—N$^6$-(cyclopropyl)-(4S*,7R*)-[4,7-ethenylene-spiro[2.4]heptane]-5,6-dicarboxamide;

(5R*)—N$^5$-(4-Bromophenyl)-(6R*)—N$^6$-(butyl)-(4S*,7R*)-[4,7-ethenylene-spiro[2.4]heptane]-5,6-dicarboxamide;

(5R*)—N$^5$-(4-Bromophenyl)-(6R*)—N$^6$-(hexyl)-(4S*,7R*)-[4,7-ethenylene-spiro[2.4]heptane]-5,6-dicarboxamide;

(5R*)—N$^5$-(4-Bromophenyl)-(6R*)—N$^6$-(2-(1-ethyl-3-methyl-1H-pyrazol-5-yl)-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-(2-phenyl-2-morpholino-ethyl)-(4S*,7R*)-[4,7-ethenylene-spiro[2.4]-heptane]-5,6-dicarboxamide;

(5R*)—N$^5$-(4-Bromophenyl)-(6R*)—N$^6$-(3-diethylamino-propyl)-(4S*,7R*)-[4,7-ethenylene-spiro[2.4]heptane]-5,6-dicarboxamide;

(5R*)—N$^5$-(4-Bromophenyl)-(6R*)—N$^6$-(N-tert-butoxycarbonyl-pyrrolidin-2-yl-methyl)-(4S*,7R*)-[4,7-ethenylene-spiro[2.4]heptane]-5,6-dicarboxamide;

(5R*)—N$^5$-(4-Bromophenyl)-(6R*)—N$^6$-(2-morpholino-ethyl)-(4S*,7R*)-[4,7-ethenylene-spiro[2.4]heptane]-5,6-dicarboxamide;

(5R)—N$^5$-(4-Bromophenyl)-(6R*)—N$^6$-(2-carbamoyl-cyclohexyl)-(4S*,7R*)-[4,7-ethenylene-spiro[2.4]heptane]-5,6-dicarboxamide;

(5R*)—N$^5$-(4-Bromophenyl)-(6R*)—N$^6$-(1-piperidin-1-yl-propan-1-on-2-yl)-(4S*,7R*)-[4,7-ethenylene-spiro[2.4]heptane]-5,6-dicarboxamide;

(5R*)—N$^5$-(4-Bromophenyl)-(6R*)—N$^6$-(N-benzyl-piperidin-4-yl)-(4S*,7R*)-[4,7-ethenylene-spiro[2.4]heptane]-5,6-dicarboxamide;

(5R*)—N$^5$-(4-Bromophenyl)-(6R*)—N$^6$-methyl-N$^6$-hexyl-(4S*,7R*)-[4,7-ethenylene-spiro[2.4]heptane]-5,6-dicarboxamide;

(5R*)—N$^5$-(4-Bromophenyl)-(6R*)—N$^6$-(3,3-dimethyl-butyl)-(4S*,7R*)-[4,7-ethenylene-spiro[2.4]heptane]-5,6-dicarboxamide;

(5R*)—N$^5$-(4-Bromophenyl)-(6R")-N$^6$-(N-methyl-piperidin-4-yl)-(4S*,7R*)-[4,7-ethenylene-spiro[2.4]heptane]-5,6-dicarboxamide;

(5R*)—N$^5$-(4-Bromophenyl)-(6R*)—N$^6$-(3-morpholino-propyl)-(4S*,7R*)-[4,7-ethenylene-spiro[2.4]heptane]-5,6-dicarboxamide;

(5R*)—N$^5$-(4-Bromophenyl)-(6R*)—N$^6$-(3-(5-methyl-1H-pyrazol-4-yl)-propyl)-(4S*,7R*)-[4,7-ethenytene-spiro[2.4]heptane]-5,6-dicarboxamide;

(5R*)—N$^5$-(4-Bromophenyl)-(6R*)—N$^6$-(3-tert-butoxycarbonyl-propyl)-(4S*,7R*)-[4,7-ethenylene-spiro[2.4]heptane]-5,6-dicarboxamide;

(5R*)—N$^5$-(4-Bromophenyl)-(6R*)—N$^6$-{[(3-N-tert-butoxycarbonyl-aminomethyl)-phenyl]-methyl}-(4S*,7R*)-[4,7-ethenylene-spiro[2.4]heptane]-5,6-dicarboxarnide;

(5R*)—N$^5$-(4-Bromophenyl)-(6R*)—N$^6$-propyl-N$^6$-(cyclopropylmethyl)-(4S*,7R*)-[4,7-ethenylene-spiro[2.4]heptane]-5,6-dicarboxamide;

(5R*)—N$^5$-(4-Bromophenyl)-(6R*)—N$^6$-(N-tert-butoxycarbonyl-piperidin-4-yl-methyl)-(4S*,7R*)-[4,7-ethenylene-spiro[2.4]heptane]-5,6-dicarboxamide;

(5R*)—N$^5$-(4-Bromophenyl)-(6R*)—N$^6$-(cyclohexyl)-(4S*,7R*)-[4,7-ethenylene-spiro[2.4]heptane]-5,6-dicarboxamide;

(5R*)—N$^5$-(4-Bromophenyl)-(6R*)—N$^6$-(N-tert-butoxycarbonyl-piperidin-4-yl)-(4S*,7R*)-[4,7-ethenylene-spiro[2.4]heptane]-5,6-dicarboxamide;

(5R*)—N$^5$-(4-Bromophenyl)-(6R*)—N$^6$-[(1S)-1-carbamoyl-2-phenyl-ethyl]-(4S*,7R*)-[4,7-ethenylene-spiro[2.4]heptane]-5,6-dicarboxamide;

(5R*)—N$^5$-(4-Bromophenyl)-(6R*)—N$^6$-[(2S)-3,3-dimethyl-1-(methylamino)-1-oxobutan-2-yl]-(4S*,7R*)-[4,7-ethenylene-spiro[2.4]heptane]-5,6-dicarboxamide;

(5R*)—N$^5$-(4-Bromophenyl)-(6R*)—N$^6$-[(4-N-tert-butoxycarbonyl-aminomethyl-phenyl)-methyl]-(4S*,7R*)-[4,7-ethenylene-spiro[2.4]heptane]-5,6-dicarboxamide;

(5R*)—N$^5$-(4-Bromophenyl)-(6R*)—N$^6$-(N-tert-butoxycarbonyl-azetidin-3-yl)-(4S*,7R*)-[4,7-ethenylene-spiro[2.4]heptane]-5,6-dicarboxamide;

(5R*)—N$^5$-(4-Bromophenyl)-(6R*)—N$^6$-(2-(N-tert-butoxycarbonyl-piperidin-3-yl)-ethyl)-(4S*,7R*)-[4,7-ethenylene-spiro[2.4]heptane]-5,6-dicarboxamide;

(5R*)—N$^5$-(4-Bromophenyl)-(6R*)—N$^6$-[(1S)-2-methoxy-1-benzyl-ethyl]-(4S*,7R*)-[4,7-ethenylene-spiro[2.4]heptane]-5,6-dicarboxamide;

(5R*)—N$^5$-(4-Bromophenyl)-(6R*)—N$^6$-[(5-methyl-3-phenyl-isoxazol-4-yl)-methyl]-(4S*,7R*)-[4,7-ethenylene-spiro[2.4]heptane]-5,6-dicarboxamide;

(5R*)—N$^5$-(4-Bromophenyl)-(6R*)—N$^6$-(2-carbamoyl-ethyl)-(4S*,7R*)-[4,7-ethylene-spiro[2.4]heptane]-5,6-dicarboxamide;

(5R*)—N$^5$-(4-Bromophenyl)-(6R*)—N$^6$-(3-methoxy-propyl)-(4S*,7R*)-[4,7-ethylene-spiro[2.4]heptane]-5,6-dicarboxamide;

(5R*)—N$^5$-(4-Bromophenyl)-(6R*)—N$^6$-(tetrahydrofuran-2-yl-methyl)-(4S*,7R*)-[4,7-ethylene-spiro[2.4]heptane]-5,6-dicarboxamide;

(5R*)—$N^5$-(4-Bromophenyl)-(6R*)—$N^6$-[(2-imidazolidin-2-on-1-yl)-ethyl]-(4S*,7R*)-[4,7-ethylene-spiro[2.4]heptane]-5,6-dicarboxamide;

(5R*)—$N^5$-(4-Bromophenyl)-(6R*)—$N^6$-(cyclopropyl)-(4S*,7R*)-[4,7-ethylene-spiro[2.4]heptane]-5,6-dicarboxamide;

(5R*)—$N^5$-(4-Bromophenyl)-(6R*)—$N^6$-(3-hydroxypropyl)-(4S*,7R*)-[4,7-ethylene-spiro[2.4]heptane]-5,6-dicarboxamide;

(5R*)—$N^5$-(4-Bromophenyl)-(6R*)—$N^6$-(3-(1H-imidazol-1-)-propyl)-(4S*,7R*)-[4,7-ethylene-spiro[2.4]heptane]-5,6-dicarboxamide;

(5R*)—$N^5$-(4-Bromophenyl)-(6R*)—$N^6$-(5-(dimethylamino)-pentyl)-(4S*,7R*)-[4,7-ethylene-spiro[2.4]heptane]-5,6-dicarboxamide;

(5R*)—$N^5$-(4-Bromophenyl)-(6R*)—$N^6$-(3-pyrrolidin-1-yl-propyl)-(4S*,7R*)-[4,7-ethylene-spiro[2.4]heptane]-5,6-dicarboxamide;

(5R*)—$N^5$-(4-Bromophenyl)-(6R*)—$N^6$-(3-(4-methylpiperazin-1-yl)-propyl)-(4S*,7R*)-[4,7-ethylene-spiro[2.4]heptane]-5,6-dicarboxamide;

(5R*)—$N^5$-(4-Bromophenyl)-(6R*)—$N^6$-(2-(4,5-dimethyl-1H-imidazol-2-yl)-ethyl)-(4S*,7R*)-[4,7-ethylene-spiro[2.4]heptane]-5,6-dicarboxamide;

(5R)—$N^5$-(4-Bromophenyl)-(6R)—$N^6$-(4-pyrrolidin-1-yl-butyl)-(4S,7R)-[4,7-ethylene-spiro[2.4]heptane]-5,6-dicarboxamide;

(5R*)—$N^5$-(2-Bromopyridin-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(4-Methoxyphenyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Chloro-pyridin-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(Benzothiazol-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(4-Bromophenyl-methyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Bromo-pyridin-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Bromo-thiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Methyl-pyridin-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-Pentyl-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-[(4-Methyl-phenyl1)-methyl]-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Methoxycarbonyl-ethyl)-(6R*)—$N^6$-(4-pyrrolidin-1-yl-btriyl)-(4S*,7R*)-[4,7-ethenylene-spiro[2.4]heptane]-5,6-dicarboxamide;

(5R*)—$N^5$-(Cyclohexyl-methyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(4-Methyl-cyclohex-1-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Oxo-hexyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Nitro-thiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Chloro-thiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Cyano-thiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(Furan-2-yl-methyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(1-(4-Bromophenyl)-ethyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(4-Trifluoromethoxyphenyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Phenoxy-ethyl)-(6R*)-$1V^6$-(4-pyrrolidin-1-yl-butyl)-(4S*,7R*)-[4,7-ethenylene-spiro[2.4]heptane]-5,6-dicarboxamide;

(5R*)—$N^5$-(3-Methyl-butyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-Butyl-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-Methyl-furan-2-yl-methyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Methyl-benzothiazol-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Phenyl-ethyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(4-Oxo-pentyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(3-(1H-Imidazol-1-yl)-propyl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(2-Chloro-pyrimidin-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(3-Bromophenyl-methyl)-(6R*)—$N^6$-(4-pyrrolidin-1-yl-butyl)-(4S*,7R*)-[4,7-ethenylene-spiro[2.4]heptane]-5,6-dicaxboxamide;

(5R*)—$N^5$-(Benzothiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(5-tert-Butyl-isoxazol-3-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(3-Methyl-benzo[d]isothiazol-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(1H-Indol-5-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—$N^5$-(6-Fluoro-benzothiazol-2-yl)-(6R*)—$N^6$-(4-pyrrolidin-1-yl-butyl)-(4S*,7R*)-[4,7-ethenylene-spiro[2.4]heptane]-5,6-dicarboxamide;

(5R*)—N$^5$-(2-Ethyl-butyl)-(6R1-N$^6$-(4-pyrrolidin-1-yl-butyl)-(4S*,7R*)-[4,7-ethenylene-spiro[2.4]heptane]-5,6-dicarboxamide;

(5R*)—N$^5$-(4-(4-Chlorophenyl)-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(Benzo[2,1,3]oxadiazol-4-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-tert-Butyl-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(3-Phenyl-[1,2,4]thiadiazol-5-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(6-Chloro-benzothiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(3-(2-Methyl-1H-indol-1-yl)-propyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(1-Methyl-1H-benzoimidazol-2-yl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(1H-Indol-1-yl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-(2-Methoxy-phenyl)-ethyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-Bromo-phenyl)-(6R*)-6-[(3-(3,5-dimethyl-pyrazol-1-yl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(5-phenyl-isoxazole-4-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(4-(2-oxo-pyrrolidin-1-yl)-butyrylamino)-methyl]-(4S*,7R*)-[4,7-ethenylene-spiro[2.4]heptane]-5-carboxamide;

(5R*)—N$^5$-(4-Bromo-phenyl)-(6R*)-6-[(2-(2-chloro-phenyl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-methoxy-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(N,N-dimethyl-aminocarbonyl)-propionyl-amino)-methyl]-(4S*,7R*)-[4,7-ethenylene-spiro[2.4]heptane]-5-carboxamide;

(5R*)—N$^5$-(4-Bromo-phenyl)-(6R*)-6-{[(2,2-dichloro-1-methyl-cyclopropylcarbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(4-methoxycarbonyl-butanoyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-(pentanoylamino-methyl)-(4S*,7R*)-[4,7-ethenylene-spiro[2.4]heptane]-5-carboxamide;

(5R*)—N$^5$-(4-Bromo-phenyl)-(6R*)-6-[(2-(2,5-dimethyl-thiazol-4-yl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-{[1-phenyl-1H-pyrazole-5-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(3-aminocarbonyl-propionyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(4-methyl-pyridine-3-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(isobutyrylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(N-ethyl-piperidine-4-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(3-pyridin-3-yl-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-{[N-(3-methoxy-propionyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(2-chloro-3-fluoro-phenyl-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(4-pynrolidin-1-yl-butanoylamino)-methyl]-(4S*,7R*)-[4,7-ethenylene-spiro[2.4]heptane]-5-carboxamide;

(5R*)—N$^5$(4-Bromo-phenyl)-(6R*)-6-{[(1,5-dimethyl-1H-pyrazole-3-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-{[(cyclopentyl-carbonyl)-amino]-methyl}-(4S*,7R*)-[4,7-ethenylene-spiro[2.4]heptane]-5-carboxamide;

(5R*)—N$^5$-(4-Bromo-phenyl)-(6R*)-6-[(2-(2-methyl-thiazol-4-yl)-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(2-(N,N-dimethyl-amino)-acetylamino)-methyl]-(4S*,7R*)-[4,7-ethenylene-spiro[2.4]heptane]-5-carboxamide;

(5R*)—N$^5$44-Bromo-phenyl)-(6R*)-6-{[N-(2-(2-chloro-phenyl)-acetyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-{[N-(1,5-dimethyl-1H-pyrazole-3-carbonyl)-N-methyl-amino]-methyl}-(4S*,7R*)-[4,7-ethenylene-spiro[2.4]heptane]-5-carboxamide;

(5R*)—N$^5$-(4-Bromo-phenyl)-(6R*)-6-[(2-cyclopropyl-acetylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(1-methyl-1H-benzoimidazol-2-yl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-1H-indol-3-yl-propionylamino)-methyl]-(4S*,7R*)-[4,7-ethenylene-spiro[2.4]heptane]-5-carboxamide;

(5R*)—N$^5$44-Bromo-phenyl)-(6R*)-6-[(butanoylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-(4-fluoro-phenyl)-propionylamino)-methyl]-(4S*,7R*)-[4,7-ethenylene-spiro[2.4]heptane]-5-carboxamide;

(5R*)—N$^5$-(4-Bromo-phenyl)-(6R*)-6-[(3-phenyl-acryloylamino)-methyl]-(4S*,7R*)-[4,7-ethenylene-spiro[2.4]heptane]-5-carboxamide;

(5R*)—N$^5$-(4-Bromo-phenyl)-(6R*)-6-{[(5-chloro-1,3-dimethyl-1H-pyrazole-4-carbonyl)-amino]-methyl}-(4S*,7R*)-[4,7-ethenylene-spiro[2.4]heptane]-5-carboxamide;

(5R*)—N⁵-(4-Acetyl-thiazol-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Acetyl-phenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-Methyl-thiazol-2-yl)-(6R*)—N⁶-(4-pyroliclin-1-yl-butyl)-(4S*,7R*))-[4,7-ethenylene-spiro[2.4]heptane]-5,6-dicarboxamide;

(5R*)—N⁵-(5-Acetyl-thiophen-2-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R)—N⁵-(5-Acetyl-furan-2-yl-methyl)-(6R)—N⁶-(4-pyrrolidin-1-yl-butyl)-(4S,7R)-[4,7-ethenylene-spiro[2.4]heptane]-5,6-dicarboxamide;

(5R*)—N⁵-(5-Acetyl-furan-2-yl-methyl)-(6R)—N⁶-(4-pyrrolidin-1-yl-butyl)-(4S,7R)-[4,7-ethylene-spiro[2.4]heptane]-5,6-dicarboxamide;

(5R*)—N⁵-(4-Trifluoromethyl-phenyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Acetyl-oxazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-(4,5-Dimethyl-1H-imidazol-2-yl)-ethyl)-(6R*)—N⁶-(4-bromophenyl)-(4S*,7R*)-[4,7-ethenylene-spiro[2.4]heptane]-5,6-dicarboxamide;

(5R*)—N⁵-(4-Iodophenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(5-(iso-Butyl)-isoxazol-3-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2-Bromo-thiophen-4-yl-methyl)-(6R*)—N⁶-(4-pyrrolidin-1-yl-butyl)-(4S*,7R*)-[4,7-ethenylene-spiro[2.4]heptane]-5,6-dicarboxamide; or (5R*)—N⁵-(2-Fluoro-4-bromophenyl-methyl)-(6R*)—N⁶-(4-pyrrolidin-1-yl-butyl)-(4S*,7R*)-[4,7-ethenylene-spiro[2.4]heptane]-5,6-dicarboxamide;

or a salt thereof.

11. The compound according to claim 1, selected from:

(5R*)—N⁵-(4-Bromophenyl)-(6R*)—N⁵-(3-dimethylamino-3-oxopropyl)-(4S*,7R*)-[4,7-ethenylene-spiro[2.4]heptane]-5,6-dicarboxamide;

(5R*)—N⁵-(4-Bromophenyl)-(6R*)—N⁶-(4-amino-4-oxobutyl)-(4S*,7R*)-[4,7-ethenylene-spiro[2.4]heptane]-5,6-dicarboxamide;

(5R*)—N⁵-(4-Bromophenyl)-(6R*)—N⁶-(3-pyrrolidino-3-oxopropyl)-(4S*,7R*)-[4,7-ethenylene-spiro[2.4]heptane]-5,6-dicarboxamide;

(5R*)—N⁵-(4-Bromophenyl)-(6R*)—N⁶-(2-amino-2-oxoethyl)-(4S*,7R*)-[4,7-ethenylene-spiro[2.4]heptane]-5,6-dicarboxamide;

(5R)—N⁵-(4-Bromophenyl)-(6R)—N⁶-(4-(4-ethyl-piperazin-1-yl)-butyl)-(4S, 7R)-[4,7-ethenylene-spiro[2.4]heptane]-5,6-dicarboxamide;

(5R)—N⁵-(4-Bromophenyl)-(6R)—N⁶-(4-piperidino-butyl)-(4S, 7R)-[4,7-ethenylene-spiro[2.4]heptane]-5,6-dicarboxamide;

(5R)—N⁵-(4-Bromophenyl)-(6R)—N⁶-(4-(azetidin-1-yl)butyl)-(4S,7R)-[4,7-ethenylene-spiro[2.4]heptane]-5,6-dicarboxamide;

(5R)—N⁵-(4-Bromophenyl)-(6R)—N⁵-(4-morpholino-butyl)-(4S,7R)-[4,7-ethenylene-spiro[2.4]heptane]-5,6-dicarboxamide;

(5R)—N⁵-(4-Bromophenyl)-(6R)—N⁶-(4-(4-methyl-1,4-diazepan-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-(4-methyl-piperazin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-pyrrolidino-4-oxobutyl)-(4S,7R)-[4,7-ethenylene-spiro[2.4]heptane]-5,6-dicarboxamide;

(5R)—N⁵-(4-Bromophenyl)-(6R)—N⁶-(2-(2-(pyrrolidin-1-yl)ethoxy)ethyl)-(4S,7R)-[4,7-ethenylene-spiro[2.4]heptane]-5,6-dicarboxamide;

(5R)—N⁵-(4-Bromophenyl)-(6R)—N⁶-((3R,6S)-6-(pyrrolidin-1-ylmethyl)tetrahydro-2H-pyran-3-yl)-(4S, 7R)-[4,7-ethenylene-spiro[2.4]heptane]-5,6-dicarboxamide;

(5R)—N⁵-(4-Bromophenyl)-(6R)—N⁶-(4-(4-acetyl-piperazin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(cis-4-(pyrrolidin-1-yl-methyl)-cyclohexyl)-(4S,7R)-[4,7-ethenylene-spiro[2.4]heptane]-5,6-dicarboxamide;

(5R)—N⁵-(4-Bromophenyl)-(6R)—N⁶-(4((3R)-fluoropyrrolidino)butyl)-(4S,7R)-[4,7-ethenylene-spiro[2.4]heptane]-5,6-dicarboxamide;

(5R)—N⁵-(4-Bromophenyl)-(6R)—N⁶-(4((3S)-fluoropyrrolidino)butyl)-(4S,7R)-[4,7-ethenylene-spiro[2.4]heptane]-5,6-dicarboxamide;

(5R)—N⁵-(4-Bromophenyl)-(6R)—N⁶-(5-pyrrolidinopentyl)-(4S,7R)-[4,7-ethenylene-spiro[2.4]heptane]-5,6-dicarboxamide;

(5R)—N⁵-(4-Bromophenyl)-(6R)—N⁶-(trans-4-(pyrrolidin-1-yl-methyl)-cyclohexyl)-(4S,7R)-[4,7-ethenylene-spiro[2.4]heptane]-5,6-dicarboxamide;

(5R*)—N⁵-(4-Bromophenyl)-(6R*)—N⁶-(3-methylamino-3-oxopropyl)-(4S*,7R*)-[4,7-ethenylene-spiro[2.4]heptane]-5,6-dicarboxamide;

(5R*)—N⁵-(2-Acetyl-thiazol-5-yl-methyl)-(6R*)—N⁶-(4-pyrrolidin-1-yl-butyl)-(4S*,7R*)-[4,7-ethenylene-spiro[2.4]heptane]-5,6-dicarboxamide;

(5R)—N⁵-(5-Bromo-thiazol-2-yl)-(6R)—N⁶-(4-pyrrolidin-1-yl-butyl)-(4S,7R)-[4,7-ethenylene-spiro[2.4]heptarie]-5,6-dicarboxamide;

(5R*)—N⁵-(2,6-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(2,3-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3-Fluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(3,5-Difluoro-4-methoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Chloro-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Fluoro-phenyl-methyl)-(6R*)—N⁶-(4-pyrolidin-1-yl-butyl)-(4S*,7R*)-[4,7-ethenylene-spiro[2.4]heptane]-5,6-dicarboxamide;

(5R*)—N⁵-(4-Trifluoromethoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N⁵-(4-Isopropoxy-phenyl-methyl)-(6R*)—N⁶-(4-pyrrolidin-1-yl-butyl)-(4S*,7R*)-[4,7-ethenylene-spiro[2.4]heptane]-5,6-dicarboxamide;

(5R*)—N$^5$-(4-Bromo-thiazol-2-yl-methyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-Acetyl-oxazol-4-yl-methyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-Bromo-phenyl-methyl)-(6R*)—N$^6$-(3-pyrrolidin-1-yl-propyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(3-pyrrolidin-1-yl-propyl)-(4S*,7R*)-[4,7-ethenylene-spiro[2.4]heptane]-5,6-dicarboxamide;

(5R)—N$^5$-(5-Bromo-thiazol-2-yl)-(6R)—N$^6$-(4-pyrrolidin-1-yl-butyl)-(4S,7R)-[4,7-ethylene-spiro[2.4]heptane]-5,6-dicarboxamide;

(5R)—N$^5$-(5-Bromo-thiazol-2-yl)-(6R)—N$^6$-(3-amino-3-oxopropyl)-(4S,7R)-[4,7-ethylene-spiro[2.4]heptane]-5,6-dicarboxamide;

(5R)—N$^5$-(5-Bromo-thiazol-2-yl)-(6R)—N$^6$-(3-amino-3-oxopropyl)-(4S,7R)-[4,7-ethenylene-spiro[2.4]heptane]-5,6-dicarboxamide;

(5R)—N$^5$-(4-Bromo-phenyl-methyl)-(6R)—N$^6$-(3-amino-3-oxopropyl)-(4S,7R)-[4,7-ethenylene-spiro[2.4]heptane]-5,6-dicarboxamide;

(5R)—N$^5$-(2-Bromo-pyrid-5-yl)-(6R)—N$^6$-(3-amino-3-oxopropyl)-(4S,7R)-[4,7-ethenylene-spiro[2.4]heptane]-5,6-dicarboxamide;

(5R*)—N$^5$-(4-Acetyl-oxazol-2-yl-methyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-Acetyl-thiazol 2-yl-methyl)-(6R*)—N$^5$-(isobutyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(isobutyl)-(4S*,7R*)-[4,7-ethenylene-spiro[2,4]heptane]-5,6-dicarboxamide;

(5R*)—N$^5$-(4-Bromo-phenyl-methyl)-(6R*)—N$^6$-(isobutyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(3-(1H-benzoimidazol-2-yl)-propyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(3-(1H-benzoimidazol-2-yl)-propyl)-(4S*,7R*)-[4,7-ethenylene-spiro[2.4]heptane]-5,6-dicarboxamide;

(5R*)—N$^5$-(4-Bromo-phenyl-methyl)-(6R*)—N$^6$-(3-(1H-benzoimidazol-2-yl)-propyl)-(4S*,7R*)-[4,7-ethenylene-spiro[2.4]heptane]-5,6-dicarboxamide;

(5R*)—N$^5$-(2-Methoxy-pyridin-5-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(2-Bromo-pyrazin-5-yl)-(5R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(5-Trifluoromethyl-pyridin-2-yl)-(6R*)—N$^6$-(4-pyrrolidin-1-yl-butyl)-(4S*,7R*)-[4,7-ethenylene-spiro[2,4]heptane]-5,6-dicarboxamide;

(5R*)—N$^5$-(2-Methyl-pyridin-5-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(Benzo[d]oxazol-6-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(5-Methyl-isoxazol-3-yl-methyl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(4-Methyl-thiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R*)—N$^5$-(5-Trifluommethyl-1,3,4-thiadiazol-2-yl)-(6R*)—N$^6$-(4-pyrrolidin-1-yl-butyl)-(4S*,7R*)-[4,7-ethenylene-spiro[2.4]heptane]-5,6-dicarboxamide;

(5R)—N$^5$-(2-Bromo-pyridin-5-yl)-(6R)—N$^5$-(4-pyrrolidin-1-yl-butyl)-(4S,7R)-[4,7-ethenylene-spiro[2.4]heptane]-5,6-dicarboxamide;

(5R*)—N$^5$-(5-Bromo-thiazol-2-yl)-(6R*)—N$^6$-(2-fluoro-ethyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-((2-imidazolidin-2-on)-1-yl-ethyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(3-amino-3-oxopropyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(4-diethylamino-butyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(3-ethoxy-propyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(3-pyrrolidino-propyl)-(4S*,7R*)-[4,7-ethenylene-spiro[2.4]heptane]-5,6-dicarboxamide;

(5R*)—N$^5$-(5-Bromothiazol-2-yl)-(6R*)—N$^6$-(3-(4-methylpiperazin-1-yl)-propyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(2-dimethylamino-ethyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(3-dimethylamino-propyl)-(4S*,7R*)-[4,7-ethenylene-spiro[2.4]heptane]-5,6-dicarboxamide;

(5R*)—N$^5$-(4-Acetyl-thiazol-2-yl-methyl)-(6R*)—N$^6$-(3-(4-methylpiperazin-1-yl)-propyl)-(4S*,7R*)-[4,7-ethenylene-spiro[2.4]heptane]-5,6-dicarboxamide;

(5R*-N$^5$-(4-Acetyl-thiazol-2-yl-methyl)-(6R*)—N$^6$-((2-imidazolidin-2-on)-1-yl-ethyl)-(4S*,7R*)-[4,7-ethenylene-spiro[2.4]heptane]-5,6-dicarboxamide;

(5R*)—N$^5$-(5-Bromothiazol-2-yl)-(6R*)—N$^6$-(4-diethylamino-butyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(2-fluoroethyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(4-diethylamino-butyl)-(4S*,7R*)-[4,7-ethenylene-spiro[2.4]heptane]-5,6-dicarboxamide;

(5R*)—N$^5$-(4-Bromophenyl-methyl)-(6R*)—N$^5$-(3-(4-methylpiperazin-1-yl)-propyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(2-dimethylamino-ethyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(2-imidazolidin-2-on)-1-yl-ethyl)-(4S*,7R*)-[4,7-ethenylene-spiro[2.4]heptane]-5,6-dicarboxamide;

(5R*)—N$^5$-(5-Bromothiazol-2-yl)-(6R*)—N$^5$-(2-methoxy-ethyl)-(4S*,7R*)-[4,7-ethenylene-spiro[2.4]heptane]-5,6-dicarboxamide;

(5R*)—N$^5$-(5-Bromothiazol-2-yl)-(6R*)—N$^6$-(3-dimethylamino-propyl)-(4S*,7R*)-[4,7-ethenylene-spiro[2.4]heptane]-5,6-dicarboxamide;

(5R)—N$^5$-(2-Bromopyrid-5-yl)-(6R)—N$^6$-(3-amino-3-oxopropyl)-(4S,7R)-[4,7-ethylene-spiro[2.4]heptane]-5,6-dicarboxamide;

(5R)—N$^5$-(2-Bromopyrid-5-yl)-(6R)—N$^6$-(4-pyrrolidino-butyl)-(4S,7R)-[4,7-ethylene-spiro[2.4]heptane]-5,6-dicarboxamide;

(5R)—N$^5$-(5-Bromopyrid-2-yl)-(6R)—N$^6$-(3-amino-3-oxopropyl)-(4S,7R)-[4,7-ethylene-spiro[2.4]heptane]-5,6-dicarboxamide;

(5R)—N$^5$-(2-Chloropyrid-5-yl)-(6R)—N$^6$-(3-amino-3-oxopropyl)-(4S,7R)-[4,7-ethylene-spiro[2.4]heptane]-5,6-dicarboxamide;

(5R)—N$^5$-(4-Bromo-2-fluorophenyl-methyl)-(6R)—N$^6$-(3-amino-3-oxopropyl)-(4S,7R)-[4,7-ethylene-spiro[2.4]heptane]-5,6-dicarboxamide;

(5R)—N$^5$-(2-Bromothiazol-5-yl-methyl)-(6R)—N$^6$-(3-amino-3-oxopropyl)-(4S,7R)-[4,7-ethylene-spiro[2.4]heptane]-5,6-dicarboxamide;

(5R)—N$^5$-(4-Bromo-2-fluorophenyl-methyl)-(6R)—N$^6$-(4-pyrrolidino-butyl)-(4S,7R)-[4,7-ethylene-spiro[2.4]heptane]-5,6-dicarboxamide;

(5R)—N$^5$-(4-Methoxyphenyl)-(6R)—N$^6$-(4-pyrrolidino-butyl)-(4S,7R)-[4,7-ethylene-spiro[2.4]heptane]-5,6-dicarboxamide;

(5R)—N$^5$-(4-Bromophenyl-methyl)-(6R)—N$^6$-(4-pyrrolidino-butyl)-(4S,7R)-[4,7-ethylene-spiro[2.4]heptane]-5,6-dicarboxamide;

(5R)—N$^5$-(4-Methoxyphenyl)-(6R)—N$^6$-(3-hydroxyl-3-oxopropyl)-(4S,7R)-[4,7-ethylene-spiro[2.4]heptane]-5,6-dicarboxamide;

(5R)—N$^5$-(4-Bromo-3-fluorophenyl)-(6R)—N$^6$-(4-pyrrolidino-butyl)-(4S,7R)-[4,7-ethylene-spiro[2.4]heptane]-5,6-dicarboxamide;

(5R)—N$^5$-(2-Chloro-pyridin-5-yl)-(6R)—N$^6$-(4-pyrrolidino-butyl)-(4S,7R)-[4,7-ethylene-spiro[2.4]heptane]-5,6-dicarboxamide;

(5R)—N$^5$-(4-Methoxyphenyl)-(6R)—N$^6$-(3-amino-3-oxopropyl)-(4S,7R)-[4,7-ethylene-spiro[2.4]heptane]-5,6-dicarboxamide;

(5R)—N$^5$-(4-Bromophenyl-methyl)-(6R)—N$^5$-(3-amino-3-oxopropyl)-(4S,7R)-[4,7-ethylene-spiro[2.4]heptane]-5,6-dicarboxamide;

(5R)—N$^5$-(4-Bromo-2-fluorophenyl-methyl)-(6R)—N$^6$-(3-amino-3-oxopropyl)-(4S,7R)-[4,7-ethylene-spiro[2.4]heptane]-5,6-dicarboxamide;

(5R)—N$^5$-(4-Methoxyphenyl)-(6R)—N$^6$-(3-amino-3-oxopropyl)-(4S,7R)-[4,7-ethylene-spiro[2.4]heptane]-5,6-dicarboxamide;

(5R)—N$^5$-(5-Bromo-pyridin-2-yl)-(6R)—N$^6$-(4-pyrrolidino-butyl)-(4S,7R)-[4,7-ethylene-spiro[2.4]heptane]-5,6-dicarboxamide;

(5R)—N$^5$-(4-Bromo-2-fluorophenyl)-(6R)—N$^6$-(4-pyrrolidino-butyl)-(4,S,7R)-[4,7-ethylene-spiro[2.4]heptane]-5,6-dicarboxamide;

(5R)—N$^5$-(4-Bromo-2-methylphenyl)-(6R)—N$^6$-(4-pyrrolidino-butyl)-(4S,7R)-[4,7-ethylene-spiro[2.4]heptane]-5,6-dicarboxamide;

(5R)—N$^5$-(4-Bromo-3-chlorophenyl)-(6R)—N$^6$-(4-pyrrolidino-butyl)-(4S,7R)-[4,7-ethylene-spiro[2.4]heptane]-5,6-dicarboxamide;

(5R)—N$^5$-(2-Chloro-pyridin-5-yl)-(6R)—N$^6$-(3-amino-3-oxopropyl)-(4S,7R)-[4,7-ethylene-spiro[2.4]heptane]-5,6-dicarboxamide;

(5R*)—N$^5$-(4-Acetyl-thiazol-2-yl-methyl)-(6R*)—N$^6$-(3-amino-propyl)-(4S*,7R*)-[4,7-ethylene-spiro[2.4]heptane]-5,6-dicarboxamide;

(5R*)—N$^5$-(4-Acetyl-thiazol-2-yl-methyl)-(6R*)—N$^6$-(piperidin-4-yl-methyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(2-methylamino-ethyl)-(4S*,7R*)-[4,7-ethenylene-spiro[2.4]heptane]-5,6-dicarboxamide;

(5R*)—N$^5$(5-Bromo-thiazol-2-yl)-(6R*)—N$^6$-(5-amino-pentyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(4-(aminomethyl)phenyl-methyl)-(4S*,7R*)-[4,7-ethenylene-spiro[2.4]heptane]-5,6-dicarboxamide;

(5R*)—N$^5$-(5-Bromo-thiazol-2-yl)-(6R*)—N$^6$-(2,2-dimethyl-3-amino-propyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(2-methylamino-ethyl)-(4S*,7R*)-[4,7-ethenylene-spiro[2.4]heptane]-5,6-dicarboxamide;

(5R*)—N$^5$-(4-Bromophenyl-methyl)-(6R*)—N$^5$-(piperidin-4-yl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(3-amino-propyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(3-(aminomethyl)phenyl-methyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(4-(aminomethyl)phenyl-methyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(2,2-dimethyl-3-amino-propyl)-(4S*,7R*)-[4,7-ethenylene-spiro[2.4]heptane]-5,6-dicarboxamide;

(5R*)—N$^5$-(4-Bromophenyl-methyl)-(6R*)—N$^6$-(piperidin-4-yl-methyl)-(4S*,7R*)-[4,7-ethenylene-spiro[2.4]heptane]-5,6-dicarboxamide;

(5R)—N$^5$-(2-Bromo-thiazol-5-yl-methyl)-(6R)—N$^6$-(4-pyrrolidino-butyl)-(4S,7R)-[4,7-ethenylene-spiro[2.4]heptane]-5,6-dicarboxamide;

(5R)—N$^5$-(5-Methyl-pyridin-2-yl)-(6R)—N$^6$-(3-amino-3-oxopropyl)-(4S,7R)-[4,7-ethenylene-spiro[2.4]heptane]-5,6-dicarboxamide;

(5R)—N$^5$-(4-Bromo-2,5-difluorophenyl)-(6R)—N$^6$-(4-pyrrolidino-butyl)-(4S,7R)-[4,7-ethenylene-spiro[2.4]heptane]-5,6-dicarboxamide;

(5R)—N$^5$-(4-Bromo-2,6-difluorophenyl)-(6R)—N$^6$-(4-pyrrolidino-butyl)-(4S,7R)-[4,7-ethenylene-spiro[2.4]heptane]-5,6-dicarboxamide;

(5R)—N$^5$-(4-Bromo-2,3-d difluorophenyl)-(6R)—N$^6$-(4-pyrrolidino-butyl)-(4S,7R)-[4,7-ethenylene-spiro[2.4]heptane]-5,6-dicarboxamide;

(5R)—N$^5$-(4-Bromo-2,6-difluorophenyl-methyl)-(6R)—N$^6$-(4-pyrrolidin-1-yl-butyl)-(4S,7R)-[4,7-ethenylene-spiro[2.4]heptane]-5,6-dicarboxamide;

(5R)—N$^5$-(4-Bromo-2-fluorophenyl-methyl)-(6R)—N$^5$-(4-pyrrolidino-butyl)-(4S,7R)-[4,7-ethylene-spiro[2.4]heptane]-5,6-dicarboxamide;

(5R)—N$^5$-(4-Bromo-2-fluorophenyl-methyl)-(6R)—N$^6$-(5-amino-pentyl)-(4S,7R)-[4,7-ethenylene-spiro[2.4]heptane]-5,6-dicarboxamide;

(5R)—N$^5$-(4-Bromo-2-fluorophenyl-methyl)-(6R)—N$^6$-(4-amino-butyl)-(4S,7R)-[4,7-ethenylene-spiro[2.4]heptane]-5,6-dicarboxamide;

(5R)—N$^5$-(4-Bromo-3-fluorophenyl-methyl)-(6R)—N$^6$-(4-pyrrolidino-butyl)-(4S,7R)-[4,7-ethenylene-spiro[2.4]heptane]-5,6-dicarboxamide;

(5R)—N⁶-(5-Bromo-thiazol-2-yl)-(6R)—N⁶-(5-aminopentyl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yhmethyl)-(4S,7R)-[4,7-ethenylene-spiro[2.4]heptane]-5,6-dicarboxamide;

(5R)—N⁵-(5-Bromo-thiazol-2-yl)-(6R)—N⁶,N⁶-(3-(aminomethyl)pentane-1,5-diyl)-(4S,7R)-[4,7-ethenylene-spiro[2.4]heptane]-5,6-diearboxamide;

(5R)—N⁵-(4-Bromo-2-fluorophenyl-methyl)-(6R)—N⁶-(5-amino-pentyl)-(4S,7R)-[4,7-ethylene-spiro[2.4]heptane]-5,6-dicarboxamide;

(5R)—N⁵-(4-Bromo-2,3-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-3,5-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-2,5-difluorophenyl-methyl)-(6R)—N⁶-(4-pyrrolidino-butyl)-(4S,7R)-[4,7-ethenylene-spiro[2.4]heptane]-5,6-dicarboxamide;

(5R)—N⁵-(5-Bromo-thiazol-2-yl)-(6R)—N⁶-(piperidin-4-yl)-(4S,7R)-[4,7-ethylene-spiro[2.4]heptane]-5,6-dicarboxamide;

(5R)—N⁵-(5-Bromo-thiazol-2-yl)-(6R)—N⁶-(isobutyl)-(4S,7R)-[4,7-ethylene-spiro[2.4]heptane]-5,6-dicarboxamide;

(5R)—N⁵-(5-Bromo-thiazol-2-yl)-(6R)—N⁶-(4-tert-butoxycarbonyl-amino-butyl)-(4S,7R)-[4,7-ethylene-spiro[2.4]heptane]-5,6-dicarboxamide;

(5R)—N⁵-(5-Bromo-thiazol-2-yl)-(6R)—N⁶-(5-tert-butoxycarbonyl-amino-pentyl)-(4S,7R)-[4,7-ethylene-spiro[2.4]heptane]-5,6-dicarboxamide;

(5R)—N⁵-(5-Bromo-thiazol-2-yl)-(6R)—N⁶-(5-aminopentyl)-(4S,7R)-[4,7-ethylene-spiro[2.4]heptane]-5,6-dicarboxamide;

(5R)—N⁵-(5-Bromo-thiazol-2-yl)-(6R)—N⁶-(4-aminobutyl)-(4S,7R)-[4,7-ethylene-spiro[2.4]heptane]-5,6-dicarboxamide;

(5R)—N⁵-(5-Bromo-thiazol-2-yl)-(6R)—N⁶,N⁶-(3-(aminomethyl)pentane-1,5-diyl)-(4S,7R)-[4,7-ethylene-spiro[2.4]heptane]-5,6-dicarboxamide;

(5R)—N⁵-(5-Bromo-thiazol-2-yl)-(6R)—N⁶-(piperidin-4-yl-methyl)-(4S,7R)-[4,7-ethylene-spiro[2.4]heptane]-5,6-dicarboxamide;

(5R)—N⁵-(2-Bromo-3-fluoro-pyridin-5-yl)-(6R)—N⁶-(4-pyrrolidino-butyl)-(4S,7R)-[4,7-ethenylene-spiro[2.4]heptane]-5,6-dicarboxamide;

(5R*)—N⁵-(4-Aminobutyl)-(6R*)—N⁶-(4-bromophenyl)-(4S*,7R*)-[4,7-ethenylene-spiro[2.4]heptane]-5,6-dicarboxamide;

(5R*)—N⁵-(5-Aminopentyl)-(6R*)—N⁶-(4-bromophenyl)-(4S*,7R*)-[4,7-ethenylene-spiro[2.4]heptane]-5,6-dicarboxamide;

(5R*)—N⁵-(2-(Cyclohexen-1-yl)ethyl)-(6R*)—N⁶-(4-pyrrolidino-butyl)-(4S*,7R*)--[4,7-ethenylene-spiro[2.4]heptane]-5,6-dicarboxamide;

(5R*)—N⁵-(4-tert-Butyl-cyclohexyl)-(6R*)—N⁵-(4-pyrrolidino-butyl)-(4S*,7R*)-[4,7-ethenylene-spiro[2.4]heptane]-5,6-dicarboxamide;

(5R*)—N⁵-(2-(Pyridin-2-yl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Acetyl-thiazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Trifluoromethyl-thiazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,4,6-Trifluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,4-Dimethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(2-Acetyl-thiazol-4-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Chloro-2-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Methyl-oxazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(5-Acetyl-thiazol-2-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Acetylphenyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Bromo-4-fluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,3,5-Trifluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(4-Methyl-1,2,5-oxadiazol-3-yemethyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Fluoro-3-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3,5-Dimethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3-Acetylphenyl-methyl)-(6R*)—N⁵-(4-pyrrolidino-butyl)-(4S*,7R*)-[4,7-ethenylene-spiro[2.4]heptane]-5,6-dicarboxamide;

(5R*)—N⁵-(3-Difluoromethoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(2-Methoxypyridin-4-yl)methyl]-(6R*)—N⁶-(4-pyrrolidino-butyl)-(4,3*,7R*)-[4,7-ethenylene-spiro[2.4]heptane]-5,6-dicarboxamide;

(5R*)—N⁵-(3-Fluoro-5-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Acetylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Chloro-5-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Fluoro-5-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4-Fluoro-3-trifluoromethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-[(2,6-Dichloropyridin-4-yl)methyl]-(6R*)—N⁶-(4-pyrrolidino-butyl)-(4S*,7R*)-[4,7-ethenylene-spiro[2.4]heptane]-5,6-dicarboxamide;

(5R*)—N⁵-(2,5-Dimethylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(4,5-Dimethyl-thiazol-2-yl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Methoxy-5-methylphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Chloro-3,6-difluorophenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Isopropoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-Chloro-6-fluoro-3-methylphenyl-methyl)-(6R*)—N⁶-(4-pyrrolidino-butyl)-(4S*,7R*)[4,7-ethenylene-spiro[2.4]heptane]-5,6-dicarboxamide;

(5R*)—N⁵-(3-Chloro-4-methoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(3,4-Dimethoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2,4-Dimethoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(3,4-Dimethoxyphenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(4-Methoxyphenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(4-Bromophenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(3,4-Dimethylphenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(4-Methylphenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(4-Fluorophenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(Benzo[d][1,3]dioxol-5-yl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(3-Bromo-4-methoxyphenyl)ethyl)-(6R*)—N⁶-(4-pyrrolidino-butyl)-(4S*,7R*)-[4,7-ethenylene-spiro[2.4]heptane]-5,6-dicarboxamide;

(5R*)—N⁵-(2-(2,4-Dimethylphenyl)ethyl)-(6R*)—N⁶-(4-pyrrohdino-butyl)-(4S*,7R*)-[4,7-ethenylene-spiro[2.4]heptane]-5,6-dicarboxamide;

(5R*)—N⁵-(4-Ethoxyphenyl-methyl)-(6R*)—N⁶-(4-pyrrolidino-butyl)-(4S*,7R*)-[4,7-ethenylene-spiro[2.4]heptane]-5,6-dicarboxamide;

(5R)—N⁵-(2-(4-Chlorophenyeethyl)-(6R)—N⁶-(4-pyrradino-butyl)-(4S,7R)-[4,7-ethenylene-spiro[2.4]heptane]-5,6-dicarboxamide;

(5R)—N⁵-(2-(4-Chlorophenyl)ethyl)-(6R)—N⁶-(2-dimethylamino-ethyl)-(4S,7R)-[4,7-ethenylene-spiro[2.4]heptane]-5,6-dicarboxamide;

(5R)—N⁵-(2-(4-Chlorophenyl)ethyl)-(6R)—N⁶-(2-(pyridin-2-yl)ethyl)-(4S,7R)-[4,7-ethenylene-spiro[2.4]heptane]-5,6-dicarboxamide;

(5R)—N⁵-(2-(4-Chlorophenypethyl)-(6R)—N⁶-(2-(4-aminosulfonyl-phenyl)-ethyl)-(4S,7R)-[4,7-ethenylene-spiro[2.4]heptane]-5,6-dicarboxamide;

(5R)—N⁵-(2-(2,4-Dichlorophenyl)ethyl)-(6R)-(4-pyrrolidino-butyl)-(4S,7R)-[4,7-ethenylene-spiro[2.4]heptane]-5,6-dicarboxamide;

(5R)—N⁵-(2-(4-Chlorophenyl)ethyl)-(6R)—N⁶-(N-isopentyl-piperidin-4-yl)-(4S,7R)-[4,7-ethenylene-spiro[2.4]heptane]-5,6-dicarboxamide;

(5R)—N⁵-(4-Bromo-3,5-difluorophenyl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-thiazol-2-yl)-(6R)—N⁶-(4-pyrrolidino-butyl)-(4S,7R)-[4,7-ethenylene-spiro[2.4]heptane]-5,6-dicarboxamide;

(5R)—N⁵-(4-Bromo-3-trifluoromethylphenyl)-(6R)—N⁶-(4-pyrrolidino-butyl)-(4S,7R)-[4,7-ethenylene-spiro[2.4]heptane]-5,6-dicarboxamide;

(5R*)—N⁵-[(4-Acetyl-thiazol-2-yl)methyl]-(6R*)—N⁶-(2-methylamino-ethyl)-(4S*,7R*)-[4,7-ethenylene-spiro[2.4]heptane]-5,6-dicarboxamide;

(5R)—N⁵-(4-Bromophenyl)-(6R)—N⁶-(4-(2,5-dimethylpyrrolidin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-(pyrrolidin-1-yl)pentyl)-(4S,7R)-[4,7-ethenylene-spiro[2.4]heptane]-5,6-dicarboxamide;

(5R)—N⁵-(4-Bromophenyl)-(6R)—N⁶-(3-fluoro-4-(pyrrolidin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-(2-(methoxymethyl)pyrrolidin-1-yl)butyl)-(4S,7R)-[4,7-ethenylene-spiro[2.4]heptane]-5,6-dicarboxamide;

(5R)—N⁵-(4-Bromophenyl)-(6R)—N⁶-(4-(3,3-difluoropyrrolidin-1-yl)butyl)-(4S,7R)-[4,7-ethenylene-spiro[2.4]heptane]-5,6-dicarboxamide;

(5R)—N⁵-(2-Bromo-3-fluoro-pyridin-5-yl)-(6R)—N⁶-(4-pyrrolidino-butyl)-(4S,7R)-[4,7-ethenylene-spiro[2.4]heptane]-5,6-dicarboxamide;

(5R)—N⁵-(5-Bromothiazol-2-yl)-(6R)—N⁶-(2-hydroxyethyl)-(4S,7R)-[4,7-ethylene-spiro[2.4]heptane]-5,6-dicarboxamide;

(5R)—N⁵-(5-Bromothiazol-2-yl)-(6R)—N⁶-(3-hydroxypropyl)-(4S,7R)-[4,7-ethylene-spiro[2.4]heptane]-5,6-dicarboxamide;

(5R)—N⁵-(5-Bromothiazol-2-yl)-(6R)—N⁶-(4-hydroxybutyl)-(4S,7R)-[4,7-ethylene-spiro[2.4]heptane]-5,6-dicarboxamide;

(5R)—N⁵-(5-Bromothiazol-2-yl)-(6R)—N⁶-(2-methyl-3-hydroxyprop-2-yl)-(4S,7R)-[4,7-ethylene-spiro[2.4]heptane]-5,6-dicarboxamide;

(5R)—N⁵-(5-Bromothiazol-2-yl)-(6R)—N⁶-(2-(2-hydroxyethoxy)ethyl)-(4S,7R)-[4,7-ethylene-spiro[2.4]heptane]-5,6-dicarboxamide;

(5R)—N⁵-(5-Bromothiazol-2-yl)-(6R)—N⁶-(4-hydroxycyclohexyl)-(4S,7R)-[4,7-ethylene-spiro[2.4]heptane]-5,6-dicarboxamide;

(5R)—N⁵-(5-Bromothiazol-2-yl)-(6R)—N⁶-[(1-hydroxycyclohexyl)methyl]-(4S,7R)-[4,7-ethylene-spiro[2.4]heptane]-5,6-dicarboxamide;

(5R)—N$^5$-(5-Bromothiazol-2-yl)-(6R)—N$^6$-(trans-4-(hydroxymethyl)-cyclohexyl)-(4S,7R)-[4,7-ethylene-spiro[2.4]heptane]-5,6-dicarboxamide;

(5R)—N$^5$-(5-Bromothiazol-2-yl)-(6R)—N$^6$-(cis-4-(hydroxymethyl)-cyclohexyl)-(4S,7R)-[4,7-ethylene-spiro[2.4]heptane]-5,6-dicarboxamide;

(5R)—N$^5$-(5-Bromothiazol-2-yl)-(6R)—N$^6$-(pyrrolidin-3-yl)-(4S,7R)-[4,7-ethylene-spiro[2.4]heptane]-5,6-dicarboxamide;

(5R)—N$^5$-(5-Bromothiazol-2-yl)-(6R)—N$^6$-(2-(N-methylamino)-ethyl)-(4S,7R)-[4,7-ethylene-spiro[2.4]heptane]-5,6-dicarboxamide;

(5R)—N$^5$-(5-Bromothiazol-2-yl)-(6R)—N$^6$-(3-(N-methylamino)-propyl)-(4S,7R)-[4,7-ethylene-spiro[2.4]heptane]-5,6-dicarboxamide;

(5R)—N$^5$-(5-Bromothiazol-2-yl)-(6R)—N$^6$-(piperidin-3-yl)-(4S,7R)-[4,7-ethylene-spiro[2.4]heptane]-5,6-dicarboxamide;

(5R)—N$^5$-(5-Bromothiazol-2-yl)-(6R)—N$^6$-[(pyrrolidin-2-yl)-methyl]-(4S,7R)-[4,7-ethylene-spiro[2.4]heptane]-5,6-dicarboxamide;

(5R)—N$^5$-(5-Bromothiazol-2-yl)-(6R)—N$^6$-[(piperidin-2-yl)-methyl]-(4S,7R)-[4,7-ethylene-spiro[2.4]heptane]-5,6-dicarboxamide;

(5R)—N$^5$-(5-Bromothiazol-2-yl)-(6R)—N$^6$-[(piperidin-3-yl)-methyl]-(4S,7R)-[4,7-ethylene-spiro[2.4]heptane]-5,6-dicarboxamide;

(5R)—N$^5$-(5-Bromothiazol-2-yl)-(6R)—N$^6$-(azetidin-3-yl)-(4S,7R)-[4,7-ethylene-spiro[2.4]heptane]-5,6-dicarboxamide;

(5R)—N$^5$-(4-Bromophenyl)-(6R)—N$^6$-(cis-4-(aminomethyl)-cyclohexyl)-(4S,7R)-[4,7-ethenylene-spiro[2.4]heptane]-5,6-dicarboxamide;

(5R)—N$^5$-(4-Bromophenyl)-(6R)—N$^6$-(trans-4-(aminomethyl)-cyclohexyl)-(4S,7R)-[4,7-ethenylene-spiro[2.4]heptane]-5,6-dicarboxamide; or (5R*)—N$^5$-(2-Trifluoromethyl-pyridin-5-yl)-(6R*)—N$^6$-(4-pyrrolidin-1-yl-butyl)-(4S*,7R*)-[4,7-ethenylene-spiro[2.4]heptane]-5,6-dicarboxamide; or a salt thereof.

12. The compound according to claim 1, wherein the salt thereof is a pharmaceutically acceptable salt thereof.

13. A pharmaceutical composition comprising, a compound according to claim 1, or a pharmaceutically acceptable salt thereof, and at least one therapeutically inert excipient.

14. A method of treating a disease comprising administering to a subject in need thereof, an effective amount of the compound according to claim 1, wherein the disease is rheumatoid arthritis, acute lung injury, severe asthma, cystic fibrosis, inflammatory bowel disease, keratoconjunctivitis sicca, or Alzheimer's disease.

15. A method of treating a disease comprising administering to a subject in need thereof, an effective amount of the composition according to claim 13, wherein the disease is rheumatoid arthritis, acute lung injury, severe asthma, cystic fibrosis, inflammatory bowel disease, keratoconjunctivitis sicca, or Alzheimer's disease.

16. The compound according to claim 1, wherein
W represents —CH$_2$CH$_2$— or —CH=CH—;
Y represents a bond or a (C$_1$-C$_4$)alkandiyl group;
R$^1$ represents an aryl-group or a heteroaryl-group, wherein the groups are independently unsubstituted, mono-, di- or tri-substituted, and wherein the substituents are independently selected from halogen, (C$_1$-C$_4$)alkyl, (C$_1$-C$_4$)alkoxy, (C$_1$-C$_2$)alkyl-carbonyl, (C$_1$-C$_2$)fluoroalkyl, (C$_1$-C$_2$)fluoroalkoxy, nitro, cyano or phenyl, wherein the phenyl is unsubstituted or mono- Substituted with halogen;

Z represents —C(O)NR$^3$—* or —CH$_2$NR$^4$C(O)—*, wherein the asterisks indicate the bond which is linked to R$^2$;

R$^2$ represents
(C$_3$-C$_6$)cycloalkyl, which is unsubstituted or mono-substituted with hydroxy or —CONH$_2$;
(C$_1$-C$_6$)alkyl, which is mono-substituted with fluorine, trifluoromethyl, (C$_1$-C$_4$)alkoxy, (C$_1$-C$_4$)alkylthio, (C$_1$-C$_4$)alkoxy-carbonyl, hydroxy, cyano, —NR$^5$R$^6$ or —C(O)NR$^7$R$^8$;
(C$_1$-C$_4$)alkyl, which is mono-substituted with heterocyclyl, wherein the heterocyclyl is unsubstituted or mono-substituted at a nitrogen atom with (C$_1$-C$_4$)alkyl; or
(C$_1$-C$_4$)alkyl, which is mono-substituted with an aryl-group or heteroaryl-group, wherein the groups are independently unsubstituted, mono-, di- or tri-substituted, and wherein the substituents are independently selected from halogen, (C$_1$-C$_4$)alkyl, —CH$_2$NH$_2$ or —SO$_2$NH$_2$; or
heterocyclyl, which is unsubstituted or mono-substituted at a nitrogen atom with (C$_1$-C$_6$)alkyl, benzyl or tert-butoxycarbonyl; or
an aryl-group or a heteroaryl-group, wherein the groups are independently unsubstituted, mono- or di-substituted, and wherein the substituents are independently selected from halogen, (C$_1$-C$_4$)alkyl or phenyl;

R$^3$ represents hydrogen, (C$_1$-C$_3$)alkyl or 2-methoxy-ethyl;
R$^4$ represents hydrogen or methyl;
R$^5$ represents hydrogen, (C$_1$-C$_3$)alkyl or tert-butoxycarbonyl;
R$^6$ represents hydrogen or (C$_1$-C$_3$)alkyl; and
R$^7$ and R$^8$ represent independently from each other hydrogen or methyl;

or a salt thereof.

17. The compound according to claim 1, wherein
Y represents a (C$_1$-C$_2$)alkandiyl group and R$^1$ represents an aryl-group, wherein the group is unsubstituted, mono-, di- or tri-substituted, and wherein the substituents are halogen, (C$_1$-C$_4$)alkyl or (C$_1$-C$_4$)alkoxy; or benzo[d][1,3]dioxolyl;
or a salt thereof.

18. The compound according to claim 17, wherein Z represents —C(O)NR$^3$—*, wherein the asterisk indicates the bond which is linked to R$^2$; or a salt thereof.

19. The compound according to claim 2, wherein R$^2$ represents (C$_1$-C$_4$)alkyl, which is mono-substituted with heterocyclyl, wherein the heterocyclyl is unsubstituted or mono-substituted at a nitrogen atom with methyl;
or a salt thereof.

20. The compound according to claim 18, wherein R$^2$ represents (C$_1$-C$_4$)alkyl, which is mono-substituted with heterocyclyl, wherein the heterocyclyl is unsubstituted or mono-substituted at a nitrogen atom with methyl;
or a salt thereof.

21. A method of treating a disease comprising administering to a subject in need thereof, an effective amount of the compound according to claim 1, wherein the disease is rheumatoid arthritis.

22. A method of treating a disease comprising administering to a subject in need thereof, an effective amount of the composition according to claim 13, wherein the disease is rheumatoid arthritis.

23. A method of treating a disease comprising administering to a subject in need thereof, an effective amount of the compound according to claim 1, wherein the disease is acute lung injury.

24. A method of treating a disease comprising administering to a subject in need thereof, an effective amount of the composition according to claim 13, wherein the disease is acute lung injury.

25. A method of treating a disease comprising administering to a subject in need thereof, an effective amount of the compound according to claim 1, wherein the disease is severe asthma.

26. A method of treating a disease comprising administering to a subject in need thereof, an effective amount of the composition according to claim 13, wherein the disease is severe asthma.

27. A method of treating a disease comprising administering to a subject in need thereof, an effective amount of the compound according to claim 1, wherein the disease is cystic fibrosis.

28. A method of treating a disease comprising administering to a subject in need thereof, an effective amount of the composition according to claim 13, wherein the disease is cystic fibrosis.

29. A method of treating a disease comprising administering to a subject in need thereof, an effective amount of the compound according to claim 1, wherein the disease is inflammatory bowel disease.

30. A method of treating a disease comprising administering to a subject in need thereof, an effective amount of the composition according to claim 13, wherein the disease is inflammatory bowel disease.

31. A method of treating a disease comprising administering to a subject in need thereof, an effective amount of the compound according to claim 1, wherein the disease is keratoconjunctivitis sicca.

32. A method of treating a disease comprising administering to a subject in need thereof, an effective amount of the composition according to claim 13, wherein the disease is keratoconjunctivitis sicca.

33. A method of treating a disease comprising administering to a subject in need thereof, an effective amount of the compound according to claim 1, wherein the disease is Alzheimer's disease.

34. A method of treating a disease comprising administering to a subject in need thereof, an effective amount of the composition according to claim 13, wherein the disease is Alzheimer's disease.

\* \* \* \* \*